US012766337B2

(12) United States Patent
Petluri et al.

(10) Patent No.: US 12,766,337 B2
(45) **Date of Patent: *Oct. 20, 2026**

(54) SWITCHABLE BIOACTIVE LIGHTING

(71) Applicant: KORRUS, INC., Los Angeles, CA (US)

(72) Inventors: Raghuram L. V. Petluri, Los Angeles, CA (US); Paul Kenneth Pickard, Los Angeles, CA (US); Benjamin Harrison, Los Angeles, CA (US)

(73) Assignee: Korrus, Inc., Anaheim, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/617,143

(22) Filed: Mar. 26, 2024

(65) Prior Publication Data

US 2024/0416142 A1 Dec. 19, 2024

Related U.S. Application Data

(63) Continuation of application No. 18/103,184, filed on Jan. 30, 2023, now Pat. No. 11,938,339, which is a (Continued)

(51) Int. Cl.
*A61N 5/06* (2006.01)
*H05B 45/22* (2020.01)

(Continued)

(52) U.S. Cl.
CPC ........... *A61N 5/0618* (2013.01); *H05B 45/22* (2020.01); *H05B 45/28* (2020.01); *H05B 47/115* (2020.01);

(Continued)

(58) Field of Classification Search
CPC .......... A61N 5/0618; A61N 2005/0626; A61N 2005/0652; A61N 2005/0663;

(Continued)

(56) References Cited

U.S. PATENT DOCUMENTS 7,748,845 B2 7/2010 Casper
8,018,135 B2 9/2011 Van De Ven (Continued)

FOREIGN PATENT DOCUMENTS

CN 106449626 A 2/2017
CN 107167962 A 9/2017

(Continued)

OTHER PUBLICATIONS

Commission Internationale de l'Éclairage. 1995. Technical Report: Method of Measuring and Specifying Colour Rendering Properties of Light Sources, CIE No. 13.3—1995. Vienna, Austria: Commission Internationale de l'Éclairage, 22 pages.

(Continued)

*Primary Examiner* — Abdullah A Riyami
*Assistant Examiner* — Syed M Kaiser
(74) *Attorney, Agent, or Firm* — FisherBroyles LLP

(57) ABSTRACT

The present disclosure provides lighting systems, which may be semiconductor light emitting devices, with two or more of blue, red and/or LRNE, short-blue-pumped cyan, long-blue-pumped cyan, yellow, and violet channels. The lighting systems can have a plurality of operational modes that provide different biological effects while having good color rendering capability. The yellow and violet channels can include violet LEDs and be used in operational modes that provide white light with lower EML values relative to operational modes using three or more of the blue, red, short-blue-pumped cyan, and long-blue-pumped cyan color channels.

17 Claims, 28 Drawing Sheets

Related U.S. Application Data continuation of application No. 17/316,264, filed on May 10, 2021, now abandoned, which is a continuation of application No. PCT/US2019/060636, filed on Nov. 8, 2019, which is a continuation-in-part of application No. 16/393,660, filed on Apr. 24, 2019, now Pat. No. 10,805,998, and a continuation-in-part of application No. PCT/US2019/013380, filed on Jan. 11, 2019, and a continuation-in-part of application No. PCT/US2019/013359, filed on Jan. 11, 2019, and a continuation-in-part of application No. PCT/US2019/013379, filed on Jan. 11, 2019, and a continuation-in-part of application No. PCT/US2019/013356, filed on Jan. 11, 2019.

(60) Provisional application No. 62/757,664, filed on Nov. 8, 2018, provisional application No. 62/757,672, filed on Nov. 8, 2018, provisional application No. 62/758,411, filed on Nov. 9, 2018, provisional application No. 62/758,447, filed on Nov. 9, 2018, provisional application No. 62/885,162, filed on Aug. 9, 2019.

(51) Int. Cl.
*H05B 45/28* (2020.01)
*H05B 47/115* (2020.01)

(52) U.S. Cl.
CPC ................ *A61N 2005/0626* (2013.01); *A61N 2005/0652* (2013.01)

(58) Field of Classification Search
CPC ...... H05B 45/22; H05B 45/28; H05B 47/115; H05B 45/20; H05B 47/105; Y02B 20/40
See application file for complete search history.

(56) References Cited

U.S. PATENT DOCUMENTS

| | | | |
|---|---|---|---|
| 8,028,706 | B2 | 10/2011 | Skene |
| 8,506,612 | B2 | 8/2013 | Ashdown |
| 8,508,127 | B2 | 8/2013 | Negley |
| 8,646,939 | B2 | 2/2014 | Bues |
| 8,791,642 | B2 | 7/2014 | Van De Ven |
| 8,921,875 | B2 | 12/2014 | Letoquin |
| 8,933,644 | B2 | 1/2015 | David |
| 9,007,495 | B1 | 4/2015 | Chin |
| 9,181,471 | B2 | 11/2015 | Kang |
| 9,192,013 | B1 | 11/2015 | Van De Ven |
| 9,289,622 | B2 | 3/2016 | Feng |
| 9,370,669 | B2 | 6/2016 | Park |
| 9,410,664 | B2 | 8/2016 | Krames |
| 9,474,111 | B2 | 10/2016 | Harris |
| 9,474,119 | B1 | 10/2016 | Chen |
| 9,526,143 | B1 | 12/2016 | Petluri |
| 9,543,363 | B2 | 1/2017 | Baek |
| 9,560,714 | B1 | 1/2017 | Hjerde |
| 9,609,715 | B1 | 3/2017 | Petluri |
| 9,719,660 | B1 | 8/2017 | Petluri |
| 9,807,843 | B2 | 10/2017 | Koo |
| 9,827,440 | B2 | 11/2017 | Moore-Ede |
| 9,839,091 | B2 | 12/2017 | Petluri |
| 9,860,956 | B2 | 1/2018 | Petluri |
| 9,900,957 | B2 | 2/2018 | Van De Ven |
| 9,990,722 | B2 | 6/2018 | Kim |
| 10,009,971 | B2 | 6/2018 | Chobot |
| 10,022,556 | B1 | 7/2018 | Holbert |
| 10,039,169 | B2 | 7/2018 | Chen |
| 10,084,320 | B2 | 9/2018 | Tanabe |
| 10,085,320 | B1 | 9/2018 | Sussman |
| 10,113,700 | B2 | 10/2018 | Soer |
| 10,128,415 | B2 | 11/2018 | Huang |
| 10,269,285 | B2 | 4/2019 | Lee |
| 10,362,654 | B2 | 7/2019 | Bong |
| 10,401,683 | B2 | 9/2019 | David |
| 10,416,496 | B2 | 9/2019 | Yang |
| 10,475,363 | B2 | 11/2019 | Chen |
| 10,485,070 | B2 | 11/2019 | Chen |
| 10,602,583 | B2 | 3/2020 | Petluri |
| 10,747,056 | B2 | 8/2020 | Yang |
| 10,750,590 | B2 | 8/2020 | Petluri |
| 10,805,998 | B2 | 10/2020 | Petluri |
| 10,946,211 | B2 | 3/2021 | Hommes |
| 11,064,585 | B2 | 7/2021 | Petluri |
| 11,073,727 | B2 | 7/2021 | David |
| 11,265,983 | B2 | 3/2022 | Petluri |
| 11,843,018 | B2 | 12/2023 | Yokogawa |
| 11,938,339 | B2 * | 3/2024 | Petluri ................ H05B 47/115 |
| 2001/0028227 | A1 | 10/2001 | Lys |
| 2005/0015122 | A1 | 1/2005 | Mott |
| 2005/0161586 | A1 | 7/2005 | Rains, Jr. |
| 2006/0221272 | A1 | 10/2006 | Negley |
| 2007/0085862 | A1 | 4/2007 | Moriya |
| 2007/0096057 | A1 | 5/2007 | Hampden-Smith |
| 2007/0205712 | A1 | 9/2007 | Radkov |
| 2007/0268234 | A1 | 11/2007 | Wakabayashi |
| 2008/0224598 | A1 | 9/2008 | Baretz |
| 2008/0275533 | A1 | 11/2008 | Powell |
| 2009/0026913 | A1 | 1/2009 | Mrakovich |
| 2009/0281604 | A1 | 11/2009 | De Boer |
| 2010/0174345 | A1 | 7/2010 | Ashdown |
| 2010/0177084 | A1 | 7/2010 | Murata |
| 2010/0182294 | A1 | 7/2010 | Roshan |
| 2010/0220269 | A1 | 9/2010 | Takama |
| 2010/0264850 | A1 | 10/2010 | Yamamoto |
| 2010/0320928 | A1 | 12/2010 | Kaihotsu |
| 2011/0043137 | A1 | 2/2011 | Negley |
| 2011/0043486 | A1 | 2/2011 | Hagiwara |
| 2011/0127930 | A1 | 6/2011 | Bennette |
| 2012/0044202 | A1 | 2/2012 | Ishizaki |
| 2012/0223657 | A1 | 9/2012 | Van De Ven |
| 2012/0259392 | A1 | 10/2012 | Feng |
| 2012/0271384 | A1 | 10/2012 | Muehlemann |
| 2012/0326627 | A1 | 12/2012 | Mcdaniel, Jr. |
| 2012/0330387 | A1 | 12/2012 | Ferraz Rigo |
| 2013/0015774 | A1 | 1/2013 | Briggs |
| 2013/0020929 | A1 | 1/2013 | Van De Ven |
| 2013/0070442 | A1 | 3/2013 | Negley |
| 2013/0140490 | A1 | 6/2013 | Fujinaga |
| 2013/0165741 | A1 | 6/2013 | Seabury |
| 2013/0301034 | A1 | 11/2013 | Olds |
| 2014/0035472 | A1 | 2/2014 | Raj |
| 2014/0048743 | A1 | 2/2014 | Le-Mercier |
| 2014/0204023 | A1 | 7/2014 | Kumar |
| 2014/0228914 | A1 | 8/2014 | Van De Ven |
| 2014/0232289 | A1 | 8/2014 | Brandes |
| 2014/0264290 | A1 | 9/2014 | Brown |
| 2015/0002034 | A1 | 1/2015 | Van De Ven |
| 2015/0062892 | A1 | 3/2015 | Krames |
| 2015/0109495 | A1 | 4/2015 | Tanaka |
| 2015/0231408 | A1 | 8/2015 | Williams |
| 2015/0295144 | A1 | 10/2015 | Weiler |
| 2015/0342457 | A1 | 12/2015 | Sanchez Ramos |
| 2015/0348468 | A1 | 12/2015 | Chen |
| 2016/0063951 | A1 | 3/2016 | Ikizyan |
| 2016/0066387 | A1 | 3/2016 | Darton |
| 2016/0140889 | A1 | 5/2016 | Wu |
| 2016/0273717 | A1 | 9/2016 | Krames |
| 2016/0286616 | A1 * | 9/2016 | van de Ven ........... H05B 47/16 |
| 2016/0316527 | A1 | 10/2016 | Allen |
| 2016/0339203 | A1 | 11/2016 | Krames |
| 2017/0027033 | A1 | 1/2017 | Chobot |
| 2017/0033309 | A1 | 2/2017 | Song |
| 2017/0069290 | A1 | 3/2017 | Lee |
| 2017/0085768 | A1 | 3/2017 | Van Der Sijde |
| 2017/0086274 | A1 | 3/2017 | Soler |
| 2017/0105265 | A1 | 4/2017 | Sadwick |
| 2017/0140145 | A1 | 5/2017 | Shah |
| 2017/0169764 | A1 | 6/2017 | Lee |
| 2017/0193880 | A1 | 7/2017 | Lee |
| 2017/0219184 | A1 | 8/2017 | Petluri |
| 2017/0223786 | A1 | 8/2017 | Petluri |

(56) References Cited

U.S. PATENT DOCUMENTS

| | | | |
|---|---|---|---|
| 2017/0231058 A1 | 8/2017 | Sadwick | |
| 2017/0236866 A1 | 8/2017 | Lee | |
| 2017/0303818 A1 | 10/2017 | Behzadi | |
| 2017/0348506 A1 | 12/2017 | Berman | |
| 2017/0354000 A1 | 12/2017 | Gordin | |
| 2017/0356624 A1 | 12/2017 | Petluri | |
| 2017/0368210 A1 | 12/2017 | David | |
| 2018/0056027 A1 | 3/2018 | Peeters | |
| 2018/0077767 A1 | 3/2018 | Soler | |
| 2018/0139817 A1 | 5/2018 | Yamakawa | |
| 2018/0311464 A1 | 11/2018 | Krames | |
| 2018/0317296 A1 | 11/2018 | Chen | |
| 2019/0041699 A1 | 2/2019 | David | |
| 2019/0189853 A1 | 6/2019 | Yoo | |
| 2019/0209806 A1 | 7/2019 | Allen | |
| 2019/0209858 A1 | 7/2019 | Slaughter | |
| 2019/0385506 A1 | 12/2019 | Andrivon | |
| 2020/0074910 A1 | 3/2020 | Chen | |
| 2020/0196411 A1 | 6/2020 | Qiu | |
| 2020/0368550 A1 | 11/2020 | Moore-Ede | |
| 2021/0060353 A1 | 3/2021 | Petluri | |
| 2021/0097943 A1 | 4/2021 | Wyatt | |
| 2022/0050331 A1 | 2/2022 | David | |
| 2024/0387481 A1 | 11/2024 | Johnson | |

FOREIGN PATENT DOCUMENTS

| | | | | |
|---|---|---|---|---|
| CN | 110970409 A | | 4/2020 | |
| CN | 108877690 B | | 1/2021 | |
| CN | 112233609 A | | 1/2021 | |
| DE | 102017204086 A1 | | 9/2018 | |
| JP | 2005063687 A | | 3/2005 | |
| KR | 101574063 B1 | | 12/2015 | |
| WO | 2012024243 | | 2/2012 | |
| WO | 2016130464 | | 8/2016 | |
| WO | 2017131693 A1 | | 8/2017 | |
| WO | 2017131703 A1 | | 8/2017 | |
| WO | 2017131706 A1 | | 8/2017 | |
| WO | 2017131715 A1 | | 8/2017 | |
| WO | 2018039433 | | 3/2018 | |
| WO | 2018039433 A1 | | 3/2018 | |
| WO | 2018130403 | | 7/2018 | |
| WO | 2018176533 A1 | | 10/2018 | |
| WO | WO-2019140326 A1 | * | 7/2019 | G09G 3/3413 |
| WO | WO-2019140327 A2 | * | 7/2019 | H05B 45/20 |
| WO | 2020155841 A1 | | 8/2020 | |
| WO | WO-2021092570 A1 | * | 5/2021 | H05B 45/20 |
| WO | 2021135752 A1 | | 7/2021 | |

OTHER PUBLICATIONS

Figueiro et al.; "Designing with Circadian Stimulus"; Illuminating Engineering Society; Oct. 2016; p. 31-34.
Rea M, Figueiro M, Bierman A, Hamner R. Modelling the spectral sensitivity of the human circadian system. Lighting Research & Technology. 2012;44(4):386-396. doi:10.1177/1477153511430474 (Year: 2012).
Royer et al. "IES Method for Evaluating Light Source Color Rendition," Illuminating Engineering Society; TM-30-15; May 18, 2015; 32 pages.
"Be the First to View Screenliner at Orgatec 2018"; https://thinkingw.com/news/be-the-first-to-view-screenliner-at-orgatec-2018/; Thinking Works Pty Ltd.; Oct. 2018; accessed Jun. 14, 2019; 4 pages.
Alkozei, A. et al., "Acute exposure to blue wavelength light during memory consolidation improces verbal memory performance," PLOS ONE, Sep. 2017, 11 pages.
Arjmandi, N., et al. (2018). "Can Light Emitted from Smartphone Screens and Taking Selfies Cause Premature Aging and Wrinkles?" Journal of Biomedical and Physical Engineering 8(4), 447-452.
Avci, P. et al. (2013). Low-level Laser (Light) Therapy (LLLT) in Skin: Stimulating, Healing, Restoring. Semin Cutan Medical Surgery (32)(1), 41-52.
Chinese Notice of Allowance mailed Feb. 2, 2024 in Chinese Application No. 201980018683.4, including English language translation, 2 pages.
Chinese Office Action mailed Apr. 26, 2023, in Application No. 201980018683.4, including partial English language translation. 7 pages.
Chinese Office Action mailed Nov. 22, 2021, in Application No. 201980018683.4, including English language translation. 8 pages.
Chinese Office Action mailed Sep. 15, 2022, in Application No. 201980018683.4, including English language translation. 7 pages.
European Communication pursuant to Article 94(3) mailed Apr. 19, 2023, in European Application No. 19738727.7, 7 pages.
Ewing et al, "Simulating Circadian Light: Multi-Dimensional Illuminance Analysts," Proceedings of the 15th IBPSA Conference, Aug. 7-9, 2017, pp. 2363-2371, 9pp.
Extended European Search Report issued Oct. 13, 2021, in European Application No. 19738727.7, 8 pages.
Gupta, A.K., Mays, et al. (2018). Efficacy of Non-Surgical Treatments for Androgenetic Alopecia: A Systematic Review and Network Meta-Analysis. Journal of The European Academy of Dermatology and Venereology 32(12), 2112-2125.
Hamblin, M.R. (2017). Mechanisms and Applications of the Anti-Inflammatory Effects of Photobiomodulation. AIMS Biophysics 4(3), 337-361.
Hennessy, M., & Hamblin, M. (2017). Photobiomodulation and the Brain: A New Paradigm. Journal of Optics 19(1):013003. 29 pages.
Hye et al. "Healthy, natural, efficient and tunable lighting: four-package white LEDs for optimizing the circadian effect, color quality and vision performance," Light: Science & Application 3.2 (2014) e141, entire document, 9 pages.
Hye Oh et al., "Healthy, natural, efficient and tunable lighting: four-package white LEDs for optimizing the circadian effect, color quality and vision performance," Light: Science & Applications 3.2 (2014); 23pp.
International Patent Application No. PCT/US2016/015318; Int'l Written Opinion and the Search Report; dated Apr. 11, 2016; 16 pages.
International Patent Application No. PCT/US2019/060634; Int'l Search Report and the Written Opinion; dated Jan. 27, 2020; 10 pages.
International Search Report mailed Apr. 18, 2019, in International Application No. PCT/US2019/013380, 3 pages.
International Search Report mailed Apr. 29, 2019, in International Application No. PCT/US2019/013356, 3 pages.
International Search Report mailed Apr. 30, 2019, in International Application No. PCT/US2019/013359, 3 pages.
International Search Report mailed Mar. 5, 2020, in International Application No. PCT/US2019/060636, 4 pages.
International Search Report mailed May 10, 2018, in International Application No. PCT/US2018/020792, 3 pages.
Kwok-Fai, et al. (2014). Effects of Low Laser Treatment on the Survival of Axotomized Retinal Ganglion Cells in Adult Hamsters. Neural Regeneration Research 9(21), 1863-1869.
Lucas et al, "Measuring and using light in the melanopsin age," Trends in Neurosciences, Jan. 2014, vol. 37, No. 1, 9pp.
Olmo-Aguado, S.,et al. (2016). "Red Light of the Visual Spectrum Attenuates Cell Death in Culture and Retinal Ganglion Cell Death in Situ." Acta Ophthalmologica 94, e481-e49.
Stefani et al., Evaluation of Human Reactions on Displays with LED Backlight and a Technical Concept of a Circadian Effective Display, SID 10 Digest, ISSN 0097-966X/10/4102-1120, 2010, 4 pgs.
Stern, M. et al, "Blue light exposure decreases systolic blood pressure, arterial stiffness, and improves endothelial function in humans," European Journal of Preventative Cardiology, Sep. 2018, 9 pages.
Tosini, G., et al. (2016). "Effects of Blue Light on the Circadian System and Eye Physiology." Molecular Vision: Biology and Genetics in Vision Research 22, 61-72.
U.S. Appl. No. 62/616,401, filed Jan. 11, 2018, Petluri et al.
U.S. Appl. No. 62/616,404, filed Jan. 11, 2018, Petluri et al.
U.S. Appl. No. 62/616,414, filed Jan. 11, 2018, Petluri et al.
U.S. Appl. No. 62/616,423, filed Jan. 11, 2018, Petluri et al.

(56) References Cited

OTHER PUBLICATIONS

U.S. Appl. No. 62/634,798, filed Feb. 23, 2018, Petluri et al.
U.S. Appl. No. 62/712,182, filed Jul. 30, 2018, Petluri et al.
U.S. Appl. No. 62/712,191, filed Jul. 30, 2018, Petluri et al.
U.S. Appl. No. 62/757,664, filed Nov. 8, 2018, Petluri et al.
U.S. Appl. No. 62/757,672, filed Nov. 8, 2018, Petluri et al.
U.S. Appl. No. 62/758,411, filed Nov. 9, 2018, Petluri et al.
Vandersee, S., et al. (2015). "Blue-Violet Light Irradiation Dose Dependently Decreases Carotenoids in Human Skin, Which Indicates the Generation of Free Radicals." Oxidative Medicine and Cellular Longevity doi: 10.1155/2015/579675. 7 pages.
Written Opinion of the International Searching Authority mailed May 10, 2018, in International Application No. PCT/US2018/020792, 5 pages.
Written Opinion of the International Searching Authority mailed Apr. 18, 2019, in International Application No. PCT/US2019/013380, 6 pages.
Written Opinion of the International Searching Authority mailed Apr. 29, 2019, in International Application No. PCT/US2019/013356, 6 pages.
Written Opinion of the International Searching Authority mailed Apr. 30, 2019, in International Application No. PCT/US2019/013359, 8 pages.
Written Opinion of the International Searching Authority mailed Mar. 5, 2020, in International Application No. PCT/US2019/060636, 8 pages.
Communication under Rule 71(3) EPC mailed Oct. 1, 2025, in European Application No. 19738727.7.

* cited by examiner

SWITCHABLE BIOACTIVE LIGHTING

CROSS-REFERENCE TO RELATED APPLICATIONS

This application claims the benefit of International Patent Application No. PCT/US2019/013359 filed Jan. 11, 2019, which claims the benefit of U.S. Provisional Patent Application No. 62/757,672 filed Nov. 8, 2018; International Patent Application No. PCT/US2019/013356 filed Jan. 11, 2019, which claims the benefit of U.S. Provisional Patent Application No. 62/757,664 filed Nov. 8, 2018: U.S. patent application Ser. No. 16/393,660 filed Apr. 24, 2019, which is a Continuation of International Patent Application No. PCT/US2019/013380 filed Jan. 11, 2019, which claims the benefit of U.S. Provisional Patent Application No. 62/758,411 filed Nov. 9, 2018: International Patent Application No. PCT/US2019/013379 filed Jan. 11, 2019, which claims the benefit of U.S. Provisional Patent Application No. 62/758,447 filed Nov. 9, 2018; and U.S. Provisional Patent Application No. 62/885,162 filed Aug. 9, 2019, the entire contents of which are incorporated by reference as if fully set forth herein.

FIELD OF THE DISCLOSURE

This disclosure is in the field of solid-state bioactive lighting. In particular, the disclosure relates to devices for use in, and methods of, providing bioactive tunable white light with high color rendering performance.

BACKGROUND

A wide variety of light emitting devices are known in the art including, for example, incandescent light bulbs, fluorescent lights, and semiconductor light emitting devices such as light emitting diodes ("LEDs").

There are a variety of resources utilized to describe the light produced from a light emitting device, one commonly used resource is 1931 CIE (Commission Internationale de l'Éclairage) Chromaticity Diagram. The 1931 CIE Chromaticity Diagram maps out the human color perception in terms of two CIE parameters x and y. The spectral colors are distributed around the edge of the outlined space, which includes all of the hues perceived by the human eye. The boundary line represents maximum saturation for the spectral colors, and the interior portion represents less saturated colors including white light. The diagram also depicts the Planckian locus, also referred to as the black body locus (BBL), with correlated color temperatures, which represents the chromaticity coordinates (i.e., color points) that correspond to radiation from a black-body at different temperatures. Illuminants that produce light on or near the BBL can thus be described in terms of their correlated color temperatures (CCT). These illuminants yield pleasing "white light" to human observers, with general illumination typically utilizing CCT values between 1,800 K and 10,000 K.

Color rendering index (CRI) is described as an indication of the vibrancy of the color of light being produced by a light source. In practical terms, the CRI is a relative measure of the shift in surface color of an object when lit by a particular lamp as compared to a reference light source, typically either a black-body radiator or the daylight spectrum. The higher the CRI value for a particular light source, the better that the light source renders the colors of various objects it is used to illuminate.

Color rendering performance may be characterized via standard metrics known in the art. Fidelity Index (Rf) and the Gamut Index (Rg) can be calculated based on the color rendition of a light source for 99 color evaluation samples ("CES"). The 99 CES provide uniform color space coverage, are intended to be spectral sensitivity neutral, and provide color samples that correspond to a variety of real objects. Rf values range from 0 to 100 and indicate the fidelity with which a light source renders colors as compared with a reference illuminant. In practical terms, the Rf is a relative measure of the shift in surface color of an object when lit by a particular lamp as compared to a reference light source, typically either a black-body radiator or the daylight spectrum. The higher the Rf value for a particular light source, the better that the light source renders the colors of various objects it is used to illuminate. The Gamut Index Rg evaluates how well a light source saturates or desaturates the 99 CES compared to the reference source.

LEDs have the potential to exhibit very high power efficiencies relative to conventional incandescent or fluorescent lights. Most LEDs are substantially monochromatic light sources that appear to emit light having a single color. Thus, the spectral power distribution of the light emitted by most LEDs is tightly centered about a "peak" wavelength, which is the single wavelength where the spectral power distribution or "emission spectrum" of the LED reaches its maximum as detected by a photo-detector. LEDs typically have a full-width half-maximum wavelength range of about 10 nm to 30 nm, comparatively narrow with respect to the broad range of visible light to the human eye, which ranges from approximately from 380 nm to 800 nm.

In order to use LEDs to generate white light, LED lamps have been provided that include two or more LEDs that each emit a light of a different color. The different colors combine to produce a desired intensity and/or color of white light. For example, by simultaneously energizing red, green and blue LEDs, the resulting combined light may appear white, or nearly white, depending on, for example, the relative intensities, peak wavelengths and spectral power distributions of the source red, green and blue LEDs. The aggregate emissions from red, green, and blue LEDs typically provide poor color rendering for general illumination applications due to the gaps in the spectral power distribution in regions remote from the peak wavelengths of the LEDs.

White light may also be produced by utilizing one or more luminescent materials such as phosphors to convert some of the light emitted by one or more LEDs to light of one or more other colors. The combination of the light emitted by the LEDs that is not converted by the luminescent material (s) and the light of other colors that are emitted by the luminescent material(s) may produce a white or near-white light.

LED lamps have been provided that can emit white light with different CCT values within a range. Such lamps utilize two or more LEDs, with or without luminescent materials, with respective drive currents that are increased or decreased to increase or decrease the amount of light emitted by each LED. By controllably altering the power to the various LEDs in the lamp, the overall light emitted can be tuned to different CCT values. The range of CCT values that can be provided with adequate color rendering values and efficiency is limited by the selection of LEDs.

The spectral profiles of light emitted by white artificial lighting can impact circadian physiology, alertness, and cognitive performance levels. Bright artificial light can be used in a number of therapeutic applications, such as in the treatment of seasonal affective disorder (SAD), certain sleep problems, depression, jet lag, sleep disturbances in those with Parkinson's disease, the health consequences associated with shift work, and the resetting of the human circadian clock. Artificial lighting may change natural processes, interfere with melatonin production, or disrupt the circadian rhythm.

Significant challenges remain in providing LED lamps that can provide white light across a range of CCT values while simultaneously achieving high efficiencies, high luminous flux, good color rendering, and acceptable color stability. It is also a challenge to provide lighting apparatuses that can provide desirable lighting performance while addressing circadian stimulating energy (CSE) performance.

DISCLOSURE

The present disclosure provides aspects of methods, systems and devices of using illumination to one of attenuate, activate, and modulate the response of biological systems in mammalians or for research and teaching models of mammalians and human forms. In some instances the action of the one spectrum of light is used as an antedate or to balance the exposure or lack of exposure to other light.

The present disclosure provides aspects of methods, systems and devices of using bioactive illumination via a plurality of semiconductor light emitting device outputting a first circadian stimulating energy (CSE); at least one external device receiving feedback comprising information associated with at least one of the semiconductor light emitting devices and the first CSE: a master device in communication with the plurality of semiconductor light emitting devices, the master device configured to adjust a parameter on at least one of the plurality of semiconductor light emitting devices based on the feedback, and cause the at least one semiconductor light emitting devices to emit a second CSE. In some instances a first, second, third, and fourth and fifth LED strings, with each LED string comprising one or more LEDs having an associated luminophoric medium.

In some instances the first, second, third, and fourth LED string together with their associated luminophoric mediums comprise red, blue, short-blue-pumped cyan, and long-blue-pumped cyan channels respectively, producing first, second, third, and fourth unsaturated color points of red within long red near infrared energy (LRNE), blue, short-blue-pumped cyan, and long-blue-pumped cyan regions on the 1931 CIE Chromaticity diagram, respectively; a control circuit is configured to adjust a sixth color point of a sixth unsaturated light that results from a combination of the first, second, third, fourth and fifth unsaturated light, with the fifth color point falls within a 7-step MacAdam ellipse around any point on the black body locus having a correlated color temperature between 1800 K and 10000 K.

In some instances the at least one external device is a mobile device, a wearable device, a sensor, a panel system, a lighting device, and a computing system. In some instances the at least one external device is configured to sense one or more of temperature, pressure, ambient lighting conditions, localized lighting conditions, lighting spectrum characteristics, humidity, UV light, sound, particles, pollutants, gases, radiation, location of objects or items, and motion. In some instances the wearable device is incorporated in at least one of armbands, wrist bands, chest bands, glasses, or clothing.

In the above disclosure the one or more external devices may be configured to sense one or more of a person's temperature, blood pressure, heart rate, oxygen saturation, activity type, activity level, galvanic skin response, respiratory rate, cholesterol level (including HDL. LDL and triglyceride), hormone or adrenal levels (e.g., Cortisol, thyroid, adrenaline, melatonin, and others), histamine levels, immune system characteristics, blood alcohol levels, drug content, macro and micro nutrients, mood, emotional state, alertness, and sleepiness. In some instances feedback is indicative of information relating to at least one of light, motion, temperature, environment, physiological data, usage patterns, user feedback, and location.

The present disclosure provides aspects of methods, systems and devices of using bioactive illumination via a plurality of semiconductor light emitting device outputting a first circadian stimulating energy (CSE); at least one external device receiving feedback comprising information associated with at least one of the semiconductor light emitting devices and the first CSE; a master device in communication with the plurality of semiconductor light emitting devices, the master device configured to adjust a parameter on at least one of the plurality of semiconductor light emitting devices based on the feedback, and cause the at least one semiconductor light emitting devices to emit a second CSE. In some instances a first, second, third, and fourth and fifth LED strings, with each LED string comprising one or more LEDs having an associated luminophoric medium and the master device is at least one of a mobile device, a wearable device, and a computing device. In some instances the master device is configured to receive user input. In some instances the parameter is associated with lighting control based on at least one of physiological factors, health conditions, emotional states, user mood, and user input. In some instances the master device is in communication with the plurality of semiconductor light emitting devices through one or more of a wired network, a wireless network, and Bluetooth communication.

The present disclosure provides aspects of methods, systems and devices of using bioactive illumination via semiconductor light emitting device including first, second, third, and fourth and fifth LED strings, with each LED string comprising one or more LEDs having an associated luminophoric medium; the first, second, third, and fourth LED strings together with their associated luminophoric mediums comprise red, blue, short-blue-pumped cyan, and long-blue-pumped cyan channels respectively, producing first, second, third, and fourth unsaturated color points of red within long red near infrared energy (LRNE), blue, short-blue-pumped cyan, and long-blue-pumped cyan regions on the 1931 CIE Chromaticity diagram, respectively; a control circuit is configured to adjust a sixth color point of a sixth unsaturated light that results from a combination of the first, second, third, fourth and fifth unsaturated light, with the fifth color point falls within a 7-step MacAdam ellipse around any point on the black body locus having a correlated color temperature between 1800 K and 10000 K.

In some instances the semiconductor light emitting device is configured to generate the fifth unsaturated light corresponding to a plurality of points along a predefined path with the light generated at each point having light with Rf greater than or equal to about 88, Rg greater than or equal to about 98 and less than or equal to about 104, or both.

In some instances the semiconductor lighting device is configured to generate the fifth unsaturated light corresponding to a plurality of points along a predefined path with the light generated at each point having light with Ra greater than or equal to about along points with correlated color temperature between about 1800 K and 10000 K, R9 greater than or equal to 87 along points with correlated color temperature between about 2000 K and about 10000 K, or both, In some instances the spectral power distribution for the LRNE channel falls within the Red minimum 1 and Red maximum 1 ranges shown in Table 1, Table 2, or both Tables 1 and 2. In some instances the spectral power distribution for the blue channel falls within the Blue minimum 1 and Blue maximum 1 ranges shown in Table 1, Table 2, or both Tables 1 and 2. In some instances the spectral power distribution for the short-blue-pumped cyan channel falls within the short-blue-pumped cyan minimum 1 and short-blue-pumped cyan maximum 1 ranges shown in Table 1, Table 2, or both Tables 1 and 2. In some instances the spectral power distribution for the short-blue-pumped cyan channel falls within the short-blue-pumped cyan minimum 1 and short-blue-pumped cyan maximum ranges shown in Table 1, Table 2, or both Tables 1 and 2. In some instances the spectral power distribution for the long-blue-pumped cyan channel falls within the long-blue-pumped cyan minimum 1 and long-blue-pumped cyan maximum 1 ranges shown in Table 1, Table 2, or both Tables 1 and 2.

The semiconductor light emitting devices described above may have a long red channel which has a spectral power distribution with spectral power in one or more of the wavelength ranges other than the reference wavelength range increased or decreased within 30% greater or less, within 20% greater or less, within 10% greater or less, or within 5% greater or less than the values of a red channel shown in one or more of Tables 3, 4, 7, 8, and 9.

The present disclosure provides aspects of methods, systems and devices of using bioactive illumination via semiconductor light emitting device including first, second, third, and fourth and fifth LED strings, with each LED string comprising one or more LEDs having an associated luminophoric medium: the first, second, third, and fourth LED strings together with their associated luminophoric mediums comprise red, blue, short-blue-pumped cyan, and long-blue-pumped cyan channels respectively, producing first, second, third, and fourth unsaturated color points of red within long red near infrared energy (LRNE), blue, short-blue-pumped cyan, and long-blue-pumped cyan regions on the 1931 CIE Chromaticity diagram, respectively; a control circuit is configured to adjust a sixth color point of a sixth unsaturated light that results from a combination of the first, second, third, fourth and fifth unsaturated light, with the fifth color point falls within a 7-step MacAdam ellipse around any point on the black body locus having a correlated color temperature between 1800 K and 10000 K and the control circuit is configured to provide three operating modes including a first operating mode that generates light only using the blue, red, and short-blue-pumped cyan channels; a second operating mode that generates light only using the blue, red, and long-blue-pumped cyan channels; and, a third operating mode that generates light only using the blue, long red, and long-blue-pumped cyan channels.

In some instances the control circuit is configured to provide three operating modes including a first operating mode that generates light only using the blue, red, and short-blue-pumped cyan channels: a second operating mode that generates light only using the blue, red, and long-blue-pumped cyan channels; and, a third operating mode that generates light only using the blue, long red, and long-blue-pumped cyan channels. In some instances the control circuit is configured to provide three operating modes including a first operating mode that generates light only using the blue, red, and short-blue-pumped cyan channels; a second operating mode that generates light only using the blue, red, and long-blue-pumped cyan channels: a third operating mode that generates visible light only using the blue, red, long red, and long-blue-pumped cyan channels; and, wherein near infrared emissions for a long red near infrared energy (LRNE) which is a non visible is added to at least one of the three operating modes.

In some instances the control circuit is configured to provide three operating modes including a first operating mode that generates light only using the blue, red, and short-blue-pumped cyan channels; a second operating mode that generates light only using the blue, red, and long-blue-pumped cyan channels; and, a third operating mode that generates light only using the blue, red, long-blue-pumped cyan channels; and, provides near infrared emissions for a long red near infrared energy (LRNE) which is a non visible channel In some instances the semiconductor light emitting device control circuit is configured to switch between the first operating mode, the second operating mode and the third operating mode to provide a sixth unsaturated light in the first operating mode and a seventh unsaturated light in the second operating mode, with the sixth unsaturated light and the seventh unsaturated light having substantially the same ccx, ccy coordinated on the 1931 CIE Chromaticity Diagram.

The present disclosure provides aspects of methods of generating bioactive white light, the methods including providing first, second, third, and fourth LED strings, with each LED string comprising one or more LEDs having an associated luminophoric medium; wherein the first, second, third, and fourth LED strings together with their associated luminophoric mediums comprise long red, blue, short-blue-pumped cyan, and long-blue-pumped cyan channels respectively: producing first, second, third, and fourth unsaturated light with color points within long red, blue, short-blue-pumped cyan, and long-blue-pumped cyan regions on the 1931 CIE Chromaticity diagram, respectively; providing a control circuit configured to adjust a fifth color point of a fifth unsaturated light that results from a combination of the first, second, third, and fourth unsaturated light, with the fifth color point falls within a 7-step MacAdam ellipse around any point on the black body locus having a correlated color temperature between 1800 K and 10000 K: generating two or more of the first, second, third, and fourth unsaturated light; and combining the two or more generated unsaturated lights to create the fifth unsaturated light.

In some instances an infrared emissions for long red near infrared energy (LRNE) which is a non visible channel is added. In some instance a control system configured to switch the control circuit based on inputs from one or more sensors to adjust at least one of the long red, short-blue-pumped cyan, and long-blue-pumped cyan strings Disclosed herein are one or more methods and systems comprising: a plurality of semiconductor light emitting device outputting a first circadian stimulating energy (CSE), at least one external device receiving feedback comprising information associated with at least one of the semiconductor light emitting devices and the first CSE, and a master device in communication with the plurality of semiconductor light emitting devices, the master device configured to adjust a parameter on at least one of the plurality of semiconductor light emitting devices based on the feedback, and cause the at least one semiconductor light emitting devices to emit a second CSE.

In aspects of the disclosure, at least one external device is a mobile device, a wearable device, a sensor, a panel system, a lighting device, and a computing system. The at least one external device may be configured to sense one or more of temperature, pressure, ambient lighting conditions, localized lighting conditions, lighting spectrum characteristics, humidity, UV light, sound, particles, pollutants, gases, radiation, location of objects or items, and motion. In an example, the wearable device is incorporated in at least one of armbands, wrist bands, chest bands, glasses, or clothing.

In another aspect, one or more external devices are configured to sense one or more of a person's temperature, blood pressure, heart rate, oxygen saturation, activity type, activity level, galvanic skin response, respiratory rate, cholesterol level (including HDL, LDL and triglyceride), hormone or adrenal levels (e.g., Cortisol, thyroid, adrenaline, melatonin, and others), histamine levels, immune system characteristics, blood alcohol levels, drug content, macro and micro nutrients, mood, emotional state, alertness, and sleepiness.

In another aspect of the disclosure, the feedback is indicative of information relating to at least one of light, motion, temperature, environment, physiological data, usage patterns, user feedback, and location. Additional aspects include the master device being at least one of a mobile device, a wearable device, and a computing device. The master device may be configured to receive user input, and the parameter may be associated with lighting control based on at least one of physiological factors, health conditions, emotional states, user mood, and user input.

The general disclosure and the following further disclosure are exemplary and explanatory only and are not restrictive of the disclosure, as defined in the appended claims. Other aspects of the present disclosure will be apparent to those skilled in the art in view of the details as provided herein. In the figures, like reference numerals designate corresponding parts throughout the different views. All callouts and annotations are hereby incorporated by this reference as if fully set forth herein.

DRAWINGS

The summary, as well as the following detailed description, is further understood when read in conjunction with the appended drawings. For the purpose of illustrating the disclosure, there are shown in the drawings exemplary implementations of the disclosure; however, the disclosure is not limited to the specific methods, compositions, and devices disclosed. In addition, the drawings are not necessarily drawn to scale. In the drawings.

Figure 1:
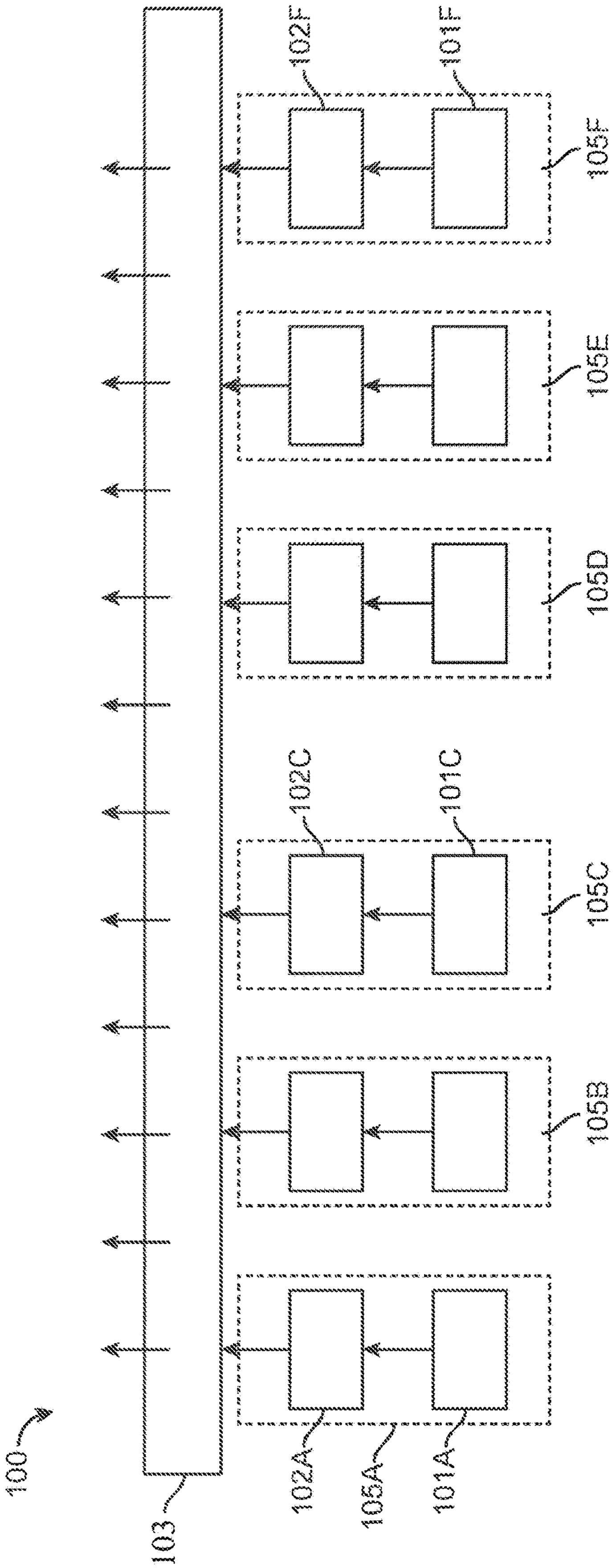
FIG. 1 illustrates aspects of light emitting devices according to the present disclosure.

All descriptions and callouts in the Figures and Tables are hereby incorporated by this reference as if fully set forth herein.

FURTHER DISCLOSURE

The present disclosure may be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular exemplars by way of example only and is not intended to be limiting of the claimed disclosure. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another exemplar includes from the one particular value and/or to the other particular value. Similarly, when values are expressed as approximations, by use of the antecedent "about," it will be understood that the particular value forms another exemplar. All ranges are inclusive and combinable.

The term "circadian-stimulating energy characteristics" refers to any characteristics of a spectral power distribution that may have biological effects on a subject. In some aspects, the circadian-stimulating energy characteristics of aspects of the lighting systems of this disclosure can include one or more of CS, CLA, EML, BLH, CER, CAF, LEF, circadian power, circadian flux, and the relative amount of power within one or more particular wavelength ranges. Circadian-stimulating energy may be referred to as "CSE". The application of CSE to biological systems in doses, amount, aliquots and volumes may be referred to as CSE therapy.

Benefits of Blue Light

Exposure to blue light including CSE affects various bio-physiological functions of the human body and may be called "bioactive". Many of these effects are beneficial. For instance, a region of what is commonly called the blue wavelength region of light may improve memory performance and cognitive function. Exposure to blue wavelength light during memory consolidation has been shown to improve subsequent delayed memory recall when compared to placebo wavelength light exposure. Alkozei, A., Smith R., Dailey N. S., Bajaj S., & Killgore W. D. S. (2017). Acute Exposure to a quantity, volume, aliquot or dose of a specific Blue Wavelength Light During Memory Consolidation Improves Verbal Memory Performance. *PLoS ONE* 12(9), 1-11. Additionally, blue wavelength light may decrease blood pressure, increase blood flow, and improve overall endothelial function. Full body irradiation with blue light has been shown to promote release nitric oxide from the skin into circulating blood. As a result, systolic blood pressure and vascular resistance have been shown to decrease. Stem, M. et al. (2018). Blue Light Exposure Decreases Systolic Blood Pressure, Arterial Stiffness, and Improves Endothelial Function in Humans. *European Journal of Preventive Cardiology* 0(00), 1-9.

Challenges of Blue Light.

In some instances exposure to a quantity of blue light may be involved in damage in human eyes. Blue Light Hazard (BLH) is a known risk and the measure of BLH provides a measure of potential for a photochemical induced retinal injury that results from radiation exposure. Such exposure is one factor which has been linked to photoreceptor damage. It has been reported that the blue light appears to decrease Adenosine Triphosphate (ATP) energy production in retinal ganglion cells. This has a negative effect on mitochondrial function and oxidative stress which has been shown to decrease survival of ganglion cells. Tosini, G., Ferguson. I., & Tsubota, K. (2016). Effects of Blue Light on the Circadian System and Eye Physiology. *Molecular Vision: Biology and Genetics in Vision Research* 22, 61-72. As ganglion cells play a major role in synchronizing circadian rhythms, their destruction inhibits the eye's ability to determine length-of-day and length-of-night. Retinal ganglion cell death further leads to impaired vision. There is also increasing evidence that excessive blue light exposure may cause damage in human skin; it may contribute to wrinkles, worsening skin laxity, and pigmentation issues. Arjmandi, N., Mortazavi G. H., Zarei, S., Faraz M., & Mortazavi, S. A. R. (2018). Can Light Emitted from Smartphone Screens and Taking Selfies Cause Premature Aging and Wrinkles? *Journal of Biomedical and Physical Engineering* 8(4), 447-452. When blue light penetrates the skin it can damage DNA, leading to inflammation, the breakdown of healthy collagen and elastin, and hyperpigmentation. Vandersee, S., Beyer, M., Lademann, J., & Darvin, M. E. (2015). Blue-Violet Light Irradiation Dose Dependently Decreases Carotenoids in Human Skin, Which Indicates the Generation of Free Radicals. *Oxidative Medicine and Cellular Longevity*. doi: 10.1155/2015/579675. It is also reported that excessive blue light at night negatively affects the human body's natural sleep cycle. Blue light, which inhibits melatonin production, reduces both quantity and quality of sleep.

Benefits of Long Red and Near IR.

Blue light is not the only light in the visible spectrum that can be used to affect bio-physiological functions (also referred to herein as "bioactive") of the human body. Recent studies indicate that therapy which may include doses of long red and near-IR: Long Red typically with a spectrum of >625 nms to <700 nms with peak wavelengths >640-nm and Near-Infrared typical ranges from >700 nms and <1400 nm (with typical peak wavelengths: 850 nm, 940 nm, 1064 nm) may affect bio-physiological functions and are also described herein as "bioactive" they may improve eye health, skin health, hair growth, and cognitive function. The spectral sensitivity corresponding to the human eye can be considered to be based on the color-matching functions of the 1931 Standard Observer (XYZ, tristimulus values for CIE 1931 2° color-matching), which show that the effect of light above nm on color perception to be substantially negligible. In other words, it will have no significant impact on the overall (ccx, ccy) color point on the 1931 CIE Chromaticity Diagram of emitted light from a lighting system. Emissions of Long Red and Near-Infrared may be referred to collectively as Long Red and Near-Infrared Energy (LRNE). How the human eye perceives red, long red and near infrared in a given individual may vary based on a plethora of factors including but not limited to age, stimulation of eye before exposure, eye health and health in general. Accordingly, there will be an overlap between the end of long red and the beginning of near infrared. Those of ordinary skill in the art and the skilled artisan will recognize variation is narrow and does not create substantial uncertainty in the terms. Hence the terminology LRNE is encompasses the entirety of both long red and near-infrared.

Additionally. LRNE may be beneficial by reducing, limiting, counteracting or ameliorating some of the negative effects associated with excessive blue light exposure. Disclosed herein are methods and systems to provide therapeutic doses of LRNE either to address a biological condition or as a prophylactic or health supplement means to limit or prevent at least one of an emotional, neurological, immune, and biological condition or system. "Bioactive Exposure" refers to one or both of LRNE and CSE and directing at least one of LRNE and CSE at a biological system which may be a specific organ or any part of the body The Bioactive Exposure may be controlled by a control system (described herein, see e.g., FIG. 28 whereby at least one controller, e.g., a computing device receives inputs including fixed, variable and dynamically changing from a variety of sources and the processor associated with the system and method applies at least one of LRNE and CSE in accordance with said control system. Control input data is at least one of input by: users, server, database, derived from a decisioning engine and collected by at least one sensor. The inputs are provided to a processor via signal communication. The processor may be local to the therapeutic device, remote from the therapeutic device or the processing may take place both locally and remote from the therapeutic device. Control systems disclosed herein may adjust the amount and timing of aliquots of bioactive Exposure. The control of aliquots and frequency in response to input may be used to dynamically adjust the therapeutic or health supplement application of one or more of CSE and LRNE to users. Dynamic adjustment of Bioactive Exposure to a user may be viewed as personalized whereby data harvested from sensors in the lighting installation environment as well as sensors that reflect information about users, such as one or more of physiological sensors (including wearable devices, such as armbands, wrist bands, chest bands, glasses, clothing, and the like), sensors on various devices used by a user, ambient sensors, and the like. The control system may have modules within the platform which may connect to or integrate with data sources of information about users as described below. The frequency of the LRNE and CSE are controllable and the range of emission spans constant on to micro-pulses of less than a tenth of a second. Light pulses can be used to provide Bioactive Exposure. Such pulse may have a duration of less than 100 ms, with a frequency between 10 Hz and 0.5 mHz and have been shown to have a bioactive effect, such pulses may vary from a single pulse up to 400,000 pulses.

Disclosed herein are additional methods and systems to provide Bioactive Exposure as one of a supplement and therapeutic dose of LRNE to:

A. Lessen the effect of age-related macular degeneration by stimulating mitochondria in retinal ganglion eye cells to produce more ATP energy. (Calaza, K. C., Kam. J. H., Hogg, C., & Jeffery G. (2015) and *Neurobiology of Aging* 36, 2869-2876.) The increase in ATP production has been shown to slow the decline in vision associated with aging. LRNE may additionally improve the effects of glaucoma, a condition that destroys ganglion eye cells, by protecting the cornea and the retina. (Olmo-Aguado, S., Núñez-Álvarez, C., & Osborne, N. N. (2016). Red Light of the Visual Spectrum Attenuates Cell Death in Culture and Retinal Ganglion Cell Death in Situ. *Acta Ophthalmologica* 94, e481-e491).

B. Address a biological condition or as a prophylactic or supplement means to limit or prevent a biological condition. Examples, include but are not limited to, to prevent fluid build-up in the front of the eye, a main complication of glaucoma known to result in cell death of ganglion cells. LRNE has been shown to prevent the death of retinal ganglion cells when the optic nerve has been damaged, thereby preventing vision loss that would otherwise occur. (Kwok-Fai, S., Leung, M. C. P., & Cui, Q. (2014). Effects of Low Laser Treatment on the Survival of Axotomized Retinal Ganglion Cells in Adult Hamsters. *Neural Regeneration Research* 9(21), 1863-1869.)

C. improve skin health and appearance by the application of LRNE therapy. LRNE can reduce acute and chronic inflammation by increasing blood flow to damaged tissues. (Hamblin. M. R. (2017). Mechanisms and Applications of the Anti-Inflammatory Effects of Photobiomodulation. *AIMS Biophysics* 4(3), 337-361.) LRNE may be applied to increase natural collagen production, resulting in younger, healthier looking skin. Rats that were exposed to doses of LRN experienced an increase in collagen synthesis and neoformed bone. Brassoliatti, P. et al. (2018). Photobiomodulation on Critical Bone Defects of Rat Calvaria: A Systematic Review. *Lasers in Medical Science* 33(9), 1841-1848. Patients dealing with acne or depigmentation conditions, such as vitiligo, may benefit from undergoing LRN therapy, as it can control sebum production (which leads to acne), and it can stimulate melanocyte proliferation (which enhances skin re-pigmentation). Skin that has been wounded, burned, or scarred also repairs more rapidly if it is exposed to LRN, as red light significantly increases tensile strength and wound contraction while decreasing inflammation. Avci, P. et al. (2013). Low-level Laser (Light) Therapy (LLLT) in Skin: Stimulating, Healing, Restoring. *Semin Cutan Medical Surgery* (32)(1), 41-52.

D. A myriad of other bio-physiological function are impacted by LRNEs, including but not limited to, hair growth and cognitive function. LRNE therapy may be used in conjunction with or as an alternative treatment to hormone regulating drugs typically used to treat hair loss. LRNE exposure has been shown to be a treatment in terms of hair regrowth. Gupta, A. K., Mays, et al. (2018). Efficacy of Non-Surgical Treatments for Androgenetic Alopecia A Systematic Review and Network Meta-Analysis. *Journal of The European Academy of Dermatology and Venereology* 32(12), 2112-2125. Research has also demonstrated that LRNE exposure may lead to improved cognitive function with few side effects. In one study, those exposed to LRNE experienced quicker reaction times, better memory, a more positive mood, and the ability to learn new information faster. These beneficial effects on the human brain may be related to LRNE's increasing cerebral blood flow and oxygen availability and boost ATP energy production. Hennessy, M., & Hamblin, M. (2017). Photobiomodulation and the Brain: A New Paradigm. *Journal of Optics* 19(J):013003.

E. LRNE therapy may be able to counteract, limit or ameliorate the negative effects from excessive CSE and blue light exposure. When humans absorb natural blue light from the sun, they also absorb natural red light from the sun-together the two provide numerous health benefits. However, an overload of artificial blue light such as CSE by itself may be determinantal. This damage can be mitigated through LRN exposure. Balancing and/or controlling an exposure of both artificial blue light and LRNE support wellness benefits similar to those that flow from natural, sunlight exposure.

It is to be appreciated that certain features of the disclosure which are, for clarity, described herein in the context of separate exemplar, may also be provided in combination in a single exemplary implementation. Conversely, various features of the disclosure that are, for brevity, described in the context of a single exemplary implementation, may also be provided separately or in any subcombination. Further, reference to values stated in ranges include each and every value within that range.

In one aspect, the present disclosure provides semiconductor light emitting devices 100 that can have a plurality of light emitting diode (LED) strings. Each LED string can have one, or more than one, LED. As depicted schematically in FIG. 1, the device 100 may comprise a plurality of lighting channels 105A-F formed from LED strings 101A-F and optionally with associated luminophoric mediums 102A-F to produce a particular light output from each of the lighting channels 105A-F. Each lighting channel can have an LED string (101A-F) that emits light (schematically shown with arrows). In some instances, the LED strings can have recipient luminophoric mediums (102A-F) associated therewith. The light emitted from the LED strings, combined with light emitted from the recipient luminophoric mediums, can be passed through one or more optical elements 103. Optical elements 103 may be one or more diffusers, lenses, light guides, reflective elements, or combinations thereof. In some implementations, one or more of the LED strings 101A-F may be provided without an associated luminophoric medium. A recipient luminophoric medium 102A-F includes one or more luminescent materials and is positioned to receive light that is emitted by an LED or other semiconductor light emitting device. In some implementations, recipient luminophoric mediums include layers having luminescent materials that are coated or sprayed directly onto a semiconductor light emitting device or on surfaces of the packaging thereof, and clear encapsulants that include luminescent materials that are arranged to partially or fully cover a semiconductor light emitting device. A recipient luminophoric medium may include one medium layer or the like in which one or more luminescent materials are mixed, multiple stacked layers or mediums, each of which may include one or more of the same or different luminescent materials, and/or multiple spaced apart layers or mediums, each of which may include the same or different luminescent materials. Suitable encapsulants are known by those skilled in the art and have suitable optical, mechanical, chemical, and thermal characteristics. In some implementations, encapsulants can include dimethyl silicone, phenyl silicone, epoxies, acrylics, and polycarbonates. In some implementations, a recipient luminophoric medium can be spatially separated (i.e., remotely located) from an LED or surfaces of the packaging thereof. In some implementations, such spatial segregation may involve separation of a distance of at least about 1 mm, at least about 2 mm, at least about 5 mm, or at least about 10 mm. In certain embodiments, conductive thermal communication between a spatially segregated luminophoric medium and one or more electrically activated emitters is not substantial. Luminescent materials can include phosphors, scintillators, day glow tapes, nanophosphors, inks that glow in visible spectrum upon illumination with light, semiconductor quantum dots, or combinations thereof. In some implementations, the luminescent materials may comprise phosphors comprising one or more of the following materials: $BaMg_2Al_{16}O_{27}:Eu^{2+}$, $BaMg_2Al_{16}O_{27}:Eu^{2+}, Mn^{2+}$, $CaSiO_3$:Pb, Mn, $CaWO_4$:Pb, $MgWO_4$, $Sr_5Cl(PO_4)_3:Eu^{2+}$, $Sr_2P_2O_7:Sn^{2+}$, $Sr_6P_5BO_{20}$:Eu, $CasF(PO_4)_3$:Sb, $(Ba,Ti)_2P_2O_7$:Ti, $Sr_5F(PO_4)_3$:Sb, Mn,$(La,Ce,Tb)PO_4$:Ce,Tb, $(Ca,Zn,Mg)_3(PO_4)_2$:Sn,$(Sr,Mg)_3(PO_4)_2$:Sn, $Y_2O_3:Eu^{3+}$, $Mg_4(F)GeO_6$:Mn, $LaMgAl_{11}O_{19}$:Ce, $LaPO_4$:Ce, $SrAl_{12}O_{19}$:Ce, $BaSi_2O_5$:Pb, $SrB_4O_7$:Eu, $Sr_2MgSi_2O_7$:Pb, $Gd_2O_2S$:Tb, $Gd_2O_2S$:Eu, $Gd_2O_2S$:Pr, $Gd_2O_2S$:Pr,Ce,F, $Y_2O_2S$:Tb, $Y_2O_2S$:Eu, $Y_2O_2S$:Pr, Zn(0.5)Cd(0.4)S:Ag, Zn(0.4)Cd(0.6)S:Ag, $Y_2SiO_5$:Ce, $YAlO_3$:Ce, $Y_3(Al,Ga)_5O_{12}$:Ce, CdS:In, ZnO:Ga, ZnO:Zn,(Zn,Cd)S:Cu,Al, ZnCdS:Ag,Cu, ZnS:Ag, ZnS:Cu, NaI:Tl, CsI:Tl, $^6LiF$/ZnS:Ag, $^6LiF$/ZnS:Cu,Al,Au, ZnS:Cu,Al, ZnS:Cu,Au,Al, $CaAlSiN_3$:Eu, $(Sr,Ca)AlSiN_3$:Eu, $(Ba,Ca,Sr,Mg)_2SiO_4$:Eu, $Lu_3Al_5O_{12}$:Ce, $Eu^{3+}(Gd_{0.9}Y_{0.1})_3Al_5O_{12}:Bi^{3+},Tb^{3+}$, $Y_3Al_5O_{12}$:Ce, $(La,Y)_3Si_6N_{11}$:Ce, $Ca_2AlSi_3O_2N_5:Ce^{3+}$, $Ca_2AlSi_3O_2N_5:Eu^{2+}$, $BaMgAl_{10}O_{17}$:Eu, $Sr_5(PO_4)_3Cl$:Eu,$(Ba,Ca,Sr,Mg)_2SiO_4$:Eu, $Si_{6-z}Al_2N_{8-z}O_z$:Eu (wherein $0<z\leq4.2$); $M_3Si_6O_{12}N_2$:Eu (wherein M=alkaline earth metal element), $(Mg,Ca,Sr,Ba)Si_2O_2N_2$:Eu, $Sr_4Al_{14}O_{25}$:Eu, $(Ba,Sr,Ca)Al_{12}O_4$:Eu, $(Sr,Ba)Al_2Si_2O_8$:Eu, $(Ba,Mg)_2SiO_4$:Eu, $(Ba,Sr,Ca)_2(Mg, Zn)Si_2O_7$:Eu, $(Ba,Ca,Sr,Mg)_9(Sc,Y,Lu,Gd)_2(Si,Ge)_6O_{24}$:Eu, $Y_2SiO_5$:CeTb, $Sr_2P_2O_7-Sr_2B_2O_5$:Eu, $Sr_2Si_3O_8-2SrCl_2$:Eu, $Zn_2SiO_4$:Mn, $CeMgAl_{11}O_{19}$:Tb, $Y_3Al_5O_{12}$:Tb, $Ca_2Y_8(SiO_4)_6O_2$:Tb, $La_3Ga_5SiO_{14}$:Tb,$(Sr,Ba,Ca)Ga_2S_4$:Eu, Tb,Sm, $Y_3(Al,Ga)_5O_{12}$:Ce, $(Y,Ga,Tb,La,Sm,Pr,Lu)_3(Al,Ga)_5O_{12}$:Ce, $Ca_3Sc_2Si_3O_{12}$:Ce, $Ca_3(Sc,Mg,Na,Li)_2Si_3O_{12}$:Ce, $CaSc_2O_4$:Ce, Eu-activated β-Sialon, $SrAl_2O_4$:Eu, $(La,Gd,Y)_2O_2S$:Tb, $CeLaPO_4$:Tb, ZnS:Cu,Al, ZnS:Cu,Au,Al,$(Y,Ga,Lu,Sc,La)BO_3$:Ce, Tb, $Na_2Gd_2B_2O_7$:Ce, Tb, $(Ba,Sr)_2(Ca,Mg,Zn)B_2O_6$:K,Ce,Tb, $CasMg(SiO_4)_4Cl_2$:Eu, Mn,$(Sr,Ca,Ba)(Al,Ga,In)_2S_4$:Eu, $(Ca,Sr)_8(Mg,Zn)(SiO_4)_4Cl_2$:Eu, Mn, $M_3Si_6O_9N_4$:Eu, $Sr_5Al_5Si_{21}O_2N_{35}$:Eu, $Sr_3Si_{13}Al_3N_{21}O_2$:Eu, $(Mg,Ca,Sr,Ba)_2Si_5N_8$:Eu, $(La,Y)_2O_2S$:Eu, $(Y,La,Gd,Lu)_2O_2S$:Eu, $Y(V,P)O_4$:Eu, $(Ba,Mg)_2SiO_4$:Eu, Mn,$(Ba,Sr, Ca,Mg)_2SiO_4$:Eu, Mn, $LiW_2O_8$:Eu, $LiW_2O_8$:Eu, Sm, $Eu_2W_2O_9$, $Eu_2W_2O_9$:Nb and $Eu_2W_2O_9$:Sm,(Ca,Sr)S:Eu, $YAlO_3$:Eu, $Ca_2Y_8(SiO_4)_6O_2$:Eu, $LiY_9(SiO_4)_6O_2$:Eu, $(Y,Gd)_3Al_5O_{12}$:Ce, $(Tb,Gd)_3Al_5O_{12}$:Ce, $(Mg,Ca,Sr,Ba)_2Si_5(N,O)_8$:Eu, $(Mg,Ca,Sr,Ba)Si(N,O)_2$:Eu, $(Mg,Ca,Sr,Ba)AlSi(N,O)_3$:Eu, $(Sr,Ca,Ba,Mg)_{10}(PO_4)_6Cl_2$:Eu, Mn, Eu,$Ba_3MgSi_2O_8$:Eu,Mn, $(Ba,Sr,Ca,Mg)_3(Zn,Mg)Si_2O_8$:Eu, Mn,(k-x)$MgO\cdot xAF_2\cdot GeO_2:yMn^{4+}$ (wherein k=2.8 to 5, x=0.1 to 0.7, y=0.005 to 0.015, A=Ca, Sr, Ba, Zn or a mixture thereof), Eu-activated α-Sialon,$(Gd,Y,Lu,La)_2O_3$:Eu,Bi, $(Gd,Y,Lu,La)_2O_2S$:Eu,Bi, $(Gd,Y,Lu,La)VO_4$:Eu,Bi, $SrY_2S_4$:Eu,Ce, $CaLa_2S_4$:Ce, Eu, $(Ba,Sr,Ca)MgP_2O_7$:Eu, Mn,$(Sr,Ca,Ba,Mg,Zn)_2P_2O_7$:Eu, Mn,$(Y,Lu)_2WO_6$:Eu, Ma, $(Ba,Sr,Ca)_xSiyN_Z$:Eu,Ce (wherein x, y and z are integers equal to or greater than 1),$(Ca,Sr,Ba,Mg)_{10}(PO_4)_6(F,Cl,Br,OH)$:Eu, Mn, $((Y,Lu,Gd,Tb)_{1-x-y}Sc_xCe_y)_2(Ca,Mg)(Mg,Zn)_{2+r}Si_{z-9}Ge_qO_{12+\delta}$, $SrAl_2Si_4N_7$, $Sr_2Al_2Si_9O_2N_{14}$:Eu, $M^1{}_a,M^2{}_bM^3{}_cO_d$ (wherein $M^1$=activator element including at least Ce, $M^2$=bivalent metal element, $M^3$=trivalent metal element, $0.000\leq a\leq0.2$, 0.85≤b1.2, $1.6\leq c\leq2.4$ and $3.2\leq d\leq4.8$), $A_{2+x}M_yMn_zF_n$ (wherein A=Na and/or K, M=Si and Al, and $-1\leq x\leq1$, $0.95\leq y+z\leq1.1$, $0.001\leq z\leq0.4$ and $5\leq n\leq7$). KSF/KSNAF, or $(La_{1-x-y}, Eu_x, Ln_y)_2O_2S$ (wherein $0.02\leq x\leq0.50$ and $0\leq y\leq0.50$, Ln=$Y^{3+}$, $Gd^{3+}$, $Lu^{3+}$, $Sc^{3+}$,$Sm^{3+}$ or $Er^{3+}$). In some preferred implementations, the luminescent materials may comprise phosphors comprising one or more of the following materials: $CaAlSiN_3$:Eu, $(Sr,Ca)AlSiN_3$:Eu, $BaMgAl_{10}O_{17}$:Eu, $(Ba,Ca,Sr,Mg)_2SiO_4$:Eu, β-SiAlON, $Lu_3Al_5O_{12}$:Ce, $Eu^{3+}(Cd_{0.9}Y_{0.1})_3Al_5O_{12}:Bi^{3+},Tb^{3+}$, $Y_3Al_5O_{12}$:Ce, $La_3Si_6N_{11}$:Ce, $(La,Y)_3Si_6N_{11}$:Ce, $Ca_2AlSi_3O_2N_5:Ce^{3+}$, $Ca_2AlSi_3O_2N_5:Ce^{3+},Eu^{2+}$, $Ca_2AlSi_3O_2N_5:Eu^{2+}$, $BaMgAl_{10}O_{17}:Eu^{2+}$, $Sr_{4.5}Eu_{0.5}(PO_4)_3Cl$, or $M^1_aM^2_bM^3_cO_d$ (wherein $M^1$=activator element comprising Ce, $M^2$=bivalent metal element, $M^3$=trivalent metal element, $0.0001 \leq a \leq 0.2$, $0.8 \leq b \leq 1.2$, $1.6 \leq c \leq 2.4$ and $3.25 \leq d \leq 4.8$). In further preferred implementations, the luminescent materials may comprise phosphors comprising one or more of the following materials: $CaAlSiN_3:Eu$, $BaMgAl_{10}O_{17}:Eu$, $Lu_3Al_5O_{12}:Ce$, or $Y_3Al_5O_{12}:Ce$.

Figure 19:
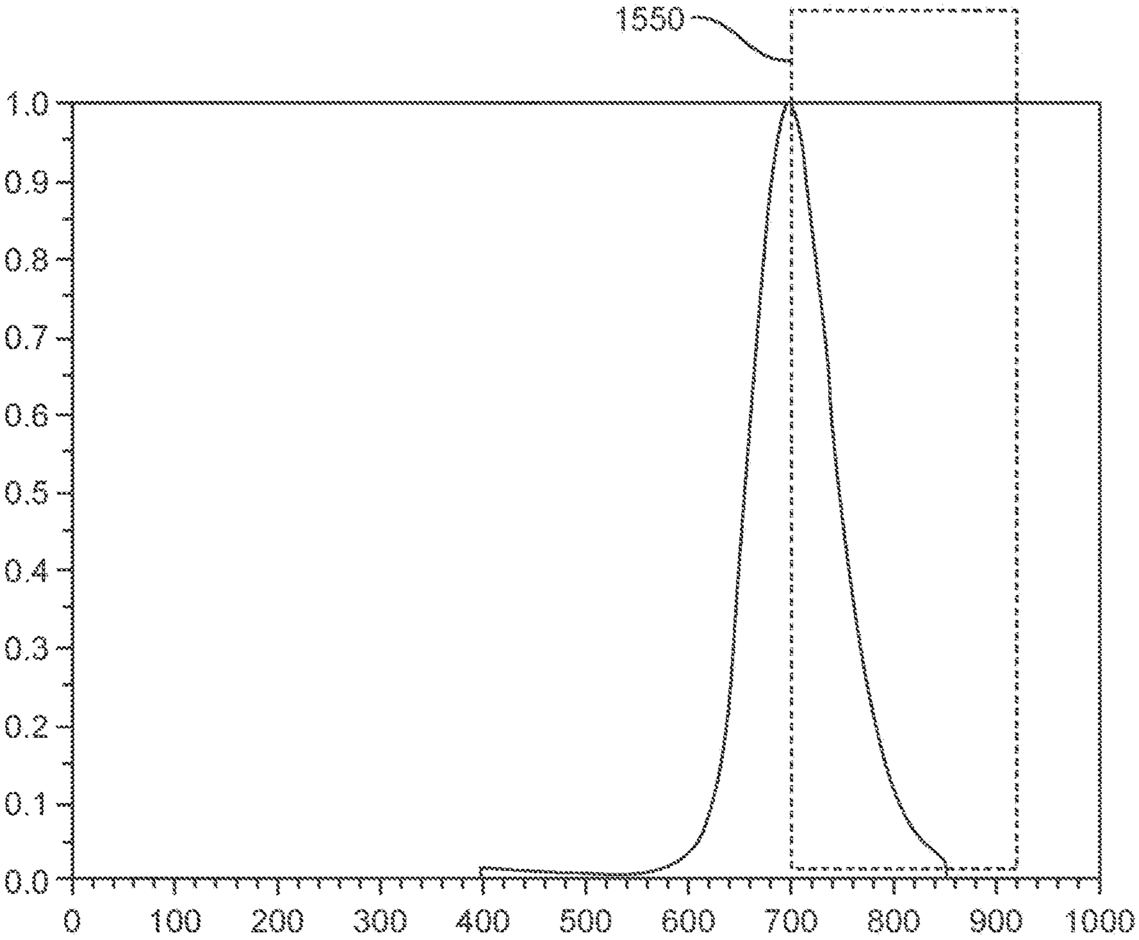
FIG. 19 illustrates some aspects of light emitting devices according to the present disclosure, including aspects of LRNE spectral power distributions for light generated by components of the devices.

In certain implementations, LRNE emissions can be generated with one or more luminescent materials that generate emissions with wavelengths between about 625 nm and about 1400 nm. In some implementations, the luminescent materials can comprise phosphors comprising one or more of the materials listed above. FIG. 19 shows an emission profile for an exemplary long-red phosphor, referred to herein as Long-Red Phosphor 700 nm, having a peak emission wavelength of about 700 nm suitable for some implementations. In certain implementations, an exemplary long-red phosphor, referred to herein as Long-Red Phosphor 675 nm, having a peak emission wavelength of about 675 nm can be used. Some aspects of the spectral power distributions of the emissions for Long-Red Phosphor 700 nm and Long-Red Phosphor 675 nm are shown in Tables 44-46.

In yet further implementations, the luminescent materials can comprise phosphors comprising one or more of the following materials excited by light at about 273 nm:$LiAlO_2:Fe^{3+}$ (peak at 770 nm), $CdS:Ag^+,Cl^-$ (peak at 800 nm), $ZnSbGaTe:Cr^{3+},Nd^{3+}$ (peak at 845 nm), $La_3In_2Ga_3O_{12}:Cr^{3+}$, $Dy^{3+}$ (peak at 905 nm), $BaGd_2ZnO_5:Yb^{3+}$ (peak at 979 nm) and $Ba(GdY)_2ZnO_5:Yb^{3+}$ (peak at 979 nm). In further implementations, the luminescent materials can comprise chemically modified versions of these phosphors having excitation bands overlapping with violet or blue LED wavelengths.

In certain implementations, the luminophoric mediums can include luminescent materials that comprise one or more quantum materials. Throughout this specification, the term "quantum material" means any luminescent material that includes: a quantum dot; a quantum wire; or a quantum well. Some quantum materials may absorb and emit light at spectral power distributions having narrow wavelength ranges, for example, wavelength ranges having spectral widths being within ranges of between about 25 nanometers and about 50 nanometers. In examples, two or more different quantum materials may be included in a lumiphor, such that each of the quantum materials may have a spectral power distribution for light emissions that may not overlap with a spectral power distribution for light absorption of any of the one or more other quantum materials. In these examples, cross-absorption of light emissions among the quantum materials of the lumiphor may be minimized. Throughout this specification, the term "quantum dot" means: a nanocrystal made of semiconductor materials that are small enough to exhibit quantum mechanical properties, such that its excitons are confined in all three spatial dimensions. Throughout this specification, the term "quantum wire" means: an electrically conducting wire in which quantum effects influence the transport properties. Throughout this specification, the term "quantum well" means: a thin layer that can confine (quasi-)particles (typically electrons or holes) in the dimension perpendicular to the layer surface, whereas the movement in the other dimensions is not restricted.

Figure 2:
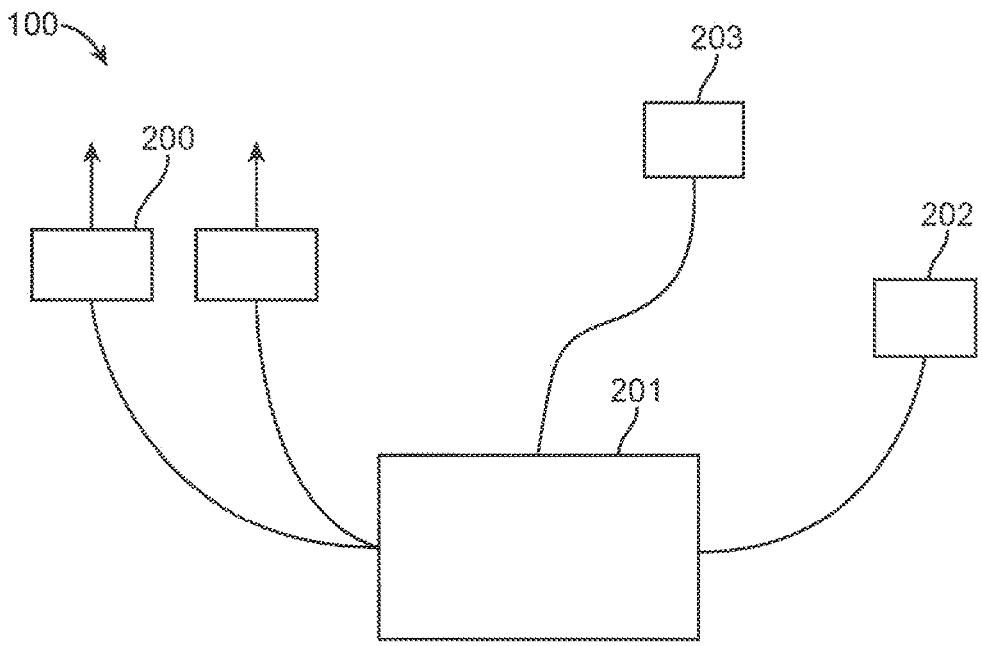
FIG. 2 illustrates aspects of light emitting devices according to the present disclosure.

Some implementations of the present invention relate to use of solid state emitter packages. A solid state emitter package typically includes at least one solid state emitter chip that is enclosed with packaging elements to provide environmental and/or mechanical protection, color selection, and light focusing, as well as electrical leads, contacts or traces enabling electrical connection to an external circuit. Encapsulant material, optionally including luminophoric material, may be disposed over solid state emitters in a solid state emitter package. Multiple solid state emitters may be provided in a single package. A package including multiple solid state emitters may include at least one of the following: a single leadframe arranged to conduct power to the solid state emitters, a single reflector arranged to reflect at least a portion of light emanating from each solid state emitter, a single submount supporting each solid state emitter, and a single lens arranged to transmit at least a portion of light emanating from each solid state emitter. Individual LEDs or groups of LEDs in a solid state package (e.g., wired in series) may be separately controlled. As depicted schematically in FIG. 2, multiple solid state packages 200 may be arranged in a single semiconductor light emitting device 100. Individual solid state emitter packages or groups of solid state emitter packages (e.g., wired in series) may be separately controlled. Separate control of individual emitters, groups of emitters, individual packages, or groups of packages, may be provided by independently applying drive currents to the relevant components with control elements known to those skilled in the art. In one embodiment, at least one control circuit 201 a may include a current supply circuit configured to independently apply an on-state drive current to each individual solid state emitter, group of solid state emitters, individual solid state emitter package, or group of solid state emitter packages. Such control may be responsive to a control signal (optionally including at least one sensor 202 arranged to sense electrical, optical, and/or thermal properties and/or environmental conditions), and a control system 203 may be configured to selectively provide one or more control signals to the at least one current supply circuit. The design and fabrication of semiconductor light emitting devices are well known to those skilled in the art, and hence further description thereof will be omitted. In various embodiments, current to different circuits or circuit portions may be pre-set, user-defined, or responsive to one or more inputs or other control parameters. The lighting systems can be controlled via methods described in U.S. Provisional Patent Application Ser. No. 62/491,137, filed Apr. 27, 2017, entitled Methods and Systems for An Automated Design, Fulfillment, Deployment and Operation Platform for Lighting Installations, U.S. Provisional Patent Application Ser. No. 62/562,714, filed Sep. 25, 2017, entitled Methods and Systems for An Automated Design, Fulfillment, Deployment and Operation Platform for Lighting Installations, and International Patent Application No. PCT/US2018/029380, filed Apr. 25, 2018 and entitled Methods and Systems for an Automated Design, Fulfillment. Deployment and Operation Platform for Lighting Installations, published as International Publication No. WO 2018/200685 A2, each of which hereby are incorporated by reference as if fully set forth herein in their entirety.

Figure 3:
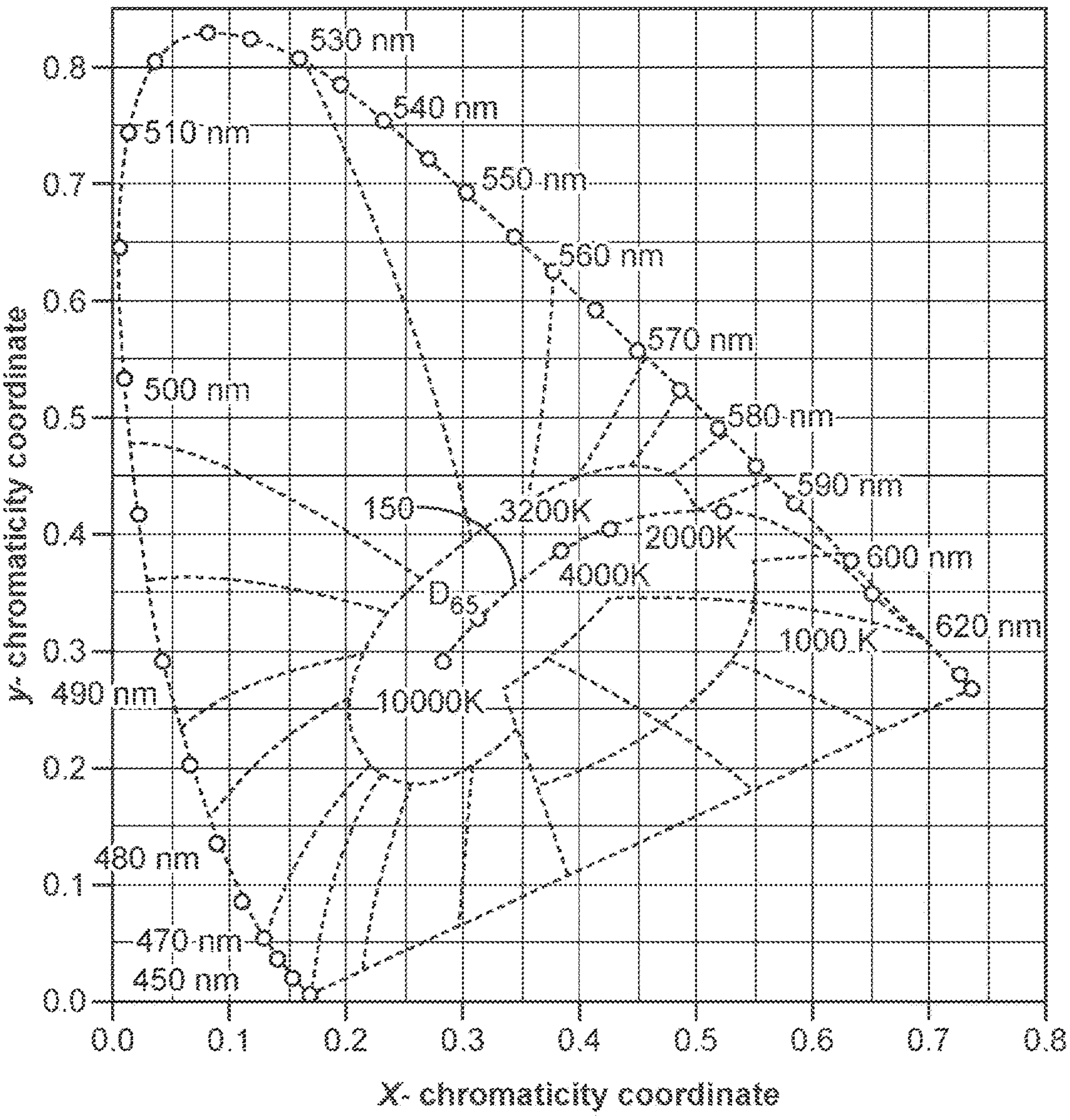
FIG. 3 (PRIOR ART)
FIG. 3 depicts a graph of a 1931 CIE Chromaticity Diagram illustrating the location of the Planckian locus.

FIG. 3 illustrates a 1931 International Commission on Illumination (CIE) chromaticity diagram. The 1931 CIE Chromaticity diagram is a two-dimensional chromaticity space in which every visible color is represented by a point having x- and y-coordinates, also referred to herein as (ccx, ccy) coordinates. Fully saturated (monochromatic) colors appear on the outer edge of the diagram, while less saturated colors (which represent a combination of wavelengths) appear on the interior of the diagram. The term "saturated", as used herein, means having a purity of at least 85%, the term "purity" having a well-known meaning to persons skilled in the art, and procedures for calculating purity being well-known to those of skill in the art. The Planckian locus, or black body locus (BBL), represented by line 150 on the diagram, follows the color an incandescent black body would take in the chromaticity space as the temperature of the black body changes from about 1000 K to 10,000 K. The black body locus goes from deep red at low temperatures (about 1000 K) through orange, yellowish white, white, and finally bluish white at very high temperatures. The temperature of a black body radiator corresponding to a particular color in a chromaticity space is referred to as the "correlated color temperature." In general, light corresponding to a correlated color temperature (CCT) of about 2700 K to about 6500 K is considered to be "white" light. In particular, as used herein, "white light" generally refers to light having a chromaticity point that is within a 10-step MacAdam ellipse of a point on the black body locus having a CCT between 2700 K and 6500 K. However, it will be understood that tighter or looser definitions of white light can be used if desired. For example, white light can refer to light having a chromaticity point that is within a seven step MacAdam ellipse of a point on the black body locus having a CCT between 2700 K and 6500 K. The distance from the black body locus can be measured in the CIE 1960 chromaticity diagram, and is indicated by the symbol Δuv, or DUV or duv as referred to elsewhere herein. If the chromaticity point is above the Planckian locus the DUV is denoted by a positive number: if the chromaticity point is below the locus, DUV is indicated with a negative number. If the DUV is sufficiently positive, the light source may appear greenish or yellowish at the same CCT. If the DUV is sufficiently negative, the light source can appear to be purple or pinkish at the same CCT. Observers may prefer light above or below the Planckian locus for particular CCT values. DUV calculation methods are well known by those of ordinary skill in the art and are more fully described in ANSI C78.377, American National Standard for Electric Lamps—Specifications for the Chromaticity of Solid State Lighting (SSL) Products, which is incorporated by reference herein in its entirety for all purposes. A point representing the CIE Standard Illuminant D65 is also shown on the diagram. The D65 illuminant is intended to represent average daylight and has a CCT of approximately 6500 K and the spectral power distribution is described more fully in Joint ISO/CIE Standard, ISO 10526:1999/CIE S005/E-1998, CIE Standard Illuminants for Colorimetry, which is incorporated by reference herein in its entirety for all purposes.

The light emitted by a light source may be represented by a point on a chromaticity diagram, such as the 1931 CIE Chromaticity Diagram, having color coordinates denoted (ccx, ccy) on the X-Y axes of the diagram. A region on a chromaticity diagram may represent light sources having similar chromaticity coordinates. The color points described in the present disclosure can be within color-point ranges defined by geometric shapes on the CIE Chromaticity Diagram that enclose a defined set of ccx, ccy color coordinates. It should be understood that any gaps or openings in any described or depicted boundaries for color-point ranges should be closed with straight lines to connect adjacent endpoints in order to define a closed boundary for each color-point range.

The ability of a light source to accurately reproduce color in illuminated objects can be characterized using the color rendering index ("CRI"), also referred to as the CIE Ra value. The Ra value of a light source is a modified average of the relative measurements of how the color rendition of an illumination system compares to that of a reference black-body radiator or daylight spectrum when illuminating eight reference colors R1-R8. Thus, the Ra value is a relative measure of the shift in surface color of an object when lit by a particular lamp. The Ra value equals 100 if the color coordinates of a set of test colors being illuminated by the illumination system are the same as the coordinates of the same test colors being irradiated by a reference light source of equivalent CCT. For CCTs less than 5000 K, the reference illuminants used in the CRI calculation procedure are the SPDs of blackbody radiators; for CCTs above 5000 K, imaginary SPDs calculated from a mathematical model of daylight are used. These reference sources were selected to approximate incandescent lamps and daylight, respectively. Daylight generally has an Ra value of nearly 100, incandescent bulbs have an Ra value of about 95, fluorescent lighting typically has an Ra value of about 70 to 85, while monochromatic light sources have an Ra value of essentially zero. Light sources for general illumination applications with an Ra value of less than 50 are generally considered very poor and are typically only used in applications where economic issues preclude other alternatives. The calculation of CIE Ra values is described more fully in Commission Internationale de l'Éclairage. 1995. Technical Report: Method of Measuring and Specifying Colour Rendering Properties of Light Sources, CIE No. 13.3-1995. Vienna, Austria: Commission Internationale de l'Éclairage, which is incorporated by reference herein in its entirety for all purposes. In addition to the Ra value, a light source can also be evaluated based on a measure of its ability to render seven additional colors R9-R15, which include realistic colors like red, yellow, green, blue, Caucasian skin color (R13), tree leaf green, and Asian skin color (R15), respectively. The ability to render the saturated red reference color R9 can be expressed with the R9 color rendering value ("R9 value"). Light sources can further be evaluated by calculating the gamut area index ("GAI"). Connecting the rendered color points from the determination of the CIE Ra value in two-dimensional space will form a gamut area. Gamut area index is calculated by dividing the gamut area formed by the light source with the gamut area formed by a reference source using the same set of colors that are used for CRI. GAI uses an Equal Energy Spectrum as the reference source rather than a black body radiator. A gamut area index related to a black body radiator ("GAIBB") can be calculated by using the gamut area formed by the blackbody radiator at the equivalent CCT to the light source.

The ability of a light source to accurately reproduce color in illuminated objects can be characterized using the metrics described in IES Method for Evaluating Light Source Color Rendition, Illuminating Engineering Society, Product ID: TM-30-15 (referred to herein as the "TM-30-15 standard") which is incorporated by reference herein in its entirety for all purposes. The TM-30-15 standard describes metrics including the Fidelity Index (Rf) and the Gamut Index (Rg) that can be calculated based on the color rendition of a light source for 99 color evaluation samples ("CES"). The 99 CES provide uniform color space coverage, are intended to be spectral sensitivity neutral, and provide color samples that correspond to a variety of real objects. Rf values range from 0 to 100 and indicate the fidelity with which a light source renders colors as compared with a reference illuminant. Rg values provide a measure of the color gamut that the light source provides relative to a reference illuminant. The range of Rg depends upon the Rf value of the light source being tested. The reference illuminant is selected depending on the CCT. For CCT values less than or equal to 4500 K, Planckian radiation is used. For CCT values greater than or equal to 5500 K, CIE Daylight illuminant is used. Between 4500 K and 5500 K a proportional mix of Planckian radiation and the CIE Daylight illuminant is used, according to the following equation:

$$S_{r,M}(\lambda, T_t) = \frac{5500 - T_t}{1000} S_{r,P}(\lambda, T_t) + \left(1 - \frac{5500 - T_t}{1000}\right) S_{r,D}(\lambda, T_t),$$

$S_{r,M}(\lambda, T_t)$ is the proportional mix reference illuminant, $S_{r,p}(\lambda, T_t)$ is Planckian radiation, and $S_{r,D}(\lambda, T_t)$ is the CIE Daylight illuminant.

Circadian illuminance (CLA) is a measure of circadian effective light, spectral irradiance distribution of the light incident at the cornea weighted to reflect the spectral sensitivity of the human circadian system as measured by acute melatonin suppression after a one-hour exposure, and CS, which is the effectiveness of the spectrally weighted irradiance at the cornea from threshold (CS=0.1) to saturation (CS=0.7). The values of CLA are scaled such that an incandescent source at 2856 K (known as CIE Illuminant A) which produces 1000 lux (visual lux) will produce 1000 units of circadian lux (CLA). CS values are transformed CLA values and correspond to relative melatonin suppression after one hour of light exposure for a 2.3 mm diameter pupil during the mid-point of melatonin production. CS is calculated from.

$$CS = 0.7\left(1 - \frac{1}{1 + \left(\frac{CLA}{355.7}\right)^{\wedge 1.126}}\right).$$

The calculation of CLA is more fully described in Rea et al., "Modelling the spectral sensitivity of the human circadian system," Lighting Research and Technology, 2011: 0:1-12, and Figueiro et al., "Designing with Circadian Stimulus", October 2016, LD+A Magazine, Illuminating Engineering Society of North America, which are incorporated by reference herein in its entirety for all purposes. Figueiro et al. describe that exposure to a CS of 0.3 or greater at the eye, for at least one hour in the early part of the day, is effective for stimulating the circadian system and is associated with better sleep and improved behavior and mood.

Equivalent Melanopic Lux (EML) provides a measure of photoreceptive input to circadian and neurophysiological light responses in humans, as described in Lucas et al., "Measuring and using light in the melanopsin age." Trends in Neurosciences, January 2014, Vol. 37, No. 1, pages 1-9, which is incorporated by reference herein in its entirety, including all appendices, for all purposes. Melanopic lux is weighted to a photopigment with λmax 480 nm with pre-receptoral filtering based on a 32 year old standard observer, as described more fully in the Appendix A, Supplementary Data to Lucas et al. (2014), User Guide: Irradiance Toolbox (Oxford 18 Oct. 2013), University of Manchester, Lucas Group, which is incorporated by reference herein in its entirety for all purposes. EML values are shown in the tables and Figures herein as the ratio of melanopic lux to luminous flux, with luminous flux considered to be 1000 lumens. It can be desirable for biological effects on users to provide illumination having higher EML in the morning, but lower EML in the late afternoon and evening.

Blue Light Hazard (BLH) provides a measure of potential for a photochemical induced retinal injury that results from radiation exposure. Blue Light Hazard is described in IEC/

EN 62471, Photobiological Safety of Lamps and Lamp Systems and Technical Report IEC/TR 62778: Application of TEC 62471 for the assessment of blue light hazard to light sources and luminaires, which are incorporated by reference herein in their entirety for all purposes. A BLH factor can be expressed in (weighted power/lux) in units of $\mu W/cm^2/lux$.

In some aspects the present disclosure relates to lighting devices and methods to provide light having particular vision energy and circadian stimulating energy (CSE) performance. Many figures of merit are known in the art, some of which are described in Ji Hye Oh, Su Ji Yang and Young Rag Do, "Healthy, natural, efficient and tunable lighting: four-package white LEDs for optimizing the circadian effect, color quality and vision performance," Light: Science & Applications (2014) 3: el41-el49, which is incorporated herein in its entirety, including supplementary information, for all purposes. Luminous efficacy of radiation ("LER") can be calculated from the ratio of the luminous flux to the radiant flux (S(λ)), i.e. the spectral power distribution of the light source being evaluated, with the following equation:

$$LER\left(\frac{\text{lm}}{W}\right) = 683\left(\frac{\text{lm}}{W}\right)\frac{\int V(\lambda)S(\lambda)d\lambda}{\int S(\lambda)d\lambda}.$$

Circadian efficacy of radiation ("CER") can be calculated from the ratio of circadian luminous flux to the radiant flux, with the following equation:

$$CER\left(\frac{blm}{W}\right) = 683\left(\frac{blm}{W}\right)\frac{\int C(\lambda)S(\lambda)d\lambda}{\int S(\lambda)d\lambda}.$$

Circadian action factor ("CAF") can be defined by the ratio of CER to LER, with the following equation:

$$\left(\frac{blm}{\text{lm}}\right) = \frac{CER\left(\frac{blm}{W}\right)}{LER\left(\frac{\text{lm}}{W}\right)}.$$

The term "blm" refers to biolumens, units for measuring circadian flux, also known as circadian lumens. The term "lm" refers to visual lumens. V(λ) is the photopic spectral luminous efficiency function and C(λ) is the circadian spectral sensitivity function. The calculations herein use the circadian spectral sensitivity function, C(A), from Gall et al., Proceedings of the CIE Symposium 2004 on Light and Health: Non-Visual Effects, 30 Sep.-2 Oct. 2004; Vienna, Austria 2004. CIE: Wien, 2004, pp 129-132, which is incorporated herein in its entirety for all purposes. By integrating the amount of light (milliwatts) within the circadian spectral sensitivity function and dividing such value by the number of photopic lumens, a relative measure of melatonin suppression effects of a particular light source can be obtained. A scaled relative measure denoted as melatonin suppressing milliwatts per hundred lumens may be obtained by dividing the photopic lumens by 100. The term "melatonin suppressing milliwatts per hundred lumens" consistent with the foregoing calculation method is used throughout this application and the accompanying figures and tables.

The melatonin suppression index (MSI) of a light source can be calculated from the ratio of the integration of cross product constant lumen spectrum of lamp with melatonin suppression action spectrum in wavelength range 380 nm to 780 nm to the integration of cross product of constant lumen spectrum of Day light spectrum at 6500 K with melatonin suppression action spectrum in 380 nm to 780 nm region. The function melatonin suppression action spectrum, "MSAS" or M(λ), is defined by Thapan K, "An action spectrum for melatonin suppression: evidence for a novel non-rod, non-cone photoreceptor system in humans", Journal of Physiology, 2001, 535: 261-267, which is incorporated herein for all purposes.

The ability of a light source to provide illumination that allows for the clinical observation of cyanosis is based upon the light source's spectral power density in the red portion of the visible spectrum, particularly around 660 nm. The cyanosis observation index ("COI") is defined by AS/NZS 1680.2.5 Interior Lighting Part 2.5: Hospital and Medical Tasks, Standards Australia, 1997 which is incorporated by reference herein in its entirety, including all appendices, for all purposes. COI is applicable for CCTs from about 3300 K to about 5500 K, and is preferably of a value less than about 3.3. If a light source's output around 660 nm is too low a patient's skin color may appear darker and may be falsely diagnosed as cyanosed. If a light source's output at 660 nm is too high, it may mask any cyanosis, and it may not be diagnosed when it is present. COI is a dimensionless number and is calculated from the spectral power distribution of the light source. The COI value is calculated by calculating the color difference between blood viewed under the test light source and viewed under the reference lamp (a 4000 K Planckian source) for 50% and 100% oxygen saturation and averaging the results. The lower the value of COI, the smaller the shift in color appearance results under illumination by the source under consideration.

The ability of a light source to accurately reproduce color in illuminated objects can be characterized by the Television Lighting Consistency Index ("TLCI-2012" or "TLCI") value Qa, as described fully in EBU Tech 3355, Method for the Assessment of the Colorimetric Properties of Luminaires, European Broadcasting Union ("EBU"), Geneva, Switzerland (2014), and EBU Tech 3355-s1, An Introduction to Spectroradiometry, which are incorporated by reference herein in their entirety, including all appendices, for all purposes. The TLCI compares the test light source to a reference luminaire, which is specified to be one whose chromaticity falls on either the Planckian or Daylight locus and having a color temperature which is that of the CCT of the test light source. If the CCT is less than 3400 K, then a Planckian radiator is assumed. If the CCT is greater than 5000 K, then a Daylight radiator is assumed. If the CCT lies between 3400 K and 5000 K, then a mixed illuminant is assumed, being a linear interpolation between Planckian at 3400 K and Daylight at 5000 K. Therefore, it is necessary to calculate spectral power distributions for both Planckian and Daylight radiators. The mathematics for both operations is known in the art and is described more fully in CIE Technical Report 15:2004, Colorimetry 3$^{rd}$ ed., International Commission on Illumination (2004), which is incorporated herein in its entirety for all purposes.

In some exemplary implementations, the present disclosure provides semiconductor light emitting devices 100 that include a plurality of LED strings, with each LED string having a recipient luminophoric medium that comprises a luminescent material. The LED(s) in each string and the luminophoric medium in each string together emit an unsaturated light having a color point within a color range in the 1931 CIE chromaticity diagram. A "color range" or "region" in the 1931 CIE chromaticity diagram refers to a bounded area defining a group of color coordinates (ccx, ccy).

In some implementations, different combinations of lighting channels 105A-F can be present in the lighting systems of the present disclosure. Each lighting channel 105A-F can emit light at a particular color point on the 1931 CIE Chromaticity Diagram and with particular spectral power characteristics. By utilizing different combinations of lighting channels, different operational modes can be provided that can provide tunable white light between particular CCT values and with particular characteristics. In some implementations, the different operational modes can provide for substantially different circadian-stimulating energy characteristics. A first LED string 101A and a first luminophoric medium 102A together can emit a first light having a first color point within a blue color range. The combination of the first LED string 101A and the first luminophoric medium 102A are also referred to herein as a "blue channel" 105A. A second LED string 101B and a second luminophoric medium 102B together can emit a second light having a second color point within a red color range. The combination of the second LED string 101A and the second luminophoric medium 102A are also referred to herein as a "red channel" 105B. A third LED string 101C and a third luminophoric medium 102C together can emit a third light having a third color point within a short-blue-pumped cyan color range. The combination of the third LED string 101C and the third luminophoric medium 102C are also referred to herein as a "short-blue-pumped cyan channel" 105C. A fourth LED string 101D and a fourth luminophoric medium 102D together can emit a fourth light having a fourth color point within a long-blue-pumped cyan color range. The combination of the fourth LED string 101D and the fourth luminophoric medium 102D are also referred to herein as a "long-blue-pumped cyan channel" 105D. A fifth LED string 101E and a fifth luminophoric medium 102E together than emit a fifth light having a fifth color point within a yellow color range. The combination of the fifth LED string 101E and the fifth luminophoric medium 102E are also referred to herein as a "yellow channel" 105E. A sixth LED string 101E and a sixth luminophoric medium 102F together than emit a sixth light having a fifth color point within a violet color range. The combination of the sixth LED string 101F and the sixth luminophoric medium 102F are also referred to herein as a "violet channel" 105F. It should be understood that the use of the terms "blue", "red", "cyan", "yellow", and "violet" for the color ranges and channels are not meant to be limiting in terms of actual color outputs, but are used as a naming convention herein, as those of skill in the art will appreciate that color points within color ranges on the 1931 CIE Chromaticity Diagram for the channels may not have the visual appearance of what may commonly be referred to as "blue" "red", "cyan", "yellow", and "violet" by laymen, and may have the appearance of other colored light or white or near-white light, for example, in some implementations.

The first, second, third, fourth, fifth, and sixth LED strings 101A-F can be provided with independently applied on-state drive currents in order to tune the intensity of the first, second, third, and fourth unsaturated light produced by each string and luminophoric medium together. By varying the drive currents in a controlled manner, the color coordinate (ccx, ccy) of the total light that is emitted from the device 100 can be tuned. In some implementations, the device 100 can provide light at substantially the same color coordinate with different spectral power distribution profiles, which can result in different light characteristics at the same CCT. In some implementations, white light can be generated in modes that produce light from different combinations of two, three, or four of the LED strings 101A-F. In some implementations, white light is generated using only the first, second, and third LED strings, i.e. the blue, red, and short-blue-pumped cyan channels, referred to herein as "high-CRI mode". In other implementations, white light is generated using the first, second, third, and fourth LED strings, i.e., the blue, red, short-blue-pumped cyan, and long-blue-pumped cyan channels, in w % bat is also referred to herein as a "highest-CRI mode". In further implementations, white light can be generated using the first, second, and fourth LED strings, i.e. the blue, red, and long-blue-pumped cyan channels, in what is also referred to herein as a "high-EML mode". In other implementations, white light can be generated using the first, second, fifth, and sixth LED strings, i.e. the blue, red, yellow, and violet channels, in what is also referred to herein as a "low-EML mode". In yet further implementations, white light can be generated using the second, fifth, and sixth LED strings, i.e. the red, yellow, and violet channels, in what is also referred to herein as a "very-low-EML mode". In some implementations, only two of the LED strings are producing light during the generation of white light in any one of the operational modes described herein, as the other two LED strings are not necessary to generate white light at the desired color point with the desired color rendering performance. In certain implementations, substantially the same color coordinate (ccx, ccy) of total light emitted from the device can be provided in two different operational modes (different combinations of two or more of the channels), but with different color-rendering, circadian, or other performance metrics, such that the functional characteristics of the generated light can be selected as desired by users.

Figure 12:
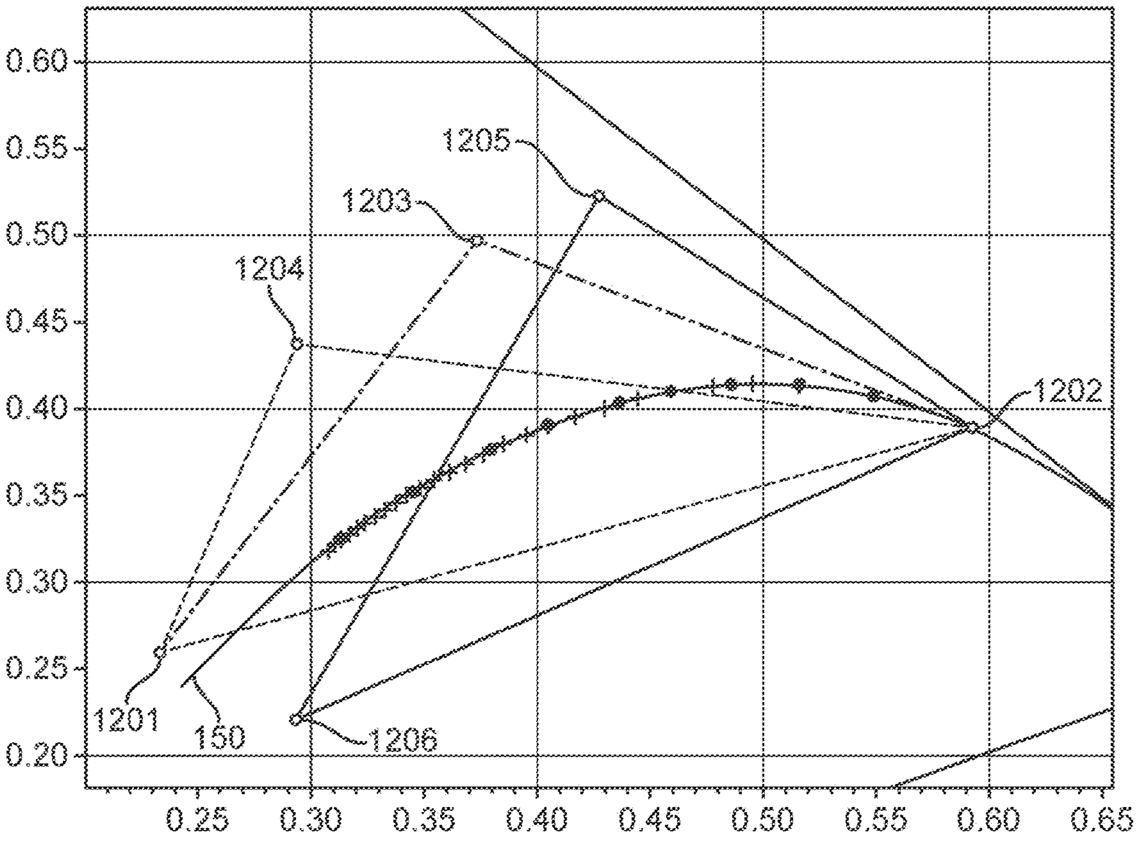
FIG. 12 illustrates some aspects of light emitting devices according to the present disclosure, including some suitable color points for light generated by components of the devices.

Non-limiting FIG. 12 shows a portion of the 1931 CIE Chromaticity Diagram with Planckian locus 150 and some exemplary color points and triangles connecting color points to depict the tunable gamut of color points from various combinations of lighting channels. FIG. 12 shows an exemplary first color point 1201 produced from a blue channel, an exemplary second color point 1202 produced from a red channel, an exemplary third color point 1203 produced from a short-blue-pumped cyan channel, an exemplary fourth color point 1204 produced from a long-blue-pumped cyan channel, an exemplary fifth color point produced from a yellow channel, and an exemplary sixth color point 1206 produced from a violet channel. In other implementations, the color points 1201, 1202, 1203, 1204, 1205, and 1206 may fall at other (ccx, ccy) coordinates within suitable color ranges for each lighting channel as describe more fully below.

Figure 11:
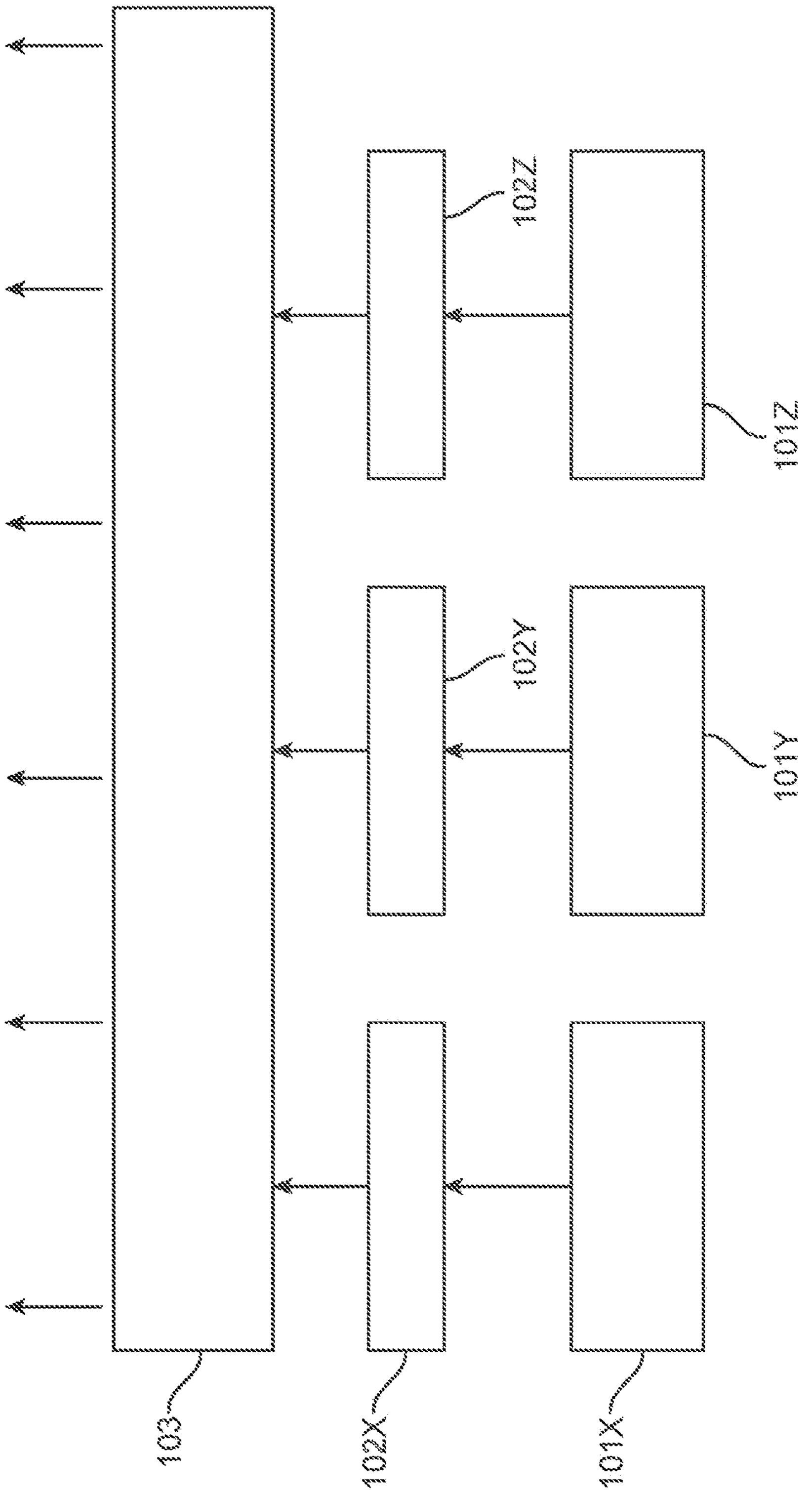
FIG. 11 illustrates aspects of light emitting devices according to the present disclosure.

In some implementations, the semiconductor light emitting devices 100 of the disclosure can comprise only three, four, or five of the lighting channels described herein. FIG. 11 illustrates a device 100 having only three LED strings 101X/101Y/101Z with associated luminophoric mediums 102X/102Y/102Z. The three channels depicted can be any combination of three of lighting channels described elsewhere throughout this disclosure. In some implementations, red, blue, and long-blue-pumped cyan channels are provided. In other implementations, red, blue, and short-blue-pumped cyan channels are provided. In other implementations, red, short-blue-pumped cyan, and long-blue-pumped cyan channels are provided. In yet other implementations, blue, short-blue-pumped cyan, and long-blue-pumped cyan channels are provided. In further implementations, red, yellow, and violet channels are provided. In further implementations, one of the three, four, or five different channels of a lighting system can be duplicated as an additional channel, so that four, five, or six channels are provided, but two of the channels are duplicates of each other.

FIGS. 4A, 4B, 5-10, 13, 14A, and 14B depict suitable color ranges for some implementations of the disclosure as described in more detail elsewhere herein. It should be understood that any gaps or openings in the described boundaries for the color ranges should be closed with straight lines to connect adjacent endpoints in order to define a closed boundary for each color range.

Blue Channels

Figure 4A:
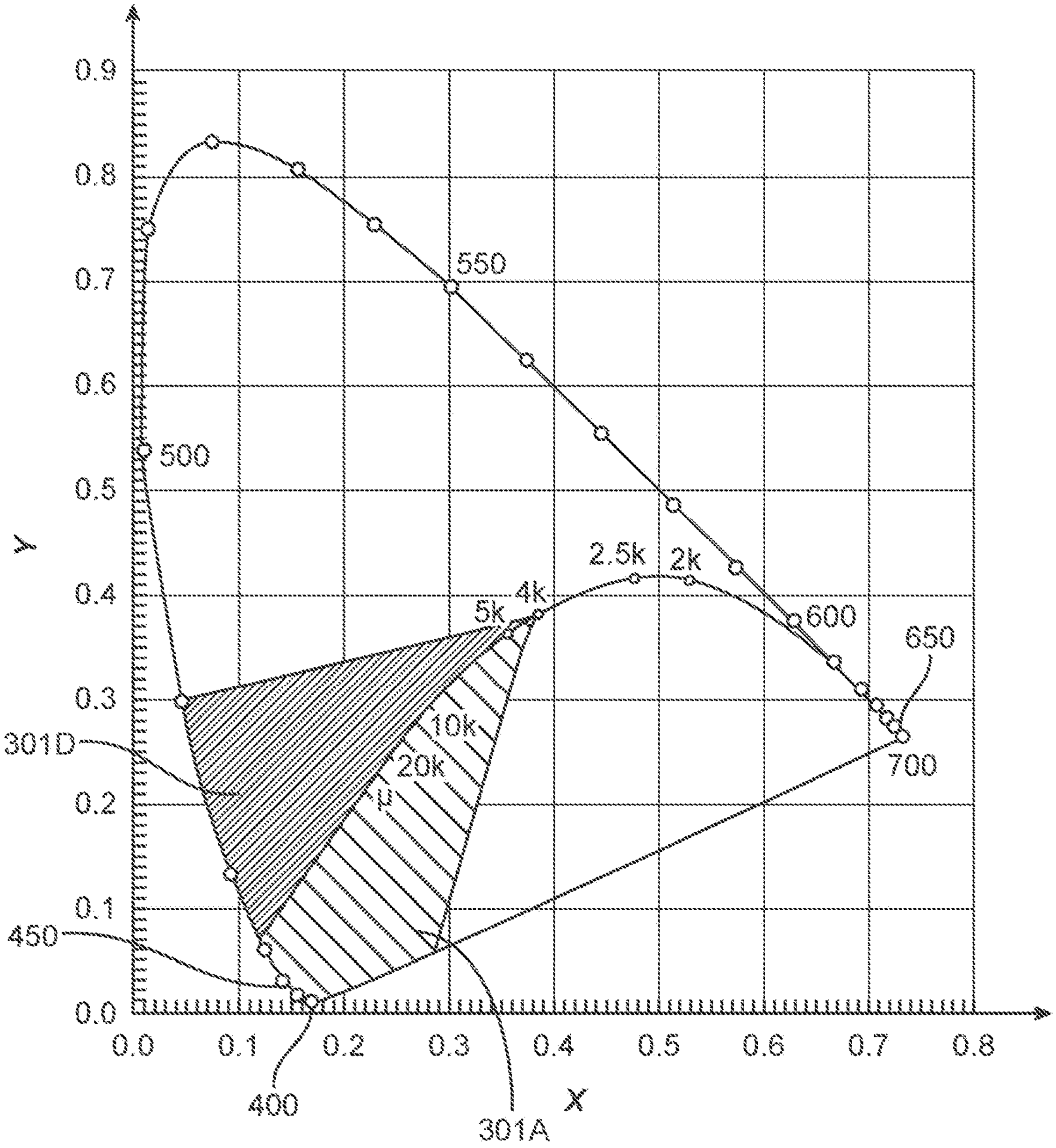
FIGS. 4A-4B illustrate some aspects of light emitting devices according to the present disclosure, including some suitable color ranges for light generated by components of the devices.
Figure 7:
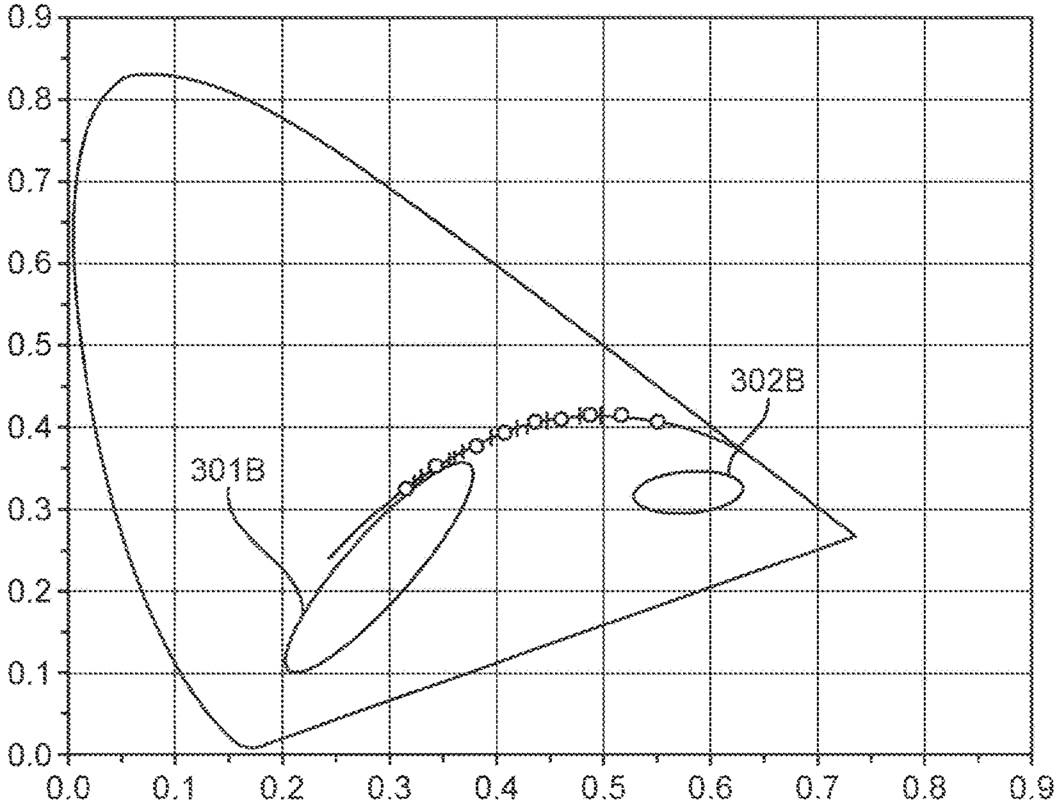
FIG. 7 illustrates some aspects of light emitting devices according to the present disclosure, including some suitable color ranges for light generated by components of the devices.
Figure 8:
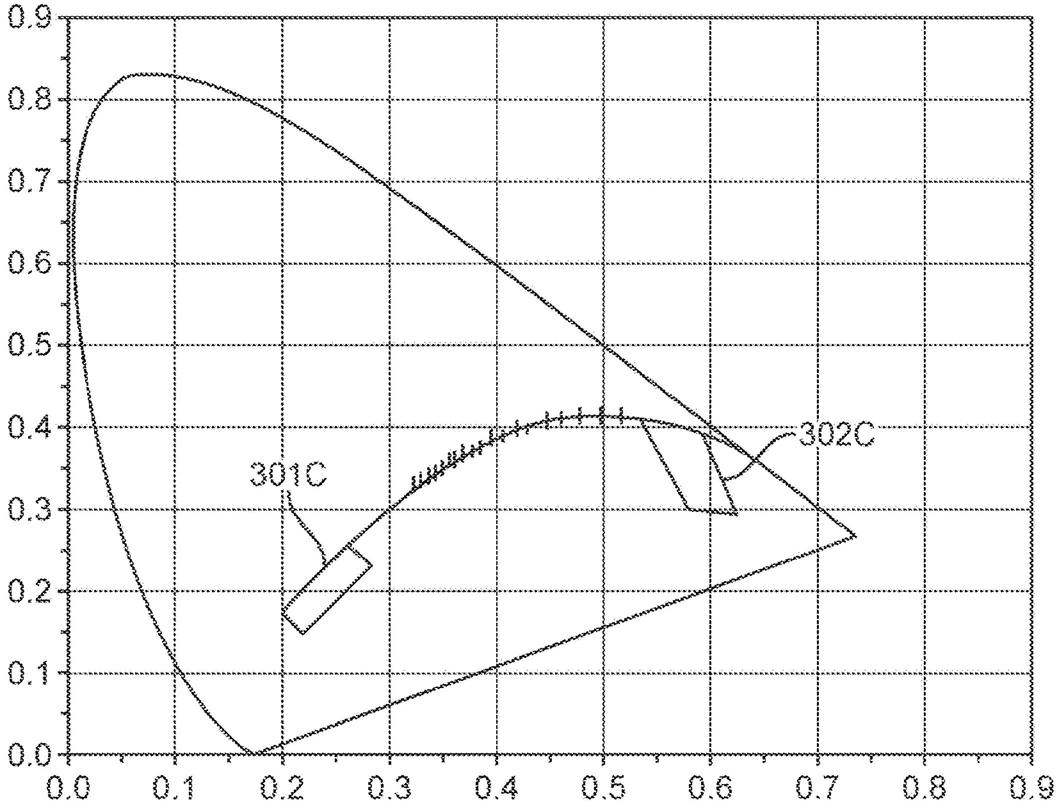
FIG. 8 illustrates some aspects of light emitting devices according to the present disclosure, including some suitable color ranges for light generated by components of the devices.
Figure 10:
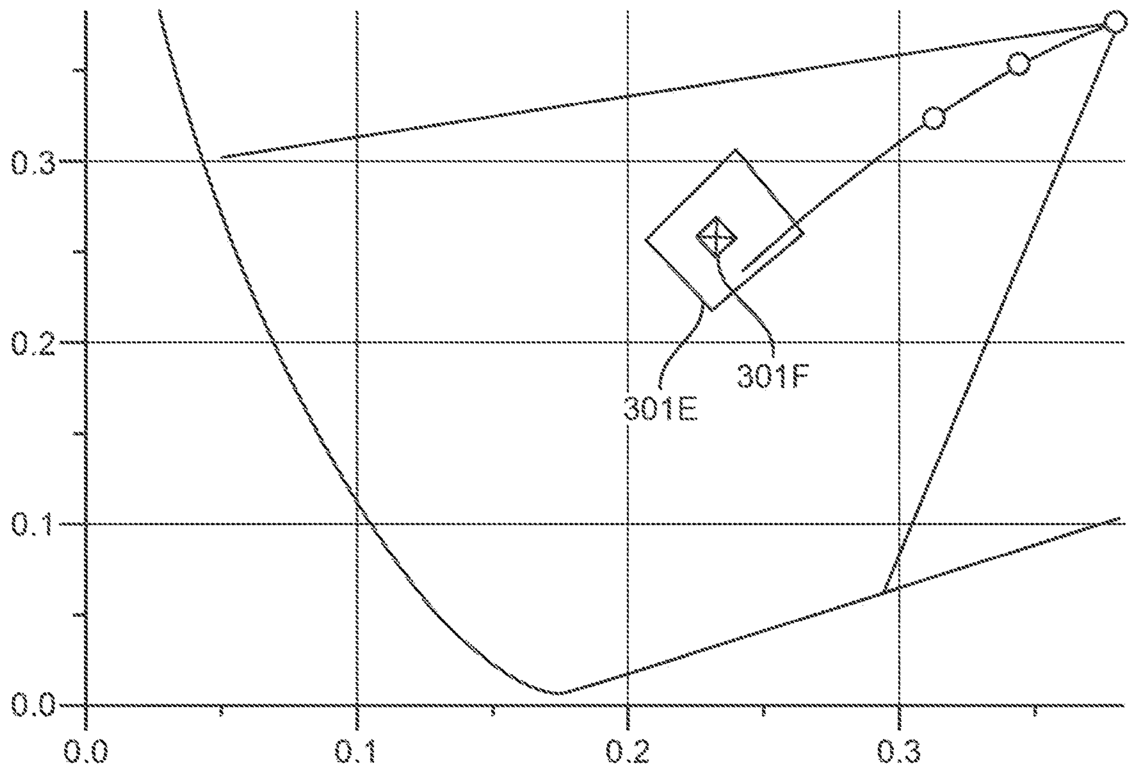
FIG. 10 illustrates some aspects of light emitting devices according to the present disclosure, including some suitable color ranges for light generated by components of the devices.

In some implementations of the present disclosure, lighting systems can include blue channels that produce light with a blue color point that falls within a blue color range. In certain implementations, suitable blue color ranges can include blue color ranges 301A-F. FIG. 4A depicts a blue color range 301A defined by a line connecting the ccx, ccy color coordinates of the infinity point of the Planckian locus (0.242, 0.24) and (0.12, 0.068), the Planckian locus from 4000 K and infinite CCT, the constant CCT line of 4000 K, the line of purples, and the spectral locus. FIG. 4A also depicts a blue color range 301D defined by a line connecting (0.3806, 0.3768) and (0.0445, 0.3), the spectral locus between the monochromatic point of 490 nm and (0.12, 0.068), a line connecting the ccx, ccy color coordinates of the infinity point of the Planckian locus (0.242, 0.24) and (0.12, 0.068), and the Planckian locus from 4000 K and infinite CCT. The blue color range may also be the combination of ranges 301A and 301D together. FIG. 7 depicts a blue color range 301B can be defined by a 60-step MacAdam ellipse at a CCT of 20000 K, 40 points below the Planckian locus. FIG. 8 depicts a blue color range 301C that is defined by a polygonal region on the 1931 CIE Chromaticity Diagram defined by the following ccx, ccy color coordinates: (0.22, 0.14),(0.19, 0.17),(0.26, 0.26),(0.28, 0.23). FIG. 10 depicts blue color ranges 301E and 301F. Blue color range 301E is defined by lines connecting (0.231, 0.218),(0.265, 0.260). (0.2405, 0.305), and (0.207, 0.256).

Red Channels

Figure 4B:
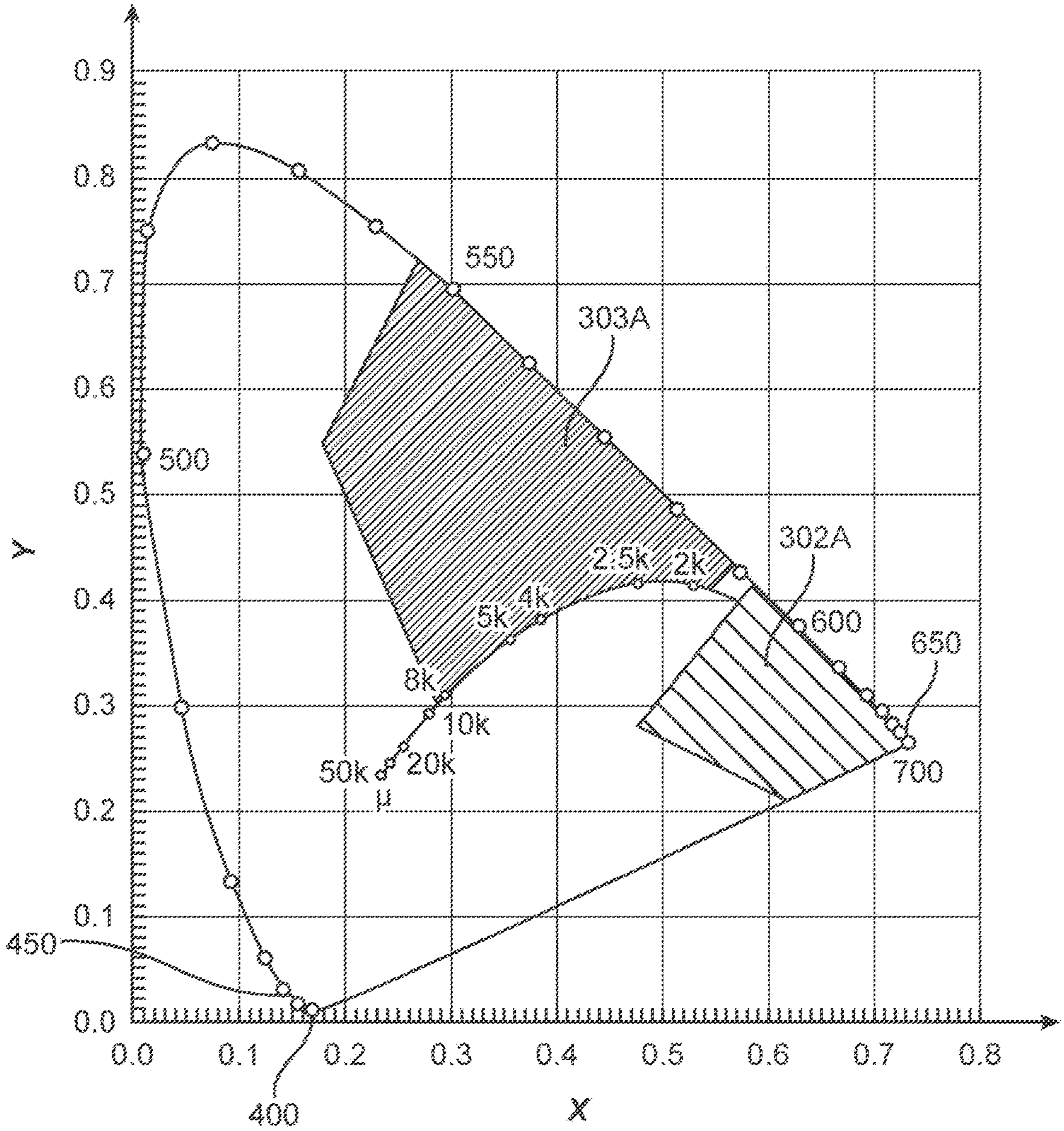
Figure 5:
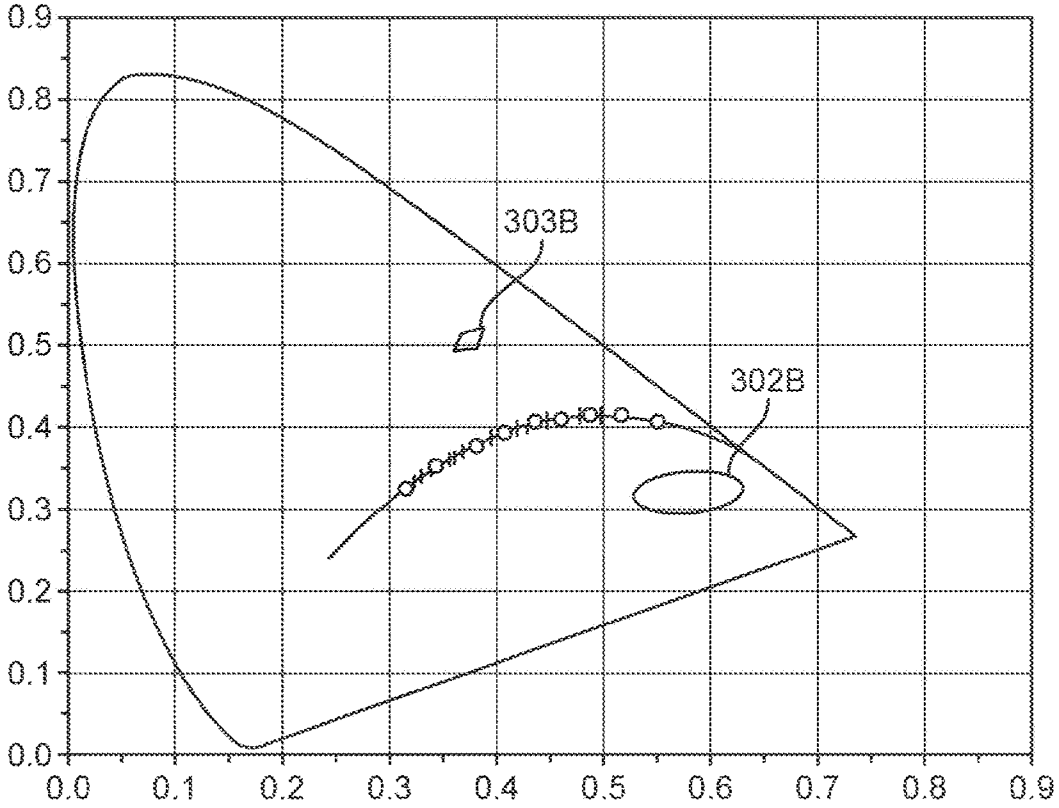
FIG. 5 illustrates some aspects of light emitting devices according to the present disclosure, including some suitable color ranges for light generated by components of the devices.
Figure 6:
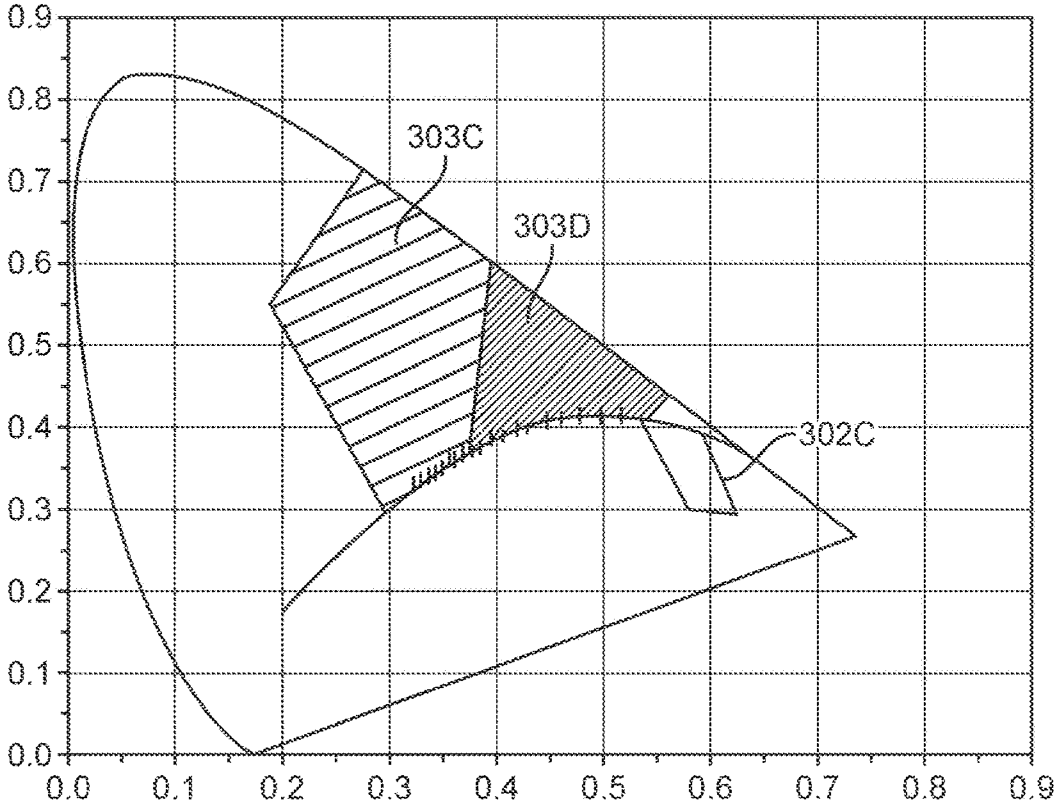
FIG. 6 illustrates some aspects of light emitting devices according to the present disclosure, including some suitable color ranges for light generated by components of the devices.
Figure 9:
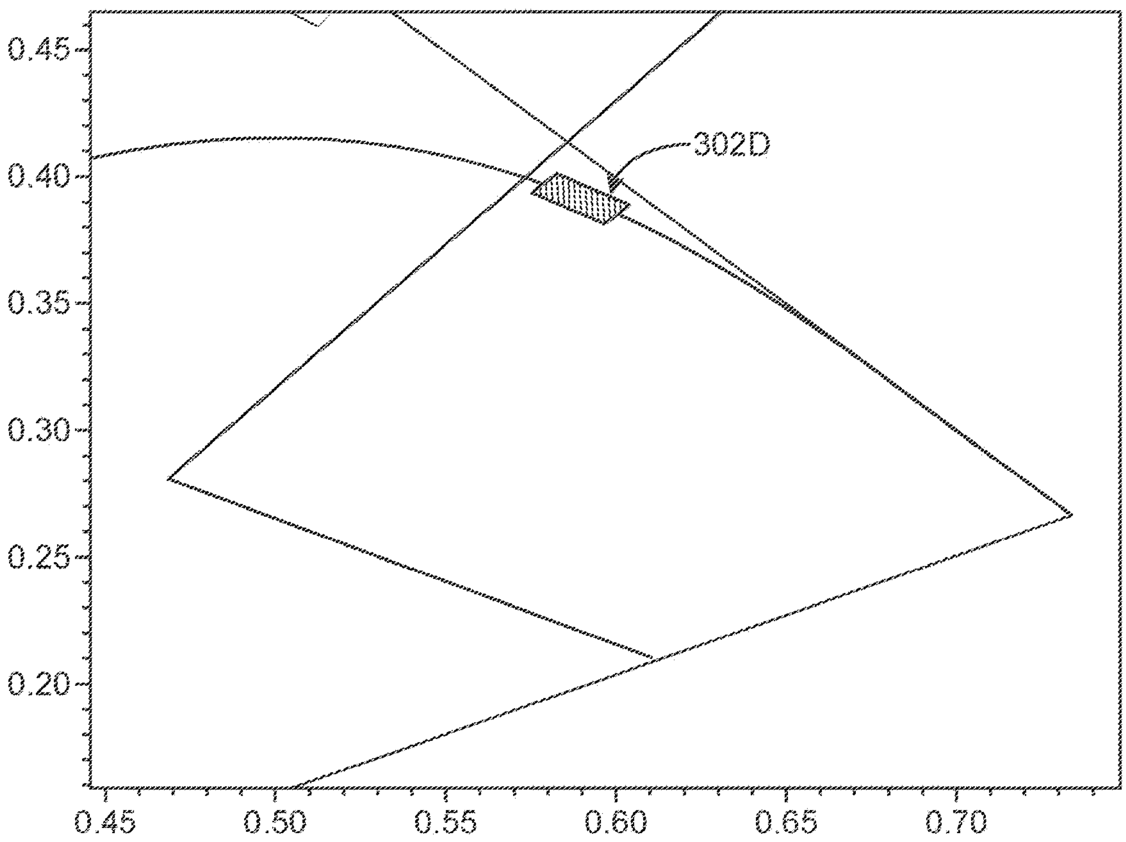
FIG. 9 illustrates some aspects of light emitting devices according to the present disclosure, including some suitable color ranges for light generated by components of the devices.

In some implementations of the present disclosure, lighting systems can include red channels that produce light with a red color point that falls within a red color range. In certain implementations, suitable red color ranges can include red color ranges 302A-D. FIG. 4B depicts a red color range 302A defined by the spectral locus between the constant CCT line of 1600 K and the line of purples, the line of purples, a line connecting the ccx, ccy color coordinates (0.61, 0.21) and (0.47, 0.28), and the constant CCT line of 1600 K. Red color ranges disclosed in the Long Red region are shown in FIG. 4B 302A. FIG. 5 depicts some suitable color ranges for some implementations of the disclosure. A red color range 302B can be defined by a 20-step MacAdam ellipse at a CCT of 1200 K, 20 points below the Planckian locus. FIG. 6 depicts some further color ranges suitable for some implementations of the disclosure. A red color range 302C is defined by a polygonal region on the 1931 CIE Chromaticity Diagram defined by the following ccx, ccy color coordinates: (0.53, 0.41),(0.59, 0.39),(0.63, 0.29), (0.58, 0.30). In FIG. 8, a red color range 302C is depicted and can be defined by a polygonal region on the 1931 CIE Chromaticity Diagram defined by the following ccx, ccy color coordinates; (0.53, 0.41),(0.59, 0.39). (0.63, 0.29), (0.58, 0.30). FIG. 9 depicts a red color range 302D defined by lines connecting the ccx, ccy coordinates (0.576, 0.393), (0.583, 0.40M),(0.604, 0.387), and (0.597, 0.380).

Long Red and Near Infrared Channel

Figure 20:
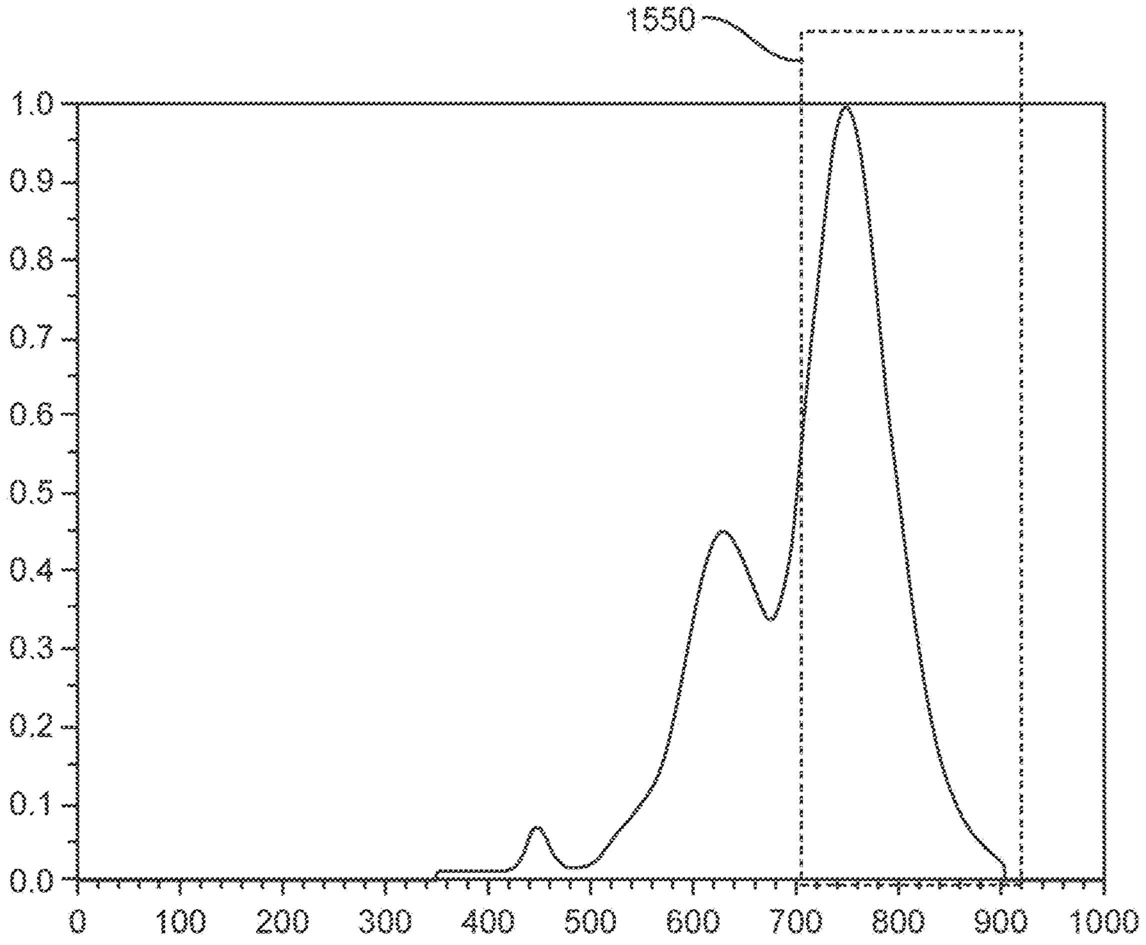
FIG. 20 illustrates some aspects of light emitting devices according to the present disclosure, including aspects of LRNE spectral power distributions for light generated by components of the devices.
Figure 21:
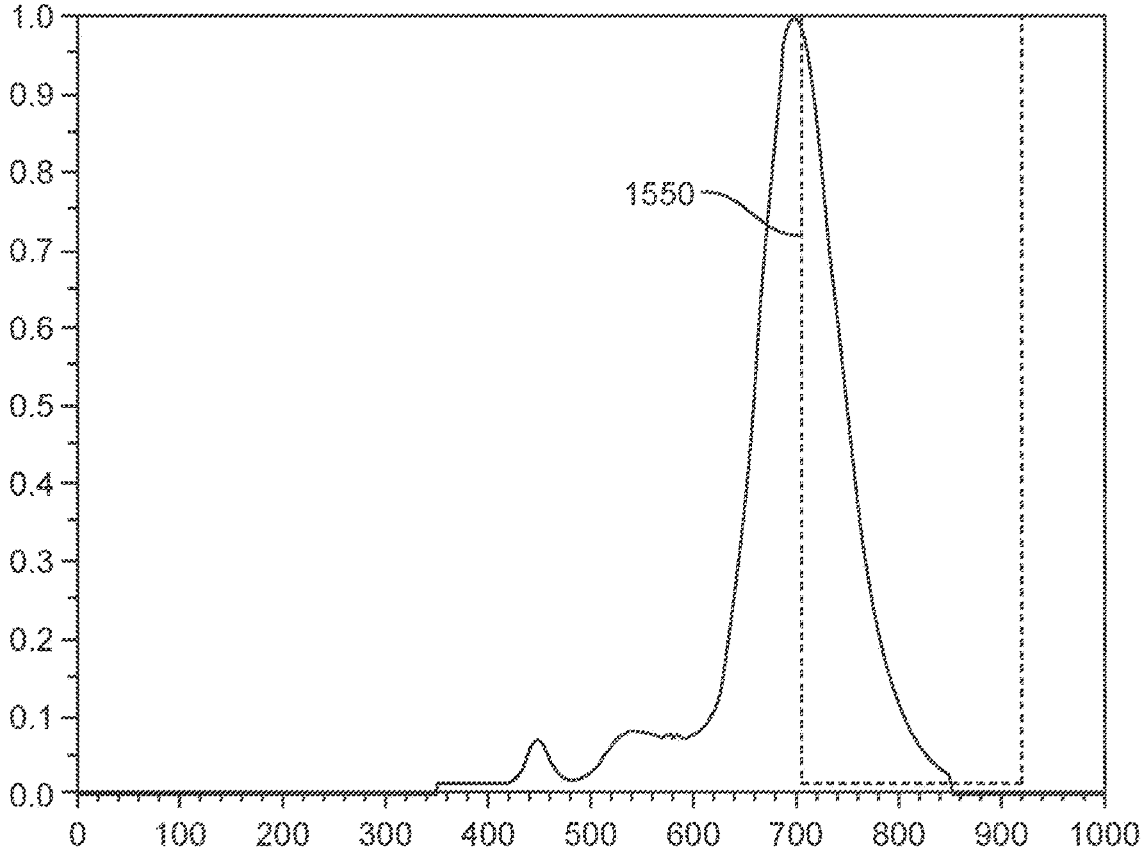
FIG. 21 illustrates some aspects of light emitting devices according to the present disclosure, including aspects of LRNE spectral power distributions for light generated by components of the devices.

In some aspects, the present disclosure relates to long red and near infrared lighting channels that can provide long red and near infrared energy ("LRNE"). Long red and near infrared channels can provide one or both of Visible LRNE and Non-Visible LRNE. Visible LRNE refers to light having spectral power in wavelengths between about 625 nm and about 700 nm. Non-Visible LRNE refers to light having spectral power in wavelengths greater than or equal to about 700 nm. The Long Red and Near Infrared Channels of the present disclosure can be part of one or more red channels involved in color-tuning and providing white light, or as separate channel that can be operated independently of color-tuning requirements. In some implementations an additional LRNE channel includes the non-visible region of the LRNE also referred to as near infrared. Although the near infrared may not be visually perceived as red such a channel it can provide benefits of LRNE as described above. In FIGS. 19-21, Region 1550 represents LRNE emissions which are considered by most to be outside the visual spectrum of humans. FIG. 19 depicts the emission spectrum of an exemplary nitride phosphor excited by violet or blue light wavelengths between about 380 nm and about 490 nm. In certain implementations red nitride phosphors having peak wavelengths between about 675 nm and about 775 nm can be included in one or more red channels or long-red channels.

Short-Blue-Pumped Cyan Channels

In some implementations of the present disclosure, lighting systems can include short-blue-pumped cyan channels that produce light with a cyan color point that falls within a cyan color range. In certain implementations, suitable cyan color ranges can include cyan color ranges 303A-D. FIG. 4B shows a cyan color range 303A defined by a line connecting the ccx, ccy color coordinates (0.18, 0.55) and (0.27, 0.72), the constant CCT line of 9000 K, the Planckian locus between 9000 K and 1800 K, the constant CCT line of 1800 K, and the spectral locus. FIG. 5 depicts some suitable color ranges for some implementations of the disclosure. A cyan color range 303B can be defined by the region bounded by lines connecting (0.360, 0.495),(0.371, 0.518),(0.388, 0.522), and (0.377, 0.499). FIG. 6 depicts some further color ranges suitable for some implementations of the disclosure. A cyan color range 303C is defined by a line connecting the ccx, ccy color coordinates (0.18, 0.55) and (0.27, 0.72), the constant CCT line of 9000 K, the Planckian locus between 9000 K and 4600 K, the constant CCT line of 4600 K, and the spectral locus. A cyan color range 303D is defined by the constant CCT line of 4600 K, the spectral locus, the constant CCT line of 1800 K, and the Planckian locus between 4600 K and 1800 K.

Long-Blue-Pumped Cyan Channels

In some implementations of the present disclosure, lighting systems can include long-blue-pumped cyan channels that produce light with a cyan color point that falls within a cyan color range. In certain implementations, suitable cyan color ranges can include cyan color ranges 303A-E. FIG. 4B shows a cyan color range 303A defined by a line connecting the ccx, ccy color coordinates (0.18, 0.55) and (0.27, 0.72), the constant CCT line of 9000 K, the Planckian locus between 9000 K and 1800 K, the constant CCT line of 1800 K, and the spectral locus. FIG. 5 depicts some suitable color ranges for some implementations of the disclosure. A cyan color range 303B can be defined by the region bounded by lines connecting (0.360, 0.495). (0.371, 0.518),(0.388, 0.522), and (0.377, 0.499). FIG. 6 depicts some further color ranges suitable for some implementations of the disclosure. A cyan color range 303C is defined by a line connecting the ccx, ccy color coordinates (0.18, 0.55) and (0.27, 0.72), the constant CCT line of 9000 K, the Planckian locus between 9000 K and 4600 K, the constant CCT line of 4600 K, and the spectral locus. A cyan color range 303D is defined by the constant CCT line of 4600 K, the spectral locus, the constant CCT line of 1800 K, and the Planckian locus between 4600 K and 1800 K. In some implementations, the long-blue-pumped cyan channel can provide a color point within a cyan color region 303E defined by lines connecting (0.497, 0.469). (0.508, 0.484),(0.524, 0.472), and (0.513, 0.459).

Yellow Channels

Figure 14A:
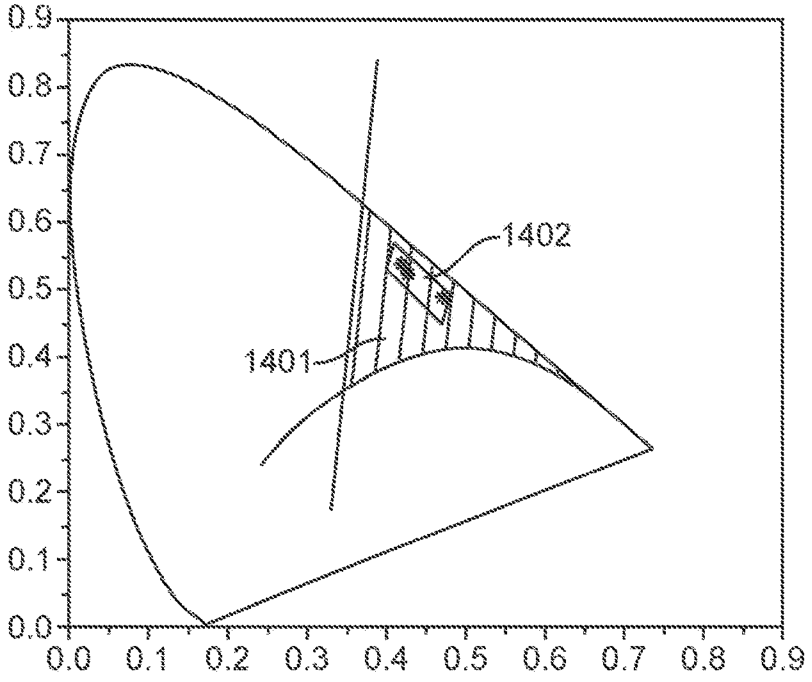
FIGS. 14A and 14B illustrate some aspects of light emitting devices according to the present disclosure, including some suitable color ranges for light generated by components of the devices.
Figure 14B:
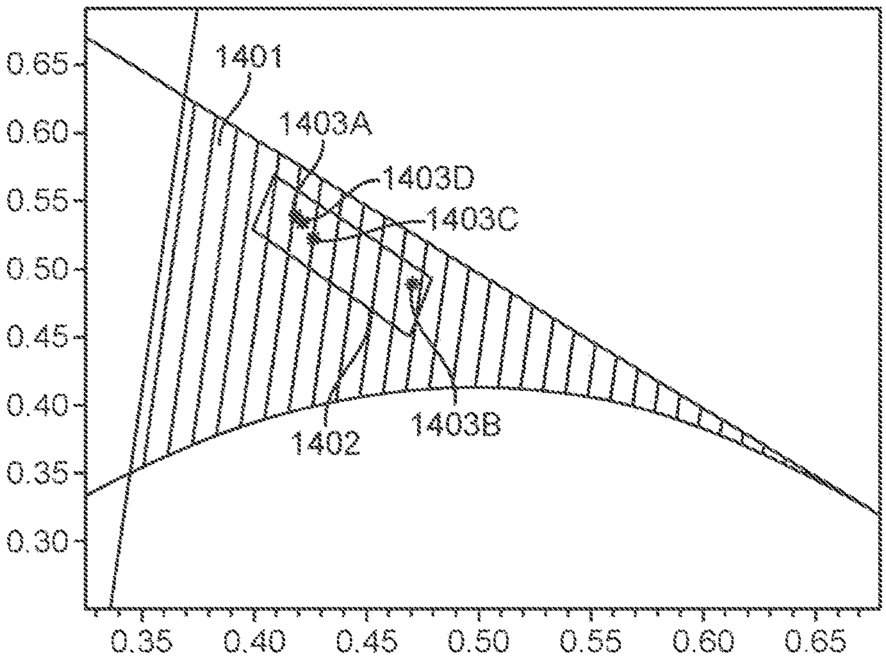

In some implementations of the present disclosure, lighting systems can include yellow channels that produce light with a yellow color point that falls within a yellow color range. Non-limiting FIGS. 14A and 14B depicts some aspects of suitable yellow color ranges for implementations of yellow channels of the present disclosure. In some implementations, the yellow channels can produce light having a yellow color point that falls within a yellow color range 1401, with boundaries defined on the 1931 CIE Chromaticity Diagram of the constant CCT line of 5000 K from the Planckian locus to the spectral locus, the spectral locus, and the Planckian locus from 5000 K to 550 K. In certain implementations, the yellow channels can produce light having a yellow color point that falls within a yellow color range 1402, with boundaries defined on the 1931 CIE Chromaticity Diagram by a polygon connecting (ccx, ccy) coordinates of (0.47, 0.45),(0.48, 0.495),(0.41, 0.57), and (0.40, 0.53). In some implementations, the yellow channels can produce light having a color point at one of the exemplary yellow color points 1403A-D shown in FIG. 14 and described more fully elsewhere herein.

Violet Channels

Figure 13:
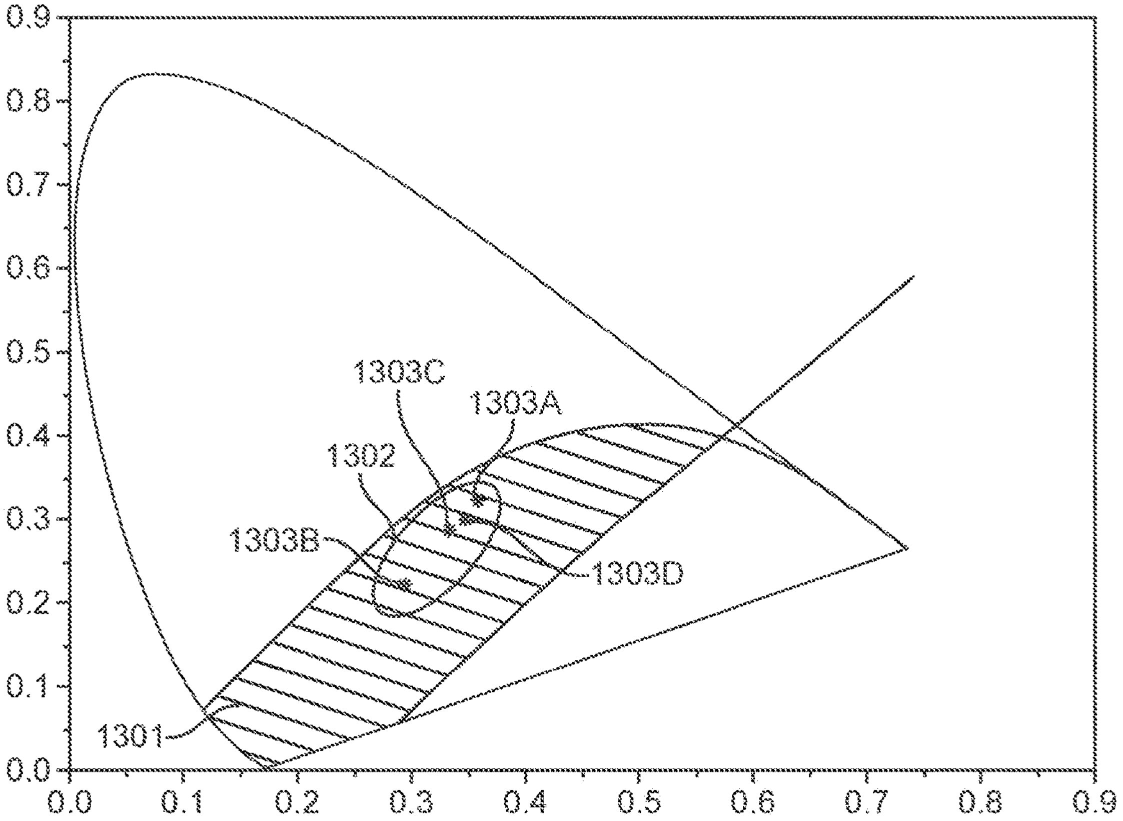
FIG. 13 illustrates some aspects of light emitting devices according to the present disclosure, including some suitable color ranges for light generated by components of the devices.

In some implementations of the present disclosure, lighting systems can include violet channels that produce light with a violet color point that falls within a violet color range. Non-limiting FIG. 13 depicts some aspects of suitable violet color ranges for implementations of violet channels of the present disclosure. In some implementations, the violet channels can produce light having a violet color point that falls within a violet color range 1301, with boundaries defined on the 1931 CIE Chromaticity Diagram of the Planckian locus between 1600 K CCT and infinite CCT, a line between the infinite CCT point on the Planckian locus and the monochromatic point of 470 nm on the spectral locus, the spectral locus between the monochromatic point of 470 nm and the line of purples, the line of purples from the spectral locus to the constant CCT line of 1600 K, and the constant CCT line of 1600 K between the line of purples and the 1600 K CCT point on the Planckian locus. In certain implementations, the violet channels can produce light having a violet color point that falls within a violet color range 1302, with boundaries defined on the 1931 CIE Chromaticity Diagram by a 40-step MacAdam ellipse centered at 6500 K CCT with DUV=−40 points. In some implementations, the violet channels can produce light having a color point at one of the exemplary violet color points 1303A-D shown in FIG. 13 and described more fully elsewhere herein.

LEDs

In some implementations, the LEDs in the first, second, third and fourth LED strings can be LEDs with peak emission wavelengths at or below about 535 nm. In some implementations, the LEDs emit light with peak emission wavelengths between about nm and about 535 nm. In some implementations, the LEDs in the first, second, third and fourth LED strings can be formed from InGaN semiconductor materials. In some preferred implementations, the first, second, and third LED strings can have LEDs having a peak wavelength between about 405 nm and about 485 nm, between about 430 nm and about 460 nm, between about 430 nm and about 455 nm, between about 430 nm and about 440 nm, between about 440 nm and about 450 nm, between about 440 nm and about 445 nm, or between about 445 nm and about 450 nm. The LEDs used in the first, second, third, and fourth LED strings may have full-width half-maximum wavelength ranges of between about nm and about 30 nm. In some preferred implementations, the first, second, and third LED strings can include one or more LUXEON Z Color Line royal blue LEDs (product code LXZ1-PR01) of color bin codes 3, 4, 5, or 6, one or more LUXEON Z Color Line blue LEDs (LXZ1-PB01) of color bin code 1 or 2, or one or more LUXEON royal blue LEDs (product code LXML-PR01 and LXML-PR02) of color bins 3, 4, 5, or 6 (Lumileds Holding B. V., Amsterdam, Netherlands).

In some implementations, the LEDs used in the fourth LED string can be LEDs having peak emission wavelengths between about 360 nm and about 535 nm, between about 380 nm and about 520 nm, between about 470 nm and about 505 nm, about 480 nm, about 470 nm, about 460 nm, about 455 nm, about 450 nm, or about 445 nm. In certain implementations, the LEDs used in the fourth LED string can have a peak wavelength between about 460 nm and 515 nm. In some implementations, the LEDs in the fourth LED string can include one or more LUXEON Rebel Blue LEDs (LXML-PB01, LXML-PB02) of color bins 1, 2, 3, 4, or 5, which have peak wavelengths ranging from 460 nm to 485 nm, or LUXEON Rebel Cyan LEDs (LXML-PE01) of color bins 1, 2, 3, 4, or 5, which have peak wavelengths raving from 460 nm to 485 nm.

In certain implementations, the LEDs used in the fifth and sixth LED strings can be LEDs having peak wavelengths of between about 380 nm and about 420 nm, such as one or more LEDs having peak wavelengths of about 380 nm, about 385 nm, about nm, about 395 nm, about 400 nm, about 405 nm, about 410 nm, about 415 nm, or about nm. In some implementations, the LEDs in the fifth and sixth LED strings can be one or more LUXEON Z UV LEDs (product codes LHUV-0380-, LHUV-0385-, LHUV-0390-, LHUV-0395-, LHUV-0400-, LHUV-0405-, LHUV-0410-, LHUV-0415-, LHUV-0420-,) (Lumileds Holding B.V., Amsterdam, Netherlands), one or more LUXEON UV FC LEDs (product codes LxF3-U410) (Lumileds Holding B.V., Amsterdam, Netherlands), one or more LUXEON UV U LEDs (product code LHUV-0415-) (Lumileds Holding B.V., Amsterdam, Netherlands), for example.

In further implementations, LRNE lighting channels can utilize commercially available LEDs with peak emission wavelengths of about 850 nm, about 940 nm, or combinations of the two. In certain implementations, the LEDs can be LUXEON Similar LEDs to those described herein from other manufacturers such as OSRAM GmbH and Cree, Inc. could also be used, provided they have peak emission and full-width half-maximum wavelengths of the appropriate values.

Spectral Power Distributions

In implementations utilizing LEDs that emit substantially saturated light at wavelengths between about 360 nm and about 535 nm, the device 100 can include suitable recipient luminophoric mediums for each LED in order to produce light having color points within the suitable blue color ranges 301A-F, red color ranges 302A-D, cyan color ranges 303A-E, violet color ranges 1301, 1302, and yellow color ranges 1401, 1402 described herein. The light emitted by each lighting channel (from each LED string, i.e., the light emitted from the LED(s) and associated recipient luminophoric medium together) can have a suitable spectral power distribution ("SPD") having spectral power with ratios of power across the visible wavelength spectrum from about 380 nm to about 780 nm or across the visible, near-visible, and non-visible wavelength spectrum from about 320 nm to about 1000 nm. While not wishing to be bound by any particular theory, it is speculated that the use of such LEDs in combination with recipient luminophoric mediums to create unsaturated light within the suitable color ranges 301A-F, 302A-D, 303A-E, 1301, 1302, 1401, and 1402 provides for improved color rendering performance for white light across a predetermined range of CCTs from a single device 100. Further, while not wishing to be bound by any particular theory, it is speculated that the use of such LEDs in combination with recipient luminophoric mediums to create unsaturated light within the suitable color ranges 301A-F, 302A-D, 303A-E, 1301, 1302, 1401, and 1402 provides for improved light rendering performance, providing higher EML performance along with color-rendering performance, for white light across a predetermined range of CCTs from a single device 100. Some suitable ranges for spectral power distribution ratios of the lighting channels of the present disclosure are shown in Tables 1-4 and 7-15. The Tables show the ratios of spectral power within wavelength ranges, with an arbitrary reference wavelength range selected for each color range and normalized to a value of 100.0.

In some implementations, the lighting channels of the present disclosure can each product a colored light that falls between minimum and maximum values in particular wavelength ranges relative to an arbitrary reference wavelength range. Tables 1, 2, and 7-15 show some exemplary minimum and maximum spectral power values for the blue, red, long-red, LRNE, short-blue-pumped cyan, long-blue-pumped cyan, yellow, and violet channels of the disclosure. In certain implementations, the blue lighting channel can produce light with spectral power distribution that falls within the values between Blue minimum 1 and Blue maximum 1 in the wavelength ranges shown in Table 1, Table 2, or both Tables 1 and 2. In some implementations, the red lighting channel can produce light with spectral power distribution that falls within the values between Red minimum 1 and Red maximum 1 in the wavelength ranges shown in Table 1, Table 2, or both Tables 1 and 2. In some implementations, the red channel can produce red light having a spectral power distribution that falls within the ranges between the Exemplary Red Channels Minimum and the Exemplary Red Channels Maximum in the wavelength ranges shown in one or more of Tables 7-9. In some implementations, the short-blue-pumped cyan can fall within the values between Short-blue-pumped cyan minimum 1 and Short-blue-pumped cyan maximum 1 in the wavelength ranges shown in Table 1, Table 2, or both Tables 1 and 2. In other implementations, the short-blue-pumped cyan can fall within the values between Short-blue-pumped cyan minimum 1 and Short-blue-pumped cyan maximum 2 in the wavelength ranges shown in Table 1. In some implementations, the Long-Blue-Pumped Cyan lighting channel can produce light with spectral power distribution that falls within the values between Long-Blue-Pumped Cyan minimum 1 and Long-Blue-Pumped Cyan maximum 1 in the wavelength ranges shown in Table 1, Table 2, or both Tables 1 and 2. In some implementations, the yellow channel can produce yellow light having a spectral power distribution that falls within the ranges between the Exemplary Yellow Channels Minimum and the Exemplary Yellow Channels Maximum in the wavelength ranges shown in one or more of Tables 13-15. In some implementations, the violet channel can produce violet light having a spectral power distribution that falls within the ranges between the Exemplary Violet Channels Minimum and the Exemplary Violet Channels Maximum in the wavelength ranges shown in one or more of Tables 10-12. While not wishing to be bound by any particular theory, it is speculated that because the spectral power distributions for generated light with color points within the blue, long-blue-pumped cyan, short-blue-pumped cyan, yellow, and violet color ranges contains higher spectral intensity across visible wavelengths as compared to lighting apparatuses and methods that utilize more saturated colors, this allows for improved color rendering for test colors other than R1-R8. International Patent Application No. PCT/US2018/020792, filed Mar. 2, 2018, discloses aspects of some additional red, blue, short-pumped-blue (referred to as "green" therein), and long-pumped-blue (referred to as "cyan" therein) channel elements that may be suitable for some implementations of the present disclosure, the entirety of which is incorporated herein for all purposes.

In some implementations, the short-blue-pumped cyan channel can produce cyan light having certain spectral power distributions. Tables 3 and 4 show the ratios of spectral power within wavelength ranges, with an arbitrary reference wavelength range selected for the short-blue-pumped cyan color range and normalized to a value of 100.0, for a short-blue-pumped cyan channel that may be used in some implementations of the disclosure. The exemplary Short-blue-pumped cyan Channel 1 has a ccx, ccy color coordinate shown in Table 5. In certain implementations, the short-blue-pumped cyan channel can have a spectral power distribution with spectral power in one or more of the wavelength ranges other than the reference wavelength range increased or decreased within 30% greater or less, within 20% greater or less, within 10% greater or less, or within 5% greater or less than the values shown in Table 3 or 4.

In some implementations, the long-blue-pumped cyan channel can produce cyan light having certain spectral power distributions. Tables 3 and 4 shows ratios of spectral power within wavelength ranges, with an arbitrary reference wavelength range selected for the long-blue-pumped cyan color range and normalized to a value of 100.0, for several non-limiting embodiments of the long-blue-pumped cyan channel. The exemplary Long-blue-pumped cyan Channel 1 has a ccx, ccy color coordinate Shown in Table 5. In certain implementations, the long-blue-pumped cyan channel can have a spectral power distribution with spectral power in one or more of the wavelength ranges other than the reference wavelength range increased or decreased within 30% greater or less, within 20% greater or less, within 10% greater or less, or within 5% greater or less than the values shown in Table 3 and 4.

In some implementations, the red channel can produce red light having certain spectral power distributions. Tables 3-4 and 7-9 show the ratios of spectral power within wavelength ranges, with an arbitrary reference wavelength range selected for the red color range and normalized to a value of 100.0, for red lighting channels, long-red lighting channels, and LRNE channels that may be used in some implementations of the disclosure. The exemplary Red Channel 1 has a ccx, ccy color coordinate of (0.5932, 0.3903). In certain implementations, the red channel can have a spectral power distribution with spectral power in one or more of the wavelength ranges other than the reference wavelength range increased or decreased within 30% greater or less, within 20% greater or less, within 10% greater or less, or within 5% greater or less than the values shown in Tables 3-4 and 7-9 for Red Channels 1-11, Long-Red Channels A-B, the Exemplary Long-Red Channel Average, and the Exemplary Red Channels Average.

In some implementations, the blue channel can produce blue light having certain spectral power distributions. Tables 3 and 4 show the ratios of spectral power within wavelength ranges, with an arbitrary reference wavelength range selected for the blue color range and normalized to a value of 100.0, for a blue channel that may be used in some implementations of the disclosure. Exemplary Blue Channel 1 has a ccx, ccy color coordinate of (0.2333, 0.2588). In certain implementations, the blue channel can have a spectral power distribution with spectral power in one or more of the wavelength ranges other than the reference wavelength range increased or decreased within 30% greater or less, within 20% greater or less, within 10% greater or less, or within 5% greater or less than the values shown in Tables 3 and 4.

In some implementations, the yellow channel can have certain spectral power distributions. Tables 13-15 show the ratios of spectral power within wavelength ranges, with an arbitrary reference wavelength range selected and normalized to a value of 100.0 for exemplary yellow lighting channels. Yellow Channels 1-6. Table 5 shows some aspects of the exemplary yellow lighting channels for some implementations of the disclosure. In certain implementations, the yellow channel can have a spectral power distribution with spectral power in one or more of the wavelength ranges other than the reference wavelength range increased or decreased within 30% greater or less, within 20% greater or less, within 10% greater or less, or within 5% greater or less than the values shown in one or more of Tables 13-15 for Yellow Channels 1-6 and the Exemplary Yellow Channels Average.

In some implementations, the violet channel can have certain spectral power distributions. Tables 13-15 show the ratios of spectral power within wavelength ranges, with an arbitrary reference wavelength range selected and normalized to a value of 100.0 for exemplary violet lighting channels, Violet Channels 1-5. Table 5 shows some aspects of the exemplary violet lighting channels for some implementations of the disclosure. In certain implementations, the violet channel can have a spectral power distribution with spectral power in one or more of the wavelength ranges other than the reference wavelength range increased or decreased within 30% greater or less, within 20% greater or less, within 10% greater or less, or within 5% greater or less than the values shown in one or more of Tables 12-15 for one or more of Violet Channels 1-6 and the Exemplary Violet Channels Average.

In some implementations, the lighting channels of the present disclosure can each product a colored light having spectral power distributions having particular characteristics. In certain implementations, the spectral power distributions of some lighting channels can have peaks, points of relatively higher intensity, and valleys, points of relatively lower intensity that fall within certain wavelength ranges and have certain relative ratios of intensity between them.

Figure 16:
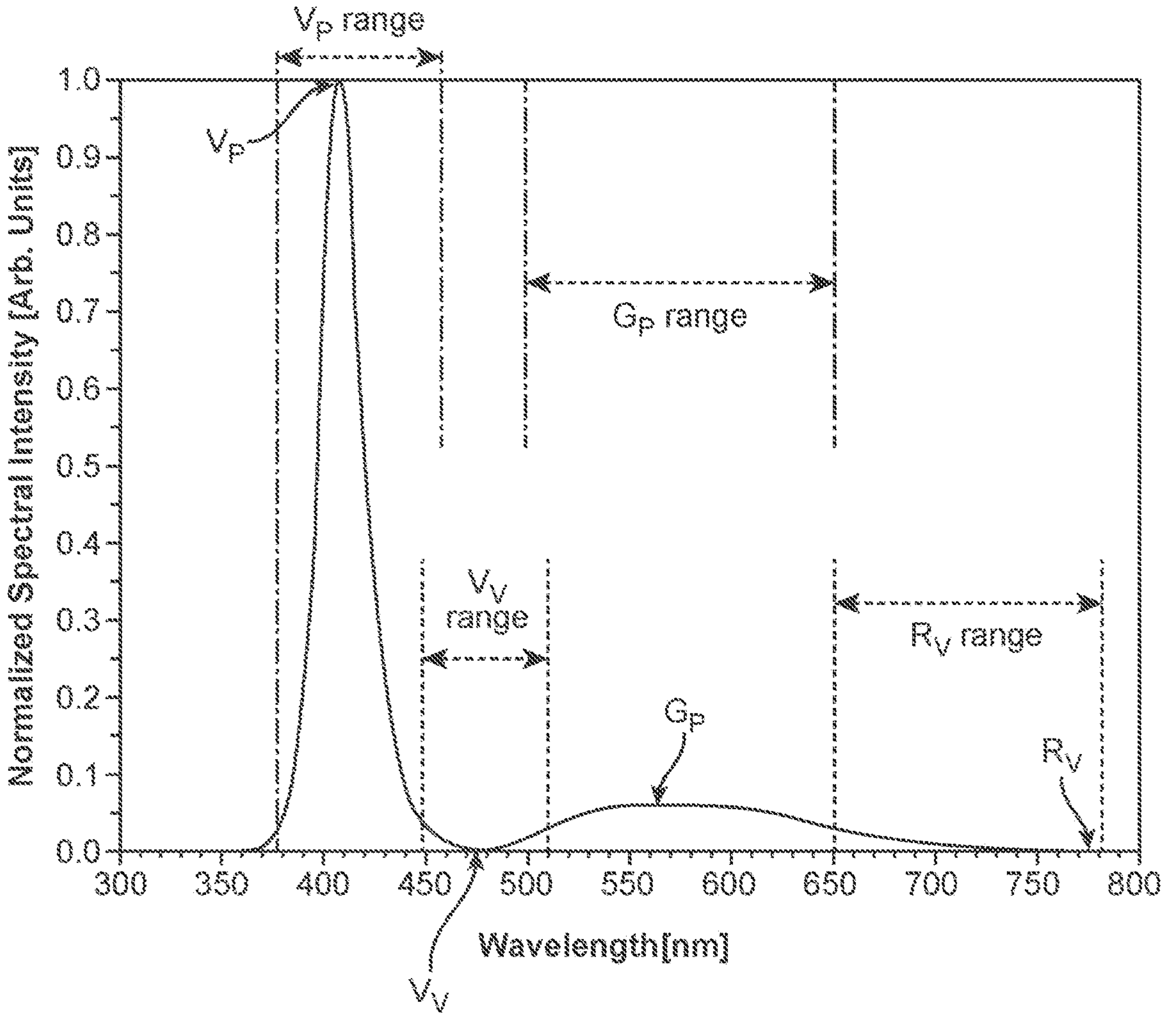
FIG. 16 illustrates some aspects of light emitting devices according to the present disclosure, including aspects of spectral power distributions for light generated by components of the devices.

Tables 38 and 39 and FIG. 16 show some aspects of exemplary violet lighting channels for some implementations of the disclosure. In certain implementations, a Violet Peak ($V_P$) is present in a range of about 380 nm to about 460 nm. In further implementations, a Violet Valley ($V_V$) is present in a range of about 450 nm to about 510 nm. In some implementations, a Green Peak ($G_P$) is present in a range of about 500 nm to about nm. In certain implementations, a Red Valley ($R_V$) is present in a range of about 650 nm to about 780 nm. Table 38 shows the relative intensities of the peaks and valleys for exemplary violet lighting channels of the disclosure, with the $V_P$ values assigned an arbitrary value of 1.0 in the table. The wavelength at which each peak or valley is present is also shown in Table 38. Table 39 shows the relative ratios of intensity between particular pairs of the peaks and valleys of the spectral power distributions for exemplary violet lighting channels and minimum, average, and maximum values thereof. In certain implementations, the violet channel can have a spectral power distribution with the relative intensities of $V_V$, $G_P$, and $R_V$ increased or decreased within 30% greater or less, within 20% greater or less, within 10% greater or less, or within 5% greater or less than the values shown in Table 38 for one or more of Violet Channels 1-5 and the Exemplary Violet Channels Average. In some implementations, the violet channel can produce violet light having a spectral power distribution with peak and valley intensities that fall between the Exemplary Violet Channels Minimum and the Exemplary Violet Channels Maximum shown in Table 38. In further implementations, the violet channel can produce violet light having a spectral power distribution with relative ratios of intensity between particular pairs of the peak and valley intensities that fall between the Exemplary Violet Channels Minimum and the Exemplary Violet Channels Maximum values shown in Table 39. In certain implementations, the violet channel can have a spectral power distribution with the relative ratios of intensity between particular pairs of the peak and valley intensities increased or decreased within 30% greater or less, within 20% greater or less, within 10% greater or less, or within 5% greater or less than the relative ratio values shown in Table 39 for one or more of Violet Channels 1-5 and the Exemplary Violet Channels Average.

Figure 17:
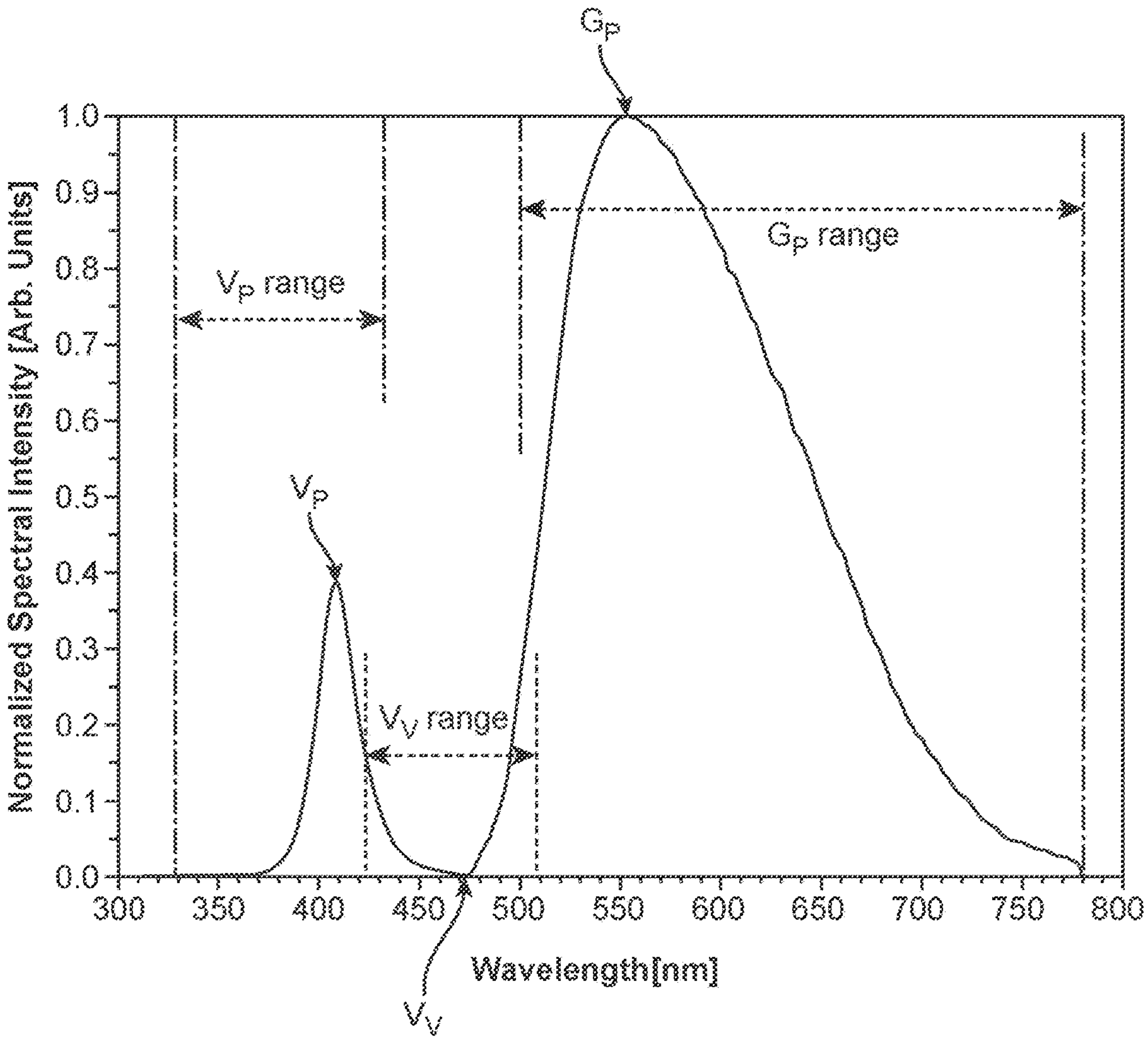
FIG. 17 illustrates some aspects of light emitting devices according to the present disclosure, including aspects of spectral power distributions for light generated by components of the devices.
Figure 18:
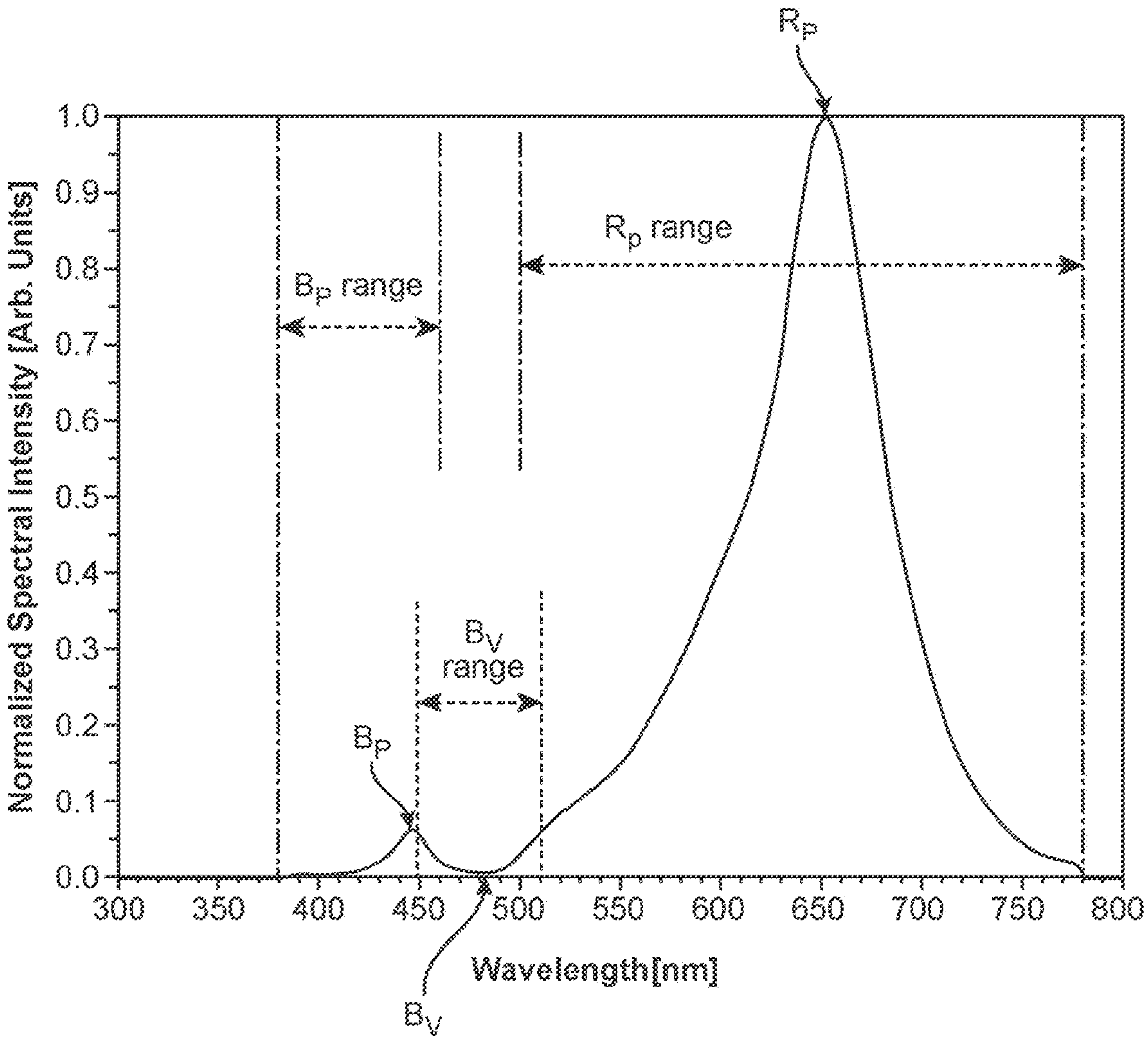
FIG. 18 illustrates some aspects of light emitting devices according to the present disclosure, including aspects of spectral power distributions for light generated by components of the devices.

Tables 40 and 41 and FIG. 17 show some aspects of exemplary yellow lighting channels for some implementations of the disclosure. In certain implementations, a Violet Peak ($V_P$) is present in a range of about 330 nm to about 430 nm. In further implementations, a Violet Valley ($V_V$) is present in a range of about 420 nm to about 510 nm. In some implementations, a Green Peak ($G_P$) is present in a range of about 500 nm to about nm. Table 40 shows the relative intensities of the peaks and valleys for exemplary yellow lighting channels of the disclosure, with the $G_P$ values assigned an arbitrary value of 1.0 in the table. The wavelength at which each peak or valley is present is also shown in Table 40. Table 41 shows the relative ratios of intensity between particular pairs of the peaks and valleys of the spectral power distributions for exemplary yellow lighting channels and minimum, average, and maximum values thereof. In certain implementations, the yellow channel can have a spectral power distribution with the relative intensities of $V_P$ and $V_V$ increased or decreased within 30% greater or less, within 20% greater or less, within 10°/o greater or less, or within 5% greater or less than the values for one or more of Yellow Channels 1-6 and the Exemplary Yellow Channels Average shown in Table 40. In some implementations, the yellow channel can produce yellow light having a spectral power distribution with peak and valley intensities that fall between the Exemplary Yellow Channels Minimum and the Exemplary Yellow Channels Maximum shown in Table 40. In further implementations, the yellow channel can produce yellow light having a spectral power distribution with relative ratios of intensity between particular pairs of the peak and valley intensities that fall between the Exemplary Yellow Channels Minimum and the Exemplary Yellow Channels Maximum values shown in Table 41. In certain implementations, the yellow channel can have a spectral power distribution with the relative ratios of intensity between particular pairs of the peak and valley intensities increased or decreased within 30% greater or less, within 20% greater or less, within 10% greater or less, or within 5% greater or less than the relative ratio values for one or more of Yellow Channels 1-6 and the Exemplary Yellow Channels Average shown in Table 41.

Tables 42-46 and FIGS. 18-21 show some aspects of exemplary red lighting channels for some implementations of the disclosure. In certain implementations, a Blue Peak ($B_P$) is present in a range of about 380 nm to about 460 nm. In further implementations, a Blue Valley ($B_V$) is present in a range of about 450 nm to about 510 nm. In some implementations, a Red Peak ($R_P$) is present in a range of about 500 nm to about 780 nm. Table 42 shows the relative intensities of the peaks and valleys for exemplary red lighting channels of the disclosure, with the $R_P$ values assigned an arbitrary value of 1.0 in the table. The wavelength at which each peak or valley is present is also shown in Table 42. Table 43 shows the relative ratios of intensity between particular pairs of the peaks and valleys of the spectral power distributions for exemplary red lighting channels and minimum, average, and maximum values thereof. In certain implementations, the red channel can have a spectral power distribution with the relative intensities of Br and By increased or decreased within 30% greater or less, within 20% greater or less, within 10% greater or less, or within 5% greater or less than the values for one or more of Red Channels 1, 3-6, and 9-17 and the Exemplary Red Channels Average shown in Table 42. In some implementations, the red channel can produce red light having a spectral power distribution with peak and valley intensities that fall between the Exemplary Red Channels Minimum and the Exemplary Red Channels Maximum shown in Table 42. In further implementations, the red channel can produce red light having a spectral power distribution with relative ratios of intensity between particular pairs of the peak and valley intensities that fall between the Exemplary Red Channels Minimum and the Exemplary Red Channels Maximum values shown in Table 43. In certain implementations, the red channel can have a spectral power distribution with the relative ratios of intensity between particular pairs of the peak and valley intensities increased or decreased within 30% greater or less, within 20% greater or less, within 10% greater or less, or within 5% greater or less than the relative ratio values for one or more of Red Channels 1, 3-6, and 9-17 and the Exemplary Red Channels Average shown in Table 43.

Luminescent Materials and Luminophoric Mediums

Blends of luminescent materials can be used in luminophoric mediums (102A-F) to create luminophoric mediums having the desired saturated color points when excited by their respective LED strings (101A-F) including luminescent materials such as those disclosed in co-pending application PCT/US2016/015318 filed Jan. 28, 2016, entitled "Compositions for LED Light Conversions", the entirety of which is hereby incorporated by this reference as if fully set forth herein. Traditionally, a desired combined output light can be generated along a tie line between the LED string output light color point and the saturated color point of the associated recipient luminophoric medium by utilizing different ratios of total luminescent material to the encapsulant material in which it is incorporated. Increasing the amount of luminescent material in the optical path will shift the output light color point towards the saturated color point of the luminophoric medium. In some instances, the desired saturated color point of a recipient luminophoric medium can be achieved by blending two or more luminescent materials in a ratio. The appropriate ratio to achieve the desired saturated color point can be determined via methods known in the art. Generally speaking, any blend of luminescent materials can be treated as if it were a single luminescent material, thus the ratio of luminescent materials in the blend can be adjusted to continue to meet a target CIE value for LED strings having different peak emission wavelengths. Luminescent materials can be tuned for the desired excitation in response to the selected LEDs used in the LED strings (101A-F), which may have different peak emission wavelengths within the range of from about 360 nm to about 535 nm. Suitable methods for tuning the response of luminescent materials are known in the art and may include altering the concentrations of dopants within a phosphor, for example. In some implementations of the present disclosure, luminophoric mediums can be provided with combinations of two types of luminescent materials. The first type of luminescent material emits light at a peak emission between about 515 nm and about 590 nm in response to the associated LED string emission. The second type of luminescent material emits at a peak emission between about nm and about 700 nm in response to the associated LED string emission. In some instances, the luminophoric mediums disclosed herein can be formed from a combination of at least one luminescent material of the first and second types described in this paragraph. In implementations, the luminescent materials of the first type can emit light at a peak emission at about 515 nm, 525 nm. 530 nm, 535 nm, 540 nm, 545 nm. 550 nm, 555 nm, 560 nm, 565 nm, 570 nm, 575 nm, 580 nm, 585 nm, or 590 nm in response to the associated LED string emission. In preferred implementations, the luminescent materials of the first type can emit light at a peak emission between about 520 nm to about 555 nm. In implementations, the luminescent materials of the second type can emit light at a peak emission at about 590 nm, about 595 nm, 600 nm. 605 nm, 610 nm, 615 nm, 620 nm, 625 nm, 630 nm, 635 nm, 640 nm, nm, 650 nm, 655 nm, 670 nm, 675 nm, 680 nm, 685 nm, 690 nm, 695 nm, or 700 nm in response to the associated LED string emission. In preferred implementations, the luminescent materials of the first type can emit light at a peak emission between about 600 nm to about 670 nm. Some exemplary luminescent materials of the first and second type are disclosed elsewhere herein and referred to as Compositions A-F. Table 6 shows aspects of some exemplar luminescent materials and properties.

Blends of Compositions A-F can be used in luminophoric mediums (102A-F) to create luminophoric mediums having the desired saturated color points when excited by their respective LED strings (101A-F). In some implementations, one or more blends of one or more of Compositions A-F can be used to produce luminophoric mediums (102A-F). In some preferred implementations, one or more of Compositions A, B. and D and one or more of Compositions C, E, and F can be combined to produce luminophoric mediums (102A-F). In some preferred implementations, the encapsulant for luminophoric mediums (102A-F) comprises a matrix material having density of about 1.1 mg/mm$^3$ and refractive index of about 1.545 or from about 1.4 to about 1.6. In some implementations, Composition A can have a refractive index of about 1.82 and a particle size from about 18 micrometers to about micrometers. In some implementations, Composition B can have a refractive index of about 1.84 and a particle size from about 13 micrometers to about 30 micrometers. In some implementations, Composition C can have a refractive index of about 1.8 and a particle size from about 10 micrometers to about 15 micrometers. In some implementations, Composition D can have a refractive index of about 1.8 and a particle size from about 10 micrometers to about 15 micrometers. Suitable phosphor materials for Compositions A, B, C, and D are commercially available from phosphor manufacturers such as Mitsubishi Chemical Holdings Corporation (Tokyo, Japan), Intematix Corporation (Fremont, CA), EMD Performance Materials of Merck KGaA (Darmstadt, Germany), and PhosphorTech Corporation (Kennesaw, GA).

Operational Modes

Figure 15:
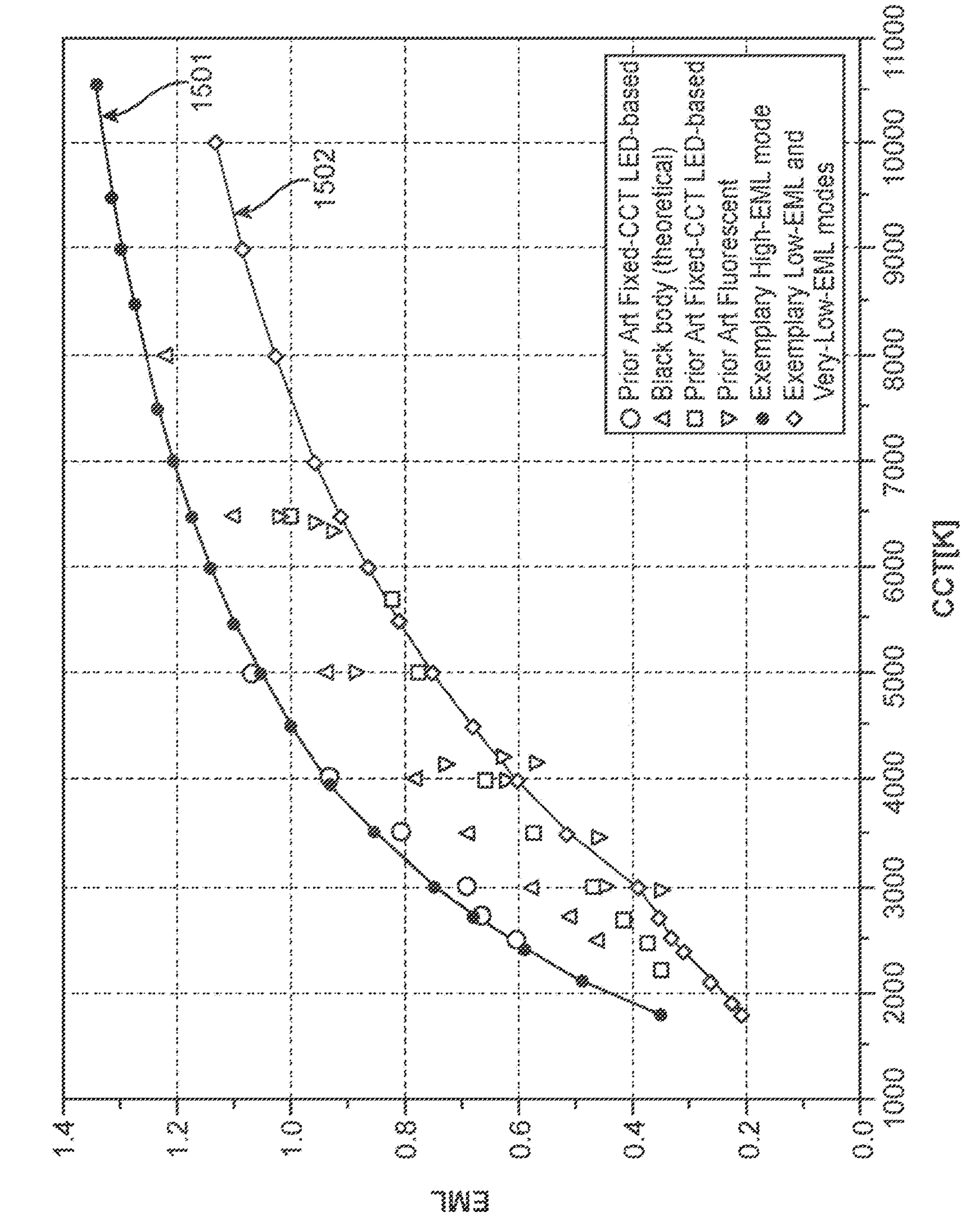
FIG. 15 illustrates some aspects of light emitting devices according to the present disclosure in comparison with some prior art and some theoretical light sources, including some light characteristics of white light generated by light emitting devices in various operational modes.

In some aspects, the present disclosure provides lighting systems that can be operated in a plurality of lighting modes. In certain implementations, the lighting systems of the present disclosure can output white light at color points along a predetermined path within a 7-step MacAdam ellipse around any point on the black body locus having a correlated color temperature between 1800 K and 10000 K. In other implementations, the lighting systems can be configured to output white light at color points along a predetermined path within a 7-step MacAdam ellipse around any point on the black body locus having a correlated color temperature within a portion of the range of 1800 K and 10000 K. In certain implementations, lighting systems can be operated in a very-low-EML mode to produce white light having CCT from about 1800 K to about 3500 K. In some implementations, the lighting systems can be operated in a low-EML mode to produce white light having CCT from about 1800 K to about 3500 K or from about 1800 K to about 10000 K. In some implementations, lighting systems can be operated in a high-EML mode to produce white light having CCT from about 1800 K to about 10000 K. In some implementations, the lighting systems can be operated in a high-CRI mode to produce white light having CCT from about 1800 K to about 10000 K. In some implementations, the lighting systems can be operated in a highest-CRI mode to produce white light having CCT from about 1800 K to about 10000 K. In certain implementations, the operation of the lighting systems of the present disclosure in a high-EML mode can be used to produce white light at a plurality of points with CCT and EML corresponding to the curve 1501 of FIG. 15. In some implementations, the operation of the lighting systems of the present disclosure in a low-EML mode can be used to produce white light at a plurality of points with CCT and EML corresponding to at least a portion of the curve 1502 of FIG. 15. In some implementations, the operation of the lighting systems of the present disclosure in a very-low-EML mode can be used to produce white light at a plurality of points with CCT and EML corresponding to at least a portion of the curve 1502 of FIG. 15. In certain implementations, the operation of the lighting systems of the present disclosure in a combination of very-low-EML and low-EML modes can be used to produce white light at a plurality of points with CCT and EML corresponding to the curve 1502 of FIG. 15.

In some aspects, the lighting systems of the present disclosure can be used to provide a plurality of white light points at different CCT values and with different EML values. It can be desirable to provide white light with substantially different EML characteristics in order to provide bioactive light configured for a biological effects to users exposed to the lighting systems. In some implementations, the lighting systems can provide a ratio of EML between a first color point produced at around 4000 K produced in a High-EML mode and a second color point produced at around 2400 K in a Low-EML or Very-Low-EML mode. In certain implementations, the ratio can be about 2.0, about 2.1, about 2.2, about 2.3, about 2.4, about 2.5, about 2.6, about 2.7, about 2.8, about 2.9, or about 3.0. In further implementations, the ratio can be between about 2.7 and about 2.9.

In some aspects, the present disclosure provides semiconductor light emitting devices capable to producing tunable white light through a range of CCT values. In some implementations, devices of the present disclosure can output white light at color points along a predetermined path within a 7-step MacAdam ellipse around any point on the black body locus having a correlated color temperature between 1800 K and 10000 K. In some implementations, the semiconductor light emitting devices can comprise first, second, third, and fourth LED strings, with each LED string comprising one or more LEDs having an associated luminophoric medium, wherein the first, second, third, and fourth LED strings together with their associated luminophoric mediums can comprise red, blue, short-blue-pumped cyan, and long-blue-pumped cyan channels respectively, producing first, second, third, and fourth unsaturated color points within red, blue, short-blue-pumped cyan, and long-blue-pumped cyan regions on the 1931 CIE Chromaticity diagram, respectively. In some implementations the devices can further include a control circuit can be configured to adjust a fifth color point of a fifth unsaturated light that results from a combination of the first, second, third, and fourth unsaturated light, with the fifth color point falls within a 7-step MacAdam ellipse around any point on the black body locus having a correlated color temperature between 1800 K and 10000 K. In some implementations the devices can be configured to generate the fifth unsaturated light corresponding to a plurality of points along a predefined path with the light generated at each point having light with Rf greater than or equal to about 88, Rg greater than or equal to about 98 and less than or equal to about 104, or both. In some implementations the devices can be configured to generate the fifth unsaturated light corresponding to a plurality of points along a predefined path with the light generated at each point having light with Ra greater than or equal to about 95 along points with correlated color temperature between about 1800 K and 10000 K, R9 greater than or equal to about 87 along points with correlated color temperature between about 2000 K and about 10000 K, or both. In some implementations the devices can be configured to generate the fifth unsaturated light corresponding to a plurality of points along a predefined path with the light generated at each point having light with R9 greater than or equal to 91 along greater than or equal to 90% of the points with correlated color temperature between about 2000 K and about 10000 K. In some implementations the devices can be configured to generate the fifth unsaturated light corresponding to a plurality of points along a predefined path with the light generated at each point having one or more of EML greater than or equal to about 0.45 along points with correlated color temperature above about 2100 K, EML greater than or equal to about 0.55 along points with correlated color temperature above about 2400 K, EML greater than or equal to about 0.7 along points with correlated color temperature above about 3000 K EML greater than or equal to about 0.9 along points with correlated color temperature above about 4000 K, and EML greater than or equal to about 1.1 along points with correlated color temperature above about 6000 K. In some implementations the devices can be configured to generate the fifth unsaturated light corresponding to a plurality of points along a predefined path with the light generated at each point having light with R13 greater than or equal to about 97, R15 greater than or equal to about 94, or both. The blue color region can comprise a region on the 1931 CIE Chromaticity Diagram comprising the combination of a region defined by a line connecting the ccx, ccy color coordinates of the infinity point of the Planckian locus (0.242, 0.24) and (0.12, 0.068), the Planckian locus from 4000 K and infinite CCT, the constant CCT line of 4000 K, the line of purples, and the spectral locus and a region defined by a line connecting (0.3806, 0.3768) and (0.0445, 0.3), the spectral locus between the monochromatic point of 490 nm and (0.12, 0.068), a line connecting the ccx, ccy color coordinates of the infinity point of the Planckian locus (0.242, 0.24) and (0.12, 0.068), and the Planckian locus from 4000 K and infinite CCT. The blue color region can comprise a region on the 1931 CIE Chromaticity Diagram defined by a line connecting the ccx, ccy color coordinates of the infinity point of the Planckian locus (0.242, 0.24) and (0.12, 0.068), the Planckian locus from 4000 K and infinite CCT, the constant CCT line of 4000 K, the line of purples, and the spectral locus. The blue color region can comprise a region on the 1931 CIE Chromaticity Diagram defined by a line connecting (0.3806, 0.3768) and (0.0445, 0.3), the spectral locus between the monochromatic point of 490 nm and (0.12, 0.068), a line connecting the ccx, ccy color coordinates of the infinity point of the Planckian locus (0.242, 0.24) and (0.12, 0.068), and the Planckian locus from 4000 K and infinite CCT. The blue color region can comprise a region on the 1931 CIE Chromaticity Diagram defined by lines connecting (0.231, 0.218),(0.265, 0.260),(0.2405, 0.305), and (0.207, 0.256). The red color region can comprise a region on the 1931 CIE Chromaticity Diagram defined by the spectral locus between the constant CCT line of 1600 K and the line of purples, the line of purples, a line connecting the ccx, ccy color coordinates (0.61, 0.21) and (0.47, 0.28), and the constant CCT line of 1600 K. The red color region can comprise a region on the 1931 CIE Chromaticity Diagram defined by lines connecting the ccx, ccy coordinates (0.576, 0.393), (0.583, 0.400),(0.604, 0.387), and (0.597, 0.380). The short-blue-pumped cyan color region, long-blue-pumped cyan color region, or both can comprise a region on the 1931 CIE Chromaticity Diagram defined by a line connecting the ccx, ccy color coordinates (0.18, 0.55) and (0.27, 0.72), the constant CCT line of 9000 K, the Planckian locus between 9000 K and 1800 K, the constant CCT line of 1800 K, and the spectral locus. The short-blue-pumped cyan color region, long-blue-pumped cyan color region, or both can comprise a region on the CIE Chromaticity Diagram defined by a line connecting the ccx, ccy color coordinates (0.18, 0.55) and (0.27, 0.72), the constant CCT line of 9000 K, the Planckian locus between 9000 K and 4600 K, the constant CCT line of 4600 K, and the spectral locus. The short-blue-pumped cyan color region, long-blue-pumped cyan color region, or both can comprise a region on the 1931 CIE Chromaticity Diagram defined by the constant CCT line of 4600 K, the spectral locus, the constant CCT line of 1800 K, and the Planckian locus between 4600 K and 1800 K. The short-blue-pumped cyan color region, long-blue-pumped cyan color region, or both can comprise a region on the 1931 CIE Chromaticity Diagram defined by the region bounded by lines connecting (0.360, 0.495),(0.371, 0.518),(0.388, 0.522), and (0.377, 0.499). The short-blue-pumped cyan color region, long-blue-pumped cyan color region, or both can comprise a region on the 1931 CIE Chromaticity Diagram defined by the region by lines connecting (0.497, 0.469). (0.508, 0.484), (0.524, 0.472), and (0.513, 0.459). In some implementations the spectral power distributions for one or more of the red channel, blue channel, short-blue-pumped cyan channel, and long-blue-pumped cyan channel can fall within the minimum and maximum ranges shown in Tables 1 and 2. In some implementations the red channel can have a spectral power distribution with spectral power in one or more of the wavelength ranges other than the reference wavelength range increased or decreased within 30% greater or less, within 20% greater or less, within 10% greater or less, or within 5% greater or less than the values of a red channel shown in Tables 3 and 4. In some implementations the blue channel can have a spectral power distribution with spectral power in one or more of the wavelength ranges other than the reference wavelength range increased or decreased within 30% greater or less, within 20% greater or less, within 10% greater or less, or within 5% greater or less than the values of a blue channel shown in Tables and 4. In some implementations the short-blue-pumped cyan channel can have a spectral power distribution with spectral power in one or more of the wavelength ranges other than the reference wavelength range increased or decreased within 30% greater or less, within 20% greater or less, within 10% greater or less, or within 5% greater or less than the values of a short-blue-pumped cyan channel shown in Table 3. In some implementations the long-blue-pumped cyan channel can have a spectral power distribution with spectral power in one or more of the wavelength ranges other than the reference wavelength range increased or decreased within 30% greater or less, within 20% greater or less, within 10% greater or less, or within 5% greater or less than the values of a long-blue-pumped cyan channel shown in Table 3. In some implementations one or more of the LEDs in the fourth LED string can have a peak wavelength of between about 480 nm and about 505 nm. In some implementations one or more of the LEDs in the first, second, and third LED strings can have a peak wavelength of between about 430 nm and about 460 nm. In some implementations, the devices can be configured to generate the fifth unsaturated light corresponding to a plurality of points along a predefined path with the light generated at each point having light with BLH factor less than 0.26 μW/cm²/lux. In some implementations, the devices can be configured to generate the fifth unsaturated light corresponding to a plurality of points along a predefined path with the light generated at each point having light with one or more of BLH factor less than or equal to about 0.05 along points with correlated color temperature below about 2100 K, BLH factor less than or equal to about 0.065 along points with correlated color temperature below about 2400 K. BLH factor less than or equal to about 0.12 along points with correlated color temperature below about 3000 K, BLH factor less than or equal to about 0.25 along points with correlated color temperature below about 4000 K, and BLH factor less than or equal to about 0.35 along points with correlated color temperature below about 6500 K. In some implementations, the devices can be configured to generate the fifth unsaturated light corresponding to a plurality of points along a predefined path with the light generated at each point having light with the ratio of the EML to the BLH factor being greater than or equal to about 2.5, greater than or equal to about 2.6, greater than or equal to about 2.7, greater than or equal to about 2.8, greater than or equal to about 2.9, greater than or equal to about 3.0, greater than or equal to about 3.1, greater than or equal to about 3.2, greater than or equal to about 3.3, greater than or equal to about 3.4, greater than or equal to about 3.5, greater than or equal to about 4.0, greater than or equal to about 4.5, or greater than or equal to about 5.0. Providing a higher ratio of the EML to the BLH factor can be advantageous to provide light that provides desired biological impacts but does not have as much potential for photochemical induced injuries to the retina or skin.

In some aspects, the present disclosure provides methods of generating white light, the methods comprising providing first, second, third, and fourth LED strings, with each LED string comprising one or more LEDs having an associated luminophoric medium, wherein the first, second, third, and fourth LED strings together with their associated luminophoric mediums comprise red, blue, short-blue-pumped cyan, and long-blue-pumped cyan channels respectively, producing first, second, third, and fourth unsaturated light with color points within red, blue, short-blue-pumped cyan, and long-blue-pumped cyan regions on the 1931 CIE Chromaticity diagram, respectively, the methods further comprising providing a control circuit configured to adjust a fifth color point of a fifth unsaturated light that results from a combination of the first, second, third, and fourth unsaturated light, with the fifth color point falls within a 7-step MacAdam ellipse around any point on the black body locus having a correlated color temperature between 1800 K and 10000 K, generating two or more of the first, second, third, and fourth unsaturated light, and combining the two or more generated unsaturated lights to create the fifth unsaturated light. In some implementations the combining generates the fifth unsaturated light corresponding to a plurality of points along a predefined path with the light generated at each point having light with Rf greater than or equal to about 85, Rg greater than or equal to about 98 and less than or equal to about 104, or both. In some implementations the combining generates the fifth unsaturated light corresponding to a plurality of points along a predefined path with the light generated at each point having light with Ra greater than or equal to about 95 along points with correlated color temperature between about 1800 K and 10000 K, R9 greater than or equal to 92 along points with correlated color temperature between about 2000 K and about 10000 K, or both. In some implementations the combining generates the fifth unsaturated light corresponding to a plurality of points along a predefined path with the light generated at each point having light with R9 greater than or equal to 95 along greater than or equal to 90% of the points with correlated color temperature between about 2000 K and about 10000 K. In some implementations the combining generates the fifth unsaturated light corresponding to a plurality of points along a predefined path with the light generated at each point having one or more of EML greater than or equal to about 0.45 along points with correlated color temperature above about 2100 K, EML greater than or equal to about 0.55 along points with correlated color temperature above about 2400 K. EML greater than or equal to about 0.70 along points with correlated color temperature above about 3000 K EML greater than or equal to about 0.9 along points with correlated color temperature above about 4000 K, and EML greater than or equal to about 1.1 along points with correlated color temperature above about 6000 K. In some implementations the combining generates the fifth unsaturated light corresponding to a plurality of points along a predefined path with the light generated at each point having light with R13 greater than or equal to about 97, R15 greater than or equal to about 94, or both. The blue color region can comprise a region on the 1931 CIE Chromaticity Diagram comprising the combination of a region defined by a line connecting the ccx, ccy color coordinates of the infinity point of the Planckian locus (0.242, 0.24) and (0.12, 0.068), the Planckian locus from 4000 K and infinite CCT, the constant CCT line of 4000 K, the line of purples, and the spectral locus and a region defined by a line connecting (0.3806, 0.3768) and (0.0445, 0.3), the spectral locus between the monochromatic point of 490 nm and (0.12, 0.068), a line connecting the ccx, ccy color coordinates of the infinity point of the Planckian locus (0.242, 0.24) and (0.12, 0.068), and the Planckian locus from 4000 K and infinite CCT. The blue color region can comprise a region on the 1931 CIE Chromaticity Diagram defined by a line connecting the ccx, ccy color coordinates of the infinity point of the Planckian locus (0.242, 0.24) and (0.12, 0.068), the Planckian locus from 4000 K and infinite CCT, the constant CCT line of 4000 K, the line of purples, and the spectral locus. The blue color region can comprise a region on the 1931 CIE Chromaticity Diagram defined by a line connecting (0.3806, 0.3768) and (0.0445, 0.3), the spectral locus between the monochromatic point of nm and (0.12, 0.068), a line connecting the ccx, ccy color coordinates of the infinity point of the Planckian locus (0.242, 0.24) and (0.12, 0.068), and the Planckian locus from 4000 K and infinite CCT. The blue color region can comprise a region on the 1931 CIE Chromaticity Diagram defined by lines connecting (0.231, 0.218),(0.265, 0.260),(0.2405, 0.305), and (0.207, 0.256). The red color region can comprise a region on the 1931 CIE Chromaticity Diagram defined by the spectral locus between the constant CCT line of 1600 K and the line of purples, the line of purples, a line connecting the ccx, ccy color coordinates (0.61, 0.21) and (0.47, 0.28), and the constant CCT line of 1600 K. The red color region can comprise a region on the 1931 CIE Chromaticity Diagram defined by lines connecting the ccx, ccy coordinates (0.576, 0.393),(0.583, 0.400),(0.604, 0.387), and (0.597, 0.380). The short-blue-pumped cyan color region, long-blue-pumped cyan color region, or both can comprise a region on the 1931 CIE Chromaticity Diagram defined by a line connecting the ccx, ccy color coordinates (0.18, 0.55) and (0.27, 0.72), the constant CCT line of 9000 K, the Planckian locus between 9000 K and 1800 K, the constant CCT line of 1800 K, and the spectral locus. The short-blue-pumped cyan color region, long-blue-pumped cyan color region, or both can comprise a region on the 1931 CIE Chromaticity Diagram defined by a line connecting the ccx, ccy color coordinates (0.18, 0.55) and (0.27, 0.72), the constant CCT line of 9000 K, the Planckian locus between 900 K and 4600 K, the constant CCT line of 4600 K, and the spectral locus. The short-blue-pumped cyan color region, long-blue-pumped cyan color region, or both can comprise a region on the 1931 CIE Chromaticity Diagram defined by the constant CCT line of 4600 K, the spectral locus, the constant CCT line of 1800 K, and the Planckian locus between 4600 K and 1800 K. The short-blue-pumped cyan color region, long-blue-pumped cyan color region, or both can comprise a region on the 1931 CIE Chromaticity Diagram defined by the region bounded by lines connecting (0.360, 0.495), (0.371, 0.518),(0.388, 0.522), and (0.377, 0.499). The short-blue-pumped cyan color region, long-blue-pumped cyan color region, or both can comprise a region on the 1931 CIE Chromaticity Diagram defined by the region by lines connecting (0.497, 0.469),(0.508, 0.484),(0.524, 0.472), and (0.513, 0.459). In some implementations the spectral power distributions for one or more of the red channel, blue channel, short-blue-pumped cyan channel, and long-blue-pumped cyan channel can fall within the minimum and maximum ranges shown in Tables 1 and 2. In some implementations the red channel can have a spectral power distribution with spectral power in one or more of the wavelength ranges other than the reference wavelength range increased or decreased within 30% greater or less, within 20% greater or less, within 10% greater or less, or within 5% greater or less than the values of a red channel shown in Tables 3 and 4. In some implementations the blue channel can have a spectral power distribution with spectral power in one or more of the wavelength ranges other than the reference wavelength range increased or decreased within 30% greater or less, within 20% greater or less, within 10% greater or less, or within 5% greater or less than the values of a blue channel shown in Tables 3 and 4. In some implementations the short-blue-pumped cyan channel can have a spectral power distribution with spectral power in one or more of the wavelength ranges other than the reference wavelength range increased or decreased within 30% greater or less, within 20% greater or less, within 10% greater or less, or within 5% greater or less than the values of a short-blue-pumped cyan channel shown in Table 3. In some implementations the long-blue-pumped cyan channel can have a spectral power distribution with spectral power in one or more of the wavelength ranges other than the reference wavelength range increased or decreased within 30% greater or less, within 20% greater or less, within 10% greater or less, or within 5% greater or less than the values of a long-blue-pumped cyan channel shown in Table 3. In some implementations one or more of the LEDs in the fourth LED string can have a peak wavelength of between about 480 nm and about 505 nm. In some implementations one or more of the LEDs in the first, second, and third LED strings can have a peak wavelength of between about 430 nm and about 460 nm. In some implementations, the combining generates the fifth unsaturated light corresponding to a plurality of points along a predefined path with the light generated at each point having light with BLH factor less than 0.25 $\mu W/cm^2/lux$. In some implementations, the combining generates the fifth unsaturated light corresponding to a plurality of points along a predefined path with the light generated at each point having light with one or more of BLH factor less than or equal to about 0.05 along points with correlated color temperature below about 2100 K, BLH factor less than or equal to about 0.065 along points with correlated color temperature below about 2400 K, BLH factor less than or equal to about 0.12 along points with correlated color temperature below about 3000 K. BLH factor less than or equal to about 0.25 along points with correlated color temperature below about 4000 K, and BLH factor less than or equal to about 0.35 along points with correlated color temperature below about 6500 K. In some implementations, the combining generates the fifth unsaturated light corresponding to a plurality of points along a predefined path with the light generated at each point having light with the ratio of the EML to the BLH factor being greater than or equal to about 2.5, greater than or equal to about 2.6, greater than or equal to about 2.7, greater than or equal to about 2.8, greater than or equal to about 2.9, greater than or equal to about 3.0, greater than or equal to about 3.1, greater than or equal to about 3.2, greater than or equal to about 3.3, greater than or equal to about 3.4, greater than or equal to about 3.5, greater than or equal to about 4.0, greater than or equal to about 4.5, or greater than or equal to about 5.0.

In some aspects, the present disclosure provides methods of generating white light with the semiconductor light emitting devices described herein. In some implementations, different operating modes can be used to generate the white light. In certain implementations, substantially the same white light points, with similar CCT values, can be generated in different operating modes that each utilize different combinations of the blue, red, short-blue-pumped cyan, long-blue-pumped cyan, yellow, and violet channels of the disclosure. In some implementations a first operating mode can use the blue, red, and short-blue-pumped cyan channels (also referred to herein as a "High-CRI mode"); a second operating mode can use the blue, red, and long-blue-pumped cyan channels of a device (also referred to herein as a "High-EML mode"); a third operating mode can use the blue, red, yellow, and violet channels (also referred to herein as a "Low-EML mode"); and a fourth operating mode can use the red, yellow, and violet channels (also referred to herein as a "Very-Low-EML mode"). In certain implementations, switching between two of the first, second, third, and fourth operating modes can increase the EML by about 5%, about 10%, about 15%, about 20%, about 25%, about 30%, about 35%, about 40%, about 45%, about 50%, about 55%, about 60%, about 65%, about 70%, about 75%, about 80%, or about 85% while providing a Ra value within about 1, about 2, about 3, about 4, about 5, about 6, about 7, about 8, about 9, or about 10 at substantially the same CCT value. In some implementations, the light output in both of the operating modes being switched between can have Ra greater than or equal to about 80. In some implementations, the light generated with both of the operating modes being switched between can be within about 1.0 standard deviations of color matching (SDCM). In some implementations, the light generated with both of the operating modes being switched between can be within about 0.5 standard deviations of color matching (SDCM). The methods of providing light under two or more operating modes can be used to provide white light that can be switched in order to provide desired biological effects to humans exposed to the light, such as by providing increased alertness and attention to workers by providing light with increased EML. Alternatively, light can be switched to a lower-EML light in order to avoid biological effects that could disrupt sleep cycles. In certain implementations, the semiconductor light emitting devices can transition among two or more of the low-EML, the very-low-EML, high-EML, and high-CRI operating modes while the devices are providing white light along a path of color points near the Planckian locus. In further implementations, the semiconductor light emitting devices can transition among two or more of the low-EML, the very-low-EML, high-EML, and high-CRI operating modes while the devices are changing the CCT of the white light along the path of color points near the Planckian locus.

In any of the above operational modes additional red channel modes which select LRNE emission may be added or used in place of. An operational mode wherein in addition to, or in lieu of a red channel a LRNE first channel and/or LRNE second channel may be included. The LRNE first channel is disclosed having emission wavelengths of Long Red (>625 to <700 nms with peak wavelengths >640-670 nms). The LRNE second channel of Near-Infrared (typical ranges from >700 and <1400 nms (with typical peak wavelengths: nm, 940 nm, 1064 nm)) as described herein.

EXAMPLES

General Simulation Method.

Devices having four LED strings with particular color points were simulated. For each device, LED strings and recipient luminophoric mediums with particular emissions were selected, and then white light rendering capabilities were calculated for a select number of representative points on or near the Planckian locus between about 1800 K and 10000 K. Ra, R9, R13, R15, LER, Rf, Rg, CLA, CS, EML, BLH factor, CAF, CER, COI, and circadian performance values were calculated at each representative point.

The calculations were performed with Scilab (Scilab Enterprises, Versailles, France), LightTools (Synopsis, Inc., Mountain View, CA), and custom software created using Python (Python Software Foundation, Beaverton, OR). Each LED string was simulated with an LED emission spectrum and excitation and emission spectra of luminophoric medium(s). For luminophoric mediums comprising phosphors, the simulations also included the absorption spectrum and particle size of phosphor particles. The LED strings generating combined emissions within blue, short-blue-pumped cyan, and red color regions were prepared using spectra of a LUXEON Z Color Line royal blue LEDs (product code LXZ1-PR01) of color bin codes 3, 4, 5, or 6, one or more LUXEON Z Color Line blue LEDs (LXZ1-PB01) of color bin code 1 or 2, or one or more LUXEON royal blue LEDs (product code LXML-PR01 and LXML-PR02) of color bins 3, 4, 5, or 6 (Lumileds Holding B.V., Amsterdam, Netherlands). The LED strings generating combined emissions with color points within the long-blue-pumped cyan regions were prepared using spectra of LUXEON Rebel Blue LEDs (LXML-PB01, LXML-PB02) of color bins 1, 2, 3, 4, or 5, which have peak wavelengths ranging from 460 nm to 485 nm, or LUXEON Rebel Cyan LEDs (LXML-PE01) of color bins 1, 2, 3, 4, or 5, which have peak wavelengths raving from 460 nm to 485 nm. Similar LEDs from other manufacturers such as OSRAM GmbH and Cree, Inc. could also be used. The LED strings generating combined emissions with color points within the yellow and violet regions were simulated using spectra of LEDs having peak wavelengths of between about 380 nm and about 420 nm, such as one or more 410 nm peak wavelength violet LEDs, one or more LUXEON Z UV LEDs (product codes LHUV-0380-, LHUV-0385-, LHUV-0390-, LHUV-0395-, LHUV-0400-, LHUV-0405-, LHUV-0410-, LHUV-0415-, LHUV-0420-,) (Lumileds Holding B.V., Amsterdam. Netherlands), one or more LUXEON UV FC LEDs (product codes LxF3-U410) (Lumileds Holding B.V., Amsterdam, Netherlands), one or more LUXEON UV U LEDs (product code LHUV-0415-) (Lumileds Holding B.V., Amsterdam, Netherlands), for example.

The emission, excitation and absorption curves are available from commercially available phosphor manufacturers such as Mitsubishi Chemical Holdings Corporation (Tokyo, Japan), Intematix Corporation (Fremont, CA), EMD Performance Materials of Merck KGaA (Darmstadt, Germany), and PhosphorTech Corporation (Kennesaw, GA). The luminophoric mediums used in the LED strings were combinations of one or more of Compositions A. B. and D and one or more of Compositions C, E, and F as described more fully elsewhere herein. Those of skill in the art appreciate that various combinations of LEDs and luminescent blends can be combined to generate combined emissions with desired color points on the 1931 CIE chromaticity diagram and the desired spectral power distributions. In any of the below examples the red channel may be deployed as one or more LRNE channels only or a red channel with at least one LRNE channel. The LRNE can be used in a device or system in conjunction with blue light providing CSE or any blue channel providing [I'm leaving "blue channel" vague to allow for a blast of blue not quite at CSE levels but a channel with lots of blue] or the LRNE may be used independently of CSE or lots of blue.

Example 1

A semiconductor light emitting device was simulated having four LED strings. A first LED string is driven by a blue LED having peak emission wavelength of approximately 450 nm to approximately 455 nm, utilizes a recipient luminophoric medium, and generates a combined emission of a blue channel having the color point and characteristics of Blue Channel 1 as described above and shown in Tables 3-5. A second LED string is driven by a blue LED having peak emission wavelength of approximately 450 nm to approximately 455 nm, utilizes a recipient luminophoric medium, and generates a combined emission of a red channel having the color point and characteristics of Red Channel 1 as described above and shown in Tables 3-5 and 7-9. A third LED string is driven by a blue LED having peak emission wavelength of approximately 450 nm to approximately 455 nm, utilizes a recipient luminophoric medium, and generates a combined emission of a short-blue-pumped cyan color channel having the color point and characteristics of Short-Blue-Pumped Cyan Channel 1 as described above and shown in Tables 3-5. A fourth LED string is driven by a cyan LED having peak emission wavelength of approximately 505 nm, utilizes a recipient luminophoric medium, and generates a combined emission of a long-blue-pumped cyan channel having the color point and characteristics of Long-Blue-Pumped Cyan Channel 1 as described above and shown in Tables 3-5.

Tables 16-19 shows light-rendering characteristics of the device for a representative selection of white light color points near the Planckian locus. Table 18 shows data for white light color points generated using only the first, second, and third LED strings in high-CRI mode. Table 16 shows data for white light color points generated using all four LED strings in highest-CRI mode. Table 17 shows data for white light color points generated using only the first, second, and fourth LED strings in high-EML mode. Table 19 show performance comparison between white light color points generated at similar approximate CCT values under high-EML mode and high-CRI mode.

Example 2

Further simulations were performed to optimize the outputs of the semiconductor light emitting device of Example 1. Signal strength ratios for the channels were calculated to generate 100 lumen total flux output white light at each CCT point. The relative lumen outputs for each of the channels is shown, along with the light-rendering characteristics, in Tables 20-22.

Example 3

A semiconductor light emitting device was simulated having four LED strings. A first LED string is driven by a blue LED having peak emission wavelength of approximately 450 nm to approximately 455 nm, utilizes a recipient luminophoric medium, and generates a combined emission of a blue channel having the color point and characteristics of Blue Channel 1 as described above and shown in Tables 3-5. A second LED string is driven by a blue LED having peak emission wavelength of approximately 450 nm to approximately 455 nm, utilizes a recipient luminophoric medium, and generates a combined emission of a red channel having the color point and characteristics of Red Channel 1 as described above and shown in Tables 3-5 and 7-9. A fifth LED string is driven by a violet LED having peak emission wavelength of about 380 nm, utilizes a recipient luminophoric medium, and generates a combined emission of a yellow color channel having the color point and characteristics of Yellow Channel 1 as described above and shown in Tables 5 and 13-15. A sixth LED string is driven by a violet LED having peak emission wavelength of about 380 nm, utilizes a recipient luminophoric medium, and generates a combined emission of a violet channel having the color point and characteristics of Violet Channel 1 as described above and shown in Tables 5 and 10-12.

Tables 23-24 shows light-rendering characteristics of the device for a representative selection of white light color points near the Planckian locus. Table 23 shows data for white light color points generated using the first, second, fifth, and sixth LED strings, i.e. the blue, red, yellow, and violet channels, in low-EML mode. Table 24 shows data for white light color points generated using the second, fifth, and sixth LED strings. i.e. the red, yellow, and violet channels, in very-low-EML mode.

Example 4

A semiconductor light emitting device was simulated having four LED strings. A first LED string is driven by a blue LED having peak emission wavelength of approximately 450 nm to approximately 455 nm, utilizes a recipient luminophoric medium, and generates a combined emission of a blue channel having the color point and characteristics of Blue Channel 1 as described above and shown in Tables 3-5. A second LED string is driven by a blue LED having peak emission wavelength of approximately 450 nm to approximately 455 nm, utilizes a recipient luminophoric medium, and generates a combined emission of a red channel having the color point and characteristics of Red Channel 1 as described above and shown in Tables 3-5 and 7-9. A fifth LED string is driven by a violet LED having peak emission wavelength of about 400 nm, utilizes a recipient luminophoric medium, and generates a combined emission of a yellow color channel having the color point and characteristics of Yellow Channel 2 as described above and shown in Tables 5 and 13-15. A sixth LED string is driven by a violet LED having peak emission wavelength of about 400 nm, utilizes a recipient luminophoric medium, and generates a combined emission of a violet channel having the color point and characteristics of Violet Channel 2 as described above and shown in Tables 5 and 10-12.

Tables 25-26 shows light-rendering characteristics of the device for a representative selection of white light color points near the Planckian locus. Table 25 shows data for white light color points generated using the first, second, fifth, and sixth LED strings, i.e. the blue, red, yellow, and violet channels, in low-EML mode. Table 26 shows data for white light color points generated using the second, fifth, and sixth LED strings, i.e. the red, yellow, and violet channels, in very-low-EML mode.

Example 5

A semiconductor light emitting device was simulated having four LED strings. A first LED string is driven by a blue LED having peak emission wavelength of approximately 450 nm to approximately 455 nm, utilizes a recipient luminophoric medium, and generates a combined emission of a blue channel having the color point and characteristics of Blue Channel 1 as described above and shown in Tables 3-5. A second LED string is driven by a blue LED having peak emission wavelength of approximately 450 nm to approximately 455 nm, utilizes a recipient luminophoric medium, and generates a combined emission of a red channel having the color point and characteristics of Red Channel 1 as described above and shown in Tables 3-5 and 7-9. A fifth LED string is driven by a violet LED having peak emission wavelength of about 410 nm, utilizes a recipient luminophoric medium, and generates a combined emission of a yellow color channel having the color point and characteristics of Yellow Channel 3 as described above and shown in Tables 5 and 13-15. A sixth LED string is driven by a violet LED having peak emission wavelength of about 410 nm, utilizes a recipient luminophoric medium, and generates a combined emission of a violet channel having the color point and characteristics of Violet Channel 3 as described above and shown in Tables 5 and 10-12.

Tables 27-28 shows light-rendering characteristics of the device for a representative selection of white light color points near the Planckian locus. Table 27 shows data for white light color points generated using the first, second, fifth, and sixth LED strings, i.e. the blue, red, yellow, and violet channels, in low-EML mode. Table 28 shows data for white light color points generated using the second, fifth, and sixth LED strings, i.e. the red, yellow, and violet channels, in very-low-EML mode.

Example 6

A semiconductor light emitting device was simulated having four LED strings. A first LED string is driven by a blue LED having peak emission wavelength of approximately 450 nm to approximately 455 nm, utilizes a recipient luminophoric medium, and generates a combined emission of a blue channel having the color point and characteristics of Blue Channel 1 as described above and shown in Tables 3-5. A second LED string is driven by a blue LED having peak emission wavelength of approximately 450 nm to approximately 455 nm, utilizes a recipient luminophoric medium, and generates a combined emission of a red channel having the color point and characteristics of Red Channel 1 as described above and shown in Tables 3-5 and 7-9. A fifth LED string is driven by a violet LED having peak emission wavelength of about 420 nm, utilizes a recipient luminophoric medium, and generates a combined emission of a yellow color channel having the color point and characteristics of Yellow Channel 4 as described above and shown in Tables 5 and 13-15. A sixth LED string is driven by a violet LED having peak emission wavelength of about 420 nm, utilizes a recipient luminophoric medium, and generates a combined emission of a violet channel having the color point and characteristics of Violet Channel 4 as described above and shown in Tables 5 and 10-12.

Table 29 shows light-rendering characteristics of the device for a representative selection of white light color points near the Planckian locus. Table 29 shows data for white light color points generated using the second, fifth, and sixth LED strings. i.e. the red, yellow, and violet channels, in very-low-EML mode.

Example 7

A semiconductor device was simulated having six lighting channels. The six lighting channels are a combination of the lighting channels of Example 1 and Example 3: Blue Channel 1, Red Channel 1, Short-Blue-Pumped Cyan Channel 1, Long-Blue-Pumped Cyan Channel 1, Yellow Chanel 1, and Violet Channel 1. As shown above with reference to Examples 1 and 3, the device can be operated in various operating modes with different combinations of lighting channels. Tables 30-31 show EML and CS values at various nominal CCT values under different operating modes and the % changes that can be achieved by switching between operating modes at the same nominal CCT.

Example 8

A semiconductor device was simulated having six lighting channels. The six lighting channels are a combination of the lighting channels of Example 1 and Example 4: Blue Channel 1, Red Channel 1, Short-Blue-Pumped Cyan Channel 1, Long-Blue-Pumped Cyan Channel 1, Yellow Chanel 2, and Violet Channel 2. As shown above with reference to Examples 1 and 4, the device can be operated in various operating modes with different combinations of lighting channels. Tables 32-33 show EML and CS values at various nominal CCT values under different operating modes and the % changes that can be achieved by switching between operating modes at the same nominal CCT.

Example 9

A semiconductor device was simulated having six lighting channels. The six lighting channels are a combination of the lighting channels of Example 1 and Example 5: Blue Channel 1, Red Channel 1, Short-Blue-Pumped Cyan Channel 1, Long-Blue-Pumped Cyan Channel 1, Yellow Chanel 3, and Violet Channel 3. As shown above with reference to Examples 1 and 5, the device can be operated in various operating modes with different combinations of lighting channels. Tables 34-35 show EML and CS values at various nominal CCT values under different operating modes and the % changes that can be achieved by switching between operating modes at the same nominal CCT.

Example 10

A semiconductor device was simulated having six lighting channels. The six lighting channels are a combination of the lighting channels of Example 1 and Example 6: Blue Channel 1, Red Channel 1, Short-Blue-Pumped Cyan Channel 1, Long-Blue-Pumped Cyan Channel 1, Yellow Chanel 4, and Violet Channel 4. As shown above with reference to Examples 1 and 6, the device can be operated in various operating modes with different combinations of lighting channels. Tables 36-37 show EML and CS values at various nominal CCT values under different operating modes and the % changes that can be achieved by switching between operating modes at the same nominal CCT.

Example 11

In some implementations, the semiconductor light emitting devices of the present disclosure can comprise three lighting channels as described elsewhere herein. In certain implementations, the three lighting channels comprise a red lighting channel, a yellow lighting channel, and a violet lighting channel. The semiconductor light emitting devices can be operated in a very-low-EML operating mode in which the red lighting channel, the yellow lighting channel, and the violet lighting channel are used. The semiconductor light emitting devices can further comprise a control system configured to control the relative intensities of light generated in the red lighting channel, the yellow lighting channel, and the violet lighting channel in order to generate white light at a plurality of points near the Planckian locus between about 4000 K and about 1400 K CCT.

Example 12

In some implementations, the semiconductor light emitting devices of the present disclosure can comprise four lighting channels as described elsewhere herein. In certain implementations, the four lighting channels comprise a red lighting channel, a yellow lighting channel, a violet lighting channel, and a blue lighting channel. In some implementations, the semiconductor light emitting devices can be operated in a very-low-EML operating mode in which the red lighting channel, the yellow lighting channel, and the violet lighting channel are used. In further implementations, the semiconductor light emitting devices can be operated in a low-EML operating mode in which the blue lighting channel, the red lighting channel, the yellow lighting channel, and the violet lighting channel are used. In certain implementations, the semiconductor light emitting devices can transition between the low-EML and the very-low-EML operating modes in one or both directions while the devices are providing white light along a path of color points near the Planckian locus. In further implementations, the semiconductor light emitting devices can transition between the low-EML and very-low-EML operating modes in one or both directions while the devices are changing the CCT of the white light along the path of color points near the Planckian locus. In some implementations the low-EML operating mode can be used in generating white light near the Planckian locus with CCT values between about 10000 K and about 1800 K. In further implementations the very-low-EML operating mode can be used in generating white light near the Planckian locus with CCT values between about 4000 K and about 1400 K.

Example 13

In some implementations, the semiconductor light emitting devices of the present disclosure can comprise five lighting channels as described elsewhere herein. In certain implementations, the five lighting channels comprise a red lighting channel, a yellow lighting channel, a violet lighting channel, a blue lighting channel, and a long-blue-pumped cyan lighting channel. In some implementations, the semiconductor light emitting devices can be operated in a very-low-EML operating mode in which the red lighting channel, the yellow lighting channel, and the violet lighting channel are used. In further implementations, the semiconductor light emitting devices can be operated in a low-EML operating mode in which the blue lighting channel, the red lighting channel, the yellow lighting channel, and the violet lighting channel are used. In yet further implementations, the semiconductor light emitting devices can be operated in a high-EML operating mode in which the blue lighting channel, the red lighting channel, and the long-blue-pumped cyan lighting channel are used. In certain implementations, the semiconductor light emitting devices can transition among two or more of the low-EML, the very-low-EML, and high-EML operating modes while the devices are providing white light along a path of color points near the Planckian locus. In further implementations, the semiconductor light emitting devices can transition among two or more of the low-EML, the very-low-EML, and high-EML operating modes while the devices are changing the CCT of the white light along the path of color points near the Planckian locus. In some implementations the low-EML operating mode can be used in generating white light near the Planckian locus with CCT values between about 10000 K and about 1800 K. In further implementations the very-low-EML operating mode can be used in generating white light near the Planckian locus with CCT values between about 4000 K and about 1400 K. In yet further implementations, the high-EML operating mode can be used in generating white light near the Planckian locus with CCT values between about 10000 K and about 1800 K.

Example 14

Figure 22:
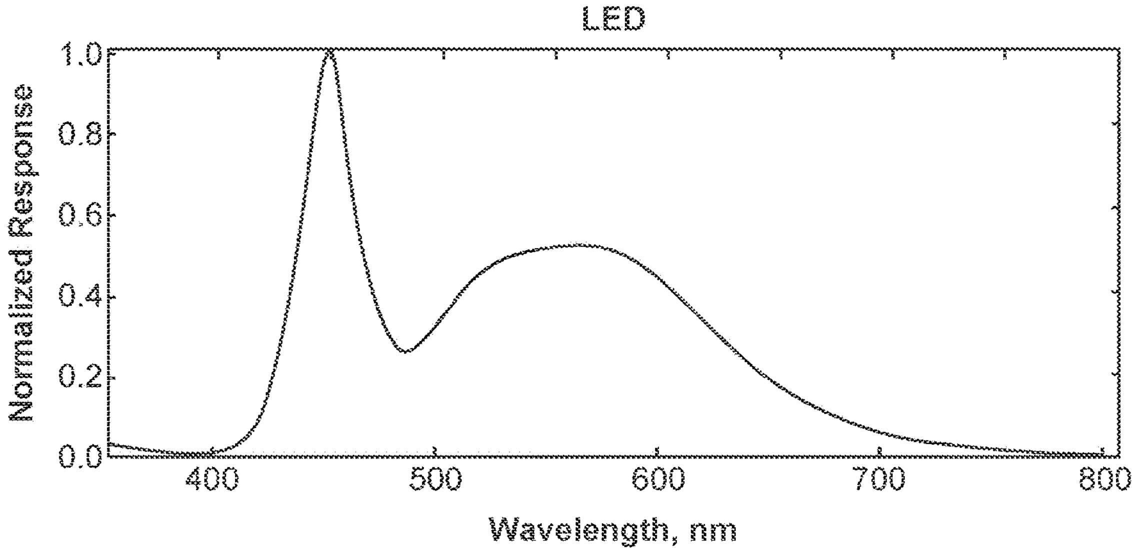
FIG. 22 illustrates some aspects of light showing the spectral power distribution.
Figure 23:
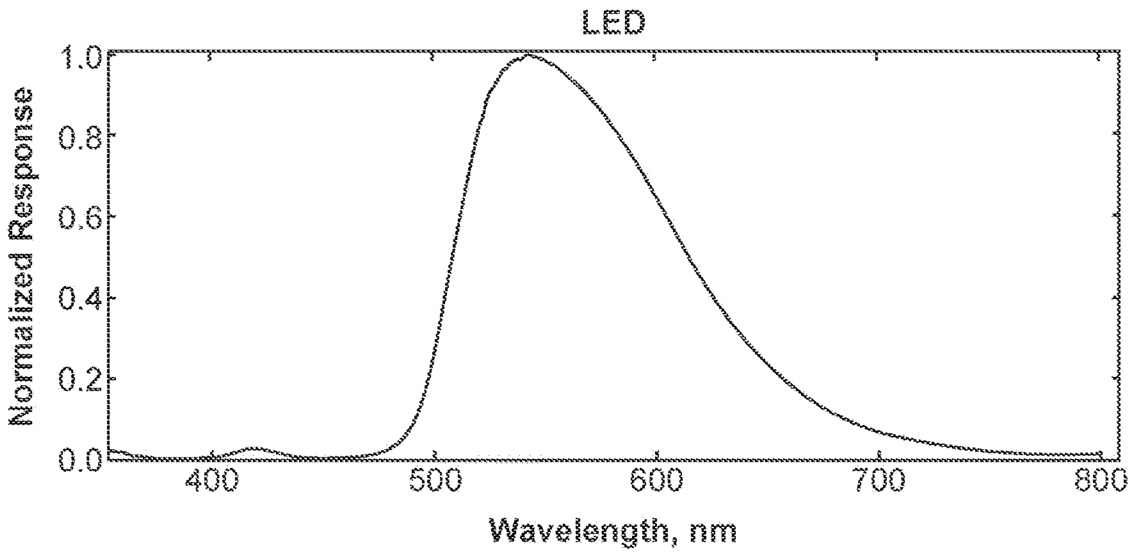
FIG. 23 illustrates some aspects of light showing the spectral power distribution.
Figure 24:
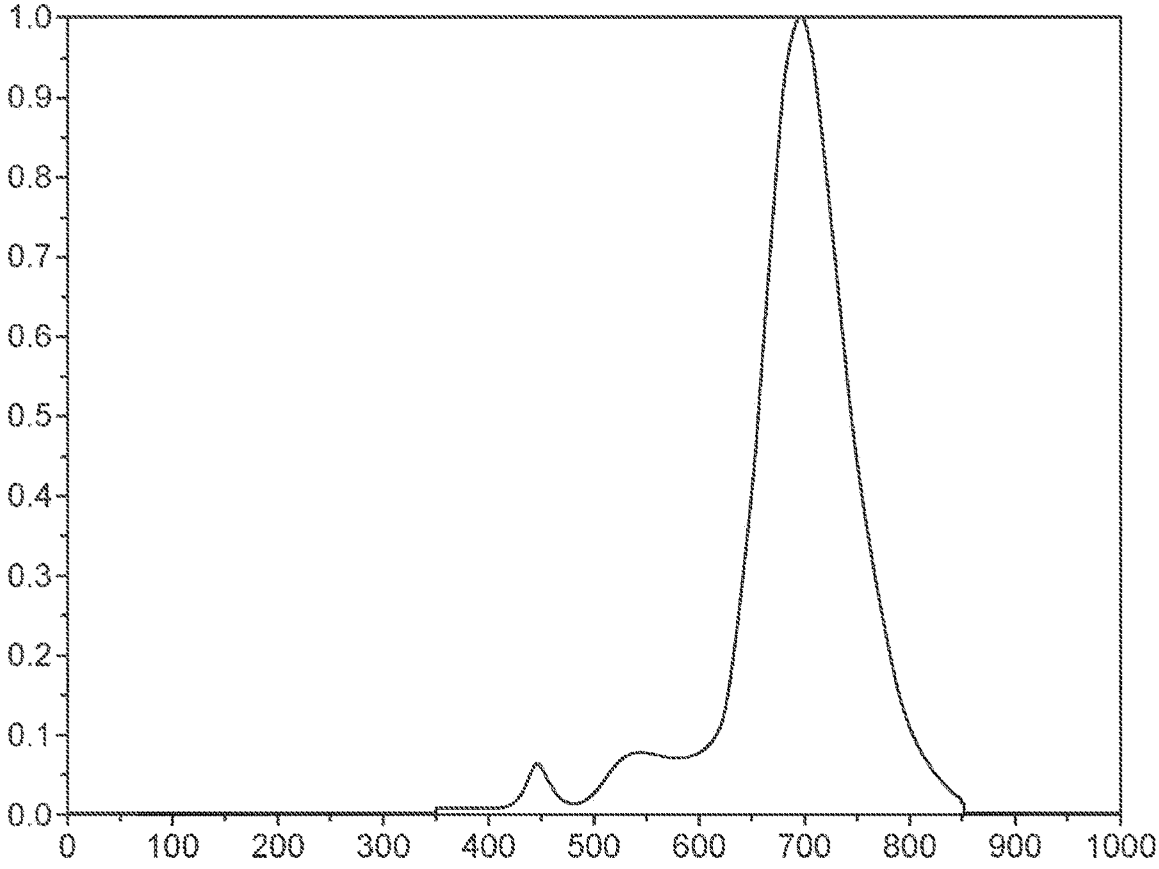
FIG. 24 illustrates some aspects of light showing the spectral power distribution for a LRNE channel.

A semiconductor light emitting device was simulated having three LED strings. A first LED string is a commercially available 6500 K white LED having a spectral power distribution as shown in FIG. 22. A second LED string is driven by a blue LED having peak emission wavelength of approximately 450 nm to approximately 455 nm, utilizes a recipient luminophoric medium, and generates a combined emission of a long-red channel having the characteristics of Long-Red Channel A as shown in Tables 7-9. The spectral power distribution for Long-Red Channel A is shown in FIG. 24. Three phosphor materials can be provided in the luminophoric medium for the second LED string, and in some implementations the phosphor materials can include a YAG phosphor, a red phosphor with emission peak at about 630 nm, and a red phosphor with an emission peak at about 700 nm. A third LED string is a commercially available "lime" LED having a spectral power distribution as shown in FIG. 23. Table 47 shows light-rendering characteristics of the device for a representative selection of white light color points near the Planckian locus.

Example 15

Figure 25:
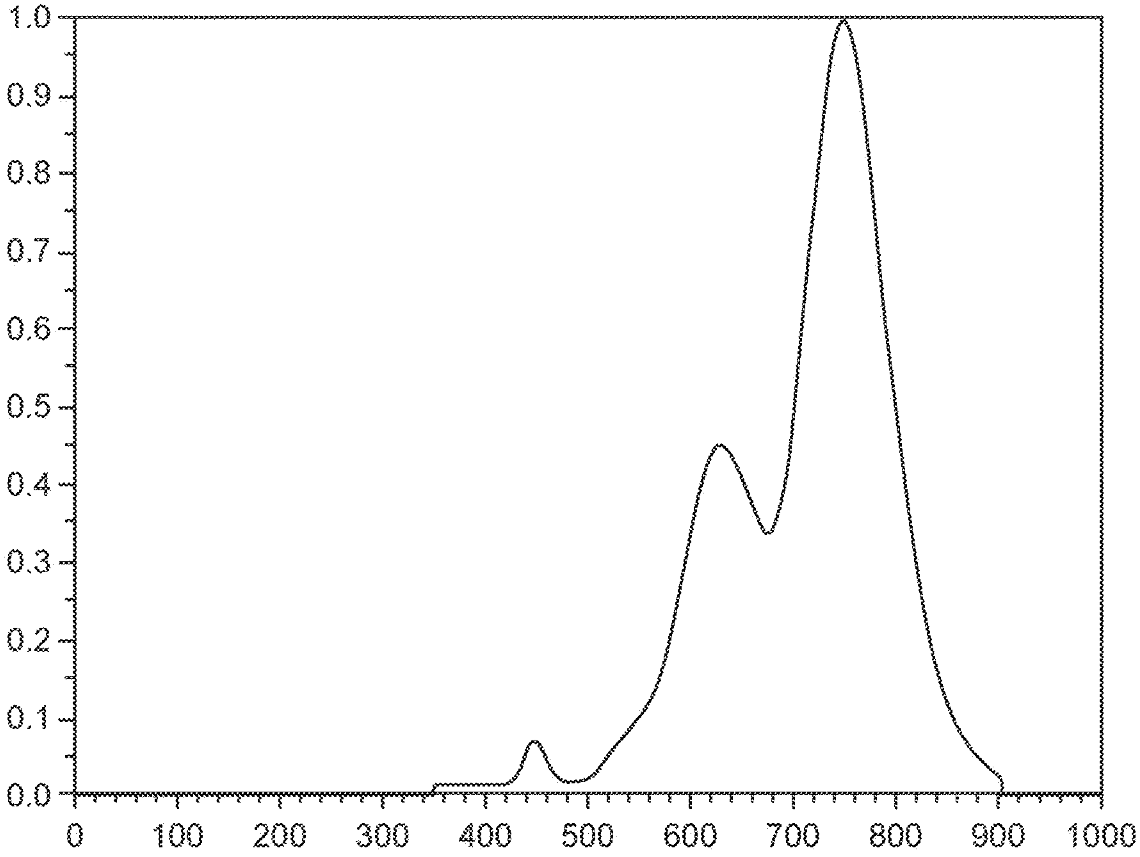
FIG. 25 illustrates some aspects of light showing the spectral power distribution for a LRNE channel.

A semiconductor light emitting device was simulated having three LED strings. A first LED string is a commercially available 6500 K white LED having a spectral power distribution as shown in FIG. 22. A second LED string is driven by a blue LED having peak emission wavelength of approximately 450 nm to approximately 455 nm, utilizes a recipient luminophoric medium, and generates a combined emission of a long-red channel having the characteristics of Long-Red Channel B as shown in Tables 7-9. The spectral power distribution for Long-Red Channel B is shown in FIG. 25. Three phosphor materials can be provided in the luminophoric medium for the second LED string, and in some implementations the phosphor materials can include a YAG phosphor, a red phosphor with emission peak at about 630 nm, and a red phosphor with an emission peak at about 750 nm. A third LED string is a commercially available "lime" LED having a spectral power distribution as shown in FIG. 23.

Table 48 shows light-rendering characteristics of the device for a representative selection of white light color points near the Planckian locus.

Control Systems

Figure 26:
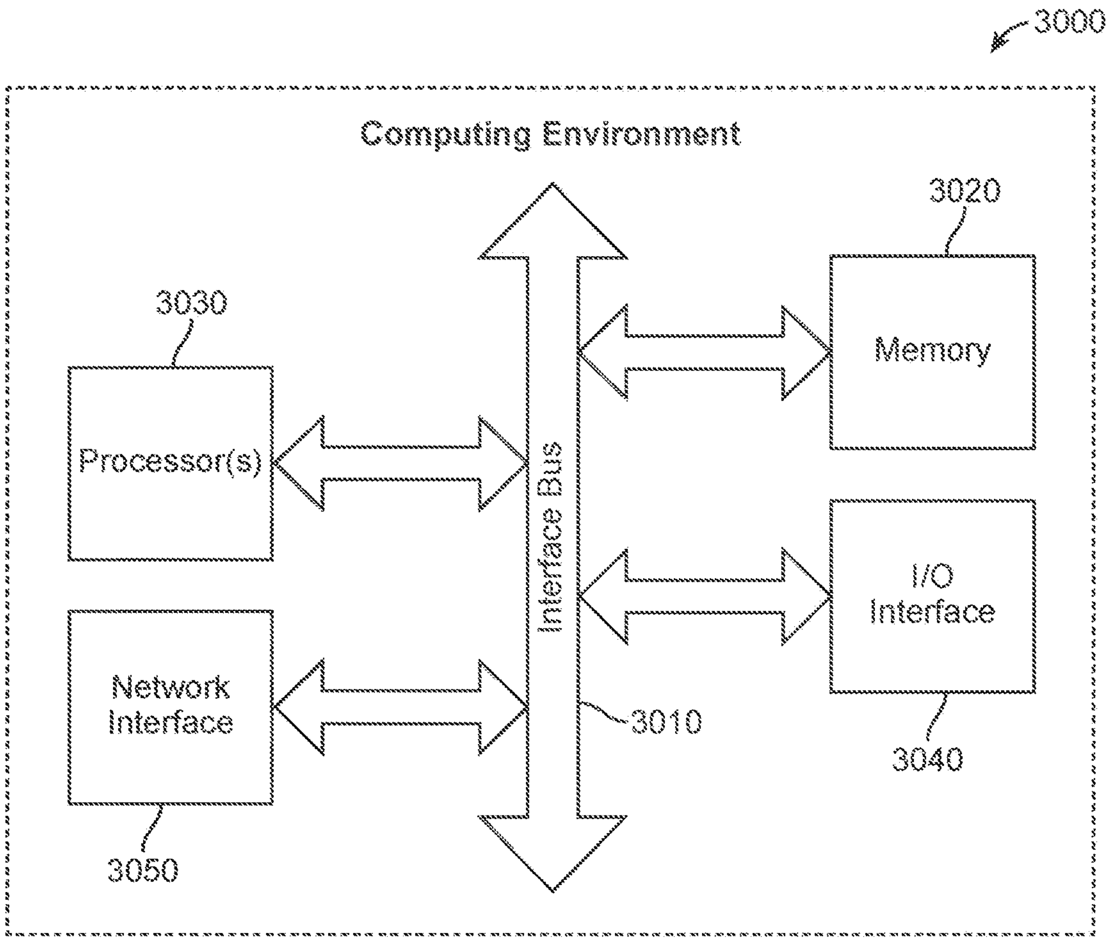
FIG. 26 depicts aspects of control of the bioactive illumination.
Figure 27:
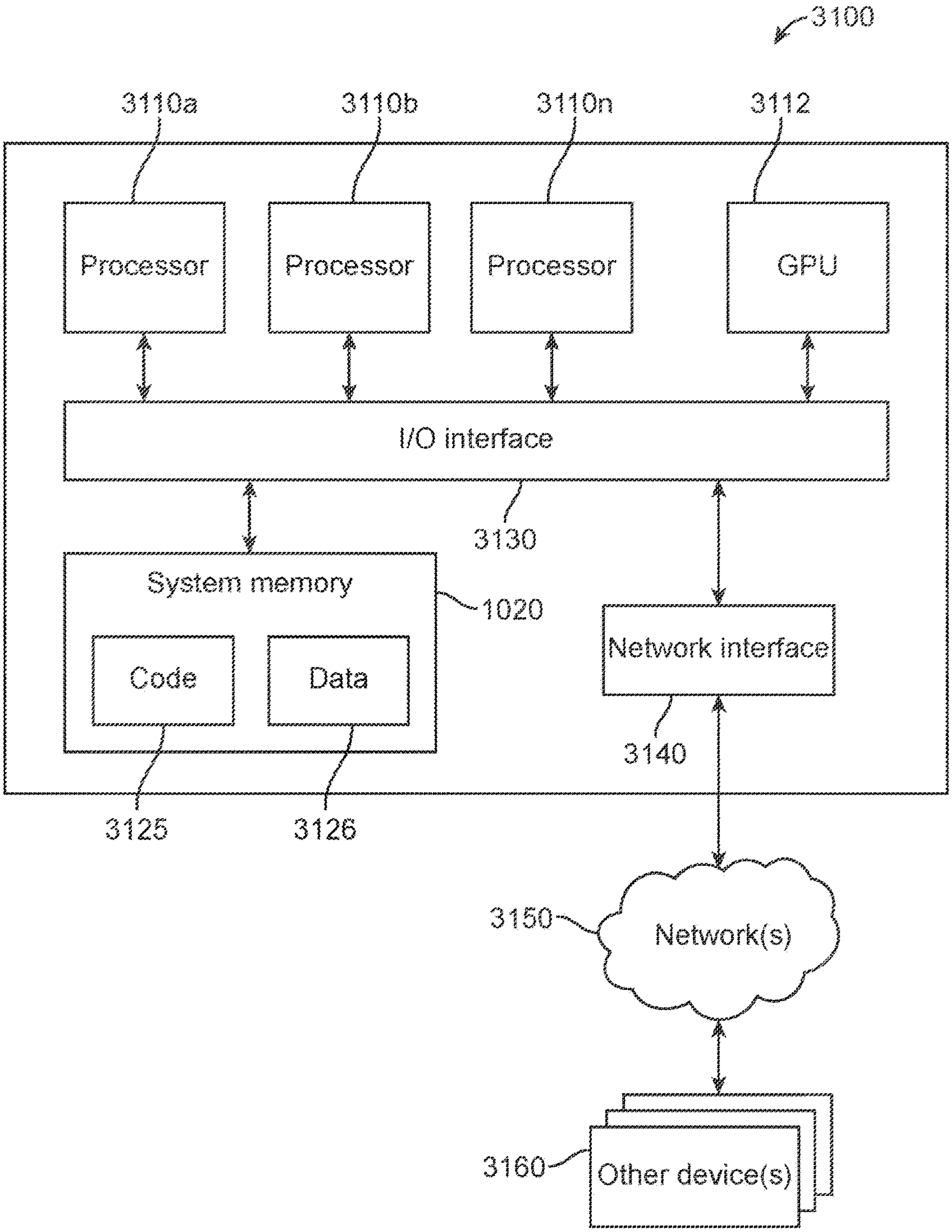
FIG. 27 is a block diagram of computing systems and methods of control of bioactive illumination.
Figure 28:
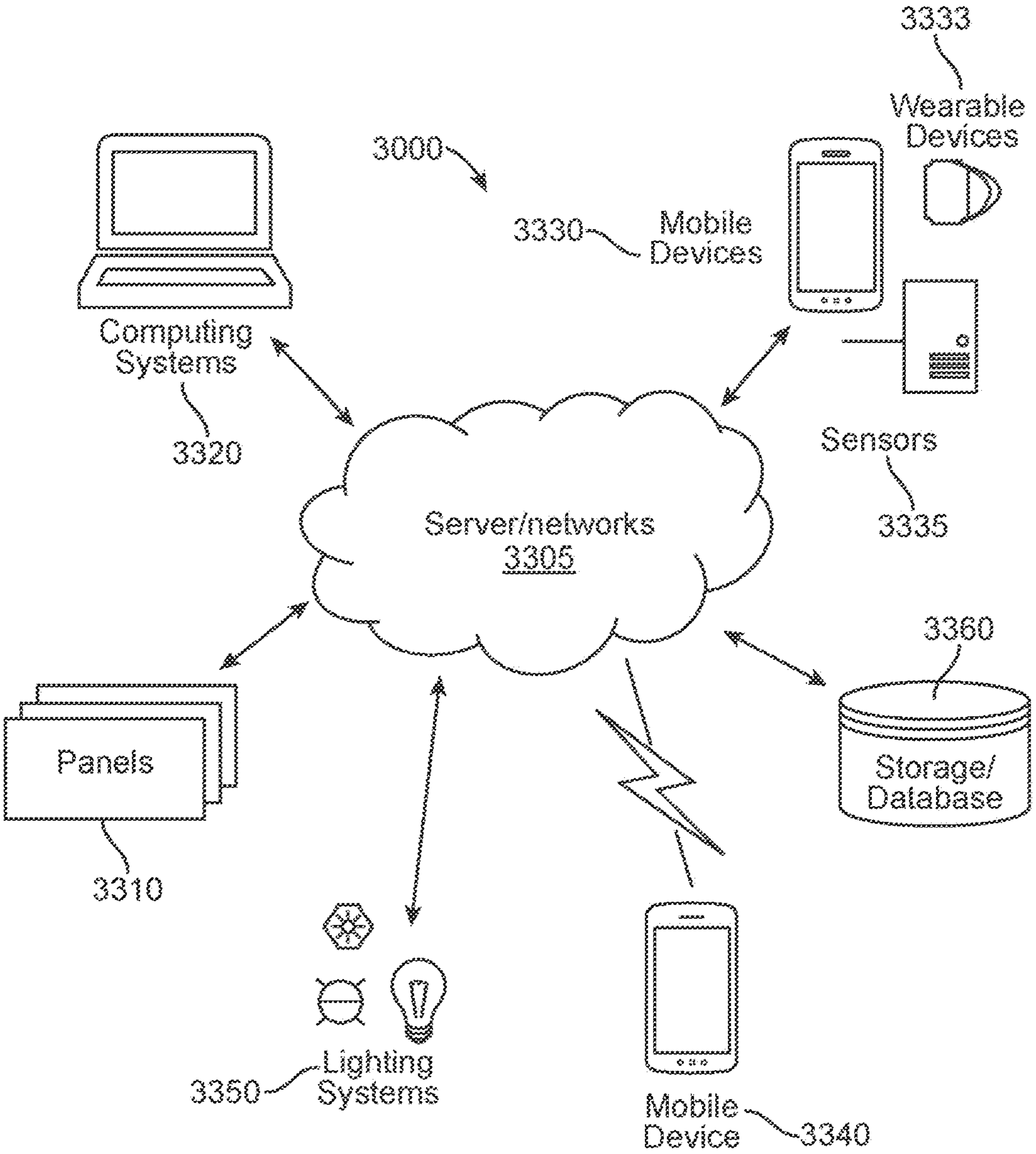
FIG. 28 is an overview of a bioactive illumination control systems and methods.

With respect to FIGS. 26-28, external systems can include, but are not limited to one or more computing environments, networks, local devices, remote devices, mobile devices, and wearable technology. In addition, each of those systems may provide the external input utilizable with control systems and embodiments discussed herein. For example, external inputs may include, but are not limited to audible, tactile, sensory, and user information through one or more sensors and other means, depending on the external system and its capabilities. As used herein, external systems and external information may also comprise the same types systems and information discussed below and in various embodiments herein.

In some embodiments, inputs may also include inputs from sensors associated with wearable devices 3330, such as enabling adjustment of lighting control parameters (autonomously or with remote or local control features) based on physiological factors, such as ones indicating health conditions, emotional states, moods, or the like. Inputs from wearable devices may be used in the operational feedback system, such as to measure reactions to lighting conditions (such as to enable automated adjustment of a lighting installation), as well as to measure impacts on mood, health conditions, energy, wellness factors, and the like.

In some embodiments, the platform may be configured to change settings or parameters for a lighting installation (including but not limited to panel systems of the present disclosure, such as by using a custom tuning system) based on a variety of real time data, with a view to having the lighting installation, including panel systems included therein, best suit its environment in a dynamic way. In embodiments, data may be obtained that serves as an indicator of the emotional state or the stress level of an environment, and the lighting installation may respond accordingly to that state or stress level. In embodiments, data about the environment may be collected by a wearable device 3333, such as a smartwatch, armband, or the like: for example, data may be collected on acceleration, location, ambient light characteristics, and heart rate, among other possibilities. In embodiments, the data may be provided to the platform for analysis, including using machine learning, such as to observe physiological indicators of stress, mood, or the like under given lighting conditions. The analysis may enable model-based controls (such as where a given mood or state of the users in a room are linked to a set of control parameters appropriate for that state). In embodiments, machine learning may be used: for example, over time, by variation of parameters for lighting objects and fixtures (such as color, color temperature, illumination patterns, lighting distributions, and many others), a machine learning system may, using feedback on outcomes based at least in part on physiological data and other data collected by a wearable device, select and/or promotion lighting installation parameters that improve various measures of stress, mood, satisfaction, or the like. This may occur in real time under control of a machine learning system based on the current conditions of users or the environment. In embodiments, data collected at least in part by a physiological monitor or wearable device may be used as an input to processing logic on a lighting object that changes lighting levels or other parameters to accommodate the 'emotional state' of the users in an environment where the lighting object is located. In embodiments, there is memory that retains and manages function with no appreciable drain on the battery.

In some embodiments, inputs may include systems that take data harvested from sensors 3335 in the lighting installation environment as well as sensors that reflect information about users, such as one or more of physiological sensors (including wearable devices, such as armbands, wrist bands, chest bands, glasses, clothing, and the like), sensors on various devices used by a user, ambient sensors, and the like. These may include sensing one or more of temperature, pressure, ambient lighting conditions, localized lighting conditions, lighting spectrum characteristics, humidity. UV light, sound, particles, pollutants, gases (e.g., oxygen, carbon dioxide, carbon monoxide and radon), radiation, location of objects or items, motion (e.g., speed, direction and/or acceleration). Where one or more wearable or physiological sensors are used, they may sense one or more of a person's temperature, blood pressure, heart rate, oxygen saturation, activity type, activity level, galvanic skin response, respiratory rate, cholesterol level (including HDL, LDL and triglyceride), hormone or adrenal levels (e.g., Cortisol, thyroid, adrenaline, melatonin, and others), histamine levels, immune system characteristics, blood alcohol levels, drug content, macro and micro nutrients, mood, emotional state, alertness, sleepiness, and the like.

In some embodiments, the platform may connect to or integrate with data sources of information about users, such as including social networks (Facebook™, LinkedIn™, Twitter™, and the like, sources of medical records (23&Me™ and the like), productivity, collaboration and/or calendaring software (Google™, Outlook™, scheduling apps and the like), information about web browsing and/or shopping activity, activity on media streaming services (Netflix™, Spotify™, YouTube™, Pandora™ and the like), health record information and other sources of insight about the preferences or characteristics of users of the space of a lighting installation, including psychographic, demographic and other characteristics.

In some embodiments, the platform may use information from sources that indicate patterns, such as patterns involving periods of time (daily patterns, weekly patterns, seasonal patterns, and the like), patterns involving cultural factors or norms (such as indicating usage patterns or preferences in different regions), patterns relating to personality and preferences, patterns relating to social groups (such as family and work group patterns), and the like. In embodiments, the platform may make use of the data harvested from various sources noted above to make recommendations and/or to optimize (such as automatically, under computer control) the design, ordering, fulfillment, deployment and/or operation of a lighting installation, such as based on understanding or prediction of user behavior. This may include recommendation or optimization relating to achieving optimal sleep time and duration, setting optimal mealtimes, satisfying natural light exposure requirements during the day, and maintaining tolerable artificial light exposure levels (such as during night time). In some embodiments, the platform may anticipate user needs and optimize the lighting installation to enhance productivity, alertness, emotional well-being, satisfaction, safety and/or sleep. In further embodiments, the platform may control one or more panel systems of the present disclosure in accordance with the user needs of the environment based on this information.

In some embodiments, the platform may store a space utilization data structure that indicates, over time, how people use the space of the lighting installation, such as indicating what hallways are more trafficked, and the like. This may inform understanding of a space, such as indicating what is an entry, what is a passage, what is a workspace, and the like, which may be used to suggest changes or updates to a lighting design. In embodiments, sensors may be used to collect and read where people have been in the space, such as using one or more video cameras, IR sensors, microwave sensors. LIDAR, ultrasound or the like. In embodiments, the platform may collect and read what adjustments people have made, such as task lamp activation and other activities that indicate how a lighting fixture is used by an individual in a space. By way of these examples, aggregate usage information may be used to optimize a lighting design and adjust other lighting designs. Based on these factors, a space may be dynamically adjusted, and the lighting model for an installation may be updated to reflect the actual installation.

In some embodiments, control capabilities of the panel systems may include dynamic configuration of control parameters, such as providing a dimming curve for a light source, including but not limited to a panel system of the present disclosure, that is customized to the preferences of a designer or other user. This may include a selection from one or more modes, such as ones described elsewhere herein that have desired effects on mood or aesthetic factors, that have desired health effects, that meet the functional requirements, or the like.

Bioactive thresholds may, in some instances, benefit from prolonged exposure to at least one of one of CSE and LRNE. In some instances a melanopic flux of at least 10:1 may be suitable, in other instances the melanopic flux may be 20:1, 50:1, 100:1, or a greater ratio. It will be appreciated in light of the disclosure that traditional systems simply adjust from a warm CCT to a cool CCT, which may only provide a 2:1 or 3:1 ratio of melanopic flux, which are below said threshold. In some implementations, the platform may include spectral tuning targets for panel systems of the present disclosure that may optimize this ratio based on local installation environments. These targets, in a first operational mode along with adjustments intensity of light (e.g., 4:1) may provide a higher ratio, such as a 10:1 ratio or greater, and thus provide greater melanopic flux ratios.

In a second operational mode and either in combination with the above mode or not, the platform may support an ability to shift the bias of light in a room. In embodiments, controlled variation of one or more panel systems of the present disclosure in a lighting environment can contribute to generating a lighting bias typical of being outside.

In some implementations, various other programmable modes may be provided, such as bioactive panel system settings where using different combinations of color light sources to achieve a given mixed color output may be optimized for efficacy, efficiency, color quality, health impact (e.g., circadian action and/or LRNE action), or to satisfy other requirements. In embodiments, the programmable modes may also include programmable dimming curves, color tuning curves, and the like (such as allowing various control interfaces, such as extra-low voltage (ELV) controllers or voltage-based dimmers to affect fixture colors, such as where a custom tuning curve provides a start point, an end point and a dimming and/or color tuning path in response to a level of dimming). In embodiments, programmable modes may use conventional tuning mechanisms, such as simple interpolation systems (which typically use two or three white color LEDs) are dimmable on a zero to ten-volt analog system, and have a second voltage-based input for adjusting the CCT of a fixture between warm and cool CCTs. The bioactive panel systems as described herein can provide for tunable ranges of color points at various x, y coordinates on the 1931 CIE chromaticity diagram. Because of the wide range of potential white or non-white colors produced by the panel systems, they may be controlled by the platform that may specify a particular x, y coordinate on the CIE diagram. Lighting control protocols like DMX™ and Dali 2.0™ may achieve this result.

In some implementations the control system described herein controls output of at least one CSE and LRNE. In some embodiments a programmable color curve for an LED driver may be input, such as through an interface of the platform, or through a desktop software interface, a mobile phone 3330, a tablet app, or the like, that enables a user to define a start and stop point to a color tuning curve and to specify how it will be controlled by a secondary input, such as a voltage-based input (e.g., a 0 to 10-volt input) to the fixture. These may include pre-defined curves, as well as the ability to set start, end, and waypoints to define custom curves. For example, an exemplary color curve can have a starting point around 8000 K biased above the black body curve, with the color curve crossing the black body around 2700 K, and finishing around 1800 K below the black body curve. Similarly, another exemplary curve could be programmed such that the start was 4000 K well above the black body, with the end being 4000 K well below the black body. By way of these examples, any adjustment would be in hue only, not CCT. Further examples may include a curve that never produces a white color, such as starting in the purple and finishing in orange. In any of these cases, these curves may be programmed into panel systems via the interface of the platform, the desk-top, mobile phone or tablet. In embodiments, the curves may be designed, saved, and then activated, such as using the secondary (supplemental) 0 to 10-volt input.

In some implementations, a three-channel warm dim operational mode may be used, such as that described more fully in U.S. Provisional Patent Application No. 62/712,182 filed Jul. 30, 2018, which is incorporated herein in its entirety for all purposes, for target applications where the "fully on" CCT falls between 3000 K and 2500 K. By way of these examples, as the fixture dims (via ELV control or in response to the 0 to 10-volt input) the CCT may be gradually decreased to between 2500 K and 1800 K. In certain embodiments, the hue adjustment may all occur below the black body curve. Alternative embodiments may use a cyan channel as described elsewhere herein, either long-blue-pumped cyan or short-blue-pumped cyan, and a red channel which may be LRNE with cyan pumped near infrared as described elsewhere herein, additionally LRNE especially in the infrared region may be produced with phosphors configured for generation of LRNE emission from a below 280 nm LED include but are not limited to: composition formula M700_rb4_lime and s_M750_rb4_M630_yag| $LiAlO_2:Fe^{3+}$ (peak at 770 nms), $CdS:Ag^+,Cl^-$ (peak at 800 nms), $ZnSbGaTe:Cr^{3+},Nd^{3+}$ (peak at 845 nms), $La_3In_2Ga_3O_{12}:Cr^{3+},Dy^{3+}$ (peak at 905 nms), $BaGd_2ZnO_5$: $Yb^{3+}$ (peak at 979 nms) and $Ba(GdY)_2ZnO_5$: $Yb^{3+}$ (peak at 979 ns), plus a 4000 K white channel as described elsewhere herein to achieve a warm dimming operational mode that allows for adjustment both above and below the black body curve. In some embodiments of the three-channel warm dim mode, the white channel can have a color point within a 7-step MacAdam ellipse around any point on the black body locus having a correlated color temperature between about 3500 K and about 6500 K.

In some implementations, the panel systems of the present disclosure can include a 4-channel color system as described elsewhere herein and in U.S. Provisional Patent Application No. 62/757,672 filed Nov. 8, 2018, and U.S. Provisional Application No. 62/712,191 filed Jul. 30, 2018, the contents of which are incorporated by reference herein in their entirety as if fully set forth herein, includes 3000 K to 1800 K CCT white color points within its range, a programmable mode may be included within the driver that adjusts color with the dimming percentage as well. In some aspects, this may be similar to a conventional control mode, except that the color control would not be on the secondary 0 to 10-volt channel, but may be activated through the primary 0 to 10-volt input channel or ELV controller. In embodiments, the "starting" color point may be the one when the fixture was "fully on." In embodiments, the "ending" color point may be the one where the fixture is maximally dimmed. It is thus possible to make full range color change, such as purple to orange, which is slaved to the 0 to 10-volt or ELV dimming signal.

In some implementations, an optimized mode may be provided. With a 4-channel color system, there are many ways to create a single x-y point on the CIE diagram. In embodiments, the maximally efficient mode may typically be one that uses the colors that have x, y coordinates closest to the target x, y coordinate. But for best color quality, utilizing a fourth channel (and thereby requiring more light from the color in the opposite "corner") may help provide a desired spectral power distribution. For the maximum melatonin suppression (for systems hoping to mimic circadian lighting), a higher cyan channel content may be required for CCTs of 3500 K and above and minimizing cyan and blue content below 3500 K. It will be appreciated in light of the disclosure that conventional systems either require expert users to understand the color balances necessary to achieve these effects (who then implement the color balances channel-by-channel) or are designed for maximum efficiency with color quality as a byproduct.

In some implementations, a digital power system is provided herein (including firmware-driven power conversion and LED current control) that controls a multichannel color system, such as a 4-channel color system, and allows for the inclusion of "modes" which may calculate the correct color balance between the various channels to provide optimized outputs. In embodiments, optimization may occur around one or more of efficacy, color quality, circadian effects, LRNE effects, and other factors. Other modes are possible, such as optimizing for contrast, particular display requirements. It will be appreciated in light of the disclosure that this is not an exhaustive list but is representative of potential modes that could be engaged through an interface of the platform (or of a mobile, tablet or desktop application) where a color tuning curve may be specified, such that the curve is used to specify an interface between a controller and the Digital PSU in a panel system. In embodiments, these modes may account for actual measured colors for each panel system and calculate the correct balance of for the chosen modes, such as based on algorithms loaded into the Digital PSU microprocessor.

In some implementations, machine learning may be used, such as based on various feedback measures, such as relating to mood (stated by the user or measured by one or more sensors), noise levels (such as indicating successful utilization of a space based on a desired level of noise), returns on investment (such as where panel systems are intended to promote retail merchandise), reported pain levels, measured health levels, performance levels of users (including fitness, wellness, and educational performance, among others), sleep levels, vitamin D levels, melatonin levels, and many others. In embodiments, the lighting installations including the panel systems may be operated or controlled based on external information, such as based on seasonal lighting conditions, weather, climate, collective mood indicators (such as based on stock market data, news feeds, or sentiment indices), analyses of social network data, and the like. This may include controlling a system to reflect, or influence, the mood of occupants.

FIG. 26 depicts an example computing environment 3000 suitable for implementing aspects of the embodiments of the present invention, including the control system, which can integrate one or more devices, computing, and lighting systems. As utilized herein, the phrase "computing system" generally refers to a dedicated computing device with processing power and storage memory, which supports operating software that underlies the execution of software, applications, and computer programs thereon. As used herein, an application is a small, in storage size, specialized program that is downloaded to the computing system or device. In some cases, the application is downloaded from an "App Store" such as APPLE's APP STORE or GOOGLE's ANDROID MARKET. After download, the application is generally installed on the computer system or computing device. As shown by FIG. 26, computing environment 3000 includes bus 3010 that directly or indirectly couples the following components: memory 3020, one or more processors 3030, I/O interface 3040, and network interface 3050. Bus 3010 is configured to communicate, transmit, and transfer data, controls, and commands between the various components of computing environment 3000.

Computing environment 3000 typically includes a variety of computer-readable media. Computer-readable media can be any available media that is accessible by computing environment 3000 and includes both volatile and nonvolatile media, removable and non-removable media. Computer-readable media may comprise both computer storage media and communication media. Computer storage media does not comprise, and in fact explicitly excludes, signals per se.

Computer storage media includes volatile and nonvolatile, removable and non-removable, tangible and non-transient media, implemented in any method or technology for storage of information such as computer-readable instructions, data structures, program modules or other data. Computer storage media includes RAM; ROM; EE-PROM: flash memory or other memory technology; CD-ROMs; DVDs or other optical disk storage; magnetic cassettes, magnetic tape, magnetic disk storage or other magnetic storage devices: or other mediums or computer storage devices which can be used to store the desired information and which can be accessed by computing environment 3000.

Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, communication media includes wired media, such as a wired network or direct-wired connection, and wireless media, such as acoustic. RF, infrared and other wireless media. Combinations of any of the above should also be included within the scope of computer-readable media.

Memory 3020 includes computer-storage media in the form of volatile and/or nonvolatile memory. The memory may be removable, non-removable, or a combination thereof. Memory 3020 may be implemented using hardware devices such as solid-state memory, hard drives, optical-disc drives, and the like. Computing environment also includes one or more processors 3030 that read data from various entities such as memory 3020, I/O interface 3040, and network interface 3050.

I/O interface 3040 enables computing environment 3000 to communicate with different input devices and output devices. Examples of input devices include a keyboard, a pointing device, a touchpad, a touchscreen, a scanner, a microphone, a joystick, and the like. Examples of output devices include a display device, an audio device (e.g., speakers), a printer, and the like. These and other I/O devices are often connected to processor 3010 through a serial port interface that is coupled to the system bus, but may be connected by other interfaces, such as a parallel port, game port, or universal serial bus (USB). A display device can also be connected to the system bus via an interface, such as a video adapter which can be part of, or connected to, a graphics processor unit. I/O interface is configured to coordinate I/O traffic between memory 3020, the one or more processors 3030, network interface 3050, and any combination of input devices and/or output devices.

Network interface 3050 enables computing environment 3000 to exchange data with other computing devices via any suitable network. In a networked environment, program modules depicted relative to computing environment 3000, or portions thereof, may be stored in a remote memory storage device accessible via network interface 3050. It will be appreciated that the network connections shown are exemplary and other means of establishing a communications link between the computers may be used.

In at least some embodiments, a server that implements a portion or all of one or more of the technologies described herein may include a general-purpose computer system that includes or is configured to access one or more computer-accessible media. FIG. depicts a general-purpose computer system that includes or is configured to access one or more computer-accessible media. In the illustrated embodiment, computing device 3100 includes one or more processors 3110*a*, 3110*b*, and/or 3110*n* (which may be referred herein singularly as a processor 1010 or in the plural as the processors 3110) coupled to a system memory 3120 via an input/output ("I/O") interface 3130. Computing device 3100 further includes a network interface 3140 coupled to I/O interface 3130.

In various embodiments, computing device 3100 may be a uniprocessor system including one processor 3110 or a multiprocessor system including several processors (e.g., two, four, eight, or another suitable number). Processors 3110 may be any suitable processors capable of executing instructions. For example, in various embodiments, processors 3110 may be general-purpose or embedded processors implementing any of a variety of instruction set architectures ("ISAs"), such as the x86, PowerPC, SPARC or MIPS ISAs, or any other suitable ISA. In multiprocessor systems, each of processors 3110 may commonly, but not necessarily, implement the same ISA.

In some embodiments, a graphics processing unit ("GPU") 3112 may participate in providing graphics rendering and/or physics processing capabilities. A GPU may, for example, comprise a highly parallelized processor architecture specialized for graphical computations. In some embodiments, processors 3110 and GPU 3112 may be implemented as one or more of the same type of device.

System memory 3120 may be configured to store instructions and data accessible by processor(s) 3110. In various embodiments, system memory 3120 may be implemented using any suitable memory technology, such as static random-access memory ("SRAM"), synchronous dynamic RAM ("SDRAM"), nonvolatile/Flash®-type memory, or any other type of memory. In the illustrated embodiment, program instructions and data implementing one or more desired functions, such as those methods, techniques, and data described above, are shown stored within system memory 3120 as code 3125 and data 3126.

In one embodiment, I/O interface 3130 may be configured to coordinate I/O traffic between processor 3110, system memory 3120, and any peripherals in the device, including network interface 3140 or other peripheral interfaces. In some embodiments, I/O interface 3130 may perform any necessary protocol, timing or other data transformations to convert data signals from one component (e.g., system memory 3120) into a format suitable for use by another component (e.g., processor 3110). In some embodiments. I/O interface may include support for devices attached through various types of peripheral buses, such as a variant of the Peripheral Component Interconnect ("PCI") bus standard or the Universal Serial Bus ("USB") standard, for example. In some embodiments, the function of V/O interface 3130 may be split into two or more separate components, such as a north bridge and a south bridge, for example. Also, in some embodiments some or all of the functionality of I/O interface 3130, such as an interface to system memory 3120, may be incorporated directly into processor 3110.

Network interface 3140 may be configured to allow data to be exchanged between computing device 3100 and other device or devices 3160 attached to a network or networks 3150, such as other computer systems or devices, for example. In various embodiments, network interface 3140 may support communication via any suitable wired or wireless general data networks, such as types of Ethernet networks, for example. Additionally, network interface 3140 may support communication via telecommunications/telephony networks, such as analog voice networks or digital fiber communications networks, via storage area networks, such as Fibre Channel SANs (storage area networks), or via any other suitable type of network and/or protocol.

In some embodiments, system memory 3120 may be one embodiment of a computer-accessible medium configured to store program instructions and data as described above for implementing embodiments of the corresponding methods and apparatus. However, in other embodiments, program instructions and/or data may be received, sent, or stored upon different types of computer-accessible media. Generally speaking, a computer-accessible medium may include non-transitory storage media or memory media, such as magnetic or optical media, e.g., disk or DVD/CD coupled to computing device 3100 via I/O interface 3130. A non-transitory computer-accessible storage medium may also include any volatile or non-volatile media, such as RAM (e.g., SDRAM, DDR SDRAM, RDRAM, SRAM, etc.), ROM, etc., that may be included in some embodiments of computing device 3100 as system memory 3120 or another type of memory. Further, a computer-accessible medium may include transmission media or signals, such as electrical, electromagnetic or digital signals, conveyed via a communication medium, such as a network and/or a wireless link, such as those that may be implemented via network interface 3140. Portions or all of multiple computing devices, such as those illustrated in FIG. 31, may be used to implement the described functionality in various embodiments; for example, software components running on a variety of different devices and servers may collaborate to provide the functionality. In some embodiments, portions of the described functionality may be implemented using storage devices, network devices or special-purpose computer systems, in addition to or instead of being implemented using general-purpose computer systems. The term "computing device," as used herein, refers to at least all these types of devices and is not limited to these types of devices.

A compute node, which may be referred to also as a computing node, may be implemented on a wide variety of computing environments, such as tablet computers, personal computers, smartphones, game consoles, commodity-hardware computers, virtual machines, web services, computing clusters, and computing appliances. Any of these computing devices or environments may, for convenience, be described as compute nodes or as computing nodes.

A network set up by an entity, such as a company or a public sector organization, to provide one or more web services (such as various types of cloud-based computing or storage) accessible via the Internet and/or other networks to a distributed set of clients may be termed a provider network. Such a provider network may include numerous data centers hosting various resource pools, such as collections of physical and/or virtualized computer servers, storage devices, networking equipment, and the like, needed to implement and distribute the infrastructure and web services offered by the provider network. The resources may in some embodiments be offered to clients in various units related to the web service, such as an amount of storage capacity for storage, processing capability for processing, as instances, as sets of related services, and the like. A virtual computing instance may, for example, comprise one or more servers with a specified computational capacity (which may be specified by indicating the type and number of CPUs, the main memory size, and so on) and a specified software stack (e.g., a particular version of an operating system, which may in turn run on top of a hypervisor).

A number of different types of computing devices may be used singly or in combination to implement the resources of the provider network in different embodiments, including general-purpose or special-purpose computer servers, storage devices, network devices, and the like. In some embodiments a client or user may be provided direct access to a resource instance, e.g., by giving a user an administrator login and password. In other embodiments the provider network operator may allow clients to specify execution requirements for specified client applications and schedule execution of the applications on behalf of the client on execution platforms (such as application server instances, Java™ virtual machines ("JVMs"), general-purpose or special-purpose operating systems, platforms that support various interpreted or compiled programming languages, such as Ruby, Perl, Python, C. C++, and the like, or high-performance computing platforms) suitable for the applications, without, for example, requiring the client to access an instance or an execution platform directly. A given execution platform may utilize one or more resource instances in some implementations; in other implementations multiple execution platforms may be mapped to a single resource instance.

In many environments, operators of provider networks that implement different types of virtualized computing, storage and/or other network-accessible functionality may allow customers to reserve or purchase access to resources in various resource acquisition modes. The computing resource provider may provide facilities for customers to select and launch the desired computing resources, deploy application components to the computing resources, and maintain an application executing in the environment. In addition, the computing resource provider may provide further facilities for the customer to quickly and easily scale up or scale down the numbers and types of resources allocated to the application, either manually or through automatic scaling, as demand for or capacity requirements of the application change. The computing resources provided by the computing resource provider may be made available in discrete units, which may be referred to as instances. An instance may represent a physical server hardware platform, a virtual machine instance executing on a server, or some combination of the two. Various types and configurations of instances may be made available, including different sizes of resources executing different operating systems ("OS") and/or hypervisors, and with various installed software applications, runtimes, and the like. Instances may further be available in specific availability zones, representing a logical region, a fault tolerant region, a data center, or other geographic location of the underlying computing hardware, for example. Instances may be copied within an availability zone or across availability zones to improve the redundancy of the instance, and instances may be migrated within a particular availability zone or across availability zones. As one example, the latency for client communications with a particular server in an availability zone may be less than the latency for client communications with a different server. As such, an instance may be migrated from the higher latency server to the lower latency server to improve the overall client experience.

In some embodiments the provider network may be organized into a plurality of geographical regions, and each region may include one or more availability zones. An availability zone (which may also be referred to as an availability container) in turn may comprise one or more distinct locations or data centers, configured in such a way that the resources in a given availability zone may be isolated or insulated from failures in other availability zones. That is, a failure in one availability zone may not be expected to result in a failure in any other availability zone. Thus, the availability profile of a resource instance is intended to be independent of the availability profile of a resource instance in a different availability zone. Clients may be able to protect their applications from failures at a single location by launching multiple application instances in respective availability zones. At the same time, in some implementations inexpensive and low latency network connectivity may be provided between resource instances that reside within the same geographical region (and network transmissions between resources of the same availability zone may be even faster).

Each of the processes, methods, and algorithms described in the preceding sections may be embodied in, and fully or partially automated by, code modules executed by one or more computers or computer processors. The code modules may be stored on any type of non-transitory computer-readable medium or computer storage device, such as hard drives, solid state memory, optical disc, and/or the like. The processes and algorithms may be implemented partially or wholly in application-specific circuitry. The results of the disclosed processes and process steps may be stored, persistently or otherwise, in any type of non-transitory computer storage, such as, e.g., volatile or non-volatile storage.

The various features and processes described above may be used independently of one another, or may be combined in various ways. All possible combinations and sub-combinations are intended to fall within the scope of this disclosure. In addition, certain methods or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

It will also be appreciated that various items are illustrated as being stored in memory or on storage while being used, and that these items or portions thereof may be transferred between memory and other storage devices for purposes of memory management and data integrity. Alternatively, in other embodiments some or all of the software modules and/or systems may execute in memory on another device and communicate with the illustrated computing systems via inter-computer communication. Furthermore, in some embodiments, some or all of the systems and/or modules may be implemented or provided in other ways, such as at least partially in firmware and/or hardware, including, but not limited to, one or more application-specific integrated circuits ("ASICs"), standard integrated circuits, controllers (e.g., by executing appropriate instructions, and including microcontrollers and/or embedded controllers), field-programmable gate arrays ("FPGAs"), complex programmable logic devices ("CPLDs"), etc. Some or all of the modules, systems, and data structures may also be stored (e.g., as software instructions or structured data) on a computer-readable medium, such as a hard disk, a memory, a network, or a portable media article to be read by an appropriate device or via an appropriate connection. The systems, modules, and data structures may also be transmitted as generated data signals (e.g., as part of a carrier wave or other analog or digital propagated signal) on a variety of computer-readable transmission media, including wireless-based and wired/cable-based media, and may take a variety of forms (e.g., as part of a single or multiplexed analog signal, or as multiple discrete digital packets or frames). Such computer program products may also take other forms in other embodiments. Accordingly, the present invention may be practiced with other computer system configurations.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

While certain example embodiments have been described, these embodiments have been presented by way of example only, and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions and changes in the form of the methods and systems described herein may be made without departing from the spirit of the inventions disclosed herein. The accompanying claims and their equivalents are intended to cover such forms or modifications as would fall within the scope and spirit of certain of the inventions disclosed herein.

TABLE 1

| | Spectral Power Distribution for Wavelength Ranges (nm) | | | | | | | | | |
|---|---|---|---|---|---|---|---|---|---|---|
| | 380 < λ ≤ 420 | 420 < λ ≤ 460 | 460 < λ ≤ 500 | 500 < λ ≤ 540 | 540 < λ ≤ 580 | 580 < λ ≤ 620 | 620 < λ ≤ 660 | 660 < λ ≤ 700 | 700 < λ ≤ 740 | 740 < λ ≤ 780 |
| Blue minimum 1 | 0.3 | 100.0 | 0.8 | 15.2 | 25.3 | 26.3 | 15.1 | 5.9 | 1.7 | 0.5 |
| Blue maximum 1 | 110.4 | 100.0 | 196.1 | 61.3 | 59.2 | 70.0 | 80.2 | 22.1 | 10.2 | 4.1 |
| Red minimum 1 | 0.0 | 10.5 | 0.1 | 0.1 | 2.2 | 36.0 | 100.0 | 2.2 | 0.6 | 0.3 |
| Red maximum 1 | 2.0 | 1.4 | 3.1 | 7.3 | 22.3 | 59.8 | 100.0 | 61.2 | 18.1 | 5.2 |
| Short-blue-pumped cyan minimum 1 | 3.9 | 100.0 | 112.7 | 306.2 | 395.1 | 318.2 | 245.0 | 138.8 | 39.5 | 10.3 |
| Short-blue-pumped cyan maximum 1 | 130.6 | 100.0 | 553.9 | 2660.6 | 4361.9 | 3708.8 | 2223.8 | 712.2 | 285.6 | 99.6 |
| Short-blue-pumped cyan maximum 2 | 130.6 | 100.0 | 553.9 | 5472.8 | 9637.9 | 12476.9 | 13285.5 | 6324.7 | 1620.3 | 344.7 |
| Long-blue-pumped cyan minimum 1 | 0.0 | 0.0 | 100.0 | 76.6 | 38.0 | 33.4 | 19.6 | 7.1 | 2.0 | 0.6 |
| Long-blue-pumped cyan maximum 1 | 1.8 | 36.1 | 100.0 | 253.9 | 202.7 | 145.0 | 113.2 | 63.1 | 24.4 | 7.3 |

TABLE 2

| Spectral Power Distribution for Wavelength Ranges (nm) | | | | |
|---|---|---|---|---|
| | 380 < λ ≤ 500 | 500 < λ ≤ 600 | 600 < λ ≤ 700 | 700 < λ ≤ 780 |
| Blue minimum 1 | 100.0 | 27.0 | 19.3 | 20.5 |
| Blue maximum 1 | 100.0 | 74.3 | 46.4 | 51.3 |
| Red minimum 1 | 100.0 | 51.4 | 575.6 | 583.7 |
| Red maximum 1 | 100.0 | 2332.8 | 8482.2 | 9476.2 |
| Short-blue-pumped cyan minimum 1 | 100.0 | 279.0 | 170.8 | 192.8 |
| Short-blue-pumped cyan maximum 1 | 100.0 | 3567.4 | 4366.3 | 4696.6 |
| Long-blue-pumped cyan minimum 1 | 100.0 | 155.3 | 41.1 | 43.5 |
| Long-blue-pumped cyan maximum 1 | 100.0 | 503.0 | 213.2 | 243.9 |

TABLE 3

| | Spectral Power Distribution for Wavelength Ranges (nm) | | | | | | | | | | |
|---|---|---|---|---|---|---|---|---|---|---|---|
| Exemplary Color Channels | 380 < λ ≤ 400 | 400 < λ ≤ 420 | 420 < λ ≤ 440 | 440 < λ ≤ 460 | 460 < λ ≤ 480 | 480 < λ ≤ 500 | 500 < λ ≤ 520 | 520 < λ ≤ 540 | 540 < λ ≤ 560 | 560 < λ ≤ 580 | 580 < λ ≤ 600 |
| Blue Channel 1 | 0.1 | 1.2 | 20.6 | 100 | 49.2 | 35.7 | 37.2 | 36.7 | 33.4 | 26.5 | 19.8 |
| Red Channel 1 | 0.0 | 0.3 | 1.4 | 1.3 | 0.4 | 0.9 | 4.2 | 9.4 | 15.3 | 26.4 | 45.8 |
| Short-Blue-Pumped Cyan Channel 1 | 0.2 | 1.2 | 8.1 | 22.2 | 17.5 | 46.3 | 88.2 | 98.5 | 100.0 | 90.2 | 73.4 |
| Long-Blue-Pumped Cyan Channel 1 | 0.0 | 0.1 | 0.7 | 9.9 | 83.8 | 100 | 75.7 | 65.0 | 62.4 | 55.5 | 43.4 |
| Blue Channel 2 | 0.4 | 2.5 | 17.2 | 100 | 60.9 | 30.9 | 29.3 | 30.2 | 28.6 | 24.3 | 20.7 |
| Red Channel 2 | 0.1 | 0.4 | 1.1 | 3.4 | 3.6 | 2.7 | 5.9 | 11.0 | 16.9 | 28.1 | 46.8 |
| Short-Blue-Pumped Cyan Channel 2 | 0.5 | 0.6 | 3.4 | 13.5 | 16.6 | 47.2 | 83.7 | 95.8 | 100.0 | 95.8 | 86.0 |
| Long-Blue-Pumped Cyan Channel 2 | 0.1 | 0.2 | 1.0 | 9.1 | 54.6 | 100.0 | 99.6 | 75.7 | 65.5 | 56.8 | 48.9 |

| | Spectral Power Distribution for Wavelength Ranges (nm) | | | | | | | | | |
|---|---|---|---|---|---|---|---|---|---|---|
| Exemplary Color Channels | 600 < λ ≤ 620 | 620 < λ ≤ 640 | 640 < λ ≤ 660 | 660 < λ ≤ 680 | 680 < λ ≤ 700 | 700 < λ ≤ 720 | 720 < λ ≤ 740 | 740 < λ ≤ 760 | 760 < λ ≤ 780 | 760 < λ ≤ 800 |
| Blue Channel 1 | 14.4 | 10.6 | 7.6 | 4.7 | 2.6 | 1.4 | 0.7 | 0.4 | 0.2 | 0.0 |
| Red Channel 1 | 66.0 | 87.0 | 100.0 | 72.5 | 42.0 | 22.3 | 11.6 | 6.1 | 3.1 | 0.0 |
| Short-Blue-Pumped Cyan Channel 1 | 57.0 | 48.1 | 41.4 | 27.0 | 15.1 | 7.9 | 4.0 | 2.1 | 1.0 | 0.0 |
| Long-Blue-Pumped Cyan Channel 1 | 30.9 | 21.5 | 14.5 | 8.5 | 4.5 | 2.4 | 1.3 | 0.7 | 0.3 | 0.0 |
| Blue Channel 2 | 18.5 | 16.6 | 13.6 | 9.5 | 6.0 | 3.5 | 2.0 | 1.2 | 0.8 | 0.0 |
| Red Channel 2 | 68.9 | 92.6 | 100.0 | 73.9 | 44.5 | 24.7 | 13.1 | 6.8 | 3.5 | 0.0 |
| Short-Blue-Pumped Cyan Channel 2 | 76.4 | 74.6 | 68.3 | 46.1 | 26.1 | 14.0 | 7.2 | 3.6 | 1.8 | 0.0 |

TABLE 3-continued

| | | | | | | | | | | |
|---|---|---|---|---|---|---|---|---|---|---|
| Long-Blue-Pumped Cyan Channel 2 | 41.3 | 33.3 | 24.1 | 15.8 | 9.4 | 5.4 | 3.0 | 1.7 | 1.1 | 0.0 |

TABLE 4

| | Spectral Power Distribution for Wavelength Ranges (nm) | | | | | | | | | |
|---|---|---|---|---|---|---|---|---|---|---|
| Exemplary Color Channels | 380 < λ ≤ 420 | 420 < λ ≤ 460 | 460 < λ ≤ 500 | 500 < λ ≤ 540 | 540 < λ ≤ 580 | 580 < λ ≤ 620 | 620 < λ ≤ 660 | 660 < λ ≤ 700 | 700 < λ ≤ 740 | 740 < λ ≤ 780 |
| Red Channel 1 | 0.2 | 1.4 | 0.7 | 7.3 | 22.3 | 59.8 | 100.0 | 61.2 | 18.1 | 4.9 |
| Red Channel 2 | 1.8 | 4.2 | 2.7 | 7.2 | 19.3 | 59.1 | 100.0 | 59.5 | 20.4 | 5.9 |
| Blue Channel 1 | 1.1 | 100.0 | 70.4 | 61.3 | 49.7 | 28.4 | 15.1 | 6.0 | 1.7 | 0.5 |
| Blue Channel 2 | 25.7 | 100.0 | 69.4 | 31.6 | 38.7 | 38.3 | 33.7 | 14.9 | 5.6 | 2.0 |
| Short-Blue-Pumped Cyan Channel 1 | 0.7 | 15.9 | 33.5 | 98.2 | 100.0 | 68.6 | 47.1 | 22.1 | 6.3 | 1.7 |
| Short-Blue-Pumped Cyan Channel 2 | 30.3 | 100.0 | 313.2 | 1842.7 | 2770.2 | 2841.2 | 2472.2 | 1119.1 | 312.7 | 77.8 |
| Long-blue-pumped cyan Channel 1 | 0.0 | 5.8 | 100.0 | 76.6 | 64.1 | 40.4 | 19.6 | 7.1 | 2.0 | 0.6 |
| Long-blue-pumped cyan Channel 2 | 0.4 | 5.3 | 100.0 | 165.3 | 105.4 | 77.0 | 49.0 | 22.7 | 8.1 | 2.3 |

TABLE 5

| Exemplary Color Channels | ccx | ccy | LED pump peak wavelength |
|---|---|---|---|
| Red Channel 1 | 0.5932 | 0.3903 | 450-455 nm |
| Blue Channel 1 | 0.2333 | 0.2588 | 450-455 nm |
| Long-Blue-Pumped Cyan Channel 1 | 0.2934 | 0.4381 | 505 nm |
| Short-Blue-Pumped Cyan Channel 1 | 0.373 | 0.4978 | 450-455 nm |
| Violet Channel 1 | 0.3585 | 0.3232 | 380 nm |
| Violet Channel 2 | 0.3472 | 0.3000 | 400 nm |
| Violet Channel 3 | 0.2933 | 0.2205 | 410 nm |
| Violet Channel 4 | 0.3333 | 0.2868 | 420 nm |

TABLE 5-continued

| Exemplary Color Channels | ccx | ccy | LED pump peak wavelength |
|---|---|---|---|
| Violet Channel 5 | | | 400 nm |
| Yellow Channel 1 | 0.4191 | 0.5401 | 380 nm |
| Yellow Channel 2 | 0.4218 | 0.5353 | 400 nm |
| Yellow Channel 3 | 0.4267 | 0.5237 | 410 nm |
| Yellow Channel 4 | 0.4706 | 0.4902 | 420 nm |
| Yellow Channel 5 | | | 400 nm |
| Yellow Channel 6 | | | 410 nm |

TABLE 6

| Designator | Exemplary Material(s) | Density (g/mL) | Emission Peak (nm) | FWHM (nm) | Emission Peak Range (nm) | FWHM Range (nm) |
|---|---|---|---|---|---|---|
| Composition "A" | Luag: Cerium doped lutetium aluminum garnet ($Lu_3Al_5O_{12}$) | 6.73 | 535 | 95 | 530-540 | 90-100 |
| Composition "B" | Yag: Cerium doped yttrium aluminum garnet ($Y_3Al_5O_{12}$) | 4.7 | 550 | 110 | 545-555 | 105-115 |
| Composition "C" | a 650 nm-peak wavelength emission phosphor: Europium doped calcium aluminum silica nitride ($CaAlSiN_3$) | 3.1 | 650 | 90 | 645-655 | 85-95 |
| Composition "D" | a 525 nm-peak wavelength emission phosphor: GBAM:$BaMgAl_{10}O_{17}$:Eu | 3.1 | 525 | 60 | 520-530 | 55-65 |
| Composition "E" | a 630 nm-peak wavelength emission quantum dot: any semiconductor quantum dot material of appropriate size for desired emission wavelengths | 5.1 | 630 | 40 | 625-635 | 35-45 |

TABLE 6-continued

| Designator | Exemplary Material(s) | Density (g/mL) | Emission Peak (nm) | FWHM (nm) | Emission Peak Range (nm) | FWHM Range (nm) |
|---|---|---|---|---|---|---|
| Composition "F" | a 610 nm-peak wavelength emission quantum dot: any semiconductor quantum dot material of appropriate size for desired emission wavelengths | 5.1 | 610 | 40 | 605-615 | 35-45 |

TABLE 7

| | 320 < λ ≤ 340 | 340 < λ ≤ 360 | 360 < λ ≤ 380 | 380 < λ ≤ 400 | 400 < λ ≤ 420 | 420 < λ ≤ 440 | 440 < λ ≤ 460 | 460 < λ ≤ 480 | 480 < λ ≤ 500 | 500 < λ ≤ 520 | 520 < λ ≤ 540 | 540 < λ ≤ 560 |
|---|---|---|---|---|---|---|---|---|---|---|---|---|
| Red Channel 11 | 0.0 | 0.0 | 0.0 | 0.6 | 0.8 | 0.9 | 3.1 | 4.9 | 2.9 | 8.5 | 14.9 | 17.6 |
| Red Channel 3 | 0.0 | 0.0 | 0.0 | 0.0 | 0.1 | 3.9 | 14.9 | 3.4 | 0.5 | 0.8 | 2.0 | 5.8 |
| Red Channel 4 | 0.0 | 0.0 | 0.0 | 25.6 | 21.1 | 16.7 | 16.4 | 15.2 | 6.0 | 10.5 | 16.8 | 18.2 |
| Red Channel 5 | 0.0 | 0.0 | 0.0 | 0.7 | 1.0 | 12.6 | 68.4 | 23.0 | 5.5 | 16.7 | 35.7 | 43.0 |
| Red Channel 6 | 0.0 | 0.0 | 0.0 | 0.0 | 0.1 | 3.9 | 14.9 | 3.4 | 0.5 | 0.8 | 2.0 | 5.8 |
| Red Channel 7 | 0.0 | 0.0 | 0.0 | 2.0 | 15.5 | 13.4 | 2.8 | 0.9 | 1.0 | 3.2 | 5.7 | 7.8 |
| Red Channel 8 | 0.0 | 0.0 | 0.0 | 0.3 | 20.3 | 17.9 | 0.2 | 0.0 | 0.0 | 0.1 | 0.1 | 0.6 |
| Red Channel 9 | 0.0 | 0.0 | 0.0 | 0.0 | 0.0 | 0.4 | 4.1 | 5.8 | 4.0 | 7.2 | 12.7 | 18.9 |
| Red Channel 10 | 0.0 | 0.0 | 0.0 | 0.1 | 0.1 | 0.7 | 4.5 | 4.9 | 3.5 | 6.7 | 11.6 | 17.6 |
| Red Channel 1 | 0.0 | 0.0 | 0.0 | 0.0 | 0.3 | 1.4 | 1.3 | 0.4 | 0.9 | 4.2 | 9.4 | 15.3 |
| Red Channel 2 | 0.0 | 0.0 | 0.0 | 0.1 | 0.4 | 1.1 | 3.4 | 3.6 | 2.7 | 5.9 | 11.0 | 16.9 |
| Long-Red Channel A | 0.0 | 1.2 | 1.8 | 1.7 | 2.1 | 6.1 | 13.2 | 4.4 | 3.5 | 10.7 | 17.7 | 18.7 |
| Long-Red Channel B | 0.0 | 1.2 | 2.1 | 2.0 | 2.1 | 6.1 | 13.4 | 4.5 | 3.1 | 7.5 | 16.3 | 25.2 |
| Exemplary Red Channels Minimum | 0.0 | 0.0 | 0.0 | 0.0 | 0.0 | 0.4 | 0.2 | 0.0 | 0.0 | 0.1 | 0.1 | 0.6 |
| Exemplary Red Channels Average | 0.0 | 0.2 | 0.3 | 2.5 | 4.9 | 6.5 | 12.4 | 5.7 | 2.6 | 6.4 | 12.0 | 16.3 |
| Exemplary Red Channels Maximum | 0.0 | 1.2 | 2.1 | 25.6 | 21.1 | 17.9 | 68.4 | 23.0 | 6.0 | 16.7 | 35.7 | 43.0 |
| Exemplary Long-Red Channel Minimum | 0.0 | 1.2 | 1.8 | 1.7 | 2.1 | 6.1 | 13.2 | 4.4 | 3.1 | 7.5 | 16.3 | 18.7 |
| Exemplary Long-Red Channel Average | 0.0 | 1.2 | 1.9 | 1.9 | 2.1 | 6.1 | 13.3 | 4.4 | 3.3 | 9.1 | 17.0 | 21.9 |
| Exemplary Long-Red Channel Maximum | 0.0 | 1.2 | 2.1 | 2.0 | 2.1 | 6.1 | 13.4 | 4.5 | 3.5 | 10.7 | 17.7 | 25.2 |

| | 560 < λ ≤ 580 | 580 < λ ≤ 600 | 600 < λ ≤ 620 | 620 < λ ≤ 640 | 640 < λ ≤ 660 | 660 < λ ≤ 680 | 680 < λ ≤ 700 | 700 < λ ≤ 720 | 720 < λ ≤ 740 | 740 < λ ≤ 760 | 760 < λ ≤ 780 | 780 < λ ≤ 800 |
|---|---|---|---|---|---|---|---|---|---|---|---|---|
| Red Channel 11 | 21.8 | 35.7 | 63.5 | 91.4 | 100.0 | 83.9 | 58.3 | 35.6 | 20.3 | 10.8 | 5.2 | 0.0 |
| Red Channel 3 | 11.8 | 30.2 | 64.2 | 94.6 | 100.0 | 83.6 | 58.7 | 36.3 | 21.0 | 11.4 | 6.0 | 0.0 |
| Red Channel 4 | 25.8 | 93.1 | 231.0 | 215.2 | 100.0 | 27.6 | 7.1 | 2.9 | 1.9 | 1.5 | 1.8 | 0.0 |
| Red Channel 5 | 47.5 | 100.0 | 478.3 | 852.3 | 100.0 | 12.4 | 4.5 | 2.7 | 1.9 | 1.5 | 1.0 | 0.0 |
| Red Channel 6 | 11.8 | 30.2 | 64.2 | 94.6 | 100.0 | 83.6 | 58.7 | 36.3 | 21.0 | 11.4 | 6.0 | 0.0 |
| Red Channel 7 | 13.0 | 28.9 | 59.4 | 89.8 | 100.0 | 84.5 | 58.8 | 36.0 | 20.5 | 10.9 | 5.2 | 0.0 |
| Red Channel 8 | 3.2 | 15.9 | 46.4 | 79.8 | 100.0 | 94.8 | 73.4 | 50.7 | 32.9 | 20.2 | 11.1 | 0.0 |
| Red Channel 9 | 29.4 | 46.9 | 72.4 | 95.7 | 100.0 | 83.0 | 57.2 | 34.7 | 19.7 | 10.8 | 5.7 | 0.0 |
| Red Channel 10 | 30.0 | 48.9 | 67.9 | 93.5 | 100.0 | 66.0 | 33.7 | 16.5 | 7.6 | 3.2 | 1.5 | 0.0 |
| Red Channel 1 | 26.4 | 45.8 | 66.0 | 87.0 | 100.0 | 72.5 | 42.0 | 22.3 | 11.6 | 6.1 | 3.1 | 0.0 |
| Red Channel 2 | 28.1 | 46.8 | 68.9 | 92.6 | 100.0 | 73.9 | 44.5 | 24.7 | 13.1 | 6.8 | 3.5 | 0.0 |
| Long-Red Channel A | 17.4 | 17.3 | 21.6 | 43.2 | 100.0 | 182.3 | 237.5 | 229.6 | 174.5 | 112.8 | 66.3 | 36.7 |
| Long-Red Channel B | 40.3 | 69.5 | 100.8 | 111.3 | 100.0 | 86.9 | 103.1 | 162.2 | 227.8 | 248.3 | 208.2 | 144.4 |
| Exemplary Red Channels Minimum | 3.2 | 15.9 | 21.6 | 43.2 | 100.0 | 12.4 | 4.5 | 2.7 | 1.9 | 1.5 | 1.0 | 0.0 |
| Exemplary Red Channels Average | 23.6 | 46.5 | 108.0 | 157.0 | 100.0 | 79.6 | 64.4 | 53.1 | 44.1 | 35.1 | 25.0 | 13.9 |
| Exemplary Red Channels Maximum | 47.5 | 100.0 | 478.3 | 852.3 | 100.0 | 182.3 | 237.5 | 229.6 | 227.8 | 248.3 | 208.2 | 144.4 |
| Exemplary Long-Red Channel Minimum | 17.4 | 17.3 | 21.6 | 43.2 | 100.0 | 86.9 | 103.1 | 162.2 | 174.5 | 112.8 | 66.3 | 36.7 |
| Exemplary Long-Red Channel Average | 28.9 | 43.4 | 61.2 | 77.2 | 100.0 | 134.6 | 170.3 | 195.9 | 201.1 | 180.5 | 137.2 | 90.6 |
| Exemplary Long-Red Channel Maximum | 40.3 | 69.5 | 100.8 | 111.3 | 100.0 | 182.3 | 237.5 | 229.6 | 227.8 | 248.3 | 208.2 | 144.4 |

TABLE 7-continued

| | 800 < λ ≤ 820 | 820 < λ ≤ 840 | 840 < λ ≤ 860 | 860 < λ ≤ 880 | 880 < λ ≤ 900 | 900 < λ ≤ 920 | 920 < λ ≤ 940 | 940 < λ ≤ 960 | 960 < λ ≤ 980 | 980 < λ ≤ 1000 |
|---|---|---|---|---|---|---|---|---|---|---|
| Red Channel 11 | 0.0 | 0.0 | 0.0 | 0.0 | 0.0 | 0.0 | 0.0 | 0.0 | 0.0 | 0.0 |
| Red Channel 3 | 0.0 | 0.0 | 0.0 | 0.0 | 0.0 | 0.0 | 0.0 | 0.0 | 0.0 | 0.0 |
| Red Channel 4 | 0.0 | 0.0 | 0.0 | 0.0 | 0.0 | 0.0 | 0.0 | 0.0 | 0.0 | 0.0 |
| Red Channel 5 | 0.0 | 0.0 | 0.0 | 0.0 | 0.0 | 0.0 | 0.0 | 0.0 | 0.0 | 0.0 |
| Red Channel 6 | 0.0 | 0.0 | 0.0 | 0.0 | 0.0 | 0.0 | 0.0 | 0.0 | 0.0 | 0.0 |
| Red Channel 7 | 0.0 | 0.0 | 0.0 | 0.0 | 0.0 | 0.0 | 0.0 | 0.0 | 0.0 | 0.0 |
| Red Channel 8 | 0.0 | 0.0 | 0.0 | 0.0 | 0.0 | 0.0 | 0.0 | 0.0 | 0.0 | 0.0 |
| Red Channel 9 | 0.0 | 0.0 | 0.0 | 0.0 | 0.0 | 0.0 | 0.0 | 0.0 | 0.0 | 0.0 |
| Red Channel 10 | 0.0 | 0.0 | 0.0 | 0.0 | 0.0 | 0.0 | 0.0 | 0.0 | 0.0 | 0.0 |
| Red Channel 1 | 0.0 | 0.0 | 0.0 | 0.0 | 0.0 | 0.0 | 0.0 | 0.0 | 0.0 | 0.0 |
| Red Channel 2 | 0.0 | 0.0 | 0.0 | 0.0 | 0.0 | 0.0 | 0.0 | 0.0 | 0.0 | 0.0 |
| Long-Red Channel A | 18.6 | 9.3 | 2.2 | 0.0 | 0.0 | 0.0 | 0.0 | 0.0 | 0.0 | 0.0 |
| Long-Red Channel B | 90.0 | 51.3 | 27.2 | 13.6 | 6.2 | 0.0 | 0.0 | 0.0 | 0.0 | 0.0 |
| Exemplary Red Channels Minimum | 0.0 | 0.0 | 0.0 | 0.0 | 0.0 | 0.0 | 0.0 | 0.0 | 0.0 | 0.0 |
| Exemplary Red Channels Average | 8.4 | 4.7 | 2.3 | 1.0 | 0.5 | 0.0 | 0.0 | 0.0 | 0.0 | 0.0 |
| Exemplary Red Channels Maximum | 90.0 | 51.3 | 27.2 | 13.6 | 6.2 | 0.0 | 0.0 | 0.0 | 0.0 | 0.0 |
| Exemplary Long-Red Channel Minimum | 18.6 | 9.3 | 2.2 | 0.0 | 0.0 | 0.0 | 0.0 | 0.0 | 0.0 | 0.0 |
| Exemplary Long-Red Channel Average | 54.3 | 30.3 | 14.7 | 6.8 | 3.1 | 0.0 | 0.0 | 0.0 | 0.0 | 0.0 |
| Exemplary Long-Red Channel Maximum | 90.0 | 51.3 | 27.2 | 13.6 | 6.2 | 0.0 | 0.0 | 0.0 | 0.0 | 0.0 |

TABLE 8

| | 320 < λ ≤ 380 | 380 < λ ≤ 420 | 420 < λ ≤ 460 | 460 < λ ≤ 500 | 500 < λ ≤ 540 | 540 < λ ≤ 580 | 580 < λ ≤ 620 | 620 < λ ≤ 660 |
|---|---|---|---|---|---|---|---|---|
| Red Channel 11 | 0.0 | 0.7 | 2.1 | 4.1 | 12.2 | 20.5 | 51.8 | 100.0 |
| Red Channel 3 | 0.0 | 0.0 | 9.6 | 2.0 | 1.4 | 9.0 | 48.5 | 100.0 |
| Red Channel 4 | 0.0 | 14.8 | 10.5 | 6.7 | 8.7 | 14.0 | 102.8 | 100.0 |
| Red Channel 5 | 0.0 | 0.2 | 8.5 | 3.0 | 5.5 | 9.5 | 60.7 | 100.0 |
| Red Channel 6 | 0.0 | 0.0 | 9.6 | 2.0 | 1.4 | 9.0 | 48.5 | 100.0 |
| Red Channel 7 | 0.0 | 9.2 | 8.6 | 1.0 | 4.6 | 11.0 | 46.5 | 100.0 |
| Red Channel 8 | 0.0 | 11.5 | 10.1 | 0.1 | 0.1 | 2.1 | 34.6 | 100.0 |
| Red Channel 9 | 0.0 | 0.0 | 2.3 | 5.0 | 10.2 | 24.7 | 61.0 | 100.0 |
| Red Channel 10 | 0.0 | 0.1 | 2.7 | 4.3 | 9.5 | 24.6 | 60.4 | 100.0 |
| Long-Red Channel A | 2.1 | 2.6 | 13.5 | 5.5 | 19.8 | 25.2 | 27.2 | 100.0 |
| Long-Red Channel B | 1.6 | 2.0 | 9.2 | 3.6 | 11.3 | 31.0 | 80.6 | 100.0 |
| Red Channel 1 | 0.0 | 0.2 | 1.4 | 0.7 | 7.3 | 22.3 | 59.8 | 100.0 |
| Red Channel 2 | 0.0 | 0.3 | 2.3 | 3.3 | 8.8 | 23.4 | 60.1 | 100.0 |
| Exemplary Red Channels Minimum | 0.0 | 0.0 | 1.4 | 0.1 | 0.1 | 2.1 | 27.2 | 100.0 |
| Exemplary Red Channels Average | 0.3 | 3.2 | 7.0 | 3.2 | 7.7 | 17.4 | 57.1 | 100.0 |
| Exemplary Red Channels Maximum | 2.1 | 14.8 | 13.5 | 6.7 | 19.8 | 31.0 | 102.8 | 100.0 |
| Exemplary Long-Red Channel Minimum | 1.6 | 2.0 | 9.2 | 3.6 | 11.3 | 25.2 | 27.2 | 100.0 |
| Exemplary Long-Red Channel Average | 1.8 | 2.3 | 11.4 | 4.5 | 15.5 | 28.1 | 53.9 | 100.0 |
| Exemplary Long-Red Channel Maximum | 2.1 | 2.6 | 13.5 | 5.5 | 19.8 | 31.0 | 80.6 | 100.0 |

| | 660 < λ ≤ 700 | 700 < λ ≤ 740 | 740 < λ ≤ 780 | 780 < λ ≤ 820 | 820 < λ ≤ 860 | 860 < λ ≤ 900 | 900 < λ ≤ 1000 |
|---|---|---|---|---|---|---|---|
| Red Channel 11 | 74.3 | 29.3 | 8.4 | 0.0 | 0.0 | 0.0 | 0.0 |
| Red Channel 3 | 73.1 | 29.5 | 9.0 | 0.0 | 0.0 | 0.0 | 0.0 |
| Red Channel 4 | 11.0 | 1.5 | 1.1 | 0.0 | 0.0 | 0.0 | 0.0 |
| Red Channel 5 | 1.8 | 0.5 | 0.3 | 0.0 | 0.0 | 0.0 | 0.0 |
| Red Channel 6 | 73.1 | 29.5 | 9.0 | 0.0 | 0.0 | 0.0 | 0.0 |
| Red Channel 7 | 75.5 | 29.8 | 8.5 | 0.0 | 0.0 | 0.0 | 0.0 |
| Red Channel 8 | 93.6 | 46.5 | 17.5 | 0.0 | 0.0 | 0.0 | 0.0 |
| Red Channel 9 | 71.7 | 27.8 | 8.4 | 0.0 | 0.0 | 0.0 | 0.0 |
| Red Channel 10 | 51.5 | 12.4 | 2.4 | 0.0 | 0.0 | 0.0 | 0.0 |
| Long-Red Channel A | 293.2 | 282.2 | 125.1 | 38.7 | 8.1 | 0.0 | 0.0 |
| Long-Red Channel B | 89.9 | 184.6 | 216.1 | 110.9 | 37.2 | 9.3 | 0.0 |
| Red Channel 1 | 61.2 | 18.1 | 4.9 | 0.0 | 0.0 | 0.0 | 0.0 |
| Red Channel 2 | 61.5 | 19.6 | 5.3 | 0.0 | 0.0 | 0.0 | 0.0 |
| Exemplary Red Channels Minimum | 1.8 | 0.5 | 0.3 | 0.0 | 0.0 | 0.0 | 0.0 |
| Exemplary Red Channels Average | 79.3 | 54.7 | 32.0 | 11.5 | 3.5 | 0.7 | 0.0 |
| Exemplary Red Channels Maximum | 293.2 | 282.2 | 216.1 | 110.9 | 37.2 | 9.3 | 0.0 |

TABLE 8-continued

| | | | | | | | |
|---|---|---|---|---|---|---|---|
| Exemplary Long-Red Channel Minimum | 89.9 | 184.6 | 125.1 | 38.7 | 8.1 | 0.0 | 0.0 |
| Exemplary Long-Red Channel Average | 191.6 | 233.4 | 170.6 | 74.8 | 22.6 | 4.7 | 0.0 |
| Exemplary Long-Red Channel Maximum | 293.2 | 282.2 | 216.1 | 110.9 | 37.2 | 9.3 | 0.0 |

TABLE 9

| | 320 < λ ≤ 400 | 400 < λ ≤ 500 | 500 < λ ≤ 600 | 600 < λ ≤ 700 | 700 < λ ≤ 800 | 800 < λ ≤ 900 | 900 < λ ≤ 1000 |
|---|---|---|---|---|---|---|---|
| Red Channel 11 | 0.2 | 3.2 | 24.8 | 100.0 | 18.1 | 0.0 | 0.0 |
| Red Channel 3 | 0.0 | 5.7 | 12.6 | 100.0 | 18.7 | 0.0 | 0.0 |
| Red Channel 4 | 4.4 | 13.0 | 28.3 | 100.0 | 1.4 | 0.0 | 0.0 |
| Red Channel 5 | 0.1 | 7.6 | 16.8 | 100.0 | 0.5 | 0.0 | 0.0 |
| Red Channel 6 | 0.0 | 5.7 | 12.6 | 100.0 | 18.7 | 0.0 | 0.0 |
| Red Channel 7 | 0.5 | 8.6 | 14.9 | 100.0 | 18.5 | 0.0 | 0.0 |
| Red Channel 8 | 0.1 | 9.8 | 5.1 | 100.0 | 29.2 | 0.0 | 0.0 |
| Red Channel 9 | 0.0 | 3.5 | 28.2 | 100.0 | 17.3 | 0.0 | 0.0 |
| Red Channel 10 | 0.0 | 3.8 | 31.8 | 100.0 | 8.0 | 0.0 | 0.0 |
| Red Channel 1 | 0.0 | 1.2 | 27.5 | 100.0 | 11.7 | 0.0 | 0.0 |
| Red Channel 2 | 0.0 | 2.9 | 28.6 | 100.0 | 12.7 | 0.0 | 0.0 |
| Long-Red Channel A | 0.8 | 5.0 | 14.0 | 100.0 | 106.0 | 5.2 | 0.0 |
| Long-Red Channel B | 1.1 | 5.8 | 31.6 | 100.0 | 197.4 | 37.5 | 0.0 |
| Exemplary Red Channels Minimum | 0.0 | 1.2 | 5.1 | 100.0 | 0.5 | 0.0 | 0.0 |
| Exemplary Red Channels Average | 0.5 | 5.8 | 21.3 | 100.0 | 35.2 | 3.3 | 0.0 |
| Exemplary Red Channels Maximum | 4.4 | 13.0 | 31.8 | 100.0 | 197.4 | 37.5 | 0.0 |
| Exemplary Long-Red Channel Minimum | 0.8 | 5.0 | 14.0 | 100.0 | 106.0 | 5.2 | 0.0 |
| Exemplary Long-Red Channel Average | 0.9 | 5.4 | 22.8 | 100.0 | 151.7 | 21.3 | 0.0 |
| Exemplary Long-Red Channel Maximum | 1.1 | 5.8 | 31.6 | 100.0 | 197.4 | 37.5 | 0.0 |

TABLE 10

| | 320 < λ ≤ 340 | 340 < λ ≤ 360 | 360 < λ ≤ 380 | 380 < λ ≤ 400 | 400 < λ ≤ 420 | 420 < λ ≤ 440 | 440 < λ ≤ 460 | 460 < λ ≤ 480 | 480 < λ ≤ 500 | 500 < λ ≤ 520 | 520 < λ ≤ 540 | 540 < λ ≤ 560 |
|---|---|---|---|---|---|---|---|---|---|---|---|---|
| Violet Channel 1 | 0.0 | 51.7 | 633.8 | 545.9 | 100.0 | 53.3 | 53.9 | 10.5 | 6.9 | 22.4 | 40.4 | 48.0 |
| Violet Channel 2 | 0.0 | 0.3 | 11.0 | 116.1 | 100.0 | 17.8 | 2.7 | 0.5 | 1.1 | 4.4 | 7.9 | 9.4 |
| Violet Channel 5 | 0.0 | 0.3 | 10.9 | 115.7 | 100.0 | 23.4 | 10.2 | 1.9 | 1.4 | 4.5 | 8.2 | 9.7 |
| Violet Channel 3 | 0.0 | 0.0 | 1.4 | 29.4 | 100.0 | 29.8 | 4.6 | 0.8 | 0.9 | 3.3 | 6.0 | 7.0 |
| Violet Channel 4 | 0.0 | 1.0 | 1.9 | 10.7 | 100.0 | 86.0 | 15.7 | 2.7 | 3.7 | 13.8 | 24.8 | 28.4 |
| Exemplary Violet Channels Minimum | 0.0 | 0.0 | 1.4 | 10.7 | 100.0 | 17.8 | 2.7 | 0.5 | 0.9 | 3.3 | 6.0 | 7.0 |
| Exemplary Violet Channels Average | 0.0 | 10.7 | 131.8 | 163.6 | 100.0 | 42.1 | 17.4 | 3.3 | 2.8 | 9.7 | 17.4 | 20.5 |
| Exemplary Violet Channels Maximum | 0.0 | 51.7 | 633.8 | 545.9 | 100.0 | 86.0 | 53.9 | 10.5 | 6.9 | 22.4 | 40.4 | 48.0 |

| Violet Channel 1 | 560 < λ ≤ 580 | 580 < λ ≤ 600 | 600 < λ ≤ 620 | 620 < λ ≤ 640 | 640 < λ ≤ 660 | 660 < λ ≤ 680 | 680 < λ ≤ 700 | 700 < λ ≤ 720 | 720 < λ ≤ 740 | 740 < λ ≤ 760 | 760 < λ ≤ 780 | 780 < λ ≤ 800 |
|---|---|---|---|---|---|---|---|---|---|---|---|---|
| Violet Channel 2 | 51.7 | 54.0 | 51.2 | 41.8 | 29.8 | 19.4 | 11.6 | 6.8 | 3.7 | 2.0 | 1.1 | 0.0 |
| Violet Channel 5 | 10.0 | 10.4 | 9.8 | 8.0 | 5.7 | 3.7 | 2.2 | 1.3 | 0.7 | 0.4 | 0.2 | 0.0 |
| Violet Channel 3 | 10.6 | 11.2 | 10.8 | 8.9 | 6.3 | 4.1 | 2.5 | 1.4 | 0.8 | 0.4 | 0.2 | 0.0 |
| Violet Channel 4 | 7.3 | 7.3 | 6.7 | 5.4 | 3.8 | 2.5 | 1.5 | 0.9 | 0.5 | 0.3 | 0.1 | 0.0 |
| Exemplary Violet Channels Minimum | 28.0 | 29.9 | 32.6 | 20.3 | 10.7 | 6.5 | 3.9 | 2.4 | 1.4 | 0.8 | 0.5 | 0.0 |
| Exemplary Violet Channels Average | 7.3 | 7.3 | 6.7 | 5.4 | 3.8 | 2.5 | 1.5 | 0.9 | 0.5 | 0.3 | 0.1 | 0.0 |
| Exemplary Violet Channels Maximum | 21.5 | 22.6 | 22.2 | 16.9 | 11.3 | 7.2 | 4.3 | 2.6 | 1.4 | 0.8 | 0.5 | 0.0 |

TABLE 11

| | 320 < λ ≤ 380 | 380 < λ ≤ 420 | 420 < λ ≤ 460 | 460 < λ ≤ 500 | 500 < λ ≤ 540 | 540 < λ ≤ 580 | 580 < λ ≤ 620 | 620 < λ ≤ 660 | 660 < λ ≤ 700 | 700 < λ ≤ 740 | 740 < λ ≤ 780 |
|---|---|---|---|---|---|---|---|---|---|---|---|
| Violet Channel 1 | 106.1 | 100.0 | 16.6 | 2.7 | 9.7 | 15.4 | 16.3 | 11.1 | 4.8 | 1.6 | 0.5 |
| Violet Channel 2 | 5.2 | 100.0 | 9.5 | 0.8 | 5.7 | 9.0 | 9.3 | 6.3 | 2.7 | 0.9 | 0.3 |
| Violet Channel 5 | 5.2 | 100.0 | 15.6 | 1.5 | 5.9 | 9.4 | 10.2 | 7.1 | 3.1 | 1.0 | 0.3 |
| Violet Channel 3 | 1.1 | 100.0 | 26.6 | 1.3 | 7.1 | 11.0 | 10.8 | 7.1 | 3.0 | 1.0 | 0.3 |
| Violet Channel 4 | 2.6 | 100.0 | 91.9 | 5.8 | 34.8 | 50.9 | 56.4 | 28.0 | 9.4 | 3.4 | 1.2 |
| Exemplary Violet Channels Minimum | 1.1 | 100.0 | 9.5 | 0.8 | 5.7 | 9.0 | 9.3 | 6.3 | 2.7 | 0.9 | 0.3 |
| Exemplary Violet Channels Average | 24.1 | 100.0 | 32.0 | 2.4 | 12.6 | 19.2 | 20.6 | 11.9 | 4.6 | 1.6 | 0.5 |
| Exemplary Violet Channels Maximum | 106.1 | 100.0 | 91.9 | 5.8 | 34.8 | 50.9 | 56.4 | 28.0 | 9.4 | 3.4 | 1.2 |

TABLE 12

| | 320 < λ ≤ 400 | 400 < λ ≤ 500 | 500 < λ ≤ 600 | 600 < λ ≤ 700 | 700 < λ ≤ 780 |
|---|---|---|---|---|---|
| Violet Channel 1 | 548.2 | 100.0 | 96.4 | 68.5 | 6.1 |
| Violet Channel 2 | 104.3 | 100.0 | 34.4 | 24.0 | 2.1 |
| Violet Channel 5 | 92.7 | 100.0 | 32.3 | 23.8 | 2.1 |
| Violet Channel 3 | 22.7 | 100.0 | 22.7 | 14.5 | 1.3 |
| Violet Channel 4 | 6.5 | 100.0 | 59.9 | 35.6 | 2.5 |
| Exemplary Violet Channels Minimum | 6.5 | 100.0 | 22.7 | 14.5 | 1.3 |
| Exemplary Violet Channels Average | 154.9 | 100.0 | 49.2 | 33.3 | 2.8 |
| Exemplary Violet Channels Maximum | 548.2 | 100.0 | 96.4 | 68.5 | 6.1 |

TABLE 13

| | 320 < λ ≤ 340 | 340 < λ ≤ 360 | 360 < λ ≤ 380 | 380 < λ ≤ 400 | 400 < λ ≤ 420 | 420 < λ ≤ 440 | 440 < λ ≤ 460 | 460 < λ ≤ 480 | 480 < λ ≤ 500 | 500 < λ ≤ 520 | 520 < λ ≤ 540 | 540 < λ ≤ 560 |
|---|---|---|---|---|---|---|---|---|---|---|---|---|
| Yellow Channel 1 | 0.0 | 2.0 | 24.3 | 20.9 | 3.9 | 2.6 | 2.8 | 1.3 | 14.6 | 55.3 | 92.6 | 100.0 |
| Yellow Channel 2 | 0.0 | 0.1 | 2.3 | 24.3 | 20.9 | 3.7 | 0.6 | 1.8 | 17.7 | 55.3 | 89.8 | 100.0 |
| Yellow Channel 5 | 0.0 | 0.1 | 2.2 | 23.4 | 20.3 | 5.4 | 3.0 | 0.9 | 11.3 | 48.1 | 87.3 | 100.0 |
| Yellow Channel 3 | 0.0 | 0.0 | 0.4 | 9.2 | 31.4 | 9.4 | 1.4 | 0.6 | 11.3 | 48.2 | 87.5 | 100.0 |
| Yellow Channel 6 | 0.0 | 0.1 | 0.6 | 9.6 | 32.4 | 9.7 | 1.6 | 0.7 | 11.3 | 47.9 | 87.1 | 100.0 |
| Yellow Channel 4 | 0.0 | 5.0 | 8.0 | 7.1 | 9.4 | 7.6 | 3.6 | 2.2 | 11.8 | 48.2 | 87.2 | 100.0 |
| Exemplary Yellow Channels Minimum | 0.0 | 0.0 | 0.4 | 7.1 | 3.9 | 2.6 | 0.6 | 0.6 | 11.3 | 47.9 | 87.1 | 100.0 |
| Exemplary Yellow Channels Average | 0.0 | 1.2 | 6.3 | 15.8 | 19.7 | 6.4 | 2.2 | 1.3 | 13.0 | 50.5 | 88.6 | 100.0 |
| Exemplary Yellow Channels Maximum | 0.0 | 5.0 | 24.3 | 24.3 | 32.4 | 9.7 | 3.6 | 2.2 | 17.7 | 55.3 | 92.6 | 100.0 |

| | 560 < λ ≤ 580 | 580 < λ ≤ 600 | 600 < λ ≤ 620 | 620 < λ ≤ 640 | 640 < λ ≤ 660 | 660 < λ ≤ 680 | 680 < λ ≤ 700 | 700 < λ ≤ 720 | 720 < λ ≤ 740 | 740 < λ ≤ 760 | 760 < λ ≤ 780 | 780 < λ ≤ 800 |
|---|---|---|---|---|---|---|---|---|---|---|---|---|
| Yellow Channel 1 | 91.4 | 77.7 | 61.5 | 44.6 | 30.0 | 19.6 | 11.8 | 7.3 | 4.1 | 2.3 | 1.3 | 0.0 |
| Yellow Channel 2 | 94.2 | 80.8 | 63.6 | 45.9 | 30.7 | 20.0 | 12.1 | 7.5 | 4.2 | 2.4 | 1.5 | 0.0 |
| Yellow Channel 5 | 96.7 | 85.5 | 69.3 | 51.0 | 34.5 | 22.6 | 13.7 | 8.4 | 4.7 | 2.7 | 1.5 | 0.0 |
| Yellow Channel 3 | 95.8 | 83.2 | 66.2 | 47.9 | 32.2 | 21.0 | 12.8 | 7.9 | 4.5 | 2.6 | 1.5 | 0.0 |
| Yellow Channel 6 | 97.4 | 88.6 | 77.3 | 64.1 | 49.6 | 35.4 | 22.7 | 14.0 | 7.9 | 4.4 | 2.4 | 0.0 |
| Yellow Channel 4 | 99.9 | 113.9 | 134.0 | 80.5 | 39.5 | 23.2 | 13.9 | 8.6 | 5.0 | 3.0 | 2.0 | 0.0 |
| Exemplary Yellow Channels Minimum | 91.4 | 77.7 | 61.5 | 44.6 | 30.0 | 19.6 | 11.8 | 7.3 | 4.1 | 2.3 | 1.3 | 0.0 |
| Exemplary Yellow Channels Average | 95.9 | 88.3 | 78.7 | 55.7 | 36.1 | 23.6 | 14.5 | 9.0 | 5.1 | 2.9 | 1.7 | 0.0 |
| Exemplary Yellow Channels Maximum | 99.9 | 113.9 | 134.0 | 80.5 | 49.6 | 35.4 | 22.7 | 14.0 | 7.9 | 4.4 | 2.4 | 0.0 |

TABLE 14

| | 320 < λ ≤ 380 | 380 < λ ≤ 420 | 420 < λ ≤ 460 | 460 < λ ≤ 500 | 500 < λ ≤ 540 | 540 < λ ≤ 580 | 580 < λ ≤ 620 | 620 < λ ≤ 660 | 660 < λ ≤ 700 | 700 < λ ≤ 740 | 740 < λ ≤ 780 |
|---|---|---|---|---|---|---|---|---|---|---|---|
| Yellow Channel 1 | 13.7 | 12.9 | 2.8 | 8.3 | 77.2 | 100.0 | 72.7 | 39.0 | 16.4 | 5.9 | 1.9 |
| Yellow Channel 2 | 1.2 | 23.3 | 2.2 | 10.1 | 74.7 | 100.0 | 74.4 | 39.5 | 16.5 | 6.0 | 2.0 |
| Yellow Channel 5 | 1.2 | 22.2 | 4.3 | 6.2 | 68.8 | 100.0 | 78.7 | 43.5 | 18.4 | 6.7 | 2.2 |
| Yellow Channel 3 | 0.2 | 20.8 | 5.5 | 6.1 | 69.3 | 100.0 | 76.3 | 40.9 | 17.3 | 6.3 | 2.1 |
| Yellow Channel 6 | 0.3 | 21.3 | 5.7 | 6.0 | 68.4 | 100.0 | 84.1 | 57.6 | 29.5 | 11.1 | 3.4 |
| Yellow Channel 4 | 6.5 | 8.3 | 5.6 | 7.0 | 67.7 | 100.0 | 124.1 | 60.1 | 18.6 | 6.8 | 2.5 |
| Exemplary Yellow Channels Minimum | 0.2 | 8.3 | 2.2 | 6.0 | 67.7 | 100.0 | 72.7 | 39.0 | 16.4 | 5.9 | 1.9 |
| Exemplary Yellow Channels Average | 3.9 | 18.1 | 4.4 | 7.3 | 71.0 | 100.0 | 85.0 | 46.7 | 19.4 | 7.1 | 2.3 |
| Exemplary Yellow Channels Maximum | 13.7 | 23.3 | 5.7 | 10.1 | 77.2 | 100.0 | 124.1 | 60.1 | 29.5 | 11.1 | 3.4 |

TABLE 15

| | 320 < λ ≤ 400 | 400 < λ ≤ 500 | 500 < λ ≤ 600 | 600 < λ ≤ 700 | 700 < λ ≤ 780 |
|---|---|---|---|---|---|
| Yellow Channel 1 | 11.3 | 6.1 | 100.0 | 40.2 | 3.6 |
| Yellow Channel 2 | 6.3 | 10.7 | 100.0 | 41.0 | 3.7 |
| Yellow Channel 5 | 6.2 | 9.8 | 100.0 | 45.8 | 4.2 |
| Yellow Channel 3 | 2.3 | 13.0 | 100.0 | 43.4 | 4.0 |
| Yellow Channel 6 | 2.4 | 13.2 | 100.0 | 59.2 | 6.8 |
| Yellow Channel 4 | 4.5 | 7.7 | 100.0 | 64.8 | 4.1 |
| Exemplary Yellow Channels Minimum | 2.3 | 6.1 | 100.0 | 40.2 | 3.6 |
| Exemplary Yellow Channels Average | 5.5 | 10.1 | 100.0 | 49.1 | 4.4 |
| Exemplary Yellow Channels Maximum | 11.3 | 13.2 | 100.0 | 64.8 | 6.8 |

TABLE 16

Simulated Performance Using 4 Channels from Example 1 (highest-CRI mode)

| ccx | ccy | CCT | duv | Ra | R9 | R13 | R15 | LER | COI |
|---|---|---|---|---|---|---|---|---|---|
| 0.280 | 0.287 | 10090 | −0.41 | 95.7 | 82.9 | 96.7 | 91.0 | 253.3 | 8.9 |
| 0.284 | 0.293 | 9450 | 0.56 | 96.2 | 88.5 | 98.0 | 92.4 | 256.9 | 8.7 |
| 0.287 | 0.286 | 8998 | 0.06 | 96.2 | 85.7 | 97.4 | 92.1 | 257.7 | 8.2 |
| 0.291 | 0.300 | 8503 | −0.24 | 96.3 | 84.2 | 97.1 | 92.0 | 259.0 | 7.6 |
| 0.300 | 0.310 | 7506 | −0.35 | 96.4 | 82.5 | 96.4 | 92.0 | 262.3 | 6.4 |
| 0.306 | 0.317 | 7017 | 0.38 | 97.0 | 86.8 | 97.6 | 93.5 | 266.0 | 6.0 |
| 0.314 | 0.325 | 6480 | 0.36 | 97.3 | 87.4 | 97.7 | 94.0 | 268.5 | 5.2 |
| 0.322 | 0.331 | 5992 | −0.56 | 96.9 | 84.2 | 96.7 | 93.3 | 269.1 | 4.2 |
| 0.332 | 0.342 | 5501 | 0.4 | 97.2 | 86.6 | 96.7 | 94.2 | 271.7 | 3.2 |
| 0.345 | 0.352 | 4991 | 0.31 | 97.0 | 87.0 | 96.7 | 93.8 | 273.3 | 2.0 |
| 0.361 | 0.365 | 4509 | 0.8 | 96.8 | 86.8 | 96.2 | 94.2 | 274.7 | 0.9 |
| 0.381 | 0.378 | 3992 | 0.42 | 96.4 | 85.7 | 95.5 | 94.3 | 274.3 | 1.0 |
| 0.405 | 0.391 | 3509 | 0.1 | 95.8 | 85.9 | 94.8 | 94.4 | 271.9 | 2.7 |
| 0.438 | 0.406 | 2997 | 0.58 | 95.3 | 89.3 | 94.3 | 95.4 | 267.0 | |
| 0.460 | 0.410 | 2701 | −0.07 | 95.3 | 92.6 | 94.3 | 96.3 | 260.7 | |
| 0.487 | 0.415 | 2389 | −0.06 | 95.7 | 98.7 | 95.0 | 98.3 | 252.3 | |
| 0.517 | 0.416 | 2097 | 0.39 | 95.7 | 90.2 | 96.9 | 97.8 | 241.4 | |
| 0.549 | 0.409 | 1808 | 0.25 | 95.7 | 73.3 | 97.7 | 91.4 | 227.4 | |
| 0.571 | 0.400 | 1614 | −0.19 | 91.7 | 58.7 | 92.7 | 85.6 | 214.4 | |

TABLE 17

Simulated Performance Using the Blue, Red, and Long-Blue-Pumped Cyan Channels from Example 1 (High-EML mode)

| ccx | ccy | CCT | duv | Ra | R9 | R13 | R15 | LER | COI | CLA | CS | Rf | Rg |
|---|---|---|---|---|---|---|---|---|---|---|---|---|---|
| 0.280 | 0.288 | 10124 | 0.56 | 95.9 | 86.9 | 97.4 | 91.6 | 254.2 | 9.1 | 2236 | 0.6190 | 89 | 98 |
| 0.287 | 0.296 | 8993 | 0.58 | 95.8 | 83.3 | 96.2 | 91.1 | 256.6 | 8.0 | 2094 | 0.6130 | 90 | 99 |
| 0.295 | 0.305 | 7999 | −0.03 | 95.2 | 77.3 | 94.3 | 89.9 | 258.2 | 6.7 | 1947 | 0.6070 | 90 | 99 |
| 0.306 | 0.317 | 7026 | 0.5 | 94.3 | 76.0 | 93.2 | 89.7 | 261.3 | 5.3 | 1761 | 0.5980 | 89 | 99 |
| 0.314 | 0.325 | 6490 | 0.52 | 93.4 | 74.3 | 92.3 | 89.3 | 262.7 | 4.4 | 1643 | 0.5910 | 89 | 99 |
| 0.322 | 0.332 | 6016 | 0.08 | 92.5 | 71.9 | 91.2 | 88.5 | 263.3 | 3.4 | 1533 | 0.5830 | 89 | 99 |
| 0.332 | 0.342 | 5506 | 0.73 | 91.7 | 73.1 | 90.7 | 88.9 | 265.2 | 2.5 | 1386 | 0.5720 | 88 | 99 |
| 0.345 | 0.352 | 5000 | 0.39 | 90.1 | 71.6 | 89.8 | 87.9 | 265.6 | 1.3 | 1238 | 0.5590 | 86 | 97 |
| 0.361 | 0.364 | 4510 | 0.51 | 88.8 | 70.2 | 88.6 | 87.5 | 265.9 | 0.9 | 1070 | 0.5400 | 83 | 96 |
| 0.381 | 0.378 | 4002 | 0.66 | 87.3 | 69.5 | 87.3 | 87.2 | 265.2 | 2.0 | 877 | 0.5110 | 81 | 94 |
| 0.405 | 0.392 | 3507 | 0.48 | 85.9 | 70.1 | 86.0 | 87.1 | 262.6 | 3.6 | 1498 | 0.5810 | 79 | 93 |
| 0.438 | 0.407 | 2998 | 0.84 | 84.7 | 74.5 | 85.3 | 88.3 | 257.7 | | 1292 | 0.5640 | 75 | 89 |
| 0.460 | 0.411 | 2700 | 0.23 | 84.7 | 79.1 | 85.5 | 89.6 | 252.0 | | 1155 | 0.5500 | 73 | 87 |
| 0.482 | 0.408 | 2399 | −2.21 | 86.2 | 86.4 | 86.3 | 91.7 | 242.7 | | 1009 | 0.5320 | 77 | 90 |
| 0.508 | 0.404 | 2103 | −3.59 | 88.2 | 97.6 | 89.2 | 96.2 | 232.3 | | 831 | 0.5030 | 82 | 94 |

TABLE 17-continued

Simulated Performance Using the Blue, Red, and Long-Blue-Pumped Cyan Channels from Example 1 (High-EML mode)

| | | | | | | | | | | | | | |
|---|---|---|---|---|---|---|---|---|---|---|---|---|---|
| 0.542 | 0.398 | 1794 | −3.34 | 91.2 | 79.1 | 96.6 | 95.0 | 219.6 | | 590 | 0.4450 | 87 | 99 |
| 0.583 | 0.392 | 1505 | −0.7 | 88.2 | 49.0 | 89.0 | 81.5 | 205.5 | | 290 | 0.3110 | 80 | 103 |

| ccx | ccy | CCT | duv | GAI | GAI 15 | GAI_BB | circadian power [mW] | circadian flux | CER | CAF | EML | BLH |
|---|---|---|---|---|---|---|---|---|---|---|---|---|
| 0.280 | 0.288 | 10124 | 0.56 | 106.0 | 298.4 | 99.0 | 0.06 | 0.03 | 298.6 | 1.17 | 1.324 | 0.251 |
| 0.287 | 0.296 | 8993 | 0.58 | 105.2 | 293.1 | 99.2 | 0.06 | 0.03 | 287.6 | 1.12 | 1.284 | 0.257 |
| 0.295 | 0.305 | 7999 | −0.03 | 104.5 | 287.8 | 99.8 | 0.07 | 0.03 | 274.8 | 1.06 | 1.240 | 0.264 |
| 0.306 | 0.317 | 7026 | 0.5 | 101.7 | 277.0 | 99.4 | 0.07 | 0.03 | 259.6 | 0.99 | 1.188 | 0.276 |
| 0.314 | 0.325 | 6490 | 0.52 | 99.8 | 269.8 | 99.3 | 0.08 | 0.03 | 249.1 | 0.95 | 1.153 | 0.285 |
| 0.322 | 0.332 | 6016 | 0.08 | 98.0 | 263.0 | 99.6 | 0.08 | 0.03 | 238.4 | 0.90 | 1.117 | 0.293 |
| 0.332 | 0.342 | 5506 | 0.73 | 94.0 | 250.7 | 98.7 | 0.09 | 0.04 | 225.2 | 0.85 | 1.074 | 0.310 |
| 0.345 | 0.352 | 5000 | 0.39 | 90.1 | 238.4 | 98.6 | 0.10 | 0.04 | 209.9 | 0.79 | 1.024 | 0.330 |
| 0.361 | 0.364 | 4510 | 0.51 | 84.2 | 221.8 | 97.7 | 0.11 | 0.04 | 192.6 | 0.72 | 0.967 | 0.320 |
| 0.381 | 0.378 | 4002 | 0.66 | 76.0 | 199.7 | 96.1 | 0.09 | 0.03 | 171.5 | 0.65 | 0.897 | 0.245 |
| 0.405 | 0.392 | 3507 | 0.48 | 66.0 | 174.1 | 94.6 | 0.08 | 0.03 | 148.0 | 0.56 | 0.815 | 0.178 |
| 0.438 | 0.407 | 2998 | 0.84 | 51.4 | 138.2 | 90.2 | 0.06 | 0.02 | 119.4 | 0.46 | 0.711 | 0.115 |
| 0.460 | 0.411 | 2700 | 0.23 | 43.3 | 118.5 | 90.1 | 0.05 | 0.01 | 101.7 | 0.40 | 0.640 | 0.085 |
| 0.482 | 0.408 | 2399 | −2.21 | 39.4 | 109.3 | 102.3 | 0.04 | 0.01 | 85.0 | 0.35 | 0.560 | 0.066 |
| 0.508 | 0.404 | 2103 | −3.59 | 33.6 | 95.4 | 119.4 | 0.03 | 0.01 | 66.3 | 0.28 | 0.462 | 0.048 |
| 0.542 | 0.398 | 1794 | −3.34 | 24.2 | 71.4 | 142.3 | 0.02 | 0.00 | 43.4 | 0.20 | 0.330 | 0.030 |
| 0.583 | 0.392 | 1505 | −0.7 | | | | | | | | | |

TABLE 18

Simulated Performance Using the Blue, Red, and Short-Blue-Pumped Cyan Channels from Example 1 (High-CRI mode)

| ccx | ccy | CCT | duv | GAI | GAI 15 | GAL_BB | circadian power [mW] | circadian flux | CER | CAF | EML | BLH |
|---|---|---|---|---|---|---|---|---|---|---|---|---|
| 0.2795 | 0.2878 | 10154.39 | 0.45 | 105.7 | 299.6 | 99.3 | 0.1 | 0.0 | 297.7 | 1.2 | 1.287392 | 0.242465 |
| 0.2835 | 0.2927 | 9463.51 | 0.57 | 105.1 | 296.8 | 99.5 | 0.1 | 0.0 | 291.0 | 1.1 | 1.255256 | 0.243167 |
| 0.2868 | 0.2963 | 8979.72 | 0.48 | 104.8 | 294.9 | 99.8 | 0.1 | 0.0 | 285.6 | 1.1 | 1.230498 | 0.243703 |
| 0.2904 | 0.3008 | 8501.8 | 0.69 | 104.0 | 292.0 | 99.9 | 0.1 | 0.0 | 279.7 | 1.1 | 1.202935 | 0.244396 |
| 0.3006 | 0.31 | 7485.85 | −0.27 | 103.4 | 287.3 | 101.3 | 0.1 | 0.0 | 263.9 | 1.0 | 1.138359 | 0.245866 |
| 0.3064 | 0.3159 | 7006.5 | −0.29 | 102.4 | 283.1 | 101.7 | 0.1 | 0.0 | 255.1 | 1.0 | 1.101543 | 0.246923 |
| 0.3137 | 0.3232 | 6489.8 | −0.31 | 100.8 | 277.6 | 102.2 | 0.1 | 0.0 | 244.2 | 0.9 | 1.057241 | 0.24832 |
| 0.322 | 0.3308 | 6006.26 | −0.45 | 99.1 | 271.4 | 102.9 | 0.1 | 0.0 | 232.5 | 0.9 | 1.01129 | 0.2499 |
| 0.3324 | 0.3414 | 5501.95 | 0.21 | 95.8 | 261.3 | 102.9 | 0.1 | 0.0 | 218.1 | 0.8 | 0.954284 | 0.252421 |
| 0.3452 | 0.3514 | 4993.84 | −0.12 | 92.5 | 251.2 | 104.0 | 0.1 | 0.0 | 201.4 | 0.7 | 0.893796 | 0.25518 |
| 0.361 | 0.3635 | 4492.22 | −0.07 | 87.6 | 237.1 | 104.7 | 0.1 | 0.0 | 182.1 | 0.7 | 0.82457 | 0.259194 |
| 0.3806 | 0.3773 | 3999.36 | 0.24 | 80.7 | 218.2 | 105.0 | 0.1 | 0.0 | 159.8 | 0.6 | 0.746244 | 0.265169 |
| 0.4044 | 0.3896 | 3509.79 | −0.28 | 72.6 | 196.8 | 106.8 | 0.1 | 0.0 | 135.5 | 0.5 | 0.663096 | 0.198253 |
| 0.4373 | 0.4046 | 2997.87 | 0.16 | 59.3 | 162.9 | 106.3 | 0.1 | 0.0 | 105.4 | 0.4 | 0.558039 | 0.127844 |
| 0.4581 | 0.4081 | 2705 | −0.79 | 52.4 | 145.2 | 110.1 | 0.0 | 0.0 | 89.0 | 0.3 | 0.498973 | 0.097229 |
| 0.4858 | 0.4142 | 2400.92 | −0.13 | 40.5 | 114.8 | 107.3 | 0.0 | 0.0 | 68.7 | 0.3 | 0.42121 | 0.064438 |
| 0.5162 | 0.4156 | 2104.13 | 0.3 | 28.4 | 82.4 | 102.9 | 0.0 | 0.0 | 49.3 | 0.2 | 0.339504 | 0.039198 |
| 0.5487 | 0.4058 | 1789.82 | −0.69 | 19.6 | 57.8 | 116.1 | 0.0 | 0.0 | 32.4 | 0.1 | 0.252508 | 0.023439 |
| 0.5742 | 0.399 | 1593.58 | 0.05 | | | | | | | | | |

| ccx | ccy | CCT | duv | Ra | R9 | R13 | R15 | LER | COI | CLA | CS | Rf | Rg |
|---|---|---|---|---|---|---|---|---|---|---|---|---|---|
| 0.2795 | 0.2878 | 10154.39 | 0.45 | 95.77 | 95.05 | 99.27 | 93.65 | 257.2 | 9.6 | 2199 | 0.617 | 89 | 98 |
| 0.2835 | 0.2927 | 9463.51 | 0.57 | 95.91 | 95.56 | 99.15 | 94.08 | 259.63 | 9.12 | 2104 | 0.614 | 89 | 99 |
| 0.2868 | 0.2963 | 8979.72 | 0.48 | 96.05 | 94.99 | 99.24 | 94.34 | 261.19 | 8.69 | 2033 | 0.6110 | 89 | 100 |
| 0.2904 | 0.3008 | 8501.8 | 0.69 | 96.11 | 95.94 | 99.02 | 94.76 | 263.35 | 8.28 | 1952 | 0.6070 | 90 | 100 |
| 0.3006 | 0.31 | 7485.85 | −0.27 | 96.32 | 91.29 | 99.44 | 94.86 | 266.03 | 6.95 | 1774 | 0.5980 | 90 | 101 |
| 0.3064 | 0.3159 | 7006.5 | −0.29 | 96.33 | 91.45 | 99.45 | 95.26 | 268.18 | 6.3 | 1670 | 0.5920 | 91 | 101 |
| 0.3137 | 0.3232 | 6489.8 | −0.31 | 96.34 | 91.81 | 99.44 | 95.76 | 270.59 | 5.51 | 1546 | 0.5840 | 91 | 102 |
| 0.322 | 0.3308 | 6006.26 | −0.45 | 96.33 | 91.92 | 99.38 | 96.16 | 272.63 | 4.65 | 1420 | 0.5750 | 92 | 102 |
| 0.3324 | 0.3414 | 5501.95 | 0.21 | 96.39 | 95.57 | 99.13 | 97.53 | 276.11 | 3.73 | 1260 | 0.5610 | 92 | 102 |
| 0.3452 | 0.3514 | 4993.84 | −0.12 | 96.8 | 95.19 | 98.84 | 96.57 | 277.51 | 2.51 | 1100 | 0.5440 | 92 | 102 |
| 0.361 | 0.3635 | 4492.22 | −0.07 | 96.83 | 94.58 | 99.18 | 97.25 | 278.89 | 1.16 | 919 | 0.5180 | 93 | 102 |
| 0.3806 | 0.3773 | 3999.36 | 0.24 | 96.85 | 94.73 | 99.44 | 97.96 | 279.47 | 0.46 | 719 | 0.4790 | 94 | 102 |
| 0.4044 | 0.3896 | 3509.79 | −0.28 | 96.77 | 93.51 | 99.01 | 97.87 | 276.46 | 2.34 | 522 | 0.4230 | 94 | 103 |
| 0.4373 | 0.4046 | 2997.87 | 0.16 | 96.89 | 96.02 | 98.46 | 98.58 | 271.21 | | 1020 | 0.5330 | 95 | 103 |
| 0.4581 | 0.4081 | 2705 | −0.79 | 96.85 | 97.34 | 97.5 | 98.4 | 263.76 | | 906 | 0.5160 | 95 | 104 |
| 0.4858 | 0.4142 | 2400.92 | −0.13 | 97.27 | 96.43 | 97.97 | 99.32 | 255.71 | | 756 | 0.4880 | 95 | 104 |
| 0.5162 | 0.4156 | 2104.13 | 0.3 | 97.2 | 87.34 | 99.31 | 96.46 | 244.06 | | 601 | 0.4490 | 93 | 102 |

TABLE 18-continued

Simulated Performance Using the Blue, Red, and Short-Blue-Pumped Cyan Channels from Example 1 (High-CRI mode)

| | | | | | | | | | | | | |
|---|---|---|---|---|---|---|---|---|---|---|---|---|
| 0.5487 | 0.4058 | 1789.82 | −0.69 | 95.09 | 72.11 | 97.24 | 91.09 | 225.81 | 444 | 0.3930 | 87 | 104 |
| 0.5742 | 0.399 | 1593.58 | 0.05 | 91.03 | 56.48 | 91.54 | 84.56 | 213.34 | 316 | 0.3270 | 83 | 101 |

TABLE 19

Comparison of EML Between 3-Channel Operation Modes

| Red, Blue, and Short-Blue-Pumped Cyan (High-CRI mode) | | Red, Blue, and Long-Blue-Pumped Cyan (High-EML mode) | | Change in EML between High-CRI and High-EML modes at same approxi- |
|---|---|---|---|---|
| CCT | EML | CCT | EML | mate CCT |
| 10154.39 | 1.287392 | 10124.15 | 1.323599 | 2.8% |
| 9463.51 | 1.255256 | | | |
| 8979.72 | 1.230498 | 8993.02 | 1.284446 | 4.4% |
| 8501.8 | 1.202935 | | | |
| | | 7998.71 | 1.240274 | |
| 7485.85 | 1.138359 | | | |
| 7006.5 | 1.101543 | 7025.83 | 1.188225 | 7.9% |
| 6489.8 | 1.057241 | 6490.37 | 1.153187 | 9.1% |
| 6006.26 | 1.01129 | 6015.98 | 1.117412 | 10.5% |
| 5501.95 | 0.954284 | 5505.85 | 1.074033 | 12.5% |
| 4993.84 | 0.893796 | 4999.87 | 1.023649 | 14.5% |
| 4492.22 | 0.82457 | 4509.8 | 0.966693 | 17.2% |
| 3999.36 | 0.746244 | 4001.99 | 0.896774 | 20.2% |
| 3509.79 | 0.663096 | 3507.13 | 0.815304 | 23.0% |
| 2997.87 | 0.558039 | 2998.02 | 0.711335 | 27.5% |
| 2705 | 0.498973 | 2700.47 | 0.639906 | 28.2% |
| 2400.92 | 0.42121 | 2398.75 | 0.5596 | 32.9% |
| 2104.13 | 0.339504 | 2102.54 | 0.461974 | 36.1% |
| 1789.82 | 0.252508 | 1794.12 | 0.330184 | 30.8% |
| 1593.58 | | 1505.05 | | |

TABLE 20

Simulated Performance Using 4 Channels from Example 1 (Highest-CRI mode) with Relative Signal Strengths Calculated for 100 Lumens Flux Output from the Device

| Blue | Red | Short-Blue-Pumped Cyan | Long-Blue-Pumped Cyan | CCT | duv | flux total | Ra | R9 | EML |
|---|---|---|---|---|---|---|---|---|---|
| 0.72 | 0.15 | 0.04 | 0.08 | 9997 | 0.99 | 100.0073 | 95.1 | 96.1 | 1.306 |
| 0.70 | 0.15 | 0.06 | 0.08 | 9501 | 0.99 | 100.0074 | 95.3 | 96.3 | 1.283 |
| 0.67 | 0.16 | 0.09 | 0.08 | 9002 | 0.99 | 100.0075 | 95.5 | 96.3 | 1.257 |
| 0.65 | 0.16 | 0.11 | 0.08 | 8501 | 0.99 | 100.0075 | 95.7 | 96.4 | 1.229 |
| 0.58 | 0.17 | 0.16 | 0.08 | 7499 | 0.99 | 100.0077 | 96.2 | 96.4 | 1.163 |
| 0.55 | 0.18 | 0.19 | 0.09 | 6999 | 0.99 | 100.0079 | 96.5 | 96.0 | 1.125 |
| 0.51 | 0.19 | 0.22 | 0.09 | 6499 | 0.99 | 100.008 | 96.8 | 95.7 | 1.082 |
| 0.46 | 0.20 | 0.25 | 0.09 | 5998 | 0.99 | 100.0082 | 97.1 | 94.8 | 1.035 |
| 0.41 | 0.22 | 0.27 | 0.10 | 5498 | 0.99 | 100.0085 | 97.5 | 93.7 | 0.983 |
| 0.35 | 0.24 | 0.30 | 0.11 | 4999 | 0.99 | 100.0089 | 97.7 | 92.3 | 0.925 |
| 0.30 | 0.26 | 0.35 | 0.09 | 4499 | 0.99 | 100.0091 | 98.0 | 92.7 | 0.848 |
| 0.24 | 0.29 | 0.38 | 0.08 | 3999 | 0.99 | 100.0096 | 97.9 | 92.2 | 0.769 |
| 0.18 | 0.34 | 0.42 | 0.07 | 3499 | 0.99 | 100.0102 | 97.7 | 92.9 | 0.675 |
| 0.11 | 0.41 | 0.44 | 0.04 | 2999 | 0.99 | 100.0111 | 97.4 | 95.6 | 0.567 |
| 0.08 | 0.46 | 0.43 | 0.03 | 2699 | 0.99 | 100.0118 | 97.5 | 98.8 | 0.495 |
| 0.04 | 0.54 | 0.40 | 0.02 | 2399 | 1.00 | 100.0127 | 97.7 | 95.7 | 0.419 |
| 0.02 | 0.64 | 0.34 | 0.01 | 2100 | 1.00 | 100.0141 | 97.4 | 86.6 | 0.337 |
| 0.00 | 0.78 | 0.19 | 0.03 | 1800 | 0.15 | 100.0161 | 95.6 | 73.0 | 0.261 |

TABLE 21

Simulated Performance Using the Blue, Red, and Long-Blue-Pumped Cyan Channels from Example 1 (High-EML mode) with Relative Signal Strengths Calculated for 100 Lumens Flux Output from the Device

| Blue | Red | Long-Blue-Pumped Cyan | CCT | duv | flux total | Ra | R9 | EML |
|---|---|---|---|---|---|---|---|---|
| 0.71 | 0.16 | 0.13 | 10468 | 0.77 | 99.24986 | 94.7 | 97.3 | 1.300 |
| 0.66 | 0.17 | 0.17 | 9001 | 0.99 | 100.008 | 94.9 | 90.1 | 1.285 |
| 0.59 | 0.18 | 0.23 | 7998 | 0.99 | 100.0085 | 94.5 | 86.7 | 1.242 |
| 0.51 | 0.21 | 0.29 | 6999 | 0.99 | 100.0091 | 93.8 | 82.6 | 1.187 |
| 0.46 | 0.22 | 0.32 | 6498 | 0.99 | 100.0095 | 93.1 | 80.4 | 1.154 |
| 0.41 | 0.24 | 0.35 | 5998 | 0.99 | 100.0099 | 92.3 | 78.0 | 1.116 |
| 0.36 | 0.26 | 0.39 | 5498 | 0.99 | 100.0104 | 91.3 | 75.6 | 1.073 |
| 0.29 | 0.28 | 0.43 | 4999 | 0.99 | 100.0109 | 90.2 | 73.3 | 1.023 |
| 0.23 | 0.31 | 0.46 | 4499 | 0.99 | 100.0115 | 88.8 | 71.4 | 0.965 |
| 0.18 | 0.35 | 0.47 | 3999 | −0.35 | 100.0122 | 87.3 | 68.2 | 0.897 |
| 0.11 | 0.41 | 0.48 | 3499 | −1.01 | 100.013 | 86.0 | 68.6 | 0.816 |
| 0.05 | 0.48 | 0.47 | 2999 | −1.01 | 100.014 | 85.1 | 73.3 | 0.715 |
| 0.01 | 0.53 | 0.45 | 2700 | −1.01 | 100.0146 | 85.1 | 78.7 | 0.642 |
| 0.02 | 0.61 | 0.37 | 2400 | −4.00 | 100.0153 | 86.5 | 85.8 | 0.564 |
| 0.01 | 0.69 | 0.30 | 2100 | −4.00 | 100.0161 | 88.2 | 97.6 | 0.462 |
| 0.00 | 0.81 | 0.19 | 1800 | −3.28 | 100.0172 | 91.2 | 79.3 | 0.333 |

TABLE 22

Simulated Performance Using the Blue, Red, and Short-Blue-Pumped Cyan Channels from Example 1 (High-CRI mode) with Relative Signal Strengths Calculated for 100 Lumens Flux Output from the Device

| Blue | Red | Short-Blue-Pumped Cyan | CCT | duv | flux total | Ra | R9 | EML |
|---|---|---|---|---|---|---|---|---|
| 0.75 | 0.14 | 0.11 | 10144 | 0.47 | 100 | 94.9 | 98.0 | 1.287 |
| 0.72 | 0.14 | 0.14 | 9458 | 0.59 | 100 | 95.0 | 98.0 | 1.255 |
| 0.69 | 0.15 | 0.16 | 8976 | 0.50 | 100 | 95.2 | 98.2 | 1.230 |
| 0.66 | 0.15 | 0.19 | 8498 | 0.70 | 100 | 95.2 | 97.8 | 1.203 |
| 0.61 | 0.17 | 0.23 | 7481 | −0.26 | 100 | 96.1 | 96.5 | 1.138 |
| 0.57 | 0.17 | 0.26 | 7003 | −0.28 | 100 | 96.3 | 96.4 | 1.101 |
| 0.53 | 0.18 | 0.29 | 6487 | −0.29 | 100 | 96.5 | 96.2 | 1.057 |
| 0.49 | 0.20 | 0.32 | 5989 | −0.54 | 100 | 96.8 | 94.9 | 1.010 |
| 0.43 | 0.21 | 0.36 | 5499 | 0.23 | 100 | 96.7 | 97.3 | 0.954 |
| 0.38 | 0.23 | 0.39 | 4993 | −0.12 | 100 | 96.8 | 95.4 | 0.894 |
| 0.32 | 0.25 | 0.42 | 4491 | −0.09 | 100 | 96.9 | 94.8 | 0.825 |
| 0.26 | 0.29 | 0.45 | 3999 | 0.25 | 100 | 96.9 | 95.0 | 0.746 |
| 0.20 | 0.34 | 0.46 | 3509 | −0.29 | 100 | 96.9 | 93.8 | 0.663 |
| 0.13 | 0.40 | 0.47 | 2998 | 0.18 | 100 | 97.0 | 96.3 | 0.558 |
| 0.10 | 0.46 | 0.44 | 2705 | −0.79 | 100 | 96.9 | 97.6 | 0.499 |
| 0.06 | 0.54 | 0.40 | 2401 | −0.16 | 100 | 97.3 | 96.2 | 0.421 |
| 0.02 | 0.63 | 0.34 | 2104 | 0.32 | 100 | 97.2 | 87.1 | 0.340 |
| 0.01 | 0.78 | 0.21 | 1790 | −0.70 | 100 | 95.0 | 71.9 | 0.253 |

TABLE 23

| Violet Channel 1 | Blue Channel 1 | Red Channel 1 | Yellow Channel 1 | x | y | CCT | duv | Ra | R9 | R13 | R15 | LER | COI | GAI |
|---|---|---|---|---|---|---|---|---|---|---|---|---|---|---|
| 1 | 0.4863 | 0.0275 | 0.0145 | 0.2808 | 0.2878 | 10006.64 | −0.32 | 88.93 | 56.99 | 89.55 | 90.02 | 170.08 | 13.12 | 101.1 |
| 1 | 0.4798 | 0.0307 | 0.0275 | 0.2866 | 0.2961 | 9012.09 | 0.49 | 88.11 | 52.29 | 88.39 | 88.34 | 175.4 | 12.56 | 99.5 |
| 1 | 0.4410 | 0.0339 | 0.0404 | 0.2947 | 0.3059 | 8001.65 | 0.89 | 87.29 | 48.58 | 87.25 | 86.96 | 178.35 | 11.77 | 97.8 |
| 1 | 0.3667 | 0.0371 | 0.0501 | 0.3062 | 0.3176 | 6993.76 | 0.67 | 86.47 | 46.21 | 86.2 | 85.94 | 177.6 | 10.66 | 95.9 |
| 1 | 0.3247 | 0.0404 | 0.0533 | 0.3136 | 0.3239 | 6498.08 | 0.15 | 86.23 | 46.62 | 85.94 | 85.88 | 176.16 | 9.89 | 94.9 |
| 1 | 0.2892 | 0.0468 | 0.0565 | 0.3220 | 0.3305 | 6007.62 | −0.62 | 86.21 | 48.62 | 86.01 | 86.26 | 175.26 | 8.94 | 94.0 |
| 1 | 0.2375 | 0.0468 | 0.0630 | 0.3324 | 0.3414 | 5501.83 | 0.25 | 84.55 | 41.19 | 83.93 | 83.37 | 174.38 | 8.24 | 90.5 |
| 1 | 0.2118 | 0.0630 | 0.0727 | 0.3448 | 0.3513 | 5008.33 | −0.03 | 84.47 | 43.2 | 83.93 | 83.42 | 178.14 | 6.84 | 88.0 |
| 1 | 0.1664 | 0.0727 | 0.0759 | 0.3608 | 0.3632 | 4497.73 | −0.17 | 84.23 | 45.18 | 83.67 | 83.11 | 176.16 | 5.48 | 83.7 |
| 1 | 0.0953 | 0.0727 | 0.0727 | 0.3808 | 0.3780 | 3999.57 | 0.49 | 82.44 | 40.62 | 81.71 | 80.76 | 168.6 | 4.28 | 76.8 |
| 1 | 0.0307 | 0.0727 | 0.0598 | 0.4055 | 0.3901 | 3489.48 | −0.33 | 80.86 | 39.01 | 80.4 | 79.43 | 154.51 | 3.21 | 69.4 |

| CCT | GAI 15 | GAI_BB | Circadian power [mW] | Circadian flux | CER | CAF | EML | CLA | CS | Rf | Rg | BLH | energy in 440-490/ total |
|---|---|---|---|---|---|---|---|---|---|---|---|---|---|
| 10006.64 | 289.2 | 96.1 | 0.046 | 0.014 | 234.3 | 1.128 | 1.2035 | 2140 | 0.6150 | 85 | 97 | 0.1520 | 24.31% |
| 9012.09 | 283.7 | 96.0 | 0.047 | 0.014 | 227.9 | 1.069 | 1.1519 | 1987 | 0.6090 | 85 | 98 | 0.1502 | 23.42% |
| 8001.65 | 277.5 | 96.3 | 0.046 | 0.013 | 216.7 | 0.997 | 1.0863 | 1805 | 0.6000 | 84 | 97 | 0.1408 | 21.93% |
| 6993.76 | 270.4 | 97.2 | 0.042 | 0.011 | 199.5 | 0.913 | 1.0044 | 1592 | 0.5870 | 84 | 98 | 0.1231 | 19.70% |
| 6498.08 | 266.6 | 98.2 | 0.041 | 0.010 | 189.1 | 0.866 | 0.9583 | 1477 | 0.5790 | 84 | 99 | 0.1132 | 18.38% |
| 6007.62 | 262.6 | 99.6 | 0.039 | 0.009 | 178.5 | 0.818 | 0.9105 | 1358 | 0.5700 | 83 | 100 | 0.1049 | 17.06% |
| 5501.83 | 252.5 | 99.5 | 0.037 | 0.008 | 164.5 | 0.751 | 0.8453 | 1189 | 0.5540 | 82 | 100 | 0.0927 | 15.23% |
| 5008.33 | 244.2 | 100.9 | 0.037 | 0.008 | 153.2 | 0.688 | 0.7870 | 1034 | 0.5350 | 82 | 100 | 0.0883 | 13.83% |
| 4497.73 | 231.7 | 102.3 | 0.034 | 0.007 | 136.0 | 0.614 | 0.7117 | 850 | 0.5060 | 82 | 100 | 0.0762 | 11.69% |
| 3999.57 | 212.4 | 102.3 | 0.031 | 0.005 | 116.1 | 0.525 | 0.6178 | 634 | 0.4580 | 79 | 101 | 0.0604 | 8.87% |
| 3489.48 | 191.0 | 104.4 | 0.026 | 0.004 | 91.3 | 0.436 | 0.5147 | 426 | 0.3850 | 74 | 102 | 0.0444 | 5.89% |

TABLE 24

| Violet Channel 1 | Red Channel 1 | Yellow Channel 1 | x | y | CCT | duv | Ra | R9 | R13 | R15 | LER | COI | GAI |
|---|---|---|---|---|---|---|---|---|---|---|---|---|---|
| 1 | 0.01 | 0.0307 | 0.3798 | 0.3755 | 4006.89 | −0.39 | 72.72 | −1.48 | 70.29 | 67.32 | 119.13 | 7.63 | 75.0 |
| 1 | 0.0404 | 0.0436 | 0.4048 | 0.3901 | 3506.88 | −0.13 | 76.74 | 22.68 | 75.58 | 73.83 | 135.43 | 4.36 | 68.6 |
| 1 | 0.1115 | 0.0662 | 0.4373 | 0.4055 | 3004.86 | 0.51 | 81.38 | 44.89 | 81.5 | 80.46 | 158.17 | 3.08 | 57.6 |
| 1 | 0.1955 | 0.0824 | 0.4602 | 0.4109 | 2697.63 | 0.09 | 84.56 | 56.59 | 85.48 | 84.52 | 171.67 | 4.98 | 50.0 |
| 1 | 0.3603 | 0.1082 | 0.4863 | 0.415 | 2400.85 | 0.11 | 87.56 | 64.45 | 88.99 | 87.52 | 186.8 | 7.75 | 40.4 |

TABLE 24-continued

| | | | | | | | | | | | | | |
|---|---|---|---|---|---|---|---|---|---|---|---|---|---|
| 1 | 0.7124 | 0.1373 | 0.5152 | 0.4136 | 2100.63 | −0.32 | 90.1 | 67.4 | 91.71 | 89.07 | 197.99 | 11.39 | 30.5 |
| 0.4378 | 1 | 0.105 | 0.5503 | 0.4097 | 1800.92 | 0.49 | 90.94 | 62.65 | 92.01 | 87.32 | 210.12 | 16 | 17.4 |
| 0.1276 | 1 | 0.0468 | 0.5739 | 0.4011 | 1605.63 | 0.52 | 89.19 | 53.54 | 89.58 | 83.84 | 209.15 | 19.91 | |
| 0 | 1 | 0.01 | 0.5904 | 0.3926 | 1472.77 | 0.48 | 86.22 | 43.73 | 85.8 | 79 | 204.65 | 23.1 | |

| CCT | GAI 15 | GAI_BB | Circadian power [mW] | Circadian flux | CER | CAF | EML | CLA | CS | Rf | Rg | BLH | energy in 440-490/ total |
|---|---|---|---|---|---|---|---|---|---|---|---|---|---|
| 4006.89 | 209.1 | 100.7 | 0.0219 | 0.0026 | 91.2 | 0.510 | 0.5409 | 614 | 0.4520 | 66 | 99 | 0.035624 | 5.32% |
| 3506.88 | 188.7 | 102.6 | 0.0232 | 0.0028 | 83.1 | 0.429 | 0.4850 | 414 | 0.3790 | 68 | 101 | 0.036204 | 4.64% |
| 3004.86 | 157.1 | 102.3 | 0.0255 | 0.0031 | 71.3 | 0.338 | 0.4190 | 788 | 0.4940 | 71 | 103 | 0.037333 | 3.72% |
| 2697.63 | 136.1 | 103.7 | 0.0276 | 0.0034 | 62.5 | 0.287 | 0.3762 | 699 | 0.4750 | 72 | 105 | 0.038411 | 3.10% |
| 2400.85 | 110.2 | 103.1 | 0.0312 | 0.0038 | 52.1 | 0.233 | 0.3289 | 601 | 0.4480 | 74 | 105 | 0.040364 | 2.42% |
| 2100.63 | 83.9 | 105.3 | 0.0370 | 0.0045 | 40.7 | 0.181 | 0.2769 | 499 | 0.4140 | 74 | 106 | 0.04391 | 1.75% |
| 1800.92 | 47.8 | 94.0 | 0.0265 | 0.0032 | 26.8 | 0.121 | 0.2127 | 374 | 0.3600 | 77 | 103 | 0.025696 | 0.98% |
| 1605.63 | | | | | | | | 290 | 0.3110 | 77 | 100 | | 0.61% |
| 1472.77 | | | | | | | | 228 | 0.2660 | 77 | 96 | | 0.41% |

TABLE 25

| Violet Channel 2 | Blue Channel 1 | Red Channel 1 | Yellow Channel 2 | x | y | CCT | duv | Ra | R9 | R13 | R15 | LER | COI |
|---|---|---|---|---|---|---|---|---|---|---|---|---|---|
| 1 | 0.5897 | 0.0145 | 0.0533 | 0.2805 | 0.2877 | 10048.55 | −0.24 | 84.74 | 35.51 | 83.78 | 83.54 | 194.76 | 14.75 |
| 1 | 0.5669 | 0.021 | 0.0662 | 0.2872 | 0.2947 | 9004.53 | −0.61 | 84.63 | 36.9 | 83.72 | 83.62 | 198.26 | 13.89 |
| 1 | 0.5089 | 0.021 | 0.0824 | 0.2953 | 0.3043 | 8002.62 | −0.27 | 83.38 | 21.18 | 82.17 | 81.47 | 201.36 | 13.28 |
| 1 | 0.4927 | 0.0339 | 0.1082 | 0.3064 | 0.3167 | 6994.18 | 0.09 | 82.8 | 29.98 | 81.54 | 80.47 | 209.16 | 11.99 |
| 1 | 0.4637 | 0.0404 | 0.1212 | 0.3134 | 0.3249 | 6502.6 | 0.2 | 82.25 | 28.43 | 80.9 | 79.58 | 212.19 | 11.3 |
| 1 | 0.4249 | 0.0501 | 0.1341 | 0.3221 | 0.3321 | 5996.32 | 0.2 | 81.71 | 27.74 | 80.34 | 78.87 | 214.8 | 10.4 |
| 1 | 0.3893 | 0.063 | 0.1535 | 0.3326 | 0.3426 | 5491.51 | 0.71 | 80.84 | 25.11 | 79.33 | 77.43 | 219.33 | 9.4 |
| 1 | 0.3538 | 0.0889 | 0.1696 | 0.3453 | 0.3522 | 4995.38 | 0.23 | 81.06 | 29.17 | 79.63 | 77.95 | 22.48 | 7.97 |
| 1 | 0.315 | 0.1244 | 0.1955 | 0.3612 | 0.3649 | 4495.14 | 0.53 | 80.98 | 32.3 | 79.74 | 78.15 | 227.7 | 6.4 |
| 1 | 0.2342 | 0.1598 | 0.2084 | 0.3808 | 0.3783 | 4001.5 | 0.64 | 80.59 | 34.94 | 79.6 | 78.1 | 228.56 | 4.76 |
| 1 | 0.1599 | 0.2278 | 0.2213 | 0.406 | 0.3916 | 3492.72 | 0.26 | 81.11 | 41.82 | 80.74 | 79.55 | 228.66 | 2.93 |

| CCT | GAI | GAI 15 | GAI_BB | Circadian power [mW] | Circadian flux | CER | CAF | EML | CLA | CS | Rf | Rg | BLH | energy in 440-490/ total |
|---|---|---|---|---|---|---|---|---|---|---|---|---|---|---|
| 10048.55 | 99.4 | 286.8 | 95.3 | 0.06561 | 0.01832 | 227.6 | 1.15226 | 1.16343 | 2214 | 0.6180 | 82 | 98 | 0.2269 | 20.57% |
| 9004.53 | 99.0 | 284.0 | 96.1 | 0.06523 | 0.01785 | 220.1 | 1.09461 | 1.11189 | 2067 | 0.6120 | 82 | 98 | 0.2212 | 19.63% |
| 8002.62 | 97.2 | 277.5 | 96.2 | 0.06317 | 0.01659 | 209.1 | 1.02377 | 1.04507 | 1888 | 0.6040 | 80 | 98 | 0.2072 | 18.14% |
| 6994.18 | 95.1 | 269.6 | 96.9 | 0.06389 | 0.01635 | 198.6 | 0.93634 | 0.97088 | 1666 | 0.5920 | 80 | 98 | 0.2030 | 16.89% |
| 6502.6 | 93.6 | 264.4 | 97.3 | 0.06322 | 0.01576 | 190.8 | 0.88706 | 0.92605 | 1542 | 0.5840 | 79 | 98 | 0.1961 | 15.91% |
| 5996.32 | 91.9 | 258.5 | 98.0 | 0.06209 | 0.01496 | 181.2 | 0.83216 | 0.87477 | 1404 | 0.5740 | 78 | 99 | 0.1871 | 14.71% |
| 5491.51 | 89.1 | 249.5 | 98.3 | 0.06152 | 0.01428 | 170.6 | 0.76736 | 0.81655 | 1242 | 0.5590 | 77 | 99 | 0.1788 | 13.41% |
| 4995.38 | 86.7 | 241.3 | 99.8 | 0.06092 | 0.01360 | 158.8 | 0.70408 | 0.75818 | 1085 | 0.5420 | 77 | 99 | 0.1707 | 12.05% |
| 4495.14 | 82.3 | 227.8 | 100.6 | 0.06079 | 0.01292 | 144.7 | 0.62725 | 0.68922 | 895 | 0.5140 | 77 | 99 | 0.1621 | 10.45% |
| 4001.5 | 76.5 | 210.3 | 101.2 | 0.05795 | 0.01128 | 126.3 | 0.54556 | 0.60853 | 697 | 0.4740 | 75 | 100 | 0.1442 | 8.27% |
| 3492.72 | 69.0 | 187.7 | 102.4 | 0.05580 | 0.00982 | 106.1 | 0.45814 | 0.52239 | 487 | 0.4100 | 72 | 101 | 0.1282 | 6.06% |

TABLE 26

| Violet Channel 2 | Red Channel 1 | Yellow Channel 2 | x | y | CCT | duv | Ra | R9 | R13 | R15 | LER | COI |
|---|---|---|---|---|---|---|---|---|---|---|---|---|
| 1 | 0.2052 | 0.1664 | 0.4371 | 0.4039 | 2996.5 | −0.07 | 77.97 | 37.32 | 78.11 | 76.47 | 209.43 | 3.24 |
| 1 | 0.3538 | 0.1986 | 0.4592 | 0.4097 | 2702.82 | −0.25 | 81.29 | 49.05 | 82.14 | 80.83 | 217.13 | 4.6 |
| 1 | 0.6704 | 0.2536 | 0.4861 | 0.4144 | 2399.16 | −0.08 | 84.77 | 58.13 | 86.1 | 84.59 | 224.1 | 7.33 |
| 0.6898 | 1 | 0.2375 | 0.5162 | 0.4152 | 2101.05 | 0.18 | 87.89 | 62.54 | 89.28 | 86.86 | 226.74 | 10.95 |
| 0.2633 | 1 | 0.1147 | 0.5494 | 0.4075 | 1795.06 | −0.17 | 89.46 | 59.71 | 90.5 | 86.24 | 219.6 | 15.9 |
| 0 | 1 | 0.0145 | 0.5884 | 0.3941 | 1490.7 | 0.58 | 86.53 | 44.85 | 86.19 | 79.53 | 206.45 | 22.61 |

| CCT | GAI | GAI 15 | GAI_BB | Circadian power [mW] | Circadian flux | CER | CAF | EML | CLA | CS | Rf | Rg | BLH | energy in 440-490/ total |
|---|---|---|---|---|---|---|---|---|---|---|---|---|---|---|
| 2996.5 | 58.5 | 151.8 | 99.2 | 0.04468 | 0.00592 | 78.2 | 0.36760 | 0.39920 | 283 | 0.3060 | 58 | 102 | 0.0914 | 2.27% |
| 2702.82 | 51.0 | 130.9 | 99.3 | 0.04816 | 0.00634 | 68.2 | 0.31019 | 0.36006 | 686 | 0.4710 | 59 | 103 | 0.0931 | 1.94% |
| 2399.16 | 40.8 | 104.2 | 97.5 | 0.05457 | 0.00709 | 55.9 | 0.24677 | 0.31417 | 586 | 0.4440 | 61 | 103 | 0.0965 | 1.54% |

TABLE 26-continued

| | | | | | | | | | | | | | | |
|---|---|---|---|---|---|---|---|---|---|---|---|---|---|---|
| 2101.05 | 29.4 | 75.0 | 94.0 | 0.04689 | 0.00596 | 42.1 | 0.18439 | 0.26370 | 480 | 0.4070 | 64 | 104 | 0.0723 | 1.12% |
| 1795.06 | 19.0 | 48.6 | 96.7 | 0.02750 | 0.00337 | 28.3 | 0.12835 | 0.20692 | 369 | 0.3570 | 66 | 104 | 0.0354 | 0.77% |
| 1490.7 | | | | | | | | | 234 | 0.2710 | 77 | 96 | | 0.42% |

TABLE 27

| Violet Channel 3 | Blue Channel 1 | Red Channel 1 | Yellow Channel 3 | x | y | CCT | duv | Ra | R9 | R13 | R15 | LER | COI |
|---|---|---|---|---|---|---|---|---|---|---|---|---|---|
| 1 | 0.6866 | 0 | 0.0953 | 0.2803 | 0.2888 | 10001.93 | 0.51 | 81.58 | 24.85 | 80.47 | 78.99 | 215.18 | 15.35 |
| 1 | 0.6575 | 0.0112 | 0.1082 | 0.2871 | 0.295 | 9005.05 | −0.41 | 81.96 | 30.63 | 81.18 | 80.21 | 217.66 | 14.27 |
| 1 | 0.6478 | 0.0178 | 0.1341 | 0.2952 | 0.3045 | 8002.58 | −0.17 | 81.67 | 30.4 | 80.86 | 79.7 | 223.79 | 13.26 |
| 1 | 0.609 | 0.0339 | 0.1598 | 0.3063 | 0.315 | 7019.98 | −0.75 | 81.69 | 34.05 | 81.11 | 80.14 | 228.65 | 11.8 |
| 1 | 0.609 | 0.0371 | 0.1922 | 3133 | 0.3244 | 6503.68 | 0.55 | 80.8 | 28.66 | 79.85 | 78.19 | 235.52 | 11.19 |
| 1 | 0.5606 | 0.0533 | 0.2052 | 0.3219 | 0.3313 | 6009.48 | −0.15 | 80.8 | 31.77 | 80.09 | 78.64 | 237.07 | 10.13 |
| 1 | 0.5283 | 0.0792 | 0.2278 | 0.3326 | 0.3399 | 5491.1 | −0.64 | 80.89 | 34.88 | 80.39 | 79.1 | 240.29 | 8.83 |
| 1 | 0.4507 | 0.0985 | 0.2439 | 0.3447 | 0.3496 | 5008.1 | −0.83 | 80.11 | 33.91 | 79.63 | 78.13 | 241.98 | 7.68 |
| 1 | 0.3731 | 0.1308 | 0.2666 | 0.3603 | 0.3616 | 4503.83 | −0.78 | 80.05 | 37.17 | 79.68 | 78.43 | 244.41 | 6.23 |
| 1 | 0.3053 | 0.1922 | 0.3021 | 0.3804 | 0.3756 | 3993.71 | −0.48 | 80.14 | 41.23 | 80.15 | 78.96 | 247.89 | 4.43 |
| 1 | 0.1955 | 0.2666 | 0.3212 | 0.405 | 0.3901 | 3501.05 | −0.19 | 79.95 | 44.73 | 80.49 | 79.23 | 247.8 | 2.82 |
| 1 | 0.1082 | 0.4507 | 0.3731 | 0.4379 | 0.406 | 2998.46 | 0.63 | 81.09 | 51.35 | 82.25 | 80.98 | 248.85 | 2.82 |

| CCT | GAI | GAI 15 | GAI BB | Circadian power [mW] | Circadian flux | CER | CAF | EML | CLA | CS | Rf | Rg | BLH | energy in 440-490/ total |
|---|---|---|---|---|---|---|---|---|---|---|---|---|---|---|
| 10001.93 | 98.5 | 286.4 | 95.2 | 0.0717 | 0.0223 | 249.5 | 1.1560 | 1.1337 | 2207 | 0.6170 | 78 | 98 | 0.296518 | 20.4% |
| 9005.05 | 98.9 | 285.5 | 96.6 | 0.0710 | 0.0217 | 240.9 | 1.1032 | 1.0860 | 2074 | 0.6120 | 78 | 99 | 0.289375 | 19.3% |
| 8002.58 | 97.7 | 280.0 | 97.1 | 0.0718 | 0.0215 | 231.7 | 1.0321 | 1.0280 | 1894 | 0.6040 | 78 | 99 | 0.286203 | 18.3% |
| 7019.98 | 96.7 | 274.6 | 98.6 | 0.0714 | 0.0208 | 218.5 | 0.9525 | 0.9580 | 1694 | 0.5940 | 77 | 100 | 0.276619 | 16.8% |
| 6503.68 | 94.1 | 266.3 | 98.0 | 0.0729 | 0.0208 | 211.1 | 0.8933 | 0.9122 | 1544 | 0.5840 | 76 | 99 | 0.275549 | 16.0% |
| 6009.48 | 93.3 | 262.2 | 99.4 | 0.0714 | 0.0198 | 200.8 | 0.8443 | 0.8655 | 1422 | 0.5750 | 75 | 100 | 0.264517 | 14.8% |
| 5491.1 | 91.6 | 255.6 | 100.8 | 0.0712 | 0.0193 | 189.2 | 0.7848 | 0.8128 | 1274 | 0.5620 | 75 | 101 | 0.256951 | 13.5% |
| 5008.1 | 89.0 | 246.4 | 101.8 | 0.0685 | 0.0177 | 175.3 | 0.7219 | 0.7515 | 1119 | 0.5460 | 74 | 100 | 0.239709 | 11.8% |
| 4503.83 | 84.9 | 233.1 | 102.8 | 0.0663 | 0.0162 | 158.7 | 0.6472 | 0.6808 | 936 | 0.5210 | 73 | 101 | 0.222675 | 9.8% |
| 3993.71 | 78.9 | 214.3 | 103.3 | 0.0655 | 0.0149 | 139.6 | 0.5613 | 0.6032 | 726 | 0.4810 | 71 | 102 | 0.208066 | 7.8% |
| 3501.05 | 70.8 | 188.9 | 102.8 | 0.0621 | 0.0128 | 117.2 | 0.4712 | 0.5148 | 509 | 0.4180 | 67 | 102 | 0.185032 | 5.3% |
| 2998.46 | 58.4 | 151.3 | 98.8 | 0.0624 | 0.0115 | 91.6 | 0.3666 | 0.4210 | 801 | 0.4970 | 63 | 103 | 0.168008 | 3.1% |

TABLE 28

| Violet Channel 3 | Red Channel 1 | Yellow Channel 3 | x | y | CCT | duv | Ra | R9 | R13 | R15 | LER | COI |
|---|---|---|---|---|---|---|---|---|---|---|---|---|
| 1 | 0.2892 | 0.2795 | 0.4383 | 0.4089 | 2991.9 | 0.55 | 77.14 | 41.67 | 78.4 | 76.41 | 238.03 | 3 |
| 1 | 0.5153 | 0.3376 | 0.4608 | 0.4121 | 2698.81 | 0.49 | 80.67 | 52.45 | 82.44 | 80.85 | 241.24 | 4.57 |
| 1 | 1 | 0.4313 | 0.4874 | 0.4164 | 2398.27 | 0.55 | 84.41 | 60.65 | 86.4 | 84.74 | 241.7 | 7.35 |
| 0.4701 | 1 | 0.2633 | 0.5163 | 0.4156 | 2103.15 | 0.32 | 87.78 | 64.36 | 89.6 | 87.19 | 236.56 | 10.96 |
| 0.1664 | 1 | 0.1276 | 0.5494 | 0.4087 | 1801.77 | 0.14 | 89.57 | 60.8 | 90.73 | 86.57 | 224.99 | 15.78 |
| 0 | 1 | 0.0113 | 0.5893 | 0.3932 | 1481.65 | 0.48 | 86.32 | 44.22 | 85.94 | 79.25 | 205.59 | 22.85 |

| CCT | GAI | GAI 15 | GAI BB | Circadian power [mW] | Circadian flux | CER | CAF | EML | CLA | CS | Rf | Rg | BLH | energy in 440-490/ total |
|---|---|---|---|---|---|---|---|---|---|---|---|---|---|---|
| 2991.9 | 58.3 | 144.4 | 94.5 | 0.05113 | 0.00853 | 88.24 | 0.37 | 0.3906 | 271 | 0.2980 | 53 | 102 | 0.142907 | 1.3% |
| 2698.81 | 50.2 | 122.2 | 93.0 | 0.05643 | 0.00916 | 74.82 | 0.31 | 0.3524 | 670 | 0.4670 | 55 | 104 | 0.145337 | 1.2% |
| 2398.27 | 40.0 | 96.1 | 90.0 | 0.06099 | 0.00950 | 59.56 | 0.25 | 0.3088 | 574 | 0.4400 | 57 | 103 | 0.139122 | 0.9% |
| 2103.15 | 29.5 | 70.5 | 88.2 | 0.04078 | 0.00601 | 44.32 | 0.19 | 0.2618 | 476 | 0.4060 | 59 | 104 | 0.079144 | 0.7% |
| 1801.77 | 18.5 | 44.7 | 87.8 | 0.02498 | 0.00338 | 28.98 | 0.13 | 0.2064 | 367 | 0.3560 | 63 | 103 | 0.037527 | 0.6% |
| 1481.65 | | | | | | | | | 231 | 0.2680 | 76 | 96 | | 0.4% |

TABLE 29

| Violet Channel 4 | Red Channel 1 | Yellow Channel 4 | x | y | CCT | duv | Ra | R9 | R13 | R15 | LER | COI | GAI |
|---|---|---|---|---|---|---|---|---|---|---|---|---|---|
| 1 | 0.0113 | 0.454 | 0.4049 | 0.3909 | 3509.71 | 0.17 | 70.47 | −30.68 | 71.94 | 61.99 | 302.33 | 8.76 | 67.73522 |
| 1 | 0.2827 | 0.6123 | 0.4371 | 0.4039 | 2996.02 | −0.08 | 75.95 | 0.28 | 78.09 | 70.25 | 296.34 | 5.74 | 58.16243 |
| 1 | 0.6155 | 0.7318 | 0.4588 | 0.4091 | 2702.91 | −0.47 | 79.45 | 17.36 | 81.9 | 75.09 | 287.92 | 5.74 | 51.1852 |
| 1 | 1 | 0.9192 | 0.475 | 0.415 | 2534.54 | 0.56 | 81.4 | 24.99 | 83.75 | 77.16 | 284.63 | 6.43 | 43.86021 |
| 0.7221 | 1 | 0.7124 | 0.4863 | 0.4149 | 2399.5 | 0.07 | 83.09 | 32.05 | 85.51 | 79.26 | 277.26 | 7.59 | 40.40926 |
| 0.3343 | 1 | 0.399 | 0.5143 | 0.413 | 2104.82 | −0.53 | 86.42 | 43.99 | 88.69 | 82.68 | 258.79 | 11.04 | 31.31714 |
| 0.14 | 1 | 0.2601 | 0.5386 | 0.4128 | 1903.52 | 0.5 | 88.01 | 47.93 | 89.69 | 83.3 | 246.03 | 13.97 | 21.13827 |
| 0.0889 | 1 | 0.1922 | 0.5503 | 0.4097 | 1800.78 | 0.49 | 88.42 | 48.88 | 89.79 | 83.17 | 237.3 | 15.78 | 17.44622 |
| 0.0436 | 1 | 0.1341 | 0.5629 | 0.4065 | 1700.09 | 0.75 | 88.41 | 48.52 | 89.33 | 82.48 | 228.6 | 17.73 | |
| 0.0404 | 1 | 0.0727 | 0.5723 | 0.3987 | 1603.05 | −0.23 | 87.82 | 47.4 | 88.45 | 81.62 | 217.65 | 19.94 | |

| CCT | GAI 15 | GAI BB | Circadian power [mW] | Circadian flux | CER | CAF | EML | CLA | CS | Rf | Rg | BLH | energy in 440-490/ total |
|---|---|---|---|---|---|---|---|---|---|---|---|---|---|
| 3509.71 | 176.4 | 95.8 | 0.0625 | 0.0139 | 134.9 | 0.4407 | 0.4559 | 429 | 0.3860 | 56 | 99 | 0.2220 | 3.15% |
| 2996.02 | 148.4 | 97.0 | 0.0726 | 0.0152 | 105.0 | 0.3502 | 0.3966 | 754 | 0.4870 | 58 | 102 | 0.2268 | 2.43% |
| 2702.91 | 129.3 | 98.1 | 0.0647 | 0.0129 | 86.8 | 0.2984 | 0.3591 | 674 | 0.4680 | 60 | 104 | 0.1838 | 2.00% |
| 2534.54 | 110.5 | 93.4 | 0.0572 | 0.0108 | 74.0 | 0.2575 | 0.3318 | 613 | 0.4520 | 62 | 104 | 0.1452 | 1.70% |
| 2399.5 | 101.5 | 95.0 | 0.0525 | 0.0097 | 66.0 | 0.2360 | 0.3130 | 575 | 0.4410 | 62 | 104 | 0.1262 | 1.52% |
| 2104.82 | 78.6 | 98.1 | 0.0401 | 0.0068 | 48.4 | 0.1856 | 0.2667 | 483 | 0.4080 | 64 | 105 | 0.0821 | 1.14% |
| 1903.52 | 53.5 | 88.0 | 0.0284 | 0.0043 | 34.5 | 0.1392 | 0.2263 | 401 | 0.3730 | 68 | 103 | 0.0441 | 0.83% |
| 1800.78 | 44.3 | 87.1 | 0.0237 | 0.0034 | 28.8 | 0.1208 | 0.2061 | 363 | 0.3540 | 69 | 102 | 0.0324 | 0.71% |
| 1700.09 | | | | | | | | 321 | 0.3300 | 72 | 99 | | 0.59% |
| 1603.05 | | | | | | | | 292 | 0.3120 | 69 | 104 | | 0.55% |

TABLE 30

| | High-CRI mode | | High-EML mode | | Low-EML mode | | Very-Low-EML mode | |
|---|---|---|---|---|---|---|---|---|
| Nominal CCT | EML | Circadian Stimulus (CS) | EML | Circadian Stimulus (CS) | EML | Circadian Stimulus (CS) | EML | Circadian Stimulus (CS) |
| 10000 | 1.287392 | 0.617 | 1.323599 | 0.6190 | 1.203532 | 0.6150 | | |
| 9500 | 1.2552564 | 0.614 | | | | | | |
| 9000 | 1.230498 | 0.6110 | 1.284446 | 0.6130 | 1.151925 | 0.6090 | | |
| 8500 | 1.202935 | 0.6070 | | | | | | |
| 8000 | | | 1.240274 | 0.6070 | 1.08629 | 0.6000 | | |
| 7500 | 1.1383591 | 0.5980 | | | | | | |
| 7000 | 1.1015431 | 0.5920 | 1.188225 | 0.5980 | 1.004381 | 0.5870 | | |
| 6500 | 1.0572409 | 0.5840 | 1.153187 | 0.5910 | 0.958281 | 0.5790 | | |
| 6000 | 1.0112902 | 0.5750 | 1.117412 | 0.5830 | 0.910548 | 0.5700 | | |
| 5500 | 0.9542838 | 0.5610 | 1.074033 | 0.5720 | 0.845296 | 0.5540 | | |
| 5000 | 0.8937964 | 0.5440 | 1.023649 | 0.5590 | 0.786954 | 0.5350 | | |
| 4500 | 0.8245702 | 0.5180 | 0.966693 | 0.5400 | 0.711691 | 0.5060 | | |
| 4000 | 0.7462442 | 0.4790 | 0.896774 | 0.5110 | | | 0.540872 | 0.452 |
| 3500 | 0.6630957 | 0.4230 | 0.815304 | 0.5810 | | | 0.48499 | 0.3790 |
| 3000 | 0.5580387 | 0.5330 | 0.711335 | 0.5640 | | | 0.418977 | 0.4940 |
| 2700 | 0.4989732 | 0.5160 | 0.639906 | 0.5500 | | | 0.376181 | 0.4750 |
| 2500 | 0.44713093 | 0.497333 | 0.586369 | 0.538 | | | 0.344663 | 0.457 |
| 2400 | 0.4212098 | 0.4880 | 0.5596 | 0.5320 | | | 0.328904 | 0.4480 |
| 2100 | 0.339504 | 0.4490 | 0.461974 | 0.5030 | | | 0.276946 | 0.4140 |
| 1900 | 0.2815066 | 0.411667 | 0.374114 | 0.464333 | | | 0.234146 | 0.378 |
| 1800 | 0.2525079 | 0.3930 | 0.330184 | 0.4450 | | | 0.212746 | 0.3600 |
| 1700 | | | | | | | | |
| 1600 | | 0.3270 | | | | | | |

TABLE 31

| Nominal CCT | EML % changes: High-EML mode to Low-EML mode | EML % changes: High-CRI mode to Low-EML mode and Very-Low-EML mode | EML % changes: High-CRI mode to High-EML mode | CS % changes: High-EML mode to LOW-EML mode | CS % changes: High-CRI mode to Low-EML mode and Very-Low-EML mode | CS % changes: High-CRI mode to High-EML mode |
|---|---|---|---|---|---|---|
| 10000 | 10.0% | 7.0% | 2.8% | 1% | 0% | 0% |
| 9500 | | | | | | |
| 9000 | 11.5% | 6.8% | 4.4% | 1% | 0% | 0% |
| 8500 | | | | | | |
| 8000 | 14.2% | | | 1% | | |
| 7500 | | | | | | |
| 7000 | 18.3% | 9.7% | 7.9% | 2% | 1% | 1% |
| 6500 | 20.3% | 10.3% | 9.1% | 2% | 1% | 1% |
| 6000 | 22.7% | 11.1% | 10.5% | 2% | 1% | 1% |
| 5500 | 27.1% | 12.9% | 12.5% | 3% | 1% | 2% |
| 5000 | 30.1% | 13.6% | 14.5% | 4% | 2% | 3% |
| 4500 | 35.8% | 15.9% | 17.2% | 7% | 2% | 4% |
| 4000 | 65.8% | 38.0% | 20.2% | 13% | 6% | 7% |
| 3500 | 68.1% | 36.7% | 23.0% | 53% | 12% | 37% |
| 3000 | 69.8% | 33.2% | 27.5% | 14% | 8% | 6% |
| 2700 | 70.1% | 32.6% | 28.2% | 16% | 9% | 7% |
| 2500 | 70.1% | 29.7% | 31.1% | 18% | 9% | 8% |
| 2400 | 70.1% | 28.1% | 32.9% | 19% | 9% | 9% |
| 2100 | 66.8% | 22.6% | 36.1% | 21% | 8% | 12% |
| 1900 | 59.8% | 20.2% | 32.9% | 23% | 9% | 13% |
| 1800 | 55.2% | 18.7% | 30.8% | 24% | 9% | 13% |
| 1700 | | | | | | |
| 1600 | | | | | | |

TABLE 32

| Nominal CCT | High-CRI mode EML | High-CRI mode Circadian Stimulus (CS) | High-EML mode EML | High-EML mode Circadian Stimulus (CS) | Low-EML mode EML | Low-EML mode Circadian Stimulus (CS) | Very-Low-EML mode EML | Very-Low-EML mode Circadian Stimulus (CS) |
|---|---|---|---|---|---|---|---|---|
| 10000 | 1.28739 | 0.6170 | 1.32360 | 0.6190 | 1.16343 | 0.6180 | | |
| 9500 | 1.25526 | 0.6140 | | | | | | |
| 9000 | 1.23050 | 0.6110 | 1.28445 | 0.6130 | 1.11189 | 0.6120 | | |
| 8500 | 1.20294 | 0.6070 | | | | | | |
| 8000 | | | 1.24027 | 0.6070 | 1.04507 | 0.6040 | | |
| 7500 | 1.13836 | 0.5980 | | | | | | |
| 7000 | 1.10154 | 0.5920 | 1.18823 | 0.5980 | 0.97088 | 0.5920 | | |
| 6500 | 1.05724 | 0.5840 | 1.15319 | 0.5910 | 0.92605 | 0.5840 | | |
| 6000 | 1.01129 | 0.5750 | 1.11741 | 0.5830 | 0.87477 | 0.5740 | | |
| 5500 | 0.95428 | 0.5610 | 1.07403 | 0.5720 | 0.81655 | 0.5590 | | |
| 5000 | 0.89380 | 0.5440 | 1.02365 | 0.5590 | 0.75818 | 0.5420 | | |
| 4500 | 0.82457 | 0.5180 | 0.96669 | 0.5400 | 0.68922 | 0.5140 | | |
| 4000 | 0.74624 | 0.4790 | 0.89677 | 0.5110 | 0.60853 | 0.4740 | | |
| 3500 | 0.66310 | 0.4230 | 0.81530 | 0.5810 | 0.52239 | 0.4100 | | |
| 3000 | 0.55804 | 0.5330 | 0.71133 | 0.5640 | | | 0.39920 | 0.3060 |
| 2700 | 0.49897 | 0.5160 | 0.63991 | 0.5500 | | | 0.36006 | 0.4710 |
| 2500 | 0.44713 | 0.4973 | 0.58637 | 0.5380 | | | 0.32947 | 0.4530 |
| 2400 | 0.42121 | 0.4880 | 0.55960 | 0.5320 | | | 0.31417 | 0.4440 |
| 2100 | 0.33950 | 0.4490 | 0.46197 | 0.5030 | | | 0.26370 | 0.4070 |
| 1900 | 0.28151 | 0.4117 | 0.37411 | 0.4643 | | | 0.22585 | 0.3737 |
| 1800 | 0.25251 | 0.3930 | 0.33018 | 0.4450 | | | 0.20692 | 0.3570 |
| 1700 | | | | | | | | |
| 1600 | | 0.3270 | | 0.3110 | | | | 0.2710 |

TABLE 33

| Nominal CCT | EML % changes: High-EML mode to Low-EML mode | EML % changes: High-CRI mode to Low-EML mode and Very-Low-EML mode | EML % changes: High-CRI mode to High-EML mode | CS % changes: High-EML mode to Low-EML mode | CS % changes: High-CRI mode to Low-EML mode and Very-Low-EML mode | CS % changes: High-CRI mode to High-EML mode |
|---|---|---|---|---|---|---|
| 10000 | 14% | 11% | 3% | 0% | 0% | 0% |
| 9500 | | | | | | |
| 9000 | 16% | 11% | 4% | 0% | 0% | 0% |
| 8500 | | | | | | |
| 8000 | 19% | | | 0% | | |
| 7500 | | | | | | |
| 7000 | 22% | 13% | 8% | 1% | 0% | 1% |
| 6500 | 25% | 14% | 9% | 1% | 0% | 1% |
| 6000 | 28% | 16% | 10% | 2% | 0% | 1% |
| 5500 | 32% | 17% | 13% | 2% | 0% | 2% |
| 5000 | 35% | 18% | 15% | 3% | 0% | 3% |
| 4500 | 40% | 20% | 17% | 5% | 1% | 4% |
| 4000 | 47% | 23% | 20% | 8% | 1% | 7% |
| 3500 | 56% | 27% | 23% | 42% | 3% | 37% |
| 3000 | 78% | 40% | 27% | 84% | 74% | 6% |
| 2700 | 78% | 39% | 28% | 17% | 10% | 7% |
| 2500 | 78% | 36% | 31% | 19% | 10% | 8% |
| 2400 | 78% | 34% | 33% | 20% | 10% | 9% |
| 2100 | 75% | 29% | 36% | 24% | 10% | 12% |
| 1900 | 66% | 25% | 33% | 24% | 10% | 13% |
| 1800 | 60% | 22% | 31% | 25% | 10% | 13% |
| 1700 | | | | | | |
| 1600 | | | | 15% | 21% | −5% |

TABLE 34

| Nominal CCT | High-CRI mode: EML | High-CRI mode: Circadian Stimulus (CS) | High-EML mode: EML | High-EML mode: Circadian Stimulus (CS) | Low-EML mode: EML | Low-EML mode: Circadian Stimulus (CS) | Very-Low-EML mode: EML | Very-Low-EML mode: Circadian Stimulus (CS) |
|---|---|---|---|---|---|---|---|---|
| 10000 | 1.2874 | 0.617 | 1.3236 | 0.619 | 1.1337 | 0.617 | | |
| 9500 | 1.2553 | 0.614 | | | | | | |
| 9000 | 1.2305 | 0.611 | 1.2844 | 0.613 | 1.0860 | 0.612 | | |
| 8500 | 1.2029 | 0.607 | | | | | | |
| 8000 | | | 1.2403 | 0.607 | 1.0280 | 0.604 | | |
| 7500 | 1.1384 | 0.598 | | | | | | |
| 7000 | 1.1015 | 0.592 | 1.1882 | 0.598 | 0.9580 | 0.594 | | |
| 6500 | 1.0572 | 0.584 | 1.1532 | 0.591 | 0.9122 | 0.584 | | |
| 6000 | 1.0113 | 0.575 | 1.1174 | 0.583 | 0.8655 | 0.575 | | |
| 5500 | 0.9543 | 0.561 | 1.0740 | 0.572 | 0.8128 | 0.562 | | |
| 5000 | 0.8938 | 0.544 | 1.0236 | 0.559 | 0.7515 | 0.546 | | |
| 4500 | 0.8246 | 0.518 | 0.9667 | 0.540 | 0.6808 | 0.521 | | |
| 4000 | 0.7462 | 0.479 | 0.8968 | 0.511 | 0.6032 | 0.481 | | |
| 3500 | 0.6631 | 0.423 | 0.8153 | 0.581 | 0.5148 | 0.418 | | |
| 3000 | 0.5580 | 0.533 | 0.7113 | 0.564 | | | 0.3906 | 0.497 |
| 2700 | 0.4990 | 0.516 | 0.6399 | 0.550 | | | 0.3524 | 0.467 |
| 2500 | 0.4471 | 0.497 | 0.5864 | 0.538 | | | 0.3234 | 0.449 |
| 2400 | 0.4212 | 0.488 | 0.5596 | 0.532 | | | 0.3088 | 0.440 |
| 2100 | 0.3395 | 0.449 | 0.4620 | 0.503 | | | 0.2618 | 0.406 |
| 1900 | 0.2815 | 0.412 | 0.3741 | 0.464 | | | 0.2249 | 0.373 |
| 1800 | 0.2525 | 0.393 | 0.3302 | 0.445 | | | 0.2064 | 0.356 |
| 1700 | | | | | | | | |
| 1600 | | 0.327 | | | | | | 0.268 |

TABLE 35

| | EML % changes | | | CS % changes | | |
|---|---|---|---|---|---|---|
| Nominal CCT | High-EML mode to Low-EML mode | High-CRI mode to Low-EML mode and Very-Low-EML mode | High-CRI mode to High-EML mode | High-EML mode to Low-EML mode | High-CRI mode to Low-EML mode and Very-Low-EML mode | High-CRI mode to High-EML mode |
| 10000 | 16.7% | 13.6% | 2.8% | | | 0.3% |
| 9500 | | | | | | |
| 9000 | 18.3% | 13.3% | 4.4% | | | 0.3% |
| 8500 | | | | | | |
| 8000 | 20.6% | | | | | |
| 7500 | | | | | | |
| 7000 | 24.0% | 15.0% | 7.9% | 1% | −0.34% | 1.0% |
| 6500 | 26.4% | 15.9% | 9.1% | 1% | 0.00% | 1.2% |
| 6000 | 29.1% | 16.8% | 10.5% | 1% | 0.00% | 1.4% |
| 5500 | 32.1% | 17.4% | 12.5% | 2% | −0.18% | 2% |
| 5000 | 36.2% | 18.9% | 14.5% | 2% | −0.37% | 3% |
| 4500 | 42.0% | 21.1% | 17.2% | 4% | −0.58% | 4% |
| 4000 | 48.7% | 23.7% | 20.2% | 6% | −0.42% | 7% |
| 3500 | 58.4% | 28.8% | 23.0% | 39% | 1.20% | 37% |
| 3000 | 82.1% | 42.9% | 27.5% | 13% | 7% | 6% |
| 2700 | 81.6% | 41.6% | 28.2% | 18% | 10% | 7% |
| 2500 | 81.3% | 38.3% | 31.1% | 20% | 11% | 8% |
| 2400 | 81.2% | 36.4% | 32.9% | 21% | 11% | 9% |
| 2100 | 76.5% | 29.7% | 36.1% | 24% | 11% | 12% |
| 1900 | 66.4% | 25.2% | 32.9% | 25% | 10% | 13% |
| 1800 | 60.0% | 22.3% | 30.8% | 25% | 10% | 13% |
| 1700 | | | | | | |
| 1600 | | | | | 22% | |

TABLE 36

| | High-CRI mode | | High-EML mode | | Very-Low-EML mode | |
|---|---|---|---|---|---|---|
| Nominal CCT | EML | Circadian Stimulus (CS) | EML | Circadian Stimulus (CS) | EML | Circadian Stimulus (CS) |
| 10000 | 1.2874 | 0.6170 | 1.3236 | 0.6190 | | |
| 9500 | 1.2553 | 0.6140 | | | | |
| 9000 | 1.2305 | 0.6110 | 1.2844 | 0.6130 | | |
| 8500 | 1.2029 | 0.6070 | | | | |
| 8000 | | | 1.2403 | 0.6070 | | |
| 7500 | 1.1384 | 0.5980 | | | | |
| 7000 | 1.1015 | 0.5920 | 1.1882 | 0.5980 | | |
| 6500 | 1.0572 | 0.5840 | 1.1532 | 0.5910 | | |
| 6000 | 1.0113 | 0.5750 | 1.1174 | 0.5830 | | |
| 5500 | 0.9543 | 0.5610 | 1.0740 | 0.5720 | | |
| 5000 | 0.8938 | 0.5440 | 1.0236 | 0.5590 | | |
| 4500 | 0.8246 | 0.5180 | 0.9667 | 0.5400 | | |
| 4000 | 0.7462 | 0.4790 | 0.8968 | 0.5110 | | |
| 3500 | 0.6631 | 0.4230 | 0.8153 | 0.5810 | 0.4559 | 0.3860 |
| 3000 | 0.5580 | 0.5330 | 0.7113 | 0.5640 | 0.3966 | 0.4870 |
| 2700 | 0.4990 | 0.5160 | 0.6399 | 0.5500 | 0.3591 | 0.4680 |
| 2500 | 0.4471 | 0.4973 | 0.5864 | 0.5380 | 0.3284 | 0.4500 |
| 2400 | 0.4212 | 0.4880 | 0.5596 | 0.5320 | 0.3130 | 0.4410 |
| 2100 | 0.3395 | 0.4490 | 0.4620 | 0.5030 | 0.2667 | 0.4080 |
| 1900 | 0.2815 | 0.4117 | 0.3741 | 0.4643 | 0.2263 | 0.3720 |
| 1800 | 0.2525 | 0.3930 | 0.3302 | 0.4450 | 0.2061 | 0.3540 |
| 1600 | | 0.3270 | | | | |

TABLE 37

| | EML % changes | | | CS % changes | | |
|---|---|---|---|---|---|---|
| Nominal CCT | High-EML mode to Low-EML mode | High-CRI mode to Low-EML mode and Very-Low-EML mode | High-CRI mode to High-EML mode | High-EML mode to Low-EML mode | High-CRI mode to Low-EML mode and Very-Low-EML mode | High-CRI mode to High-EML mode |
| 3500 | 78.8% | 45.4% | 23.0% | 51% | 10% | 37% |
| 3000 | 79.3% | 40.7% | 27.5% | 16% | 9% | 6% |
| 2700 | 78.2% | 38.9% | 28.2% | 18% | 10% | 7% |
| 2500 | 78.6% | 36.2% | 31.1% | 20% | 11% | 8% |
| 2400 | 78.8% | 34.6% | 32.9% | 21% | 11% | 9% |
| 2100 | 73.2% | 27.3% | 36.1% | 23% | 10% | 12% |
| 1900 | 65.3% | 24.4% | 32.9% | 25% | 11% | 13% |
| 1800 | 60.2% | 22.5% | 30.8% | 26% | 11% | 13% |

TABLE 38

| | Violet Peak (Vp) 380 < λ ≤ 460 | | Violet Valley (Vv) 450 < λ ≤ 510 | | Green Peak (Gp) 500 < λ ≤ 650 | | Red Valley (Rv) 650 < λ ≤ 780 | |
|---|---|---|---|---|---|---|---|---|
| | λ | Vp | λ | Vv | λ | Gp | λ | Rv |
| Violet Channel 1 | 380 | 1 | 486 | 0.00485 | 596 | 0.05521 | 751 | 0.00218 |
| Violet Channel 2 | 400 | 1 | 476 | 0.00185 | 592 | 0.05795 | 751 | 0.00227 |
| Violet Channel 5 | 400 | 1 | 482 | 0.00525 | 596 | 0.06319 | 751 | 0.00252 |
| Violet Channel 3 | 410 | 1 | 477 | 0.00368 | 578 | 0.06123 | 751 | 0.00232 |
| Violet Channel 4 | 420 | 1 | 477 | 0.01032 | 608 | 0.22266 | 749 | 0.00519 |
| Exemplary Violet Channels Minimum | 380 | 1 | 476 | 0.00185 | 578 | 0.05521 | 749 | 0.00218 |
| Exemplary Violet Channels Average | 402 | 1 | 480 | 0.00519 | 594 | 0.09205 | 751 | 0.00290 |
| Exemplary Violet Channels Maximum | 420 | 1 | 486 | 0.01032 | 608 | 0.22266 | 751 | 0.00519 |

TABLE 39

| | Ratio | | | | |
|---|---|---|---|---|---|
| | Vp/Vv | Vp/Gp | Vp/Rv | Gp/Vv | Gp/Rv |
| Violet Channel 1 | 206.3 | 18.1 | 458.5 | 11.4 | 25.3 |
| Violet Channel 2 | 540.0 | 17.3 | 440.3 | 31.3 | 25.5 |
| Violet Channel 5 | 190.4 | 15.8 | 397.0 | 12.0 | 25.1 |
| Violet Channel 3 | 272.0 | 16.3 | 431.8 | 16.7 | 26.4 |
| Violet Channel 4 | 96.9 | 4.5 | 192.6 | 21.6 | 42.9 |
| Exemplary Violet Channels Minimum | 96.9 | 4.5 | 192.6 | 11.4 | 25.1 |
| Exemplary Violet Channels Average | 261.1 | 14.4 | 384.0 | 18.6 | 29.0 |
| Exemplary Violet Channels Maximum | 540.0 | 18.1 | 458.5 | 31.3 | 42.9 |

TABLE 40

| | Violet Peak 330 < λ ≤ 430 | | Violet Valley 420 < λ ≤ 510 | | Green Peak 500 < λ ≤ 780 | |
|---|---|---|---|---|---|---|
| | λ | Vp | λ | Vv | λ | Gp |
| Yellow Channel 1 | 380 | 0.37195 | 470 | 0.00534 | 548 | 1 |
| Yellow Channel 2 | 400 | 0.37612 | 458 | 0.00275 | 549 | 1 |
| Yellow Channel 5 | 400 | 0.36297 | 476 | 0.00317 | 561 | 1 |
| Yellow Channel 3 | 410 | 0.37839 | 476 | 0.00139 | 547 | 1 |
| Yellow Channel 6 | 410 | 0.38876 | 476 | 0.00223 | 561 | 1 |
| Yellow Channel 4 | 419 | 0.07831 | 476 | 0.01036 | 608 | 1 |
| Exemplary Yellow Channels Minimum | 380 | 0.07831 | 458 | 0.00139 | 547 | 1 |
| Exemplary Yellow Channels Average | 403 | 0.32608 | 472 | 0.00421 | 562 | 1 |
| Exemplary Yellow Channels Maximum | 419 | 0.38876 | 476 | 0.01036 | 608 | 1 |

TABLE 41

| | Ratio | | |
|---|---|---|---|
| | Vp/Vv | Vp/Gp | Gp/Vv |
| Yellow Channel 1 | 69.7 | 0.372 | 187.3 |
| Yellow Channel 2 | 136.9 | 0.376 | 364.0 |
| Yellow Channel 5 | 114.4 | 0.363 | 315.3 |
| Yellow Channel 3 | 273.2 | 0.378 | 722.0 |
| Yellow Channel 6 | 174.3 | 0.389 | 448.2 |
| Yellow Channel 4 | 7.6 | 0.078 | 96.5 |
| Exemplary Yellow Channels Minimum | 7.559 | 0.078 | 96.525 |
| Exemplary Yellow Channels Average | 129.336 | 0.326 | 355.556 |
| Exemplary Yellow Channels Maximum | 273.202 | 0.389 | 722.022 |

TABLE 42

| | Blue Peak 380 < λ ≤ 460 | | Blue Valley 450 < λ ≤ 510 | | Red Peak 500 < λ ≤ 780 | |
|---|---|---|---|---|---|---|
| | λ | Bp | λ | Bv | λ | Rp |
| Red Channel 11 | 461 | 0.05898 | 488 | 0.02327 | 649 | 1 |
| Red Channel 3 | 449 | 0.18404 | 497 | 0.00309 | 640 | 1 |
| Red Channel 4 | 461 | 0.07759 | 495 | 0.01753 | 618 | 1 |
| Red Channel 5 | 453 | 0.07508 | 494 | 0.00374 | 628 | 1 |
| Red Channel 6 | 449 | 0.18404 | 497 | 0.00309 | 640 | 1 |
| Red Channel 9 | 461 | 0.07737 | 489 | 0.03589 | 645 | 1 |
| Red Channel 10 | 461 | 0.06982 | 489 | 0.02971 | 645 | 1 |
| Red Channel 1 | 445 | 0.01599 | 477 | 0.00353 | 649 | 1 |
| Red Channel 12 | 445 | 0.01217 | 477 | 0.00203 | 649 | 1 |
| Red Channel 13 | 451 | 0.06050 | 479 | 0.01130 | 651 | 1 |
| Red Channel 14 | 449 | 0.06020 | 485 | 0.00612 | 653 | 1 |
| Red Channel 15 | 445 | 0.02174 | 477 | 0.00326 | 649 | 1 |
| Red Channel 16 | 450 | 0.03756 | 483 | 0.00388 | 643 | 1 |
| Red Channel 17 | 450 | 0.03508 | 485 | 0.00425 | 641 | 1 |
| Exemplary Red Channels Minimum | 445 | 0.01217 | 477 | 0.00203 | 618 | 1 |
| Exemplary Red Channels Average | 452 | 0.06930 | 487 | 0.01076 | 643 | 1 |
| Exemplary Red Channels Maximum | 461 | 0.18404 | 497 | 0.03589 | 653 | 1 |

TABLE 43

| | Ratios | | |
|---|---|---|---|
| | Bp/Bv | Bp/Rp | Rp/Bv |
| Red Channel 11 | 2.5 | 0.059 | 43.0 |
| Red Channel 3 | 59.5 | 0.184 | 323.3 |
| Red Channel 4 | 4.4 | 0.078 | 57.1 |
| Red Channel 5 | 20.1 | 0.075 | 267.7 |
| Red Channel 6 | 59.5 | 0.184 | 323.3 |
| Red Channel 9 | 2.2 | 0.077 | 27.9 |
| Red Channel 10 | 2.4 | 0.070 | 33.7 |
| Red Channel 1 | 4.5 | 0.016 | 283.3 |
| Red Channel 12 | 6.0 | 0.012 | 493.0 |
| Red Channel 13 | 5.4 | 0.061 | 88.5 |
| Red Channel 14 | 9.8 | 0.060 | 163.4 |
| Red Channel 15 | 6.7 | 0.022 | 306.3 |
| Red Channel 16 | 9.7 | 0.038 | 257.7 |
| Red Channel 17 | 8.3 | 0.035 | 235.5 |
| Exemplary Red Channels Minimum | 2.156 | 0.012 | 27.864 |
| Exemplary Red Channels Average | 14.349 | 0.069 | 207.398 |
| Exemplary Red Channels Maximum | 59.501 | 0.184 | 492.975 |

TABLE 44

| | 320 < λ ≤ 400 | 400 < λ ≤ 500 | 500 < λ ≤ 600 | 600 < λ ≤ 700 | 700 < λ ≤ 800 | 800 < λ ≤ 900 | 900 < λ ≤ 1000 |
|---|---|---|---|---|---|---|---|
| Long-Red Phosphor 675 nm | 0.25 | 0.82 | 3.08 | 100.00 | 44.06 | 1.09 | 0.00 |
| Long-Red Phosphor 700 nm | 0.01 | 1.28 | 1.66 | 100.00 | 110.30 | 5.36 | 0.00 |

TABLE 45

| | 320 < λ ≤ 380 | 380 < λ ≤ 420 | 420 < λ ≤ 460 | 460 < λ ≤ 500 | 500 < λ ≤ 540 | 540 < λ ≤ 580 | 580 < λ ≤ 620 | 620 < λ ≤ 660 |
|---|---|---|---|---|---|---|---|---|
| Long-Red Phosphor 675 nm | 0.2 | 1.0 | 0.9 | 0.8 | 0.8 | 2.3 | 20.2 | 100.0 |
| Long-Red Phosphor 700 nm | 0.0 | 1.2 | 2.2 | 2.0 | 1.8 | 2.0 | 12.1 | 100.0 |

| | 660 < λ ≤ 700 | 700 < λ ≤ 740 | 740 < λ ≤ 780 | 780 < λ ≤ 820 | 820 < λ ≤ 860 | 860 < λ ≤ 900 | 900 < λ ≤ 1000 |
|---|---|---|---|---|---|---|---|
| Long-Red Phosphor 675 nm | 145.6 | 81.9 | 28.1 | 7.4 | 0.4 | 0.0 | 0.0 |
| Long-Red Phosphor 700 nm | 314.0 | 304.1 | 134.9 | 41.7 | 8.7 | 0.0 | 0.0 |

TABLE 46

| | 320 < λ ≤ 340 | 340 < λ ≤ 360 | 360 < λ ≤ 380 | 380 < λ ≤ 400 | 400 < λ ≤ 420 | 420 < λ ≤ 440 | 440 < λ ≤ 460 | 460 < λ ≤ 480 | 480 < λ ≤ 500 | 500 < λ ≤ 520 | 520 < λ ≤ 540 | 540 < λ ≤ 560 |
|---|---|---|---|---|---|---|---|---|---|---|---|---|
| Long-Red Phosphor 675 nm | 0.0 | 0.0 | 0.2 | 0.8 | 0.7 | 0.7 | 0.7 | 0.6 | 0.6 | 0.6 | 0.6 | 1.0 |
| Long-Red Phosphor 700 nm | 0.0 | 0.0 | 0.0 | 0.1 | 1.6 | 1.6 | 1.5 | 1.4 | 1.4 | 1.3 | 1.3 | 1.3 |

| | 560 < λ ≤ 580 | 580 < λ ≤ 600 | 600 < λ ≤ 620 | 620 < λ ≤ 640 | 640 < λ ≤ 660 | 660 < λ ≤ 680 | 680 < λ ≤ 700 | 700 < λ ≤ 720 | 720 < λ ≤ 740 | 740 < λ ≤ 760 | 760 < λ ≤ 780 | 780 < λ ≤ 800 |
|---|---|---|---|---|---|---|---|---|---|---|---|---|
| Long-Red Phosphor 675 nm | 2.7 | 7.9 | 24.2 | 58.6 | 100.0 | 121.2 | 109.6 | 79.7 | 50.2 | 28.9 | 15.7 | 7.9 |
| Long-Red Phosphor 700 nm | 1.6 | 4.3 | 12.5 | 38.2 | 100.0 | 187.6 | 246.3 | 238.7 | 181.5 | 117.4 | 69.0 | 38.2 |

| | 800 < λ ≤ 820 | 820 < λ ≤ 840 | 840 < λ ≤ 860 | 860 < λ ≤ 880 | 880 < λ ≤ 900 | 900 < λ ≤ 920 | 920 < λ ≤ 940 | 940 < λ ≤ 960 | 960 < λ ≤ 980 | 980 < λ ≤ 1000 |
|---|---|---|---|---|---|---|---|---|---|---|
| Long-Red Phosphor 675 nm | 3.9 | 0.4 | 0.2 | 0.0 | 0.0 | 0.0 | 0.0 | 0.0 | 0.0 | 0.0 |
| Long-Red Phosphor 700 nm | 19.4 | 9.7 | 2.3 | 0.0 | 0.0 | 0.0 | 0.0 | 0.0 | 0.0 | 0.0 |

TABLE 47

| Relative Intensities | | | | | | | | | | | | |
|---|---|---|---|---|---|---|---|---|---|---|---|---|
| 6500K White Channel | Long-Red Channel A | Lime Channel | x | y | CCT | duv | Ra | R9 | R13 | R15 | LER | COI |
| 0.8865 | 1 | 0.1293 | 0.3449 | 0.3519 | 5008.78 | 0.23 | 88.4 | 84.75 | 88.44 | 92.55 | 192.48 | 3.49 |
| 0.5303 | 1 | 0.1293 | 0.3608 | 0.3653 | 4509.54 | 0.87 | 88.54 | 89.8 | 90.42 | 96.75 | 169.13 | 2.17 |
| 0.2955 | 1 | 0.1135 | 0.3811 | 0.3787 | 3996.84 | 0.72 | 87.37 | 58.57 | 94.39 | 93.81 | 143.52 | 4.68 |
| 0.1557 | 1 | 0.095 | 0.4044 | 0.3909 | 3520.12 | 0.27 | 84.46 | 26.26 | 98.67 | 83.99 | 120.72 | 8.27 |
| 0.58 | 1 | 0.0712 | 0.4361 | 0.4018 | 2995.9 | −0.77 | 77.86 | −10.82 | 91.38 | 70.48 | 97.24 | 12.64 |

| GAI | GAI 15 | GAI_BB from Xicato | circadian power [mW] | circadian flux | CER (Circadian power per flux) [mW/lm] | CAF | EML | CLA | CS | Rf | Rg |
|---|---|---|---|---|---|---|---|---|---|---|---|
| 89.3918 | 247.7747 | 102.3761 | 200.0924 | 68.83046 | 135.0304 | 0.688305 | 0.818667 | 1036 | 0.5350 | 77 | 113 |
| 86.36168 | 237.7839 | 104.7505 | 187.755 | 61.27427 | 105.8975 | 0.612743 | 0.749807 | 845 | 0.5050 | 82 | 108 |
| 82.4943 | 224.7706 | 108.289 | 174.3035 | 53.37002 | 78.47837 | 0.5337 | 0.675682 | 647 | 0.4610 | 84 | 105 |
| 76.99131 | 207.4282 | 112.2712 | 160.6609 | 45.65426 | 56.59859 | 0.456543 | 0.601369 | 456 | 0.3980 | 85 | 102 |
| 68.36505 | 181.6168 | 118.6679 | 144.515 | 37.06582 | 37.09475 | 0.370658 | 0.514983 | 944 | 0.5220 | 85 | 100 |

| BLH | CP | MSI |
|---|---|---|
| 685.0497 | 589.8182 | 0.6360303 |
| 598.308 | 508.7375 | 0.571554 |
| 509.4471 | 424.6709 | 0.5047331 |
| 424.4634 | 343.3108 | 0.4400915 |
| 333.168 | 254.066 | 0.3692386 |

TABLE 48

| 6500K White Channel | Long-Red Channel B | Lime Channel | x | y | CCT | duv | Ra | R9 | R13 | R15 | LER | COI |
|---|---|---|---|---|---|---|---|---|---|---|---|---|
| 1 | 0.1346 | 0.0396 | 0.3219 | 0.3314 | 6007.86 | −0.08 | 83.53 | 17.69 | 84.14 | 79.56 | 277.79 | 11.37 |
| 1 | 0.248 | 0.844 | 0.3326 | 0.3409 | 5493.5 | −0.09 | 83.69 | 21.07 | 84.14 | 79.93 | 265.75 | 9.93 |
| 1 | 0.409 | 0.1372 | 0.3448 | 0.3508 | 5006.6 | −0.28 | 83.89 | 24.77 | 84.26 | 80.42 | 251.83 | 8.37 |
| 1 | 0.6675 | 0.2296 | 0.3612 | 0.3647 | 4493.04 | 0.43 | 84.17 | 30.16 | 84.36 | 80.48 | 237.51 | 6.59 |
| 0.9156 | 1 | 0.314 | 0.3802 | 0.3778 | 4012.59 | 0.54 | 84.93 | 36.38 | 85.18 | 81.84 | 219.73 | 4.7 |
| 0.5172 | 1 | 0.2639 | 0.405 | 0.3909 | 3507.24 | 0.14 | 86.2 | 44.03 | 86.79 | 83.92 | 197.34 | 2.92 |
| 0.2612 | 1 | 0.2984 | 0.4361 | 0.4029 | 3003.81 | −0.35 | 87.59 | 50.12 | 88.69 | 85.75 | 172.6 | 3.38 |
| 0.1477 | 1 | 0.1768 | 0.4599 | 0.4104 | 2697.76 | 0.06 | 88.14 | 51.34 | 89.44 | 85.98 | 156.99 | 5.13 |
| 0.0712 | 1 | 0.1424 | 0.4847 | 0.4146 | 2416.08 | 0.03 | 88.49 | 50.71 | 89.99 | 85.57 | 141.65 | 7.51 |
| 0 | 1 | 0.1003 | 0.5189 | 0.4161 | 2083.7 | 0.52 | 87.92 | 45.4 | 89.4 | 83.48 | 122.99 | 11.29 |

| GAI | GAI 15 | GAI_BB from Xicato | circadian power [mW] | circadian flux | CER(Circadian power per flux) [mW/lm] | CAF (Circadian action factor | EML |
|---|---|---|---|---|---|---|---|
| 80.57328 | 223.6145 | 98.74652 | 184.8974 | 60.92392 | 150.7386 | 0.609239 | 0.73978 |
| 89.00904 | 248.8449 | 94.32858 | 219.2939 | 81.08612 | 229.4777 | 0.810861 | 0.927833 |
| 87.26652 | 243.1491 | 95.83119 | 209.1279 | 75.06076 | 204.6299 | 0.750608 | 0.872042 |
| 85.06854 | 236.2083 | 97.61831 | 198.4347 | 68.86227 | 179.2151 | 0.688623 | 0.813802 |
| 75.36568 | 209.2179 | 100.4704 | 171.0594 | 53.1747 | 122.7729 | 0.531747 | 0.665282 |
| 68.27042 | 190.0996 | 103.2834 | 155.1128 | 44.71606 | 93.63939 | 0.447161 | 0.58094 |
| 58.35771 | 164.1613 | 106.8799 | 137.1443 | 35.7349 | 66.11522 | 0.357349 | 0.487668 |
| 49.46872 | 141.1403 | 107.4254 | 124.2603 | 29.50503 | 49.96062 | 0.29505 | 0.421466 |
| 40.30136 | 116.8644 | 107.9179 | 111.5604 | 23.83105 | 36.61357 | 0.238311 | 0.35771 |
| 27.3726 | 80.81314 | 103.4908 | 94.56875 | 16.80205 | 22.55986 | 0.168021 | 0.27422 |

| CLA | Circadian Stimulus (CS) | Rf | Rg | BLH | CP | MSI |
|---|---|---|---|---|---|---|
| 1350 | 0.569 | 81 | 95 | 596.6085 | 515.0455 | 0.5634632 |
| 1199 | 0.555 | 81 | 96 | 826.8956 | 724.4693 | 0.7392685 |
| 1044 | 0.536 | 82 | 96 | 757.7669 | 661.628 | 0.6867125 |
| 845 | 0.505 | 82 | 96 | 687.2929 | 597.513 | 0.6326828 |
| 654 | 0.463 | 83 | 98 | 509.7835 | 435.9521 | 0.4959888 |
| 450 | 0.395 | 84 | 99 | 417.305 | 351.5219 | 0.4224674 |
| 901 | 0.515 | 85 | 101 | 321.9402 | 264.2208 | 0.3445643 |
| 770 | 0.491 | 85 | 102 | 256.9346 | 204.6135 | 0.2905909 |
| 647 | 0.461 | 84 | 103 | 200.3619 | 152.5087 | 0.2415826 |
| 488 | 0.41 | 81 | 103 | 133.7106 | 90.80759 | 0.1810649 |

Control Systems.

As illustrated in FIG. 28, various lighting systems and control system exemplars an aspects thereof may be implemented in accordance with the present disclosure. Although aspects of methods, systems and devices are discussed below, but it will be appreciated that the disclosure is not limited to those particular configurations, and may be applied to any combination of devices, computing systems, control systems, data centers, structures, and the like.

At a simplified level aspects of the system and method disclosed herein include utilizing hardware referred to as computing or smart devices which may include internet streaming, desktop computers, laptops, tablets, smart phones, and sensors, to acquire, receive, measure or otherwise capture and then transmit via signal communication data associated with biological aspects of a user or data concerning the exposure of a user to variables discussed herein.

It is appreciated by those of ordinary skill in the art that some of the circuits, components, modules, and/or devices of the system disclosed in the present application are described as being in signal communication with each other, where signal communication refers to any type of communication and/or connection between the circuits, components, modules, and/or devices that allows a circuit, component, module, and/or device to pass and/or receive signals and/or information from another circuit, component, module, and/or device. The communication and/or connection may be along any signal path between the circuits, components, modules, and/or devices that allows signals and/or information to pass from one circuit, component, module, and/or device to another and includes wireless or wired signal paths. The signal paths may be physical such as, for example, conductive wires, electromagnetic wave guides, attached and/or electromagnetic or mechanically coupled terminals, semi-conductive or dielectric materials or devices, or other similar physical connections or couplings. Additionally, signal paths may be non-physical such as free-space (in the case of electromagnetic propagation) or information paths through digital components where communication information is passed from one circuit, component, module, and/or device to another in varying analog and/or digital formats without passing through a direct electromagnetic connection. These information paths may also include analog-to-digital conversions ("ADC"), digital-to-analog ("DAC") conversions, data transformations such as, for example, fast Fourier transforms ("FFTs"), time-to-frequency conversations, frequency-to-time conversions, database mapping, signal processing steps, coding, modulations, demodulations, etc.

An integrated control system can connect one or more external systems, input, and information to provide bioactive lighting, as discussed herein, through a plurality of devices, systems, and modalities. In various examples, the control system may communicate over one or more computing systems using one or more servers and networks in communication with one another (e.g., network, Bluetooth, wired, wireless communication, etc.).

In some embodiments, lighting systems associated with each device may be managed by a master device 3340, configured to communicate various lighting levels, timing, and configuration, for example, to achieve the desired bioactive lighting. Such levels may vary based on one or more of time of day, intended effect of the lighting, individual preferences, capabilities of the device, feedback mechanisms, sensor input, and more.

As illustrated in FIG. 28, control systems may comprise a variety of devices, including but not limited to panels and panel systems 3310, computing systems 3320, laptops, mobile devices 3330, wearable devices 3333, sensors 3335, lighting systems including but not limited to home, office, vehicle, and industrial lighting systems. The master device 3340 may be a mobile device, computing systems, as discussed further below, and may be manually managed, automated, incorporated with machine learning, located in the cloud, and more.

In an example, lighting systems that may be used in a bioactive device including but not limited to wearable devices 3333, computer display system and/or bioactive panel system 3310 in accordance with the principles of the present disclosure may be controlled over time to supplement, treat or otherwise effect biological system and cycles of an exposed user throughout the day in different ways. The lighting systems may be automatically, semi-automatically or manually adjusted. The lighting systems may be adjusted based on sensor data, activity data, social media data, etc.

In some embodiments, as the panel 3310 systems are installed in the environment of a lighting installation, networking features automatically engage upon powering up one or more the panel systems, and the panel systems may automatically commission themselves, such as by connecting to an overall control platform and/or to other panel systems. Thus, the panel systems in an installation may self-commission and self-configure to create a network connection between the panel systems in the environment and a remote operator (such as in the cloud). The panel systems may configure in a master/slave, ring, mesh, or peer-to-peer network, by which autonomous control features may be engaged in the environment. In embodiments, remote control features may be engaged using the network connection to the platform or other remote operators.

In some embodiments, networked communication can be used among components in the control system 3000 in a deployed lighting installation that includes panel systems. Once installed and commissioned, control of the lighting installation may be handed over to an operator of a platform, such as a building owner, occupant, landlord, tenant, or the like. In embodiments, handoff may include using identity and authentication features, such as using keys, passwords, or the like that allow operation of the lighting installation by permitted users. In some embodiments, a remote-control interface of the platform may be used by an operator for remote operation of the lighting installation. The remote-control interface may use a lighting project data structure as a source of knowledge about the properties, configurations, control capabilities, and other elements of a lighting installation, so that the same platform used for the design of the lighting installation may be used to control the lighting installation. The remote-control interface may include operational guidance features, such as guiding users through the operation of a lighting installation.

In some embodiments, an autonomous control system may be provided for a lighting installation that includes panel systems of the present disclosure, by which the lighting installation may control various features of the lighting system, such as based on information collected locally in the environment, such as from one or more sensors 3330. For example, the autonomous control system may automatically adjust control parameters for a light source, including but not limited to panel systems, to achieve improved adherence to the overall specifications for a lighting installation, may adjust timing variables based on detected usage patterns in a space, may adjust lighting properties based on changes in a space (such as changes in colors paints, carpet and fabrics), and the like.

Under operation, the lighting installation may include an operational feedback system, configured to collect information about the lighting installation, which may include interfaces for soliciting and receiving user feedback (such as regarding satisfaction with the installation or indicating desired changes) and which may include a sensor system 3330, e.g., a lighting installation sensor system, such as including light sensors, motion sensors, temperature sensors, and others to collect information about the actual lighting conditions in the environment, activities of occupants within the environment, and the like. Information collected by the lighting installation sensor system may be relayed to a validation system of the lighting platform, such as for validation that an installation is operating as designed, including by comparison of light properties at various locations in the environment with the specifications and requirements provided in the lighting design environment, such as reflected in the lighting project data structure. In embodiments, the variances from the specifications and requirements may be provided to the autonomous control system and/or the remote-control system, so that adjustments may be made, either autonomously or by a local or remote operator of the lighting installation, to enable adjustments (such as to colors, intensities, color temperatures, beam directions, and other factors), such as to cause the lighting installation to better meet the specifications and requirements. The operational feedback system may also capture feedback that leads to revisiting the lighting design in the lighting design environment, which may induce further iteration, resulting in changes to control parameters for the panel systems, as well as automated ordering of additional or substitute panel systems, with updated installation and operational guidance.

In some embodiments, remote control may enable field programmable lighting systems, such as for transitional environments like museums (where art objects change regularly), stores (where merchandise shifts) and the like as well as for customizable environments (such as personalizing lighting in a hotel room according to a specification for a guest (which may include having the guest select an aesthetic filter) or personalized lighting for a workstation for an employee in an office setting, or personalized wearable systems. Such features may enable the lighting installation to change configurations (such as among different aesthetic filters) for multi-use environments, multi-tenant environments, and the like where lighting conditions may need to change substantially over time.

In some embodiments, a lighting system may include navigation features, such as being associated with beacons, where the lighting system interacts with one or more devices to track users within a space. The panel systems and their locations may be associated with a map, such as the map of the lighting space in the design environment. The map may be provided from the lighting design environment to one or more other location or navigation systems, such that locations of panel systems may be used as known locations or points of interest within a space.

In some embodiments, the lighting installation may be designed for an operation that is coordinated with one or more external systems, e.g., lighting, panel, and computer systems, which may serve as inputs to the lighting installation, such as music, video and other entertainment content (such as to coordinate lighting with sound). Inputs may include voice control inputs, which may include systems for assessing tone or mood from vocal patterns, such as to adjust lighting based on the same.

With respect to FIGS. 26-28 external systems can include, but are not limited to one or more computing environments, networks, local devices, remote devices, mobile devices, and wearable technology. In addition, each of those systems may provide the external input utilizable with control systems and embodiments discussed herein. For example, external inputs may include, but are not limited to audible, tactile, sensory, and user information through one or more sensors and other means, depending on the external system and its capabilities. As used herein, external systems and external information may also comprise the same types systems and information discussed below and in various embodiments herein.

In some embodiments, inputs may also include inputs from sensors associated with wearable devices 3330, such as enabling adjustment of lighting control parameters (autonomously or with remote or local control features) based on physiological factors, such as ones indicating health conditions, emotional states, moods, or the like. Inputs from wearable devices may be used in the operational feedback system, such as to measure reactions to lighting conditions (such as to enable automated adjustment of alighting installation), as well as to measure impacts on mood, health conditions, energy, wellness factors, and the like.

In some embodiments, the platform may be configured to change settings or parameters for a lighting installation (including but not limited to panel systems of the present disclosure, such as by using a custom tuning system) based on a variety of real time data, with a view to having the lighting installation, including panel systems included therein, best suit its environment in a dynamic way. In embodiments, data may be obtained that serves as an indicator of the emotional state or the stress level of an environment, and the lighting installation may respond accordingly to that state or stress level. In embodiments, data about the environment may be collected by a wearable device 3333, such as a smartwatch, armband, or the like; for example, data may be collected on acceleration, location, ambient light characteristics, and heart rate, among other possibilities. In embodiments, the data may be provided to the platform for analysis, including using machine learning, such as to observe physiological indicators of stress, mood, or the like under given lighting conditions. The analysis may enable model-based controls (such as where a given mood or state of the users in a room are linked to a set of control parameters appropriate for that state). In embodiments, machine learning may be used; for example, over time, by variation of parameters for lighting objects and fixtures (such as color, color temperature, illumination patterns, lighting distributions, and many others), a machine learning system may, using feedback on outcomes based at least in part on physiological data and other data collected by a wearable device, select and/or promotion lighting installation parameters that improve various measures of stress, mood, satisfaction, or the like. This may occur in real time under control of a machine learning system based on the current conditions of users or the environment. In embodiments, data collected at least in part by a physiological monitor or wearable device may be used as an input to processing logic on a lighting object that changes lighting levels or other parameters to accommodate the 'emotional state' of the users in an environment where the lighting object is located. In embodiments, there is memory that retains and manages function with no appreciable drain on the battery.

In some embodiments, inputs may include systems that take data harvested from sensors 3335 in the lighting installation environment as well as sensors that reflect information about users, such as one or more of physiological sensors (including wearable devices, such as armbands, wrist bands, chest bands, glasses, clothing, and the like), sensors on various devices used by a user, ambient sensors, and the like. These may include sensing one or more of temperature, pressure, ambient lighting conditions, localized lighting conditions, lighting spectrum characteristics, humidity, UV light, sound, particles, pollutants, gases (e.g., oxygen, carbon dioxide, carbon monoxide and radon), radiation, location of objects or items, motion (e.g., speed, direction and/or acceleration). Where one or more wearable or physiological sensors are used, they may sense one or more of a person's temperature, blood pressure, heart rate, oxygen saturation, activity type, activity level, galvanic skin response, respiratory rate, cholesterol level (including HDL, LDL and triglyceride), hormone or adrenal levels (e.g., Cortisol, thyroid, adrenaline, melatonin, and others), histamine levels, immune system characteristics, blood alcohol levels, drug content, macro and micro nutrients, mood, emotional state, alertness, sleepiness, and the like.

In some embodiments, the platform may connect to or integrate with data sources of information about users, such as including social networks (Facebook™, LinkedIn™, Twitter™, and the like, sources of medical records (23&Me™ and the like), productivity, collaboration and/or calendaring software (Googler-m, Outlook™, scheduling apps and the like), information about web browsing and/or shopping activity, activity on media streaming services (Netflix™, Spotify™, YouTube™, Pandora™ and the like), health record information and other sources of insight about the preferences or characteristics of users of the space of a lighting installation, including psychographic, demographic and other characteristics.

In some embodiments, the platform may use information from sources that indicate patterns, such as patterns involving periods of time (daily patterns, weekly patterns, seasonal patterns, and the like), patterns involving cultural factors or norms (such as indicating usage patterns or preferences in different regions), patterns relating to personality and preferences, patterns relating to social groups (such as family and work group patterns), and the like. In embodiments, the platform may make use of the data harvested from various sources noted above to make recommendations and/or to optimize (such as automatically, under computer control) the design, ordering, fulfillment, deployment and/or operation of a lighting installation, such as based on understanding or prediction of user behavior. This may include recommendation or optimization relating to achieving optimal sleep time and duration, setting optimal mealtimes, satisfying natural light exposure requirements during the day, and maintaining tolerable artificial light exposure levels (such as during night time). In some embodiments, the platform may anticipate user needs and optimize the lighting installation to enhance productivity, alertness, emotional well-being, satisfaction, safety and/or sleep. In further embodiments, the platform may control one or more panel systems of the present disclosure in accordance with the user needs of the environment based on this information.

In some embodiments, the platform may store a space utilization data structure that indicates, over time, how people use the space of the lighting installation, such as indicating what hallways are more trafficked, and the like. This may inform understanding of a space, such as indicating what is an entry, what is a passage, what is a workspace, and the like, which may be used to suggest changes or updates to a lighting design. In embodiments, sensors may be used to collect and read where people have been in the space, such as using one or more video cameras, IR sensors, microwave sensors. LIDAR, ultrasound or the like. In embodiments, the platform may collect and read what adjustments people have made, such as task lamp activation and other activities that indicate how a lighting fixture is used by an individual in a space. By way of these examples, aggregate usage information may be used to optimize a lighting design and adjust other lighting designs. Based on these factors, a space may be dynamically adjusted, and the lighting model for an installation may be updated to reflect the actual installation.

In some embodiments, control capabilities of the panel systems may include dynamic configuration of control parameters, such as providing a dimming curve for a light source, including but not limited to a panel system of the present disclosure, that is customized to the preferences of a designer or other user. This may include a selection from one or more modes, such as ones described elsewhere herein that have desired effects on mood or aesthetic factors, that have desired health effects, that meet the functional requirements, or the like.

Bioactive thresholds may, in some instances, benefit from prolonged exposure to at least one of one of CSE and LRNE. In some instances a melanopic flux of at least 10:1 may be suitable, in other instances the melanopic flux may be 20:1, 50:1, 100:1, or a greater ratio. It will be appreciated in light of the disclosure that traditional systems simply adjust from a warm CCT to a cool CCT, which may only provide a 2:1 or 3:1 ratio of melanopic flux, which are below said threshold. In some implementations, the platform may include spectral tuning targets for panel systems of the present disclosure that may optimize this ratio based on local installation environments. These targets, in a first operational mode along with adjustments intensity of light (e.g., 4:1) may provide a higher ratio, such as a 10:1 ratio or greater, and thus provide greater melanopic flux ratios.

In a second operational mode and either in combination with the above mode or not, the platform may support an ability to shift the bias of light in a room. In embodiments, controlled variation of one or more panel systems of the present disclosure in a lighting environment can contribute to generating a lighting bias typical of being outside.

In some implementations, various other programmable modes may be provided, such as bioactive panel system settings where using different combinations of color light sources to achieve a given mixed color output may be optimized for efficacy, efficiency, color quality, health impact (e.g., circadian action and/or LRNE action), or to satisfy other requirements. In embodiments, the programmable modes may also include programmable dimming curves, color tuning curves, and the like (such as allowing various control interfaces, such as extra-low voltage (ELV) controllers or voltage-based dimmers to affect fixture colors, such as where a custom tuning curve provides a start point, an end point and a dimming and/or color tuning path in response to a level of dimming). In embodiments, programmable modes may use conventional tuning mechanisms, such as simple interpolation systems (which typically use two or three white color LEDs) are dimmable on a zero to ten-volt analog system, and have a second voltage-based input for adjusting the CCT of a fixture between warm and cool CCTs. The bioactive panel systems as described herein can provide for tunable ranges of color points at various x, y coordinates on the 1931 CIE chromaticity diagram. Because of the wide range of potential white or non-white colors produced by the panel systems, they may be controlled by the platform that may specify a particular x, y coordinate on the CIE diagram. Lighting control protocols like DMX™ and Dali 2.0™ may achieve this result.

In some implementations the control system described herein controls output of at least one CSE and LRNE. In some embodiments a programmable color curve for an LED driver may be input, such as through an interface of the platform, or through a desktop software interface, a mobile phone 3330, a tablet app, or the like, that enables a user to define a start and stop point to a color tuning curve and to specify how it will be controlled by a secondary input, such as a voltage-based input (e.g., a 0 to 10-volt input) to the fixture. These may include pre-defined curves, as well as the ability to set start, end, and waypoints to define custom curves. For example, an exemplary color curve can have a starting point around 8000 K biased above the black body curve, with the color curve crossing the black body around 2700 K, and finishing around 1800 K below the black body curve. Similarly, another exemplary curve could be programmed such that the start was 4000 K well above the black body, with the end being 4000 K well below the black body. By way of these examples, any adjustment would be in hue only, not CCT. Further examples may include a curve that never produces a white color, such as starting in the purple and finishing in orange. In any of these cases, these curves may be programmed into panel systems via the interface of the platform, the desktop, mobile phone or tablet. In embodiments, the curves may be designed, saved, and then activated, such as using the secondary (supplemental) 0 to 10-volt input.

In some implementations, a three-channel warm dim operational mode may be used, such as that described more fully in U.S. Provisional Patent Application No. 62/712,182 filed Jul. 30, 2018, which is incorporated herein in its entirety for all purposes, for target applications w % here the "fully on" CCT falls between 3000 K and 2500 K. By way of these examples, as the fixture dims (via ELV control or in response to the 0 to 10-volt input) the CCT may be gradually decreased to between 2500 K and 1800 K. In certain embodiments, the hue adjustment may all occur below the black body curve. Alternative embodiments may use a cyan channel as described elsewhere herein, either long-blue-pumped cyan or short-blue-pumped cyan, and a red channel which may be LRNE with cyan pumped near infrared as described elsewhere herein, plus a 4000 K white channel as described elsewhere herein to achieve a warm dimming operational mode that allows for adjustment both above and below the black body curve. In some embodiments of the three-channel warm dim mode, the white channel can have a color point within a 7-step MacAdam ellipse around any point on the black body locus having a correlated color temperature between about 3500 K and about 6500 K.

In some implementations, the panel systems of the present disclosure can include a 4-channel color system as described elsewhere herein and in U.S. Provisional Patent Application No. 62/757,672 filed Nov. 8, 2018, and U.S. Provisional Application No. 62/712,191 filed Jul. 30, 2018, the contents of which are incorporated by reference herein in their entirety as if fully set forth herein, includes 3000 K to 1800 K CCT white color points within its range, a programmable mode may be included within the driver that adjusts color with the dimming percentage as well. In some aspects, this may be similar to a conventional control mode, except that the color control would not be on the secondary 0 to 10-volt channel, but may be activated through the primary 0 to 10-volt input channel or ELV controller. In embodiments, the "starting" color point may be the one when the fixture was "fully on." In embodiments, the "ending" color point may be the one where the fixture is maximally dimmed. It is thus possible to make full range color change, such as purple to orange, which is slaved to the 0 to 10-volt or ELV dimming signal.

In some implementations, an optimized mode may be provided. With a 4-channel color system, there are many ways to create a single x-y point on the CIE diagram. In embodiments, the maximally efficient mode may typically be one that uses the colors that have x, y coordinates closest to the target x, v coordinate. But for best color quality, utilizing a fourth channel (and thereby requiring more light from the color in the opposite "corner") may help provide a desired spectral power distribution. For the maximum melatonin suppression (for systems hoping to mimic circadian lighting), a higher cyan channel content may be required for CCTs of 3500 K and above and minimizing cyan and blue content below 3500 K. It will be appreciated in light of the disclosure that conventional systems either require expert users to understand the color balances necessary to achieve these effects (who then implement the color balances channel-by-channel) or are designed for maximum efficiency with color quality as a byproduct.

In some implementations, a digital power system is provided herein (including firmware-driven power conversion and LED current control) that controls a multichannel color system, such as a 4-channel color system, and allows for the inclusion of "modes" which may calculate the correct color balance between the various channels to provide optimized outputs. In embodiments, optimization may occur around one or more of efficacy, color quality, circadian effects, LRNE effects, and other factors. Other modes are possible, such as optimizing for contrast, particular display requirements. It will be appreciated in light of the disclosure that this is not an exhaustive list but is representative of potential modes that could be engaged through an interface of the platform (or of a mobile, tablet or desktop application) where a color tuning curve may be specified, such that the curve is used to specify an interface between a controller and the Digital PSU in a panel system. In embodiments, these modes may account for actual measured colors for each panel system and calculate the correct balance of for the chosen modes, such as based on algorithms loaded into the Digital PSU microprocessor.

In some implementations, machine learning may be used, such as based on various feedback measures, such as relating to mood (stated by the user or measured by one or more sensors), noise levels (such as indicating successful utilization of a space based on a desired level of noise), returns on investment (such as where panel systems are intended to promote retail merchandise), reported pain levels, measured health levels, performance levels of users (including fitness, wellness, and educational performance, among others), sleep levels, vitamin D levels, melatonin levels, and many others. In embodiments, the lighting installations including the panel systems may be operated or controlled based on external information, such as based on seasonal lighting conditions, weather, climate, collective mood indicators (such as based on stock market data, news feeds, or sentiment indices), analyses of social network data, and the like. This may include controlling a system to reflect, or influence, the mood of occupants.

FIG. 26 depicts an example computing environment 3000 suitable for implementing aspects of the embodiments of the present disclosure, including the control system, which can integrate one or more devices, computing, and lighting systems. As utilized herein, the phrase "computing system" generally refers to a dedicated computing device with processing power and storage memory, which supports operating software that underlies the execution of software, applications, and computer programs thereon. As used herein, an application is a small, in storage size, specialized program that is downloaded to the computing system or device. In some cases, the application is downloaded from an "App Store" such as APPLE's APP STORE or GOOGLE's ANDROID MARKET. After download, the application is generally installed on the computer system or computing device. As shown by FIG. 26, computing environment 3000 includes bus 3010 that directly or indirectly couples the following components: memory 3020, one or more processors 3030. I/O interface 3040, and network interface 3050. Bus 3010 is configured to communicate, transmit, and transfer data, controls, and commands between the various components of computing environment 3000.

Computing environment 3000 typically includes a variety of computer-readable media. Computer-readable media can be any available media that is accessible by computing environment 3000 and includes both volatile and nonvolatile media, removable and non-removable media. Computer-readable media may comprise both computer storage media and communication media. Computer storage media does not comprise, and in fact explicitly excludes, signals per se.

Computer storage media includes volatile and nonvolatile, removable and non-removable, tangible and non-transient media, implemented in any method or technology for storage of information such as computer-readable instructions, data structures, program modules or other data. Computer storage media includes RAM; ROM: EE-PROM; flash memory or other memory technology: CD-ROMs; DVDs or other optical disk storage: magnetic cassettes, magnetic tape, magnetic disk storage or other magnetic storage devices: or other mediums or computer storage devices which can be used to store the desired information and which can be accessed by computing environment 3000.

Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, communication media includes wired media, such as a wired network or direct-wired connection, and wireless media, such as acoustic, RF, infrared and other wireless media. Combinations of any of the above should also be included within the scope of computer-readable media.

Memory 3020 includes computer-storage media in the form of volatile and/or nonvolatile memory. The memory may be removable, non-removable, or a combination thereof. Memory 3020 may be implemented using hardware devices such as solid-state memory, hard drives, optical-disc drives, and the like. Computing environment also includes one or more processors 3030 that read data from various entities such as memory 3020, I/O interface 3040, and network interface 3050.

I/O interface 3040 enables computing environment 3000 to communicate with different input devices and output devices. Examples of input devices include a keyboard, a pointing device, a touchpad, a touchscreen, a scanner, a microphone, a joystick, and the like. Examples of output devices include a display device, an audio device (e.g., speakers), a printer, and the like. These and other I/O devices are often connected to processor 3010 through a serial port interface that is coupled to the system bus, but may be connected by other interfaces, such as a parallel port, game port, or universal serial bus (USB). A display device can also be connected to the system bus via an interface, such as a video adapter which can be part of, or connected to, a graphics processor unit. I/O interface is configured to coordinate I/O traffic between memory 3020, the one or more processors 3030, network interface 3050, and any combination of input devices and/or output devices.

Network interface 3050 enables computing environment 3000 to exchange data with other computing devices via any suitable network. In a networked environment, program modules depicted relative to computing environment 3000, or portions thereof, may be stored in a remote memory storage device accessible via network interface 3050. It will be appreciated that the network connections shown are exemplary and other means of establishing a communications link between the computers may be used.

In at least some embodiments, a server that implements a portion or all of one or more of the technologies described herein may include a general-purpose computer system that includes or is configured to access one or more computer-accessible media. FIG. depicts a general-purpose computer system that includes or is configured to access one or more computer-accessible media. In the illustrated embodiment, computing device 3100 includes one or more processors 3110*a*. 3110*b*, and/or 3110*n* (which may be referred herein singularly as a processor 1010 or in the plural as the processors 3110) coupled to a system memory 3120 via an input/output ("I/O") interface 3130. Computing device 3100 further includes a network interface 3140 coupled to I/O interface 3130.

In various embodiments, computing device 3100 may be a uniprocessor system including one processor 3110 or a multiprocessor system including several processors (e.g., two, four, eight, or another suitable number). Processors 3110 may be any suitable processors capable of executing instructions. For example, in various embodiments, processors 3110 may be general-purpose or embedded processors implementing any of a variety of instruction set architectures ("ISAs"), such as the x86. PowerPC, SPARC or MIPS ISAs, or any other suitable ISA. In multiprocessor systems, each of processors 3110 may commonly, but not necessarily, implement the same ISA.

In some embodiments, a graphics processing unit ("GPU") 3112 may participate in providing graphics rendering and/or physics processing capabilities. A GPU may, for example, comprise a highly parallelized processor architecture specialized for graphical computations. In some embodiments, processors 3110 and GPU 3112 may be implemented as one or more of the same type of device.

System memory 3120 may be configured to store instructions and data accessible by processor(s) 3110. In various embodiments, system memory 3120 may be implemented using any suitable memory technology, such as static random-access memory ("SRAM"), synchronous dynamic RAM ("SDRAM"), nonvolatile/Flash®-type memory, or any other type of memory. In the illustrated embodiment, program instructions and data implementing one or more desired functions, such as those methods, techniques, and data described above, are shown stored within system memory 3120 as code 3125 and data 3126.

In one embodiment, I/O interface 3130 may be configured to coordinate I/O traffic between processor 3110, system memory 3120, and any peripherals in the device, including network interface 3140 or other peripheral interfaces. In some embodiments, I/O interface 3130 may perform any necessary protocol, timing or other data transformations to convert data signals from one component (e.g., system memory 3120) into a format suitable for use by another component (e.g., processor 3110). In some embodiments, I/O interface may include support for devices attached through various types of peripheral buses, such as a variant of the Peripheral Component Interconnect ("PCI") bus standard or the Universal Serial Bus ("USB") standard, for example. In some embodiments, the function of I/O interface 3130 may be split into two or more separate components, such as a north bridge and a south bridge, for example. Also, in some embodiments some or all of the functionality of I/O interface 3130, such as an interface to system memory 3120, may be incorporated directly into processor 3110.

Network interface 3140 may be configured to allow data to be exchanged between computing device 3100 and other device or devices 3160 attached to a network or networks 3150, such as other computer systems or devices, for example. In various embodiments, network interface 3140 may support communication via any suitable wired or wireless general data networks, such as types of Ethernet networks, for example. Additionally, network interface 3140 may support communication via telecommunications/telephony networks, such as analog voice networks or digital fiber communications networks, via storage area networks, such as Fibre Channel SANs (storage area networks), or via any other suitable type of network and/or protocol.

In some embodiments, system memory 3120 may be one embodiment of a computer-accessible medium configured to store program instructions and data as described above for implementing embodiments of the corresponding methods and apparatus. However, in other embodiments, program instructions and/or data may be received, sent, or stored upon different types of computer-accessible media. Generally speaking, a computer-accessible medium may include non-transitory storage media or memory media, such as magnetic or optical media, e.g., disk or DVD/CD coupled to computing device 3100 via I/O interface 3130. A non-transitory computer-accessible storage medium may also include any volatile or non-volatile media, such as RAM (e.g., SDRAM, DDR SDRAM, RDRAM. SRAM, etc.), ROM, etc., that may be included in some embodiments of computing device 3100 as system memory 3120 or another type of memory. Further, a computer-accessible medium may include transmission media or signals, such as electrical, electromagnetic or digital signals, conveyed via a communication medium, such as a network and/or a wireless link, such as those that may be implemented via network interface 3140. Portions or all of multiple computing devices, such as those illustrated in FIG. 28, may be used to implement the described functionality in various embodiments; for example, software components running on a variety of different devices and servers may collaborate to provide the functionality. In some embodiments, portions of the described functionality may be implemented using storage devices, network devices or special-purpose computer systems, in addition to or instead of being implemented using general-purpose computer systems. The term "computing device," as used herein, refers to at least all these types of devices and is not limited to these types of devices.

A compute node, which may be referred to also as a computing node, may be implemented on a wide variety of computing environments, such as tablet computers, personal computers, smartphones, game consoles, commodity-hardware computers, virtual machines, web services, computing clusters, and computing appliances. Any of these computing devices or environments may, for convenience, be described as compute nodes or as computing nodes.

A network set up by an entity, such as a company or a public sector organization, to provide one or more web services (such as various types of cloud-based computing or storage) accessible via the Internet and/or other networks to a distributed set of clients may be termed a provider network. Such a provider network may include numerous data centers hosting various resource pools, such as collections of physical and/or virtualized computer servers, storage devices, networking equipment, and the like, needed to implement and distribute the infrastructure and web services offered by the provider network. The resources may in some embodiments be offered to clients in various units related to the web service, such as an amount of storage capacity for storage, processing capability for processing, as instances, as sets of related services, and the like. A virtual computing instance may, for example, comprise one or more servers with a specified computational capacity (which may be specified by indicating the type and number of CPUs, the main memory size, and so on) and a specified software stack (e.g., a particular version of an operating system, which may in turn run on top of a hypervisor).

A number of different types of computing devices may be used singly or in combination to implement the resources of the provider network in different embodiments, including general-purpose or special-purpose computer servers, storage devices, network devices, and the like. In some embodiments a client or user may be provided direct access to a resource instance, e.g., by giving a user an administrator login and password. In other embodiments the provider network operator may allow clients to specify execution requirements for specified client applications and schedule execution of the applications on behalf of the client on execution platforms (such as application server instances, Java™ virtual machines ("JVMs"), general-purpose or special-purpose operating systems, platforms that support various interpreted or compiled programming languages, such as Ruby, Perl, Python, C. C++, and the like, or high-performance computing platforms) suitable for the applications, without, for example, requiring the client to access an instance or an execution platform directly. A given execution platform may utilize one or more resource instances in some implementations: in other implementations multiple execution platforms may be mapped to a single resource instance.

In many environments, operators of provider networks that implement different types of virtualized computing, storage and/or other network-accessible functionality may allow customers to reserve or purchase access to resources in various resource acquisition modes. The computing resource provider may provide facilities for customers to select and launch the desired computing resources, deploy application components to the computing resources, and maintain an application executing in the environment. In addition, the computing resource provider may provide further facilities for the customer to quickly and easily scale up or scale down the numbers and types of resources allocated to the application, either manually or through automatic scaling, as demand for or capacity requirements of the application change. The computing resources provided by the computing resource provider may be made available in discrete units, which may be referred to as instances. An instance may represent a physical server hardware platform, a virtual machine instance executing on a server, or some combination of the two. Various types and configurations of instances may be made available, including different sizes of resources executing different operating systems ("OS") and/or hypervisors, and with various installed software applications, runtimes, and the like. Instances may further be available in specific availability zones, representing a logical region, a fault tolerant region, a data center, or other geographic location of the underlying computing hardware, for example. Instances may be copied within an availability zone or across availability zones to improve the redundancy of the instance, and instances may be migrated within a particular availability zone or across availability zones. As one example, the latency for client communications with a particular server in an availability zone may be less than the latency for client communications with a different server. As such, an instance may be migrated from the higher latency server to the lower latency server to improve the overall client experience.

In some embodiments the provider network may be organized into a plurality of geographical regions, and each region may include one or more availability zones. An availability zone (which may also be referred to as an availability container) in turn may comprise one or more distinct locations or data centers, configured in such a way that the resources in a given availability zone may be isolated or insulated from failures in other availability zones. That is, a failure in one availability zone may not be expected to result in a failure in any other availability zone. Thus, the availability profile of a resource instance is intended to be independent of the availability profile of a resource instance in a different availability zone. Clients may be able to protect their applications from failures at a single location by launching multiple application instances in respective availability zones. At the same time, in some implementations inexpensive and low latency network connectivity may be provided between resource instances that reside within the same geographical region (and network transmissions between resources of the same availability zone may be even faster).

Each of the processes, methods, and algorithms described in the preceding sections may be embodied in, and fully or partially automated by, code modules executed by one or more computers or computer processors. The code modules may be stored on any type of non-transitory computer-readable medium or computer storage device, such as hard drives, solid state memory, optical disc, and/or the like. The processes and algorithms may be implemented partially or wholly in application-specific circuitry. The results of the disclosed processes and process steps may be stored, persistently or otherwise, in any type of non-transitory computer storage, such as, e.g., volatile or non-volatile storage.

The various features and processes described above may be used independently of one another, or may be combined in various ways. All possible combinations and sub-combinations are intended to fall within the scope of this disclosure. In addition, certain methods or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

It will also be appreciated that various items are illustrated as being stored in memory or on storage while being used, and that these items or portions thereof may be transferred between memory and other storage devices for purposes of memory management and data integrity. Alternatively, in other embodiments some or all of the software modules and/or systems may execute in memory on another device and communicate with the illustrated computing systems via inter-computer communication. Furthermore, in some embodiments, some or all of the systems and/or modules may be implemented or provided in other ways, such as at least partially in firmware and/or hardware, including, but not limited to, one or more application-specific integrated circuits ("ASICs"), standard integrated circuits, controllers (e.g., by executing appropriate instructions, and including microcontrollers and/or embedded controllers), field-programmable gate arrays ("FPGAs"), complex programmable logic devices ("CPLDs"), etc. Some or all of the modules, systems, and data structures may also be stored (e.g., as software instructions or structured data) on a computer-readable medium, such as a hard disk, a memory, a network, or a portable media article to be read by an appropriate device or via an appropriate connection. The systems, modules, and data structures may also be transmitted as generated data signals (e.g., as part of a carrier wave or other analog or digital propagated signal) on a variety of computer-readable transmission media, including wireless-based and wired/cable-based media, and may take a variety of forms (e.g., as part of a single or multiplexed analog signal, or as multiple discrete digital packets or frames). Such computer program products may also take other forms in other embodiments. Accordingly, the present invention may be practiced with other computer system configurations.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

While certain example embodiments have been described, these embodiments have been presented by way of example only, and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions and changes in the form of the methods and systems described herein may be made without departing from the spirit of the inventions disclosed herein. The accompanying claims and their equivalents are intended to cover such forms or modifications as would fall within the scope and spirit of certain of the inventions disclosed herein.

Those of ordinary skill in the art will appreciate that a variety of materials can be used in the manufacturing of the components in the devices and systems disclosed herein. Any suitable structure and/or material can be used for the various features described herein, and a skilled artisan will be able to select an appropriate structures and materials based on various considerations, including the intended use of the systems disclosed herein, the intended arena within which they will be used, and the equipment and/or accessories with which they are intended to be used, among other considerations. Conventional polymeric, metal-polymer composites, ceramics, and metal materials are suitable for use in the various components. Materials hereinafter discovered and/or developed that are determined to be suitable for use in the features and elements described herein would also be considered acceptable.

When ranges are used herein for physical properties, such as molecular weight, or chemical properties, such as chemical formulae, all combinations, and subcombinations of ranges for specific exemplar therein are intended to be included.

The disclosures of each patent, patent application, and publication cited or described in this document are hereby incorporated herein by reference, in its entirety.

Those of ordinary skill in the art will appreciate that numerous changes and modifications can be made to the exemplars of the disclosure and that such changes and modifications can be made without departing from the spirit of the disclosure. It is, therefore, intended that the appended claims cover all such equivalent variations as fall within the true spirit and scope of the disclosure.

What is claimed is:

1. A lighting system comprising:

a plurality of LED lights, at least a portion of said LED strings comprising one or more LEDs having an associated luminophoric medium;

said plurality of LED lights being configured to emit at least cyan, red, LRNE, and violet light; and a controller for independently controlling said plurality of LED lights in at least three modes, a first mode in which a selection of said plurality of LED lights are powered to emit a relatively low EML light, a second mode in which a selection of said plurality of LED lights are powered to emit a relatively high EML light, and a third mode in which at least one of LRNE light or said relatively high EML light is pulsed.

2. The lighting system of claim 1, wherein said relatively low EML light, said relatively high EML light, and said high fidelity light all are within a 7-step MacAdam ellipse around any point on the black body locus having a correlated color temperature between 1800K and 10000K.

3. The lighting system of claim 1, wherein said control system is configured to switch among said first, second and third modes based on inputs from one or more sensors.

4. The lighting system of claim 1, wherein said relatively low EML light and said relatively high EML light have an Ra of at least 80.

5. The lighting system of claim 1, wherein said high fidelity light have an Ra of at least 95.

6. The lighting system of claim 1, wherein said at least one of LRNE light or said relatively high EML light is pulsed to provide bioactive exposure.

7. The lighting system of claim 1, wherein said at least one of LRNE light or said relatively high EML light is pulsed at a frequency that is controllable and ranges from constant on to micro-pulses of less than a tenth of a second.

8. The lighting system of claim 1, wherein each pulse has a duration of less than 100 ms.

9. The lighting system of claim 8, wherein said frequency between 10 Hz and 0.5 mHz.

10. The lighting system of claim 8, wherein said each pulse ranges from a single pulse up to 400,000 pulses.

11. The lighting system of claim 1, wherein said controller pulses said at least one of LRNE light or said relatively high EML light in response to a control signal based on input data.

12. The lighting system of claim 11, wherein said input data is at least one of input by one or more of a user, a server, a database, or a decisioning engine based on data collected by at least one sensor.

13. The lighting system of claim 11, wherein said input is provided to a processor, wherein said processor is integrated in said lighting system, remote from said lighting system or a combination thereof.

14. The lighting system of claim 11, wherein said at least one of LRNE light or said relatively high EML light is pulsed at a frequency based on said input to dynamically adjust the therapeutic or health supplement to a user.

15. The lighting system of claim 11, wherein an adjustment is based on data harvested from at least one sensor in a user's lighting environment and at least one sensor reflecting information about a user.

16. The lighting system of claim 15, wherein said at least one sensor reflecting information about a user is one or more of a wearable device, a display device used by a user, or an ambient sensor.

17. The lighting system of claim 1, wherein said controller is configured to power said plurality of LED lights to emit a high fidelity light having an Ra of at least 90.

* * * * *